(12) United States Patent
Williams et al.

(10) Patent No.: US 11,317,833 B2
(45) Date of Patent: *May 3, 2022

(54) DISPLAYING USER INTERFACES ASSOCIATED WITH PHYSICAL ACTIVITIES

(71) Applicant: Apple Inc., Cupertino, CA (US)

(72) Inventors: Aled Hywel Williams, San Francisco, CA (US); Gary Ian Butcher, San Jose, CA (US); Matthew J. Sundstrom, Campbell, CA (US); Molly Pray Wiebe, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/894,309

(22) Filed: Jun. 5, 2020

(65) Prior Publication Data

US 2020/0297249 A1 Sep. 24, 2020

Related U.S. Application Data

(63) Continuation of application No. 16/144,849, filed on Sep. 27, 2018, now Pat. No. 10,674,942.

(Continued)

(51) Int. Cl.
*G06F 3/0482* (2013.01)
*A61B 5/11* (2006.01)
(Continued)

(52) U.S. Cl.
CPC ............ *A61B 5/1118* (2013.01); *A61B 5/681* (2013.01); *A63B 71/0619* (2013.01);
(Continued)

(58) Field of Classification Search
CPC .................. A61B 5/1118; A61B 5/681; A61B 2562/0219; A61B 5/11; A61B 5/00;
(Continued)

(56) References Cited

U.S. PATENT DOCUMENTS 4,205,628 A 6/1980 Null
4,842,266 A 6/1989 Sweeney et al.
(Continued)

FOREIGN PATENT DOCUMENTS

CA 2815518 A1 5/2012
CN 1337638 A 2/2002
(Continued)

OTHER PUBLICATIONS

Advisory Action received for U.S. Appl. No. 16/144,864, dated Jul. 29, 2019, 6 pages.

(Continued)

*Primary Examiner* — Tuyetlien T Tran
(74) *Attorney, Agent, or Firm* — Dentons US LLP

(57) ABSTRACT

The present disclosure generally relates to user interfaces and more specifically to techniques for displaying user interfaces associated with physical activities. Exemplary user interfaces related to activity competitions are described. Exemplary user interfaces related to a friends list for activity sharing are described. Exemplary user interfaces associated with alerts presented to a user in response to automatically determining a boundary of a workout are described. Exemplary user interfaces associated with configuring a pace alert for a workout application are described.

54 Claims, 119 Drawing Sheets

Related U.S. Application Data

(60) Provisional application No. 62/679,906, filed on Jun. 3, 2018, provisional application No. 62/688,159, filed on May 7, 2018.

(51) Int. Cl.

| | |
|---|---|
| *A61B 5/00* | (2006.01) |
| *H04W 4/029* | (2018.01) |
| *G06F 1/16* | (2006.01) |
| *A63B 71/06* | (2006.01) |
| *G06F 3/04847* | (2022.01) |
| *G06F 3/0485* | (2022.01) |
| *G06F 3/04883* | (2022.01) |
| *G06F 3/0481* | (2022.01) |
| *G06F 3/0488* | (2022.01) |
| *H04L 67/04* | (2022.01) |
| *H04M 1/72469* | (2021.01) |

(52) U.S. Cl.
CPC ............ *G06F 1/163* (2013.01); *G06F 3/0481* (2013.01); *G06F 3/0482* (2013.01); *G06F 3/0485* (2013.01); *G06F 3/0488* (2013.01); *G06F 3/04847* (2013.01); *G06F 3/04883* (2013.01); *H04W 4/029* (2018.02); *A61B 2562/0219* (2013.01); *H04L 67/04* (2013.01); *H04M 1/72469* (2021.01)

(58) Field of Classification Search
CPC .. G06F 3/04883; G06F 3/0481; G06F 3/0488; G06F 3/0482; G06F 3/04847; G06F 3/0485; G06F 1/163; G06F 3/041; G06F 2203/04106; G06F 2203/04104; G06F 3/016; G06F 3/0483; G06F 3/0362; G06F 1/1626; G06F 1/1643; G06F 2203/04105; G06F 3/0484; G06F 3/048; A63B 71/0619; A63B 24/00; H04W 4/029; H04L 67/04; H04M 1/72583
See application file for complete search history.

(56) References Cited

U.S. PATENT DOCUMENTS

| | | |
|---|---|---|
| 5,423,863 A | 6/1995 | Felblinger et al. |
| 5,458,548 A | 10/1995 | Crossing et al. |
| 5,474,077 A | 12/1995 | Suga |
| 5,515,344 A | 5/1996 | Ng |
| 5,642,731 A | 7/1997 | Kehr |
| 5,685,723 A | 11/1997 | Ladin et al. |
| 5,788,655 A | 8/1998 | Yoshimura et al. |
| 6,013,008 A | 1/2000 | Fukushima |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,244,988 B1 | 6/2001 | Delman |
| 6,302,789 B2 | 10/2001 | Harada et al. |
| 6,416,471 B1 | 7/2002 | Kumar et al. |
| 6,600,696 B1 | 7/2003 | Lynn |
| 6,603,477 B1 | 8/2003 | Tittle |
| 6,639,584 B1 | 10/2003 | Li |
| 6,705,972 B1 | 3/2004 | Takano et al. |
| 6,837,827 B1 | 1/2005 | Lee et al. |
| 6,866,613 B1 | 3/2005 | Brown et al. |
| 6,950,839 B1 | 9/2005 | Green et al. |
| 7,128,693 B2 | 10/2006 | Brown et al. |
| 7,166,078 B2 | 1/2007 | Saini et al. |
| 7,251,454 B2 | 7/2007 | White |
| 7,302,272 B2 | 11/2007 | Ackley |
| 7,662,065 B1 | 2/2010 | Kahn et al. |
| 7,695,406 B2 | 4/2010 | Waters |
| 7,739,148 B2 | 6/2010 | Suzuki et al. |
| 8,060,229 B2 | 11/2011 | Gupta et al. |
| 8,105,208 B2 | 1/2012 | Oleson et al. |
| 8,321,006 B1 | 11/2012 | Snyder et al. |
| 8,341,557 B2 | 12/2012 | Pisula et al. |
| 8,475,339 B2 | 7/2013 | Hwang et al. |
| 8,496,563 B2 | 7/2013 | Komatsu et al. |
| 8,676,170 B2 | 3/2014 | Porrati et al. |
| 8,725,527 B1 | 5/2014 | Kahn et al. |
| 8,758,262 B2 | 6/2014 | Rhee et al. |
| 8,784,115 B1 | 7/2014 | Chuang |
| 8,825,445 B2 | 9/2014 | Hollman et al. |
| 8,888,707 B2 | 11/2014 | Shirasaki et al. |
| 8,934,963 B1 | 1/2015 | Farazi |
| 8,990,006 B1 | 3/2015 | Wallace et al. |
| 9,020,538 B1 | 4/2015 | White et al. |
| 9,026,927 B2 | 5/2015 | Brumback et al. |
| 9,224,291 B2 | 12/2015 | Moll-carrillo et al. |
| 9,230,076 B2 | 1/2016 | King et al. |
| 9,557,881 B1 | 1/2017 | Jain et al. |
| 9,579,060 B1 | 2/2017 | Lisy et al. |
| 9,589,445 B2 | 3/2017 | White et al. |
| 9,672,715 B2 | 6/2017 | Roberts et al. |
| 9,712,629 B2 | 7/2017 | Molettiere et al. |
| 9,721,066 B1 | 8/2017 | Funaro et al. |
| 9,730,621 B2 | 8/2017 | Cohen et al. |
| 9,734,477 B2 | 8/2017 | Weast et al. |
| 9,801,562 B1 | 10/2017 | Host-madsen |
| 9,808,206 B1 | 11/2017 | Zhao et al. |
| 9,813,642 B1 | 11/2017 | Chen et al. |
| 9,817,481 B2 | 11/2017 | Pantelopoulos et al. |
| 9,854,653 B1 | 12/2017 | Ackmann et al. |
| 9,880,805 B1 | 1/2018 | Guralnick |
| 9,940,682 B2 | 4/2018 | Hoffman et al. |
| 10,056,006 B1 | 8/2018 | Hsu-Hoffman et al. |
| 10,175,781 B2 | 1/2019 | Karagozler et al. |
| 10,220,258 B2 | 3/2019 | Gu et al. |
| 10,226,195 B2 | 3/2019 | Briante et al. |
| 10,254,911 B2 | 4/2019 | Yang |
| 10,300,334 B1 | 5/2019 | Chuang |
| 10,304,347 B2 | 5/2019 | Wilson et al. |
| 10,339,830 B2 | 7/2019 | Han et al. |
| 10,398,381 B1 | 9/2019 | Heneghan et al. |
| 10,489,508 B2 | 11/2019 | Zhai et al. |
| 10,576,327 B2 | 3/2020 | Kim et al. |
| 10,602,964 B2 | 3/2020 | Kerber |
| 10,635,267 B2 | 4/2020 | Williams |
| 10,674,942 B2 | 6/2020 | Williams et al. |
| 10,736,543 B2 | 8/2020 | Chen et al. |
| 10,762,990 B1 | 9/2020 | Schilling et al. |
| 10,764,700 B1 | 9/2020 | Felton |
| 10,777,314 B1 | 9/2020 | Williams et al. |
| 10,796,549 B2 | 10/2020 | Roberts et al. |
| 11,107,569 B1 | 8/2021 | Devoto |
| 11,107,580 B1 | 8/2021 | Felton et al. |
| 2001/0049470 A1 | 12/2001 | Mault et al. |
| 2002/0045960 A1 | 4/2002 | Phillips et al. |
| 2002/0086774 A1 | 7/2002 | Warner |
| 2002/0095292 A1 | 7/2002 | Mittal et al. |
| 2002/0118121 A1 | 8/2002 | Lehrman et al. |
| 2003/0023178 A1 | 1/2003 | Bischoff et al. |
| 2003/0064860 A1 | 4/2003 | Yamashita et al. |
| 2003/0134714 A1 | 7/2003 | Oishi et al. |
| 2003/0179229 A1 | 9/2003 | Van et al. |
| 2003/0181291 A1 | 9/2003 | Ogawa |
| 2003/0182628 A1 | 9/2003 | Lira |
| 2003/0191609 A1 | 10/2003 | Bernardi et al. |
| 2003/0200483 A1 | 10/2003 | Sutton |
| 2003/0216971 A1 | 11/2003 | Sick et al. |
| 2003/0226695 A1 | 12/2003 | Mault |
| 2004/0014567 A1 | 1/2004 | Mendel |
| 2004/0017300 A1 | 1/2004 | Kotzin et al. |
| 2004/0077462 A1 | 4/2004 | Brown et al. |
| 2004/0077958 A1 | 4/2004 | Kato et al. |
| 2004/0128286 A1 | 7/2004 | Yasushi et al. |
| 2004/0190729 A1 | 9/2004 | Yonovitz et al. |
| 2004/0193069 A1 | 9/2004 | Takehara |
| 2004/0236189 A1 | 11/2004 | Hawthorne et al. |
| 2005/0010117 A1 | 1/2005 | Agutter et al. |
| 2005/0027208 A1 | 2/2005 | Shiraishi et al. |

(56) References Cited

U.S. PATENT DOCUMENTS

| | | |
|---|---|---|
| 2005/0075214 A1 | 4/2005 | Brown et al. |
| 2005/0079905 A1 | 4/2005 | Martens |
| 2005/0113650 A1 | 5/2005 | Pacione et al. |
| 2005/0124324 A1 | 6/2005 | Thomas et al. |
| 2005/0139852 A1 | 6/2005 | Chen et al. |
| 2005/0149362 A1 | 7/2005 | Peterson et al. |
| 2005/0165627 A1 | 7/2005 | Fotsch et al. |
| 2005/0172311 A1 | 8/2005 | Hjelt et al. |
| 2005/0197063 A1 | 9/2005 | White et al. |
| 2005/0216867 A1 | 9/2005 | Marvit et al. |
| 2005/0228735 A1 | 10/2005 | Duquette |
| 2005/0244013 A1 | 11/2005 | Battenberg et al. |
| 2005/0272564 A1 | 12/2005 | Pyles et al. |
| 2006/0020174 A1 | 1/2006 | Matsumura et al. |
| 2006/0052727 A1 | 3/2006 | Palestrant |
| 2006/0094969 A1 | 5/2006 | Nissila |
| 2006/0098109 A1 | 5/2006 | Ooki |
| 2006/0106741 A1 | 5/2006 | Janarthanan |
| 2006/0136173 A1 | 6/2006 | Case et al. |
| 2006/0149144 A1 | 7/2006 | Lynn et al. |
| 2006/0152372 A1 | 7/2006 | Stout |
| 2006/0182287 A1 | 8/2006 | Schulein et al. |
| 2006/0184800 A1 | 8/2006 | Rosenberg |
| 2006/0205564 A1 | 9/2006 | Peterson |
| 2006/0235319 A1 | 10/2006 | Belohlavek et al. |
| 2006/0240959 A1 | 10/2006 | Huang |
| 2006/0250524 A1 | 11/2006 | Roche |
| 2006/0274908 A1 | 12/2006 | Choi |
| 2007/0016440 A1 | 1/2007 | Stroup |
| 2007/0021269 A1 | 1/2007 | Shum |
| 2007/0032733 A1 | 2/2007 | Burton |
| 2007/0033069 A1 | 2/2007 | Rao et al. |
| 2007/0056727 A1 | 3/2007 | Newman |
| 2007/0071256 A1 | 3/2007 | Ito |
| 2007/0113726 A1 | 5/2007 | Oliver et al. |
| 2007/0136093 A1 | 6/2007 | Rankin et al. |
| 2007/0143433 A1 | 6/2007 | Daigle |
| 2007/0169614 A1 | 7/2007 | Sasaki et al. |
| 2007/0249949 A1 | 10/2007 | Hadley |
| 2007/0271065 A1 | 11/2007 | Gupta et al. |
| 2008/0012701 A1 | 1/2008 | Kass et al. |
| 2008/0020803 A1 | 1/2008 | Rios et al. |
| 2008/0027673 A1 | 1/2008 | Trumm |
| 2008/0051919 A1 | 2/2008 | Sakai et al. |
| 2008/0052945 A1 | 3/2008 | Matas et al. |
| 2008/0058626 A1 | 3/2008 | Miyata et al. |
| 2008/0076637 A1 | 3/2008 | Gilley et al. |
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0141135 A1 | 6/2008 | Mason et al. |
| 2008/0146892 A1 | 6/2008 | Leboeuf et al. |
| 2008/0150731 A1 | 6/2008 | Laukkanen et al. |
| 2008/0159547 A1 | 7/2008 | Schuler et al. |
| 2008/0161161 A1 | 7/2008 | Pipinich et al. |
| 2008/0161707 A1 | 7/2008 | Farringdon et al. |
| 2008/0200312 A1 | 8/2008 | Tagliabue |
| 2008/0205660 A1 | 8/2008 | Goldstein |
| 2008/0228045 A1 | 9/2008 | Gao et al. |
| 2008/0229226 A1 | 9/2008 | Rowbottom et al. |
| 2008/0240519 A1 | 10/2008 | Nagamitsu |
| 2008/0254767 A1 | 10/2008 | Jin |
| 2008/0300110 A1 | 12/2008 | Smith et al. |
| 2009/0007017 A1 | 1/2009 | Anzures et al. |
| 2009/0007596 A1 | 1/2009 | Goldstein et al. |
| 2009/0012988 A1 | 1/2009 | Brown |
| 2009/0052677 A1 | 2/2009 | Smith |
| 2009/0065578 A1 | 3/2009 | Peterson et al. |
| 2009/0118100 A1 | 5/2009 | Oliver et al. |
| 2009/0164567 A1 | 6/2009 | Hara |
| 2009/0170532 A1 | 7/2009 | Lee et al. |
| 2009/0180631 A1 | 7/2009 | Michael et al. |
| 2009/0192823 A1 | 7/2009 | Hawkins et al. |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0233771 A1 | 9/2009 | Quatrochi et al. |
| 2009/0245537 A1 | 10/2009 | Morin |
| 2009/0259134 A1 | 10/2009 | Levine |
| 2009/0262088 A1 | 10/2009 | Moll-carrillo et al. |
| 2009/0287103 A1 | 11/2009 | Pillai |
| 2009/0287327 A1 | 11/2009 | Hsu et al. |
| 2009/0290721 A1 | 11/2009 | Goldstein et al. |
| 2009/0319243 A1 | 12/2009 | Suarez-rivera et al. |
| 2010/0003951 A1 | 1/2010 | Ray et al. |
| 2010/0010832 A1 | 1/2010 | Boute et al. |
| 2010/0017489 A1 | 1/2010 | Birnbaum et al. |
| 2010/0027807 A1 | 2/2010 | Jeon |
| 2010/0031202 A1 | 2/2010 | Morris et al. |
| 2010/0042949 A1 | 2/2010 | Chen |
| 2010/0046767 A1 | 2/2010 | Bayley et al. |
| 2010/0048358 A1 | 2/2010 | Tchao et al. |
| 2010/0060586 A1 | 3/2010 | Pisula et al. |
| 2010/0062818 A1 | 3/2010 | Haughay et al. |
| 2010/0062905 A1 | 3/2010 | Rottier et al. |
| 2010/0064255 A1 | 3/2010 | Rottier et al. |
| 2010/0076331 A1 | 3/2010 | Chan et al. |
| 2010/0079291 A1 | 4/2010 | Kroll et al. |
| 2010/0099539 A1 | 4/2010 | Haataja |
| 2010/0119093 A1 | 5/2010 | Uzuanis et al. |
| 2010/0121700 A1 | 5/2010 | Wigder et al. |
| 2010/0131298 A1 | 5/2010 | Buttner et al. |
| 2010/0137106 A1 | 6/2010 | Oshima et al. |
| 2010/0145209 A1 | 6/2010 | Lee et al. |
| 2010/0150378 A1 | 6/2010 | Lee et al. |
| 2010/0179832 A1 | 7/2010 | Van et al. |
| 2010/0194692 A1 | 8/2010 | Orr et al. |
| 2010/0198453 A1 | 8/2010 | Dorogusker et al. |
| 2010/0222645 A1 | 9/2010 | Nadler et al. |
| 2010/0281374 A1 | 11/2010 | Schulz et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0312138 A1 | 12/2010 | Regas |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0032105 A1 | 2/2011 | Hoffman et al. |
| 2011/0066051 A1 | 3/2011 | Moon et al. |
| 2011/0071869 A1 | 3/2011 | Obrien et al. |
| 2011/0074699 A1 | 3/2011 | Marr et al. |
| 2011/0093481 A1 | 4/2011 | Hussam |
| 2011/0098928 A1 | 4/2011 | Hoffman et al. |
| 2011/0106553 A1 | 5/2011 | Tanaka et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0152656 A1 | 6/2011 | Weinert et al. |
| 2011/0159469 A1 | 6/2011 | Hwang et al. |
| 2011/0166631 A1 | 7/2011 | Breining |
| 2011/0167369 A1 | 7/2011 | Van Os |
| 2011/0201911 A1 | 8/2011 | Johnson et al. |
| 2011/0213276 A1 | 9/2011 | Sarussi et al. |
| 2011/0214162 A1 | 9/2011 | Brakensiek et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0245623 A1 | 10/2011 | Chutani et al. |
| 2011/0246509 A1 | 10/2011 | Migita et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2012/0002510 A1 | 1/2012 | Berman, Jr. |
| 2012/0015778 A1 | 1/2012 | Lee et al. |
| 2012/0015779 A1 | 1/2012 | Powch et al. |
| 2012/0029303 A1 | 2/2012 | Shaya |
| 2012/0030623 A1 | 2/2012 | Hoellwarth |
| 2012/0034897 A1 | 2/2012 | Kreitzer et al. |
| 2012/0038651 A1 | 2/2012 | Case et al. |
| 2012/0041767 A1 | 2/2012 | Hoffman et al. |
| 2012/0042039 A1 | 2/2012 | Mark |
| 2012/0059664 A1 | 3/2012 | Georgiev et al. |

(56) References Cited

U.S. PATENT DOCUMENTS

| | | |
|---|---|---|
| 2012/0065480 A1 | 3/2012 | Badilini et al. |
| 2012/0071770 A1 | 3/2012 | Grey et al. |
| 2012/0092383 A1 | 4/2012 | Hysek et al. |
| 2012/0105225 A1 | 5/2012 | Valtonen |
| 2012/0112908 A1 | 5/2012 | Prykaeri et al. |
| 2012/0116550 A1 | 5/2012 | Hoffman et al. |
| 2012/0150759 A1 | 6/2012 | Tarjan |
| 2012/0159380 A1 | 6/2012 | Kocienda et al. |
| 2012/0179319 A1 | 7/2012 | Gilman et al. |
| 2012/0203124 A1 | 8/2012 | Lim |
| 2012/0215115 A1 | 8/2012 | Takahashi |
| 2012/0232414 A1 | 9/2012 | Mollicone et al. |
| 2012/0245447 A1 | 9/2012 | Karan et al. |
| 2012/0253485 A1 | 10/2012 | Weast et al. |
| 2012/0274508 A1 | 11/2012 | Brown et al. |
| 2012/0283524 A1 | 11/2012 | Kiani et al. |
| 2012/0283587 A1 | 11/2012 | Gosh et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0302843 A1 | 11/2012 | Otsubo et al. |
| 2012/0317167 A1 | 12/2012 | Rahman et al. |
| 2012/0321094 A1 | 12/2012 | Schiller et al. |
| 2012/0326873 A1 | 12/2012 | Utter, II |
| 2013/0002425 A1 | 1/2013 | Hatch et al. |
| 2013/0011819 A1 | 1/2013 | Horseman |
| 2013/0012788 A1 | 1/2013 | Horseman |
| 2013/0013331 A1 | 1/2013 | Horseman |
| 2013/0033376 A1 | 2/2013 | Seyed et al. |
| 2013/0054150 A1 | 2/2013 | Sacks et al. |
| 2013/0054720 A1 | 2/2013 | Kang et al. |
| 2013/0065569 A1 | 3/2013 | Leipzig et al. |
| 2013/0067050 A1 | 3/2013 | Kotteri et al. |
| 2013/0072765 A1 | 3/2013 | Kahn et al. |
| 2013/0073960 A1 | 3/2013 | Eppolito et al. |
| 2013/0081083 A1 | 3/2013 | Yu et al. |
| 2013/0093715 A1 | 4/2013 | Marsden et al. |
| 2013/0095459 A1 | 4/2013 | Tran |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0114100 A1 | 5/2013 | Torii et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0144653 A1 | 6/2013 | Poe et al. |
| 2013/0151285 A1 | 6/2013 | Mclaren et al. |
| 2013/0158367 A1 | 6/2013 | Pacione et al. |
| 2013/0158416 A1 | 6/2013 | Hatlestad et al. |
| 2013/0184613 A1 | 7/2013 | Homsi et al. |
| 2013/0185097 A1 | 7/2013 | Saria et al. |
| 2013/0187923 A1 | 7/2013 | Yoshimoto et al. |
| 2013/0188322 A1 | 7/2013 | Lowe et al. |
| 2013/0197679 A1 | 8/2013 | Balakrishnan et al. |
| 2013/0198672 A1 | 8/2013 | Yoon et al. |
| 2013/0202121 A1 | 8/2013 | Georgiou et al. |
| 2013/0203475 A1 | 8/2013 | Shin et al. |
| 2013/0215042 A1 | 8/2013 | Messerschmidt et al. |
| 2013/0215119 A1 | 8/2013 | Vanhoecke |
| 2013/0217979 A1 | 8/2013 | Blackadar et al. |
| 2013/0231575 A1 | 9/2013 | Erkkila et al. |
| 2013/0231711 A1 | 9/2013 | Kaib |
| 2013/0231947 A1 | 9/2013 | Shusterman |
| 2013/0233097 A1 | 9/2013 | Hayner et al. |
| 2013/0262155 A1 | 10/2013 | Hinkamp |
| 2013/0263719 A1 | 10/2013 | Watterson et al. |
| 2013/0268398 A1 | 10/2013 | Agami et al. |
| 2013/0274628 A1 | 10/2013 | Fausti et al. |
| 2013/0304616 A1 | 11/2013 | Raleigh et al. |
| 2013/0317380 A1 | 11/2013 | Liley et al. |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0330694 A1 | 12/2013 | Watterson |
| 2013/0332286 A1 | 12/2013 | Medelius et al. |
| 2013/0345978 A1 | 12/2013 | Lush et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0067096 A1 | 3/2014 | Aibara |
| 2014/0073486 A1 | 3/2014 | Ahmed et al. |
| 2014/0081118 A1 | 3/2014 | Reinhold et al. |
| 2014/0081666 A1 | 3/2014 | Teller et al. |
| 2014/0088995 A1 | 3/2014 | Damani |
| 2014/0089836 A1 | 3/2014 | Daman et al. |
| 2014/0108998 A1 | 4/2014 | Chaudhri et al. |
| 2014/0127996 A1 | 5/2014 | Park et al. |
| 2014/0129007 A1 | 5/2014 | Utter, II |
| 2014/0129243 A1 | 5/2014 | Utter, II |
| 2014/0135592 A1 | 5/2014 | Ohnemus et al. |
| 2014/0139637 A1 | 5/2014 | Mistry et al. |
| 2014/0142403 A1 | 5/2014 | Brumback et al. |
| 2014/0143678 A1 | 5/2014 | Mistry et al. |
| 2014/0164611 A1 | 6/2014 | Molettiere et al. |
| 2014/0176335 A1 | 6/2014 | Brumback et al. |
| 2014/0176346 A1 | 6/2014 | Brumback et al. |
| 2014/0176475 A1 | 6/2014 | Myers et al. |
| 2014/0180595 A1 | 6/2014 | Brumback et al. |
| 2014/0180786 A1 | 6/2014 | Sullivan |
| 2014/0184422 A1 | 7/2014 | Mensinger et al. |
| 2014/0189510 A1 | 7/2014 | Ozcan |
| 2014/0189584 A1 | 7/2014 | Weng et al. |
| 2014/0197946 A1 | 7/2014 | Park et al. |
| 2014/0200426 A1 | 7/2014 | Taub et al. |
| 2014/0200691 A1 | 7/2014 | Lee et al. |
| 2014/0218369 A1 | 8/2014 | Yuen et al. |
| 2014/0228647 A1 | 8/2014 | Sakamoto et al. |
| 2014/0239065 A1 | 8/2014 | Zhou et al. |
| 2014/0240122 A1* | 8/2014 | Roberts ............... A61B 5/7455 340/539.11 |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0266776 A1 | 9/2014 | Miller et al. |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0275856 A1 | 9/2014 | Kohlrausch et al. |
| 2014/0277628 A1 | 9/2014 | Nieminen et al. |
| 2014/0278220 A1 | 9/2014 | Yuen |
| 2014/0278229 A1 | 9/2014 | Hong et al. |
| 2014/0282153 A1 | 9/2014 | Christiansen et al. |
| 2014/0288680 A1 | 9/2014 | Hoffman et al. |
| 2014/0297217 A1 | 10/2014 | Yuen |
| 2014/0310598 A1 | 10/2014 | Sprague et al. |
| 2014/0310643 A1 | 10/2014 | Karmanenko et al. |
| 2014/0327527 A1 | 11/2014 | Goldstein et al. |
| 2014/0331314 A1 | 11/2014 | Fujioka |
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0344687 A1 | 11/2014 | Durham et al. |
| 2014/0344723 A1 | 11/2014 | Malik et al. |
| 2014/0344951 A1 | 11/2014 | Brewer |
| 2014/0354494 A1 | 12/2014 | Katz |
| 2014/0358012 A1 | 12/2014 | Richards et al. |
| 2014/0358473 A1 | 12/2014 | Goel et al. |
| 2014/0358584 A1 | 12/2014 | Worden et al. |
| 2014/0371887 A1 | 12/2014 | Hoffman et al. |
| 2015/0004578 A1 | 1/2015 | Gilley et al. |
| 2015/0018632 A1 | 1/2015 | Khair |
| 2015/0046814 A1 | 2/2015 | Haughay et al. |
| 2015/0057943 A1 | 2/2015 | Self et al. |
| 2015/0058263 A1 | 2/2015 | Landers |
| 2015/0065095 A1 | 3/2015 | Seo et al. |
| 2015/0065302 A1 | 3/2015 | Ou et al. |
| 2015/0067513 A1 | 3/2015 | Zambetti et al. |
| 2015/0067811 A1 | 3/2015 | Agnew et al. |
| 2015/0074571 A1 | 3/2015 | Marti et al. |

(56) References Cited

U.S. PATENT DOCUMENTS

| | | |
|---|---|---|
| 2015/0081059 A1 | 3/2015 | Hwang et al. |
| 2015/0081060 A1 | 3/2015 | Hwang et al. |
| 2015/0081210 A1 | 3/2015 | Yeh et al. |
| 2015/0081529 A1 | 3/2015 | Lee et al. |
| 2015/0083970 A1 | 3/2015 | Koh et al. |
| 2015/0089536 A1 | 3/2015 | Byerley |
| 2015/0098309 A1 | 4/2015 | Adams et al. |
| 2015/0099991 A1 | 4/2015 | Yamaguchi et al. |
| 2015/0100245 A1 | 4/2015 | Huang et al. |
| 2015/0106025 A1 | 4/2015 | Keller et al. |
| 2015/0110277 A1 | 4/2015 | Pidgeon et al. |
| 2015/0110279 A1 | 4/2015 | Tejerina |
| 2015/0112700 A1 | 4/2015 | Sublett et al. |
| 2015/0113553 A1 | 4/2015 | Pan |
| 2015/0118657 A1 | 4/2015 | Shrake et al. |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0127365 A1 | 5/2015 | Rizvi et al. |
| 2015/0130830 A1 | 5/2015 | Nagasaki et al. |
| 2015/0142689 A1 | 5/2015 | Squires |
| 2015/0153943 A1 | 6/2015 | Wang |
| 2015/0164349 A1 | 6/2015 | Gopalakrishnan et al. |
| 2015/0179186 A1 | 6/2015 | Swierk et al. |
| 2015/0180746 A1 | 6/2015 | Day et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0193805 A1 | 7/2015 | Filipiak |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0205947 A1 | 7/2015 | Berman et al. |
| 2015/0216448 A1 | 8/2015 | Lotan et al. |
| 2015/0217163 A1 | 8/2015 | Amis et al. |
| 2015/0220883 A1 | 8/2015 | Bfar et al. |
| 2015/0230717 A1 | 8/2015 | Wan |
| 2015/0251053 A1 | 9/2015 | Hoffman et al. |
| 2015/0262499 A1 | 9/2015 | Wicka et al. |
| 2015/0269848 A1 | 9/2015 | Yuen et al. |
| 2015/0286800 A1 | 10/2015 | Kanagala et al. |
| 2015/0287421 A1 | 10/2015 | Benway et al. |
| 2015/0288944 A1 | 10/2015 | Nistico et al. |
| 2015/0289823 A1 | 10/2015 | Rack-gomer et al. |
| 2015/0293592 A1 | 10/2015 | Cheong et al. |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0343709 A1 | 12/2015 | Gerstle et al. |
| 2015/0347690 A1 | 12/2015 | Keen et al. |
| 2015/0347711 A1 | 12/2015 | Soli et al. |
| 2015/0350799 A1 | 12/2015 | Schnaare et al. |
| 2015/0350861 A1 | 12/2015 | Soli et al. |
| 2015/0351655 A1 | 12/2015 | Coleman |
| 2015/0374310 A1 | 12/2015 | Lee |
| 2015/0379198 A1 | 12/2015 | Tambasco, Jr. |
| 2016/0000379 A1 | 1/2016 | Pougatchev et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0048298 A1 | 2/2016 | Choi et al. |
| 2016/0055420 A1 | 2/2016 | Karanam et al. |
| 2016/0058313 A1 | 3/2016 | Sato |
| 2016/0058336 A1* | 3/2016 | Blahnik .............. G06F 19/3481 600/595 |
| 2016/0058337 A1 | 3/2016 | Blahnik et al. |
| 2016/0062582 A1* | 3/2016 | Wilson .................. G06F 3/0482 715/772 |
| 2016/0063215 A1 | 3/2016 | Zamer |
| 2016/0065505 A1 | 3/2016 | Iskander |
| 2016/0070275 A1 | 3/2016 | Anderson et al. |
| 2016/0072896 A1 | 3/2016 | Petersen et al. |
| 2016/0085937 A1 | 3/2016 | Dettinger et al. |
| 2016/0086500 A1 | 3/2016 | Kaleal, III |
| 2016/0098522 A1 | 4/2016 | Weinstein |
| 2016/0106398 A1 | 4/2016 | Kuppuswami |
| 2016/0107031 A1 | 4/2016 | Palatsi et al. |
| 2016/0109961 A1 | 4/2016 | Parshionikar |
| 2016/0132046 A1 | 5/2016 | Beoughter et al. |
| 2016/0135719 A1 | 5/2016 | Von Kraus et al. |
| 2016/0135731 A1 | 5/2016 | Drennan |
| 2016/0140828 A1 | 5/2016 | Deforest |
| 2016/0150978 A1 | 6/2016 | Yuen et al. |
| 2016/0156584 A1 | 6/2016 | Hum et al. |
| 2016/0166181 A1 | 6/2016 | Shennib |
| 2016/0174857 A1 | 6/2016 | Eggers et al. |
| 2016/0180026 A1 | 6/2016 | Kim et al. |
| 2016/0189051 A1 | 6/2016 | Mahmood |
| 2016/0196635 A1 | 7/2016 | Cho et al. |
| 2016/0210099 A1 | 7/2016 | Hampapuram et al. |
| 2016/0220225 A1 | 8/2016 | Wang et al. |
| 2016/0235325 A1 | 8/2016 | Chou |
| 2016/0235374 A1 | 8/2016 | Miller et al. |
| 2016/0246880 A1 | 8/2016 | Battiah et al. |
| 2016/0249857 A1 | 9/2016 | Choi et al. |
| 2016/0250517 A1 | 9/2016 | Vis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0270717 A1 | 9/2016 | Luna et al. |
| 2016/0275990 A1 | 9/2016 | Vassort |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0287177 A1 | 10/2016 | Huppert et al. |
| 2016/0292373 A1 | 10/2016 | Spors et al. |
| 2016/0299769 A1 | 10/2016 | Hunter et al. |
| 2016/0301761 A1 | 10/2016 | Sanchez-sandoval et al. |
| 2016/0301794 A1 | 10/2016 | Schlakman et al. |
| 2016/0302666 A1 | 10/2016 | Shaya |
| 2016/0302717 A1 | 10/2016 | Tawa et al. |
| 2016/0314670 A1 | 10/2016 | Roberts et al. |
| 2016/0314683 A1 | 10/2016 | Felch et al. |
| 2016/0317341 A1 | 11/2016 | Galvan |
| 2016/0324457 A1 | 11/2016 | Dagum |
| 2016/0324488 A1 | 11/2016 | Olsen |
| 2016/0328736 A1 | 11/2016 | Wang et al. |
| 2016/0328991 A1 | 11/2016 | Simpson et al. |
| 2016/0332025 A1 | 11/2016 | Repka |
| 2016/0346607 A1 | 12/2016 | Rapfogel |
| 2016/0360100 A1 | 12/2016 | Kim et al. |
| 2016/0360972 A1 | 12/2016 | Kusakabe et al. |
| 2016/0371464 A1 | 12/2016 | Bricker |
| 2016/0375306 A1 | 12/2016 | Gu et al. |
| 2016/0379511 A1 | 12/2016 | Dawson et al. |
| 2017/0000348 A1 | 1/2017 | Karsten et al. |
| 2017/0000359 A1 | 1/2017 | Kohli et al. |
| 2017/0001073 A1 | 1/2017 | Krueger et al. |
| 2017/0007159 A1 | 1/2017 | Dieffenderfer et al. |
| 2017/0007167 A1 | 1/2017 | Kostic et al. |
| 2017/0011210 A1 | 1/2017 | Cheong et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0039327 A1 | 2/2017 | Bitran et al. |
| 2017/0043214 A1 | 2/2017 | Higashi |
| 2017/0046024 A1 | 2/2017 | Dascola et al. |
| 2017/0053542 A1* | 2/2017 | Wilson .................... G09B 5/02 |
| 2017/0065224 A1 | 3/2017 | Rahko et al. |
| 2017/0071551 A1 | 3/2017 | Jain et al. |
| 2017/0075551 A1 | 3/2017 | Robinson et al. |
| 2017/0086693 A1 | 3/2017 | Peterson et al. |
| 2017/0095695 A1 | 4/2017 | Mangusson et al. |
| 2017/0127997 A1 | 5/2017 | Hyde et al. |
| 2017/0132395 A1 | 5/2017 | Futch |
| 2017/0136297 A1 | 5/2017 | Penie |
| 2017/0143262 A1 | 5/2017 | Kurunmäki et al. |
| 2017/0147197 A1 | 5/2017 | Yang et al. |
| 2017/0150917 A1 | 6/2017 | Brief et al. |

(56) References Cited

U.S. PATENT DOCUMENTS

| | | |
|---|---|---|
| 2017/0153606 A1 | 6/2017 | Pitis et al. |
| 2017/0153804 A1 | 6/2017 | Kim et al. |
| 2017/0156593 A1 | 6/2017 | Ferber et al. |
| 2017/0161014 A1 | 6/2017 | Kikugawa et al. |
| 2017/0172522 A1 | 6/2017 | Insler et al. |
| 2017/0177797 A1 | 6/2017 | Kurniawan et al. |
| 2017/0181645 A1 | 6/2017 | Mahalingam et al. |
| 2017/0188841 A1 | 7/2017 | Ma et al. |
| 2017/0188893 A1 | 7/2017 | Venkatraman et al. |
| 2017/0188979 A1 | 7/2017 | Volpe |
| 2017/0202496 A1 | 7/2017 | Ramanathan |
| 2017/0209766 A1 | 7/2017 | Riley et al. |
| 2017/0235443 A1 | 8/2017 | Suzuki |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0258455 A1 | 9/2017 | Qi |
| 2017/0266494 A1 | 9/2017 | Crankson et al. |
| 2017/0269792 A1 | 9/2017 | Xu et al. |
| 2017/0274149 A1 | 9/2017 | Aeschlimann |
| 2017/0274267 A1* | 9/2017 | Blahnik ............... G06F 3/0484 |
| 2017/0281026 A1 | 10/2017 | Nick et al. |
| 2017/0281057 A1 | 10/2017 | Blahnik et al. |
| 2017/0293727 A1 | 10/2017 | Klaassen et al. |
| 2017/0294174 A1 | 10/2017 | Albadawi et al. |
| 2017/0300186 A1 | 10/2017 | Kuhar et al. |
| 2017/0301039 A1 | 10/2017 | Dyer et al. |
| 2017/0303844 A1 | 10/2017 | Baker et al. |
| 2017/0319184 A1 | 11/2017 | Sano |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0333752 A1 | 11/2017 | Korkala et al. |
| 2017/0337033 A1 | 11/2017 | Duyan et al. |
| 2017/0348562 A1 | 12/2017 | Jung et al. |
| 2017/0354845 A1 | 12/2017 | Williams et al. |
| 2017/0357329 A1 | 12/2017 | Park et al. |
| 2017/0357520 A1 | 12/2017 | De Vries et al. |
| 2018/0000426 A1 | 1/2018 | Li |
| 2018/0001184 A1 | 1/2018 | Tran et al. |
| 2018/0011686 A1 | 1/2018 | Zhao et al. |
| 2018/0032234 A1 | 2/2018 | Michalske |
| 2018/0042559 A1 | 2/2018 | Cabrera et al. |
| 2018/0047277 A1 | 2/2018 | Thyroff |
| 2018/0049659 A1 | 2/2018 | Briante et al. |
| 2018/0049696 A1 | 2/2018 | Eom et al. |
| 2018/0053200 A1 | 2/2018 | Cronin et al. |
| 2018/0055490 A1 | 3/2018 | Lee et al. |
| 2018/0056132 A1 | 3/2018 | Foley et al. |
| 2018/0060522 A1 | 3/2018 | Petterson et al. |
| 2018/0064356 A1 | 3/2018 | Mendenhall et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0081918 A1 | 3/2018 | Nites et al. |
| 2018/0096739 A1 | 4/2018 | Sano |
| 2018/0107962 A1 | 4/2018 | Lundin et al. |
| 2018/0117414 A1 | 5/2018 | Miyasaka et al. |
| 2018/0120985 A1 | 5/2018 | Wallace et al. |
| 2018/0126248 A1 | 5/2018 | Dion et al. |
| 2018/0132768 A1 | 5/2018 | Sasahara et al. |
| 2018/0137937 A1 | 5/2018 | Gass et al. |
| 2018/0140211 A1 | 5/2018 | Nakazawa et al. |
| 2018/0140903 A1 | 5/2018 | Poure et al. |
| 2018/0140927 A1 | 5/2018 | Kito et al. |
| 2018/0150709 A1 | 5/2018 | Ha |
| 2018/0154212 A1 | 6/2018 | Park et al. |
| 2018/0189077 A1 | 7/2018 | Gupta et al. |
| 2018/0206766 A1 | 7/2018 | Blahnik et al. |
| 2018/0211020 A1 | 7/2018 | Fukuda |
| 2018/0239869 A1 | 8/2018 | Laing et al. |
| 2018/0255159 A1 | 9/2018 | Cohen et al. |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263510 A1 | 9/2018 | Cronin et al. |
| 2018/0263517 A1 | 9/2018 | Kubo |
| 2018/0272190 A1 | 9/2018 | Miura et al. |
| 2018/0279885 A1 | 10/2018 | Bulut |
| 2018/0294053 A1 | 10/2018 | Runyon et al. |
| 2018/0318647 A1 | 11/2018 | Foley et al. |
| 2018/0329584 A1 | 11/2018 | Williams et al. |
| 2018/0336530 A1 | 11/2018 | Johnson et al. |
| 2018/0339195 A1 | 11/2018 | Bernotas |
| 2018/0345078 A1 | 12/2018 | Blahnik et al. |
| 2018/0350451 A1 | 12/2018 | Ohnemus et al. |
| 2018/0368814 A1 | 12/2018 | R. Kudtarkar |
| 2018/0376107 A1 | 12/2018 | Shibaev et al. |
| 2019/0008467 A1 | 1/2019 | Averina et al. |
| 2019/0012898 A1 | 1/2019 | Wittrup |
| 2019/0014205 A1 | 1/2019 | Miloseski et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0034494 A1 | 1/2019 | Bradley et al. |
| 2019/0043337 A1 | 2/2019 | Liu et al. |
| 2019/0073618 A1 | 3/2019 | Kanukurthy et al. |
| 2019/0089701 A1 | 3/2019 | Mercury et al. |
| 2019/0090800 A1 | 3/2019 | Bosworth et al. |
| 2019/0090816 A1 | 3/2019 | Horseman |
| 2019/0104951 A1 | 4/2019 | Valys et al. |
| 2019/0122523 A1 | 4/2019 | Roberts et al. |
| 2019/0138696 A1 | 5/2019 | Carpenter et al. |
| 2019/0150854 A1 | 5/2019 | Chung et al. |
| 2019/0184234 A1 | 6/2019 | Packles et al. |
| 2019/0192086 A1 | 6/2019 | Menon et al. |
| 2019/0206538 A1 | 7/2019 | Xing et al. |
| 2019/0209777 A1 | 7/2019 | O'connell et al. |
| 2019/0223843 A1 | 7/2019 | Vitti |
| 2019/0228179 A1 | 7/2019 | Rakshit et al. |
| 2019/0228640 A1 | 7/2019 | Freedman et al. |
| 2019/0232110 A1 | 8/2019 | Williams et al. |
| 2019/0232111 A1 | 8/2019 | Williams et al. |
| 2019/0240534 A1 | 8/2019 | Black |
| 2019/0252054 A1 | 8/2019 | Dirani et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0278556 A1 | 9/2019 | Usher et al. |
| 2019/0279520 A1 | 9/2019 | Wilson et al. |
| 2019/0298230 A1 | 10/2019 | Nicholson et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339849 A1 | 11/2019 | Williams et al. |
| 2019/0342616 A1 | 11/2019 | Domm et al. |
| 2019/0365332 A1 | 12/2019 | Fedichev et al. |
| 2019/0380624 A1 | 12/2019 | Ota et al. |
| 2019/0385708 A1 | 12/2019 | Hong et al. |
| 2019/0387982 A1 | 12/2019 | Buller |
| 2020/0000441 A1 | 1/2020 | Lafon et al. |
| 2020/0014967 A1 | 1/2020 | Putnam |
| 2020/0069258 A1 | 3/2020 | Grinberg |
| 2020/0098278 A1 | 3/2020 | Doti et al. |
| 2020/0100693 A1 | 4/2020 | Veto |
| 2020/0101365 A1 | 4/2020 | Wilson et al. |
| 2020/0126673 A1 | 4/2020 | Tanabe et al. |
| 2020/0245928 A1 | 8/2020 | Kang et al. |
| 2020/0261011 A1 | 8/2020 | Seppänen et al. |
| 2020/0273566 A1 | 8/2020 | Bhowmik et al. |
| 2020/0315544 A1 | 10/2020 | Levine |
| 2020/0356687 A1 | 11/2020 | Salzman et al. |
| 2020/0357522 A1 | 11/2020 | Pahwa et al. |
| 2020/0374682 A1 | 11/2020 | Newman et al. |
| 2020/0379611 A1 | 12/2020 | Dryer et al. |
| 2020/0381099 A1 | 12/2020 | Crowley et al. |
| 2020/0381100 A1 | 12/2020 | Williams et al. |
| 2020/0381123 A1 | 12/2020 | Dryer et al. |
| 2020/0382613 A1 | 12/2020 | Sundstrom et al. |
| 2020/0382866 A1 | 12/2020 | Felton |

(56) References Cited

U.S. PATENT DOCUMENTS

| | | |
|---|---|---|
| 2020/0382867 A1 | 12/2020 | Felton |
| 2020/0384314 A1 | 12/2020 | Lee et al. |
| 2021/0007632 A1 | 1/2021 | Blahnik et al. |
| 2021/0007633 A1 | 1/2021 | Blahnik et al. |
| 2021/0068714 A1 | 3/2021 | Crowley et al. |
| 2021/0110908 A1 | 4/2021 | Blahnik et al. |
| 2021/0113116 A1 | 4/2021 | Chen et al. |
| 2021/0113137 A1 | 4/2021 | Soli et al. |
| 2021/0145321 A1 | 5/2021 | Chen et al. |
| 2021/0191584 A1 | 6/2021 | Williams et al. |
| 2021/0193293 A1 | 6/2021 | Blahnik et al. |
| 2021/0225482 A1 | 7/2021 | Crowley et al. |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255758 A1 | 8/2021 | Devine et al. |
| 2021/0255826 A1 | 8/2021 | Devine et al. |
| 2021/0350900 A1 | 11/2021 | Blahnik et al. |
| 2021/0369130 A1 | 12/2021 | Felton et al. |
| 2021/0373746 A1 | 12/2021 | Felton et al. |
| 2021/0373747 A1 | 12/2021 | Felton et al. |
| 2021/0373748 A1 | 12/2021 | Felton et al. |
| 2021/0375157 A1 | 12/2021 | Sundstrom et al. |
| 2021/0375450 A1 | 12/2021 | Felton et al. |

FOREIGN PATENT DOCUMENTS

| | | |
|---|---|---|
| CN | 1397904 A | 2/2003 |
| CN | 1585943 A | 2/2005 |
| CN | 101150810 A | 3/2008 |
| CN | 101541387 A | 9/2009 |
| CN | 101651870 A | 2/2010 |
| CN | 101836894 A | 9/2010 |
| CN | 101978374 A | 2/2011 |
| CN | 102339201 A | 2/2012 |
| CN | 102448555 A | 5/2012 |
| CN | 102804238 A | 11/2012 |
| CN | 102989159 A | 3/2013 |
| CN | 103191557 A | 7/2013 |
| CN | 103212197 A | 7/2013 |
| CN | 103370924 A | 10/2013 |
| CN | 103403627 A | 11/2013 |
| CN | 103561640 A | 2/2014 |
| CN | 104288983 A | 1/2015 |
| CN | 104501043 A | 4/2015 |
| CN | 104508426 A | 4/2015 |
| CN | 104720765 A | 6/2015 |
| CN | 104815428 A | 8/2015 |
| CN | 105260078 A | 1/2016 |
| CN | 105388998 A | 3/2016 |
| CN | 105721667 A | 6/2016 |
| CN | 106164808 A | 11/2016 |
| CN | 106537397 A | 3/2017 |
| CN | 106709235 A | 5/2017 |
| CN | 106725384 A | 5/2017 |
| CN | 106878550 A | 6/2017 |
| CN | 107278138 A | 10/2017 |
| CN | 107361755 A | 11/2017 |
| CN | 107454831 A | 12/2017 |
| CN | 107591211 A | 1/2018 |
| CN | 107713981 A | 2/2018 |
| EP | 1935339 A1 | 6/2008 |
| EP | 2025368 A2 | 2/2009 |
| EP | 2391004 A1 | 11/2011 |
| EP | 2568409 A1 | 3/2013 |
| EP | 2921899 A2 | 9/2015 |
| EP | 3042606 A1 | 7/2016 |
| EP | 3096235 A1 | 11/2016 |
| EP | 3101882 A2 | 12/2016 |
| EP | 3122038 A1 | 1/2017 |
| EP | 3557590 A1 | 10/2019 |
| JP | 6-187118 A | 7/1994 |
| JP | 2001-76078 A | 3/2001 |
| JP | 2002-190007 A | 7/2002 |
| JP | 2003-337863 A | 11/2003 |
| JP | 2004-102609 A | 4/2004 |
| JP | 2004-113466 A | 4/2004 |
| JP | 2005-79814 A | 3/2005 |
| JP | 2006-230679 A | 9/2006 |
| JP | 2007-260288 A | 10/2007 |
| JP | 2007-330513 A | 12/2007 |
| JP | 2008-11865 A | 1/2008 |
| JP | 2008-104758 A | 5/2008 |
| JP | 2008-183339 A | 8/2008 |
| JP | 2009-78134 A | 4/2009 |
| JP | 2010-12335 A | 1/2010 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-200575 A | 10/2011 |
| JP | 2011-206323 A | 10/2011 |
| JP | 2011-259253 A | 12/2011 |
| JP | 2012-35071 A | 2/2012 |
| JP | 2012-59264 A | 3/2012 |
| JP | 2012-524640 A | 10/2012 |
| JP | 2012-230503 A | 11/2012 |
| JP | 2012-239808 A | 12/2012 |
| JP | 2013-103020 A | 5/2013 |
| JP | 2013-117690 A | 6/2013 |
| JP | 2013-544140 A | 12/2013 |
| JP | 2014-500740 A | 1/2014 |
| JP | 2015-213686 A | 12/2015 |
| JP | 2016-502875 A | 2/2016 |
| JP | 2016-52512 A | 4/2016 |
| JP | 2016-528016 A | 9/2016 |
| JP | 2016-177151 A | 10/2016 |
| JP | 2016-202751 A | 12/2016 |
| JP | 2017-134689 A | 8/2017 |
| JP | 2017-526073 A | 9/2017 |
| JP | 2017-182393 A | 10/2017 |
| JP | 2017-529880 A | 10/2017 |
| JP | 2017-211994 A | 11/2017 |
| JP | 2017-532069 A | 11/2017 |
| KR | 10-2002-0060421 A | 7/2002 |
| KR | 10-2006-0117570 A | 11/2006 |
| KR | 10-2008-0051460 A | 6/2008 |
| KR | 10-2011-0017076 A | 2/2011 |
| KR | 10-2012-0023657 A | 3/2012 |
| KR | 10-2012-0076559 A | 7/2012 |
| KR | 10-2013-0043698 A | 5/2013 |
| KR | 10-2013-0111569 A | 10/2013 |
| KR | 10-2013-0111570 A | 10/2013 |
| KR | 10-2013-0135282 A | 12/2013 |
| KR | 10-2015-0026635 A | 3/2015 |
| KR | 10-2015-0115385 A | 10/2015 |
| KR | 10-1594486 B1 | 2/2016 |
| KR | 10-2016-0028351 A | 3/2016 |
| KR | 10-2016-0076264 A | 6/2016 |
| KR | 10-2017-0003608 A | 1/2017 |
| KR | 10-2017-0029014 A | 3/2017 |
| KR | 10-2019-0094795 A | 8/2019 |
| WO | 1999/41682 A2 | 8/1999 |
| WO | 2002/27530 A2 | 4/2002 |
| WO | 2003/067202 A2 | 8/2003 |
| WO | 2005/070289 A1 | 8/2005 |
| WO | 2006/046648 A1 | 5/2006 |
| WO | 2008/073359 A2 | 6/2008 |
| WO | 2009/129402 A1 | 10/2009 |
| WO | 2010/126825 A1 | 11/2010 |
| WO | 2012/021507 A2 | 2/2012 |
| WO | 2012/060588 A2 | 5/2012 |
| WO | 2012/061438 A2 | 5/2012 |
| WO | 2012/061440 A2 | 5/2012 |
| WO | 2012/078079 A2 | 6/2012 |
| WO | 2012/086910 A1 | 6/2012 |
| WO | 2013/052789 A1 | 4/2013 |
| WO | 2013/103570 A1 | 7/2013 |
| WO | 2013/109762 A1 | 7/2013 |

(56) References Cited

FOREIGN PATENT DOCUMENTS

| | | |
|---|---|---|
| WO | 2013/109777 A1 | 7/2013 |
| WO | 2013/109916 A1 | 7/2013 |
| WO | 2013/173838 A2 | 11/2013 |
| WO | 2014/015378 A1 | 1/2014 |
| WO | 2014/144258 A2 | 9/2014 |
| WO | 2014/207294 A1 | 12/2014 |
| WO | 2014/207875 A1 | 12/2014 |
| WO | 2015/027133 A1 | 2/2015 |
| WO | 2015/153803 A1 | 10/2015 |
| WO | 2015/179592 | 11/2015 |
| WO | 2015/183828 A1 | 12/2015 |
| WO | 2015/187799 A1 | 12/2015 |
| WO | 2015/198488 A1 | 12/2015 |
| WO | 2016/036472 A1 | 3/2016 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2016/179559 A2 | 11/2016 |
| WO | 2016/207745 A1 | 12/2016 |
| WO | 2017/003045 A1 | 1/2017 |
| WO | 2017/037242 A1 | 3/2017 |
| WO | 2017/062621 A1 | 4/2017 |
| WO | 2017/087642 A1 | 5/2017 |
| WO | 2017/090810 A1 | 6/2017 |
| WO | 2017/215203 A1 | 12/2017 |
| WO | 2018/132507 A1 | 7/2018 |
| WO | 2018/148356 A1 | 8/2018 |
| WO | 2018/222313 A1 | 12/2018 |
| WO | 2019/017508 A1 | 1/2019 |
| WO | 2019/020977 A1 | 1/2019 |
| WO | 2019/024603 A1 | 2/2019 |
| WO | 2019/168956 A1 | 9/2019 |
| WO | 2019/231982 A1 | 12/2019 |

OTHER PUBLICATIONS

Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 14/839,922, dated Mar. 24, 2017, 4 pages.
Advisory Action received for U.S. Appl. No. 16/143,909, dated Nov. 7, 2019, 5 pages.
Advisory Action received for U.S. Appl. No. 16/143,997, dated Dec. 26, 2019, 7 pages.
Advisory Action received for U.S. Appl. No. 16/144,849, dated Aug. 12, 2019, 5 pages.
Applicant Initiated Interview Summary received for U.S. Appl. No. 15/627,069, dated Nov. 4, 2019, 6 pages.
Applicant Initiated Interview Summary received for U.S. Appl. No. 16/144,849, dated Jan. 21, 2020, 6 pages.
Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Applicant-Initiated Interview Summary received for U.S. Appl. No. 15/705,849, dated Feb. 14, 2020, 3 pages.
Certificate of Examination received for Australian Patent Application No. 2018101855, dated Aug. 6, 2019, 2 pages.
Certificate of Examination received for Australian Patent Application No. 2019100222, dated Aug. 29, 2019, 2 pages.
Certification of Examination received for Australian Patent Application No. 2018100158, dated Oct. 23, 2018, 2 pages.
Corrected Notice of Allowance received for U.S. Appl. No. 14/732,773, dated Feb. 10, 2020, 3 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.
Corrected Notice of Allowance received for U.S. Appl. No. 15/600,243, dated Feb. 5, 2020, 3 pages.
Corrected Notice of Allowance received for U.S. Appl. No. 16/143,909, dated Feb. 20, 2020, 3 pages.
Corrected Notice of Allowance received for U.S. Appl. No. 16/143,959, dated Dec. 13, 2019, 2 pages.
Decision to Grant received for Danish Patent Application No. PA201870600, dated Oct. 17, 2019, 2 pages.
Decision to Refuse received for European Application No. 13811085.3, dated Sep. 11, 2018, 21 pages.
Decision to Refuse received for European Patent Application No. 15771747.1, dated Aug. 10, 2018, 22 pages.
Dwprogressbar v2: Stepping and Events, davidwalsh.name/dwprogressbar-2-stepping-events-mootools-progress-bar, retrieved from the Wayback Machine, Aug. 31, 2008, 4 pages.
Extended European Search Report received for European Patent Application No. 16837432.0, dated Mar. 11, 2019, 10 pages.
Extended European Search Report received for European Patent Application No. 18154145.9, dated Mar. 2, 2018, 8 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 14/839,922, dated Dec. 14, 2016, 22 pages.
Final Office Action received for U.S. Appl. No. 15/608,848, dated Jun. 26, 2019, 27 pages.
Final Office Action received for U.S. Appl. No. 15/925,652, dated Aug. 1, 2019, 30 Pages.
Final Office Action received for U.S. Appl. No. 16/143,909, dated Aug. 28, 2019, 20 pages.
Final Office Action received for U.S. Appl. No. 16/143,997, dated Sep. 30, 2019, 16 pages.
Final Office Action received for U.S. Appl. No. 16/144,030, dated Feb. 13, 2020, 11 pages.
Final Office Action received for U.S. Appl. No. 16/144,030, dated Oct. 1, 2019, 13 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Fitbit App, Available online at: <http://web.archive.org/web/20180114083150/https://www.fitbit.com/au/app>, Jan. 14, 2018, 8 pages.
Graphs and Charts, Online available at: <https://www.teachervision.com/lesson-planning/graph-chart-teacher-resources, retrieved on Dec. 12, 2018, 4 pages.
Intention to Grant received for Danish Patent Application No. PA201570668, dated Mar. 27, 2017, 2 pages.
Intention to Grant received for Danish Patent Application No. PA201870600, dated Jul. 10, 2019, 2 pages.
International Preliminary Report on Patentability received for PCT Application No. PCT/US2016/037686, dated Mar. 1, 2018, 12 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/047282, dated Mar. 16, 2017, 26 pages.
International Preliminary Report on Patentability received for PCT Patent Application No. PCT/US2017/035554, dated Dec. 20, 2018, 39 pages.
International Preliminary Report on Patentability received for PCT Patent Application No. PCT/US2018/031662, dated Nov. 28, 2019, 12 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.

(56) References Cited

OTHER PUBLICATIONS

International Search Report and Written Opinion received for PCT Patent Application No. PCT/US2017/035554, dated Sep. 22, 2017, 42 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2019/019694, dated Sep. 2, 2019, 17 pages.
International Search Report and Written Opinion received for PCT Patent Application No. PCT/US2019/024570, dated Aug. 8, 2019, 18 pages.
International Written Opinion received for PCT Patent Application No. PCT/US2013/073195, dated Jun. 23, 2014, 8 pages.
Invitation to Pay Addition Fees and Partial International Search Report received for PCT Patent Application No. PCT/US2018/031662, dated Jul. 16, 2018, 13 pages.
Invitation to Pay Additional Fees received for PCT Patent Application No. PCT/US2017/035554, dated Jul. 20, 2017, 2 pages.
Invitation to Pay Additional Fees received for PCT Patent Application No. PCT/US2019/019694, dated Jul. 10, 2019, 12 pages.
Invitation to Pay Search Fees received for European Patent Application No. 19726205.8, dated Feb. 14, 2020, 5 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
Mugs, Online Available at: https://web.archive.org/web/20151029034349/http://le-mugs.com/, Oct. 29, 2015, 14 pages.
Multi-Set Bar Chart, The Data Visualization Catalogue, Available Online at: https://datavizcatalogue.com/methods/multiset_barchart.html, Feb. 8, 2014, 3 pages.
My CalStep, http://www.surprisesoftware.com/mycalstep/, retrieved from the Wayback Machine, May 9, 2007, 2 pages.
Non-Final Office Action Received for U.S. Appl. No. 16/144,864, dated Dec. 18, 2018, 19 pages.
Non-Final Office Action received for U.S. Appl. No. 15/608,848, dated Nov. 2, 2018, 21 pages.
Non-Final Office Action received for U.S. Appl. No. 14/732,773, dated Feb. 8, 2019, 32 pages.
Non-Final Office Action received for U.S. Appl. No. 14/732,773, dated Jan. 19, 2018., 45 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 15/183,663, dated Jul. 9, 2018, 13 pages.
Non-Final Office Action received for U.S. Appl. No. 15/600,243, dated Jun. 27, 2019, 17 Pages.
Non-Final Office Action received for U.S. Appl. No. 15/608,848, dated Feb. 6, 2020, 12 pages.
Non-Final Office Action received for U.S. Appl. No. 15/627,069, dated Jun. 21, 2019, 22 pages.
Non-Final Office Action received for U.S. Appl. No. 15/705,849, dated Nov. 12, 2019, 15 pages.
Non-Final Office Action received for U.S. Appl. No. 15/925,652, dated Apr. 5, 2019, 28 pages.
Non-Final Office Action received for U.S. Appl. No. 16/143,909, dated Apr. 19, 2019, 16 pages.
Non-Final Office Action received for U.S. Appl. No. 16/143,959, dated Apr. 17, 2019, 15 pages.
Non-Final Office Action received for U.S. Appl. No. 16/143,997, dated May 21, 2019, 15 pages.
Non-Final Office Action received for U.S. Appl. No. 16/144,030, dated Apr. 12, 2019, 8 pages.
Non-Final Office Action received for U.S. Appl. No. 16/144,735, dated Feb. 19, 2020, 10 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action received for U.S. Appl. No. 16/144,864, dated Jan. 31, 2020, 29 pages.
Notice of Acceptance received for Australian Patent Application No. 2015312215, dated Oct. 9, 2017, 3 pages.
Notice of Acceptance received for Australian Patent Application No. 2019201583, dated Jul. 15, 2019, 3 pages.
Notice of Allowance received for Chinese Patent Application No. 201580037927.5, dated Oct. 17, 2019, 3 pages.
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages.
Notice of Allowance received for Japanese Patent Application No. 2016-557650, dated Apr. 9, 2019, 4 pages.
Notice of Allowance received for Japanese Patent Application No. 2018-068846, dated Dec. 9, 2019, 4 pages.
Notice of Allowance received for Korean Patent Application No. 10-2016-7014577, dated May 30, 2019, 5 pages.
Notice of Allowance received for Korean Patent Application No. 10-2016-7033638, dated May 31, 2017, 5 pages.
Notice of Allowance received for Taiwanese Patent Application No. 104128685, dated May 3, 2017, 3 pages.
Notice of Allowance received for U.S. Appl. No. 14/732,773, dated Dec. 18, 2019, 21 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 15/183,663, dated Jan. 17, 2019, 6 pages.
Notice of Allowance received for U.S. Appl. No. 15/600,243, dated Dec. 12, 2019, 7 pages.
Notice of Allowance received for U.S. Appl. No. 15/616,480, dated Jan. 3, 2019, 8 pages.
Notice of Allowance received for U.S. Appl. No. 16/143,909, dated Jan. 21, 2020, 9 pages.
Notice of Allowance received for U.S. Appl. No. 16/143,959, dated Oct. 31, 2019, 10 pages.
Notice of Allowance received for U.S. Appl. No. 16/144,671, dated Feb. 10, 2020, 17 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Office Action received for Australian Patent Application No. 2015312215, dated Oct. 13, 2016, 3 pages.
Office Action received for Australian Patent Application No. 2017100667, dated Aug. 3, 2017, 9 pages.
Office Action received for Australian Patent Application No. 2018100158, dated Apr. 23, 2018, 5 pages.
Office Action received for Australian Patent Application No. 2018101855, dated Feb. 22, 2019, 4 pages.
Office Action received for Australian Patent Application No. 2018200428, dated Mar. 7, 2018, 4 pages.
Office Action received for Australian Patent Application No. 2018200428, dated Nov. 15, 2018, 4 pages.
Office Action received for Australian Patent Application No. 2019100222, dated May 24, 2019, 6 pages.
Office Action received for Australian Patent Application No. 2019100495, dated Mar. 6, 2020, 3 pages.

(56) References Cited

OTHER PUBLICATIONS

Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Chinese Patent Application No. 201380081349.6, dated Feb. 26, 2019, 12 pages.
Office Action received for Chinese Patent Application No. 201380081349.6, dated Jan. 16, 2020, 11 pages.
Office Action received for Chinese Patent Application No. 201380081349.6, dated Jul. 15, 2019, 10 pages.
Office Action received for Chinese Patent Application No. 201580037927.5, dated Apr. 22, 2019, 9 pages.
Office Action received for Chinese Patent Application No. 201580037927.5, dated Jul. 20, 2018, 21 pages.
Office Action received for Chinese Patent Application No. 201680047983.1, dated Mar. 18, 2019, 18 pages.
Office Action received for Chinese Patent Application No. 201680047983.1, dated Nov. 28, 2019, 9 pages.
Office Action received for Chinese Patent Application No. 201810105846.X, dated Aug. 27, 2019, 12 pages.
Office Action received for Chinese Patent Application No. 201810105846.X, dated Feb. 25, 2019, 10 pages.
Office Action received for Chinese Patent Application No. 201810105846.X, dated Nov. 28, 2019, 9 pages.
Office Action Received for Danish Patent Application No. PA201670656, dated Nov. 3, 2016, 8 pages.
Office Action received for Danish Patent Application No. PA201570666, dated Jun. 27, 2016, 4 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action Received for Danish Patent Application No. PA201670656, dated May 2, 2019, 4 pages.
Office Action Received for Danish Patent Application No. PA201670656, dated May 30, 2018, 5 pages.
Office Action received for Danish Patent Application No. PA201770191, dated Jan. 25, 2018, 3 pages.
Office Action received for Danish Patent Application No. PA201770191, dated Nov. 21, 2018, 4 pages.
Office Action received for Danish Patent Application No. PA201770191, dated Oct. 25, 2019, 4 pages.
Office Action received for Danish Patent Application No. PA201770423, dated Jun. 12, 2018, 7 pages.
Office Action received for Danish Patent Application No. PA201770423, dated Mar. 29, 2019, 6 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201870599, dated Dec. 20, 2019, 5 pages.
Office Action received for Danish Patent Application No. PA201870600, dated May 8, 2019, 3 pages.
Office Action received for Danish Patent Application No. PA201870601, dated Dec. 13, 2018, 8 pages.
Office Action received for Danish Patent Application No. PA201870601, dated Jan. 14, 2020, 3 pages.
Office Action received for Danish Patent Application No. PA201870601, dated Jun. 25, 2019, 3 pages.
Office Action received for Danish Patent Application No. PA201870602, dated Feb. 5, 2020, 3 pages.
Office Action received for Danish Patent Application No. PA201870602, dated Jun. 26, 2019, 3 Pages.
Office Action received for European Patent Application No. 13811085.3, dated Apr. 20, 2018, 15 pages.
Office Action received for European Patent Application No. 16837432.0, dated Jan. 10, 2020, 7 pages.
Office Action received for European Patent Application No. 17810749.6, dated Aug. 20, 2019, 9 pages.
Office Action received for European Patent Application No. 18154145.9, dated Apr. 3, 2018, 6 pages.
Office Action received for European Patent Application No. 19721883.7, dated Jan. 10, 2020, 4 pages.
Office Action received for European Patent Application No. 15771747.1, dated Oct. 31, 2017, 7 pages.
Office Action received for German Patent Application No. 112015002326.7, dated Feb. 20, 2019, 7 pages.
Office Action received for Japanese Patent Application No. 2016-535045, dated May 12, 2017, 10 pages.
Office Action received for Japanese Patent Application No. 2016-557650, dated Apr. 13, 2018, 9 pages.
Office Action received for Japanese Patent Application No. 2016-557650, dated Aug. 10, 2017, 10 pages.
Office Action received for Japanese Patent Application No. 2016-557650, dated Nov. 9, 2018, 6 pages.
Office Action received for Japanese Patent Application No. 2018-014096, dated Jan. 6, 2020, 17 pages.
Office Action received for Japanese Patent Application No. 2018-014096, dated Jun. 29, 2018, 20 pages.
Office Action received for Japanese Patent Application No. 2018-014096, dated May 8, 2019, 14 pages.
Office Action received for Japanese Patent Application No. 2018-014096, dated Nov. 6, 2018, 15 pages.
Office Action received for Japanese Patent Application No. 2018-068846, dated Jan. 8, 2019, 6 pages.
Office Action received for Japanese Patent Application No. 2019-162293, dated Jan. 31, 2020, 8 pages.
Office Action received for Korean Patent Application No. 10-2016-7014577, dated Dec. 26, 2017, 14 pages.
Office Action received for Korean Patent Application No. 10-2016-7014577, dated Oct. 31, 2018, 11 pages.
Office Action received for Korean Patent Application No. 10-2016-7033638, dated Jan. 31, 2017, 6 pages.
Office Action received for Korean Patent Application No. 10-2019-7025538, dated Feb. 17, 2020, 12 pages.
Office Action received for Korean Patent Application No. 10-2019-7025781, dated Nov. 26, 2019, 10 pages.
Office Action received for Taiwanese Patent Application No. 104128685, dated Jan. 4, 2017, 40 pages.
Partial Supplementary European Search Report received for European Patent Application No. 17810749.6, dated Apr. 25, 2019, 8 pages.
Search report and opinion received for Danish Patent Application No. PA201770191, dated Jun. 30, 2017, 9 pages.
Search Report and Opinion received for Danish Patent Application No. PA201770423, dated Oct. 4, 2017, 10 pages.
Search Report and Opinion received for Danish Patent Application No. PA201870378, dated Sep. 10, 2018, 9 pages.
Search Report and Opinion received for Danish Patent Application No. PA201870599, dated Dec. 21, 2018, 9 pages.
Search Report and Opinion received for Danish Patent Application No. PA201870600, dated Jan. 31, 2019, 8 pages.
Search Report and Opinion received for Danish Patent Application No. PA201870602, dated Dec. 19, 2018, 8 pages.
Summons to attend oral proceedings received for European Patent Application No. 13811085.3, mailed on Jan. 26, 2018, 14 pages.
Summons to Attend Oral Proceedings received for European Patent Application No. 15771747.1, mailed on May 25, 2018, 17 pages.
Supplemental Notice of Allowance received for U.S. Appl. No. 15/616,480, dated Mar. 28, 2019, 2 pages.
Supplemental Notice of Allowance received for U.S. Appl. No. 16/144,849, dated Mar. 31, 2020, 2 pages.

(56) References Cited

OTHER PUBLICATIONS

Supplementary European Search Report received for European Patent Application No. 17810749.6, dated Aug. 6, 2019, 6 pages.
SUUNTO Spartan Trainer Wrist HR 1.12, Online Available at:—https://web.archive.org/web/20180127155200/https://ns.suunto.com/Manuals/Spartan_Tra iner_WristHR/Userguides/Suunto_Spartan_Trainer_WristHR_UserGuide_EN.pdf, Jan. 17, 2018, 47 pages.
Utilization of Galaxy S4-S Health, ChatOn and Samsung Hub, Available at: http://seeit.kr/1263, Jun. 12, 2013, 25 pages.
Visual Pace Alarm app, Available Online at: https://apps.garmin.com/en-US/apps/3940f3a2-4847-4078-a911-d77422966c82, Oct. 19, 2016, 1 page.
Final Office Action received for U.S. Appl. No. 12/205,847, dated Apr. 25, 2012, 42 pages.
Non-Final Office Action received for U.S. Appl. No. 12/205,847, dated Oct. 3, 2011, 59 pages.
Notice of Allowance received for U.S. Appl. No. 12/205,847, dated Aug. 20, 2012, 13 pages.
Non-Final Office Action received for U.S. Appl. No. 14/839,916, dated Feb. 4, 2016, 19 pages.
Non-Final Office Action received for U.S. Appl. No. 14/839,922, dated Feb. 25, 2016, 20 pages.
Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Casella Cel Casella, "The Casella dBadge2—World's First Truly Wireless Noise Dosimeter and Airwave App!", Retrieved from URL <https://www.youtube.com/watch?v=Xvy2fl3cgYo>, May 27, 2015, 3 pages.
Cho H.S., "Satisfactory Innovative Smart-watch (Fitbit Force) . . . review after seven days of use, such as the amount of sleep and movement (improving sleep is the object of X-Blue", Online Available at: <https://x-blueuv.blogspot.com/2013/12/fitbit-force.html>, Dec. 3, 2013, 8 pages.
Codrington Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.
Evergreen et al., "Bar Chart", Better Evaluation, Available Online at: https://www.betterevaluation.org/en/evaluation-options/BarChart, Oct. 31, 2014, 8 pages.
Garmin, "Fenix 5x Owner's Manual", Online Available at:—https://web.archive.org/web/20180127170640/https://static.garmin.com/pumac/fenix5x_OM_EN.pdf, Jan. 27, 2018, 42 pages.
JENBSJOURNEY, "Wondering About a Fitbit?", Available at: https://jenbsjourney.blogspot.kr/2013/08/wondering-about-fitbit.html, Aug. 6, 2013, 12 pages.
MEGADEPOT, "Casella dBadge2 Noise Dosimeter", Retrieved from URL: <https://www.youtube.com/watch?v=pHiHLiYCD08>, Jun. 12, 2018, 3 pages.
MYFLO App, "Functional Medicine Period Tracker and Hormone Balancing App", Available online at <https://web.archive.org/web/20170127104125/https://myflotracker.com/>, Jan. 2017, 14 pages.
MYFLO Tutorial, "How to change the start date of your current period", Available online at <https://www.youtube.com/watch?v=uQQ-odlBJB4>, Jan. 23, 2017, 3 pages.
MYFLO Tutorial, "Setting and changing the end date of your period", Available online at <https://www.youtube.com/watch?v=UvAA4OgqL3E>, Jan. 23, 2017, 3 pages.
Office Action received for Danish Patent Application No. PA201570666, dated Feb. 2, 2016, 9 pages.
Office Action received for Danish Patent Application No. PA201570668, dated Apr. 8, 2016, 8 pages.
International Search Report received for PCT Patent Application No. PCT/US2013/073195, dated Jun. 23, 2014, 3 pages.
Invitation to Pay Additional Fees received for PCT Patent Application No. PCT/US2015/047282, dated Dec. 22, 2015, 7 pages.
Razykdreviews, "In Depth Review of Apple Watch Activity and Workout App", available at <URL: https://www.youtube.com/watch?v=GkKI3qlKOow>, Category: X Claims: 1-5 Category: L Reason: Internet citation/video, May 11, 2015, 1 page.
Rizknows, "Garmin Connect Mobile App—Review #2", https://www.youtube.com/watch?v=7my3wMpeRbE, Category: X Claims: 1-5 Category: L Reason: Internet citation/video, Oct. 22, 2015, 1 page.
Rizknows, "Tom Tom Multisport Cardio Review", Online available at:—https://www.youtube.com/watch?v=WoVCzLrSN9A, Sep. 4, 2015, 1 page.
Smith, "Garmin Fenix 5 Activity/Smart Watch Review", Online Available at:—https://www.youtube.com/watch?v=6PkQxXQxpoU, Sep. 2, 2017, 1 page.
SPORTSTECHGUIDES, "Garmin Fenix 5: How to Add Power Data Fields", Online Available at:—https://www.youtube.com/watch?v=ZkPptnnXEiQ, Apr. 29, 2017, 2 pages.
SPORTSTECHGUIDES, "Garmin Fenix 5: How to Set up Run Alerts", Online Available at:—https://www.youtube.com/watch?v=gSMwv8vlhB4, May 13, 2017, 2 pages.
STUDIOSIXDIGITAL, "Dosimeter", Retrieved from URL: <https://studiosixdigital.com/audiotools-modules-2/spl-modules/dosimeter.html>, Mar. 3, 2017, 6 pages.
Suunto, "Suunto Spartan—Heart Rate Zones", Online Available at:—https://www.youtube.com/watch?v=aixfoCnS0OU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TomTom, "TomTom Runner & Multi-Sport Reference Guide", Online available at:<https://web.archive.org/web/20150908075934/http://download.tomtom.com/open/manuals/Runner_Multi-Sport/refman/TomTom-Runner-Multi-Sport-RG-en-GB.pdf, Sep. 8, 2015, 44 pages.
Wesley, "Apple Watch Series 1", online available at:—http://toolbox.info/blog/archives/1737-unknown.html, May 28, 2015, 5 pages.
Youtube, "Apple Watch Series 3", Online available at:—https://www.youtube.com/watch?v=iBPr9gEfkK8, Nov. 21, 2017, 15 pages.
Zlelik, "Garmin Fenix 5 Open Water Swimming Activity Demo", Online Available at:—https://www.youtube.com/watch?v=iSVhdvw2dcs, Jun. 9, 2017, 1 page.
Applicant-Initiated Interview Summary received for U.S. Appl. No. 15/627,069, dated Jul. 20, 2020, 5 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Notice of Allowance received for U.S. Appl. No. 16/144,735, dated Jul. 21, 2020, 13 pages.
Office Action received for Australian Patent Application No. 2018268972, dated Jul. 9, 2020, 4 pages.
Office Action received for Chinese Patent Application No. 201910972529.2, dated Jun. 28, 2020, 8 pages (1 page of English Translation and 7 pages of Official Copy).
Applicant-Initiated Interview Summary received for U.S. Appl. No. 16/584,186, dated Feb. 3, 2020, 4 pages.
Corrected Notice of Allowance received for U.S. Appl. No. 16/584,186, dated Jul. 31, 2020, 2 pages.
Decision to Grant received for Danish Patent Application No. PA201870601, dated Aug. 17, 2020, 2 pages.
Decision to Grant received for Danish Patent Application No. PA201870602, dated Aug. 18, 2020, 2 pages.
Extended European Search Report received for European Patent Application No. 20180592.6, dated Aug. 11, 2020, 10 pages.
Final Office Action received for U.S. Appl. No. 15/608,848, dated Aug. 21, 2020, 15 pages.
Final Office Action received for U.S. Appl. No. 16/138,809, dated Aug. 27, 2020, 24 pages.
International Search Report and written Opinion received for PCT Patent Application No. PCT/US2020/025768, dated Aug. 10, 2020, 11 pages.
Non-Final Office Action received for U.S. Appl. No. 16/584,186, dated Dec. 6, 2019, 13 pages.
Non-Final Office Action received for U.S. Appl. No. 16/880,552, dated Jul. 23, 2020, 19 pages.

(56) References Cited

OTHER PUBLICATIONS

Notice of Allowance received for U.S. Appl. No. 16/584,186, dated Mar. 24, 2020, 10 pages.
Office Action received for Australian Patent Application No. 2017277971, dated Aug. 12, 2020, 3 pages.
Office Action received for Chinese Patent Application No. 201380081349.6, dated Jul. 15, 2020, 9 pages (4 pages of English Translation and 5 pages of Official Copy).
Office Action received for Danish Patent Application No. PA201970534, dated Jun. 29, 2020, 2 pages.
Office Action received for Korean Patent Application No. 10-2019-7025538, dated Aug. 15, 2020, 8 pages (4 pages of English Translation and 4 pages of Official Copy).
Search Report and Opinion received for Danish Patent Application No. PA201970534, dated Sep. 23, 2019, 6 pages.
Decision to Grant received for Danish Patent Application No. PA201870379, dated Jul. 5, 2019, 2 pages.
Intention to Grant received for Danish Patent Application No. PA201870379, dated May 2, 2019, 2 pages.
Office Action received for Danish Patent Application No. PA201870379, dated Feb. 28, 2019, 3 pages.
Search Report and Opinion received for Danish Patent Application No. PA201870379, dated Sep. 14, 2018, 9 pages.
CNET, "Google Fit's automatic activity tracking is getting smarter on Android Wear", Available online at: https://www.youtube.com/watch?v=lttzlCid_d8, May 18, 2016, 1 page.
DC Rainmaker, "Garmin Fenix3 New Auto Climb Functionality", Available online at: https://www.youtube.com/watch?v=iuavOSNpVRc, Feb. 19, 2015, 1 page.
Advisory Action received for U.S. Appl. No. 16/144,864, dated Jul. 6, 2020, 6 pages.
Applicant Initiated Interview Summary received for U.S. Appl. No. 15/608,848, dated May 12, 2020, 5 pages.
Applicant Initiated Interview Summary received for U.S. Appl. No. 16/144,735, dated Jun. 18, 2020, 3 pages.
Applicant Initiated Interview Summary received for U.S. Appl. No. 16/144,753, dated Jun. 18, 2020, 3 pages.
Applicant Initiated Interview Summary received for U.S. Appl. No. 16/144,864, dated Apr. 29, 2020, 4 pages.
Applicant-Initiated Interview Summary received for U.S. Appl. No. 15/705,849, dated Jun. 29, 2020, 3 pages.
Applicant-Initiated Interview Summary received for U.S. Appl. No. 16/138,809, dated Jun. 9, 2020, 4 pages.
Applicant-Initiated Interview Summary received for U.S. Appl. No. 16/144,864, dated Jun. 22, 2020, 3 pages.
Corrected Notice of Allowance received for U.S. Appl. No. 14/732,773, dated Mar. 24, 2020, 3 pages.
Corrected Notice of Allowance received for U.S. Appl. No. 15/600,243, dated Mar. 13, 2020, 3 pages.
Corrected Notice of Allowance received for U.S. Appl. No. 15/600,243, dated Mar. 31, 2020, 5 pages.
Corrected Notice of Allowance received for U.S. Appl. No. 16/143,909, dated Mar. 18, 2020, 3 pages.
Final Office Action received for U.S. Appl. No. 15/627,069, dated Mar. 2, 2020, 22 pages.
Final Office Action received for U.S. Appl. No. 15/705,849, dated May 1, 2020, 17 pages.
Final Office Action received for U.S. Appl. No. 16/144,735, dated May 4, 2020, 12 pages.
Final Office Action received for U.S. Appl. No. 16/144,864, dated May 28, 2020, 29 pages.
Intention to Grant received for Danish Patent Application No. PA201870601, dated Apr. 24, 2020, 2 pages.
Intention to Grant received for Danish Patent Application No. PA201870602, dated Apr. 24, 2020, 2 pages.
Non-Final Office Action received for U.S. Appl. No. 15/627,069, dated May 26, 2020, 25 pages.
Non-Final Office Action received for U.S. Appl. No. 16/138,809, dated Feb. 28, 2020, 22 pages.
Non-Final Office Action received for U.S. Appl. No. 16/144,753, dated Mar. 5, 2020, 9 pages.
Non-Final Office Action received for U.S. Appl. No. 16/377,892, dated May 21, 2020, 9 pages.
Non-Final Office Action received for U.S. Appl. No. 16/378,136, dated Jun. 2, 2020, 8 pages.
Non-Final Office Action received for U.S. Appl. No. 16/418,786, dated Apr. 24, 2020, 16 pages.
Notice of Acceptance received for Australian Patent Application No. 2019222943, dated May 5, 2020, 3 pages.
Notice of Allowance received for Chinese Patent Application No. 201810105846.X, dated Feb. 18, 2020, 2 pages (1 page of English Translation and 1 page of Official Copy).
Office Action received for Australian Patent Application No. 2017277971, dated Jun. 3, 2020, 3 pages.
Office Action received for Chinese Patent Application No. 201710439448.7, dated Mar. 27, 2020, 13 pages (7 pages of English Translation and 6 pages of Official Copy).
Office Action Received for Danish Patent Application No. PA201670656, dated Jul. 1, 2020, 4 pages.
Office Action received for European Patent Application No. 19721883.7, dated May 28, 2020, 11 pages.
Office Action received for European Patent Application No. 19726205.8, dated Jun. 26, 2020, 9 pages.
Office Action received for Japanese Patent Application No. 2019-044107, dated May 29, 2020, 6 pages (3 pages of English Translation and 3 pages of Official Copy).
Applicant Initiated Interview Summary received for U.S. Appl. No. 16/143,997, dated Aug. 13, 2020, 3 pages.
Extended European Search Report received for European Patent Application No. 20180581.9, dated Aug. 12, 2020, 9 pages.
Non-Final Office Action received for U.S. Appl. No. 15/925,652, dated Aug. 7, 2020, 39 pages.
Office Action received for Australian Patent Application No. 2019250251, dated Aug. 6, 2020, 3 pages.
Summons to Attend Oral Proceedings received for European Patent Application No. 17810749.6, mailed on Aug. 12, 2020, 11 pages.
Epstein et al., "Examining Menstrual Tracking to Inform the Design of Personal Informatics Tools", Proceedings of the 2017 CHI Conference on Human Factors in Computing Systems, ACM Press, Denver, CO, USA, CHI '17, May 6-11, 2017, pp. 6876-6888.
Final Office Action received for U.S. Appl. No. 16/144,753, dated Sep. 22, 2020, 9 pages.
Moglia et al., "Evaluation of Smartphone Menstrual Cycle Tracking Applications Using an Adapted Applications Scoring System", Obstetrics and Gynecology, vol. 127. No. 6, Jun. 2016, pp. 1153-1160.
Notice of Allowance received for Chinese Patent Application No. 201910972529.2, dated Sep. 14, 2020, 6 pages (3 pages of English Translation and 3 pages of Official Copy).
Summons to Attend Oral Proceedings received for European Patent Application No. 18154145.9, mailed on Sep. 17, 2020, 11 pages.
Non-Final Office Action received for U.S. Appl. No. 16/143,997, dated Jul. 27, 2020, 15 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,864, dated Jul. 28, 2020, 27 pages.
Office Action received for Chinese Patent Application No. 201680047983.1, dated Jul. 1, 2020, 6 pages (3 pages of English Translation and 3 pages of Official Copy).
International Search Report and Written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.

(56) References Cited

OTHER PUBLICATIONS

Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Chinese Patent Application No. 201910858933.7, dated Aug. 18, 2020, 14 pages (7 pages of English Translation and 7 pages of Official Copy).
Office Action received for Danish Patent Application No. PA201970532, dated May 29, 2020, 3 pages.
Office Action received for Japanese Patent Application No. 2018-014096, dated Aug. 28, 2020, 4 pages (2 pages of English Translation and 2 pages of Official Copy).
Office Action received for Japanese Patent Application No. 2019-162293, dated Jul. 27, 2020, 9 pages (5 pages of English Translation and 4 pages of Official Copy).
Result of Consultation received for European Patent Application No. 18154145.9, mailed on Sep. 4, 2020, 3 pages.
Search Report and Opinion received for Danish Patent Application No. PA201970532, dated Nov. 8, 2019, 9 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Applicant-Initiated Interview Summary received for U.S. Appl. No. 15/925,652, dated Nov. 3, 2020, 4 pages.
Applicant-Initiated Interview Summary received for U.S. Appl. No. 16/144,753, dated Nov. 4, 2020, 3 pages.
Bagala et al., "Evaluation of Accelerometer-Based Fall Detection Algorithms on Real-World Falls", PloS ONE, vol. 7, No. 5, May 16, 2012, 9 pages.
Non-Final Office Action received for U.S. Appl. No. 16/144,030, dated Nov. 5, 2020, 5 pages.
Office Action received for Australian Patent Application No. 2019234289, dated Nov. 2, 2020, 6 pages.
Office Action received for Australian Patent Application No. 2020230340, dated Nov. 2, 2020, 5 pages.
Office Action received for European Patent Application No. 20182116.2, dated Nov. 6, 2020, 9 pages.
Office Action received for Korean Patent Application No. 10-2019-7025781, dated Oct. 30, 2020, 10 pages (4 pages of English Translation and 6 pages of Official Copy).
Summons to Attend Oral Proceedings received for European Patent Application No. 19726205.8, mailed on Oct. 29, 2020, 13 pages.
Applicant-Initiated Interview Summary received for U.S. Appl. No. 16/138,809, dated Dec. 16, 2020, 7 pages.
Applicant-Initiated Interview Summary received for U.S. Appl. No. 16/880,552, dated Dec. 16, 2020, 6 pages.
Corrected Notice of Allowance received for U.S. Appl. No. 16/880,552, dated Dec. 23, 2020, 2 pages.
Non-Final Office Action received for U.S. Appl. No. 16/586,154, dated Dec. 28, 2020, 26 pages.
Non-Final Office Action received for U.S. Appl. No. 17/031,874, dated Dec. 28, 2020, 14 pages.
Result of Consultation received for European Patent Application No. 17810749.6, mailed on Dec. 15, 2020, 3 pages.
Search Report and Opinion received for Danish Patent Application No. PA202070620, dated Dec. 11, 2020, 9 pages.
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Oct. 13, 2020, 4 pages.
International Preliminary Report on Patentability received for PCT Patent Application No. PCT/US2019/019694, dated Sep. 24, 2020, 12 pages.
Non-Final Office Action received for U.S. Appl. No. 16/907,261, dated Sep. 30, 2020, 22 pages.
Notice of Allowance received for U.S. Appl. No. 16/144,864, dated Sep. 29, 2020, 2 pages.
Result of Consultation received for European Patent Application No. 19721883.7, mailed on Oct. 7, 2020, 3 pages.
CBS This Morning, "This smart mirror puts a personal trainer in your reflection", Available on: https://www.youtube.com/watch?v=nSmTTZcpVGg, Oct. 13, 2018, 4 pages.
Final Office Action received for U.S. Appl. No. 16/143,997, dated Feb. 9, 2021, 16 pages.
International Search Report and Written Opinion received for PCT Patent Application No. PCT/US2020/042439, dated Oct. 9, 2020, 14 pages.
Non-Final Office Action received for U.S. Appl. No. 15/608,848, dated Feb. 12, 2021, 14 pages.
Notice of Allowance received for U.S. Appl. No. 16/144,753, dated Feb. 10, 2021, 8 pages.
Notice of Allowance received for U.S. Appl. No. 16/144,864, dated Feb. 9, 2021, 13 pages.
Office Action received for Korean Patent Application No. 10-2020-7026391, dated Jan. 27, 2021, 5 pages (2 pages of English Translation and 3 pages of Official Copy).
Office Action received for Korean Patent Application No. 10-2020-7026453, dated Jan. 27, 2021, 5 pages (2 pages of English Translation and 3 pages of Official Copy).
Applicant Initiated Interview Summary received for U.S. Appl. No. 16/586,154, dated Mar. 11, 2020, 4 pages.
Final Office Action received for U.S. Appl. No. 16/586,154, dated Jul. 6, 2020, 27 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2020/035199, dated Oct. 30, 2020, 20 pages.
International Search Report and Written Opinion received for PCT Patent Application No. PCT/US2020/035462, dated Sep. 11, 2020, 17 pages.
Invitation to Pay Additional Fees and Partial International Search Report received for PCT Patent Application No. PCT/US2020/035164, dated Oct. 16, 2020, 14 pages.
Invitation to Pay Additional Fees received for PCT Patent Application No. PCT/US2020/035199, dated Sep. 8, 2020, 12 pages.
Non-Final Office Action received for U.S. Appl. No. 16/586,154, dated Dec. 9, 2019, 23 pages.
Non-Final Office Action received for U.S. Appl. No. 16/880,714, dated Oct. 28, 2020, 11 pages.
Notice of Allowance received for U.S. Appl. No. 15/925,652, dated Nov. 20, 2020, 9 pages.
Notice of Allowance received for U.S. Appl. No. 16/880,552, dated Dec. 1, 2020, 7 pages.
Office Action received for Chinese Patent Application No. 201710439448.7, dated Oct. 10, 2020, 19 pages (8 pages of English Translation and 11 pages of Official Copy).
Result of Consultation received for European Patent Application No. 18154145.9, mailed on Nov. 30, 2020, 17 pages.
Applicant Initiated Interview Summary received for U.S. Appl. No. 15/608,848, dated Oct. 26, 2020, 3 pages.
Applicant-Initiated Interview Summary received for U.S. Appl. No. 16/880,552, dated Oct. 20, 2020, 6 pages.
European Search Report received for European Patent Application No. 20182116.2, dated Oct. 21, 2020, 4 pages.
Final Office Action received for U.S. Appl. No. 15/627,069, dated Oct. 20, 2020, 25 pages.
Invitation to Pay Addition Fees received for PCT Patent Application No. PCT/US2020/035474, mailed on Oct. 2, 2020, 11 pages.
Notice of Allowance received for U.S. Appl. No. 15/705,849, dated Oct. 16, 2020, 14 pages.
Notice of Allowance received for U.S. Appl. No. 16/144,735, dated Oct. 28, 2020, 13 pages.
Notice of Allowance received for U.S. Appl. No. 16/556,023, dated Oct. 15, 2020, 8 pages.

(56) References Cited

OTHER PUBLICATIONS

Office Action received for Japanese Patent Application No. 2020-104679, dated Sep. 18, 2020, 13 pages (7 pages of English Translation and 6 pages of Official Copy).
Chatrzarrin Hanieh, "Feature Extraction for the Differentiation of Dry and Wet Cough Sounds", Carleton University, Sep. 2011, 144 pages.
Haslam Oliver, "Stop Coronavirus in its Tracks by Using This Apple Watch App to Time Hand Washes", Available Online at: <https://www.imore.com/stop-coronavirus-its-tracks-using-apple-watch-app-time-hand-washes>, Mar. 12, 2020, 12 pages.
Liaqat et al., "Challenges with Real-World Smartwatch based Audio Monitoring", WearSys'18, Munich, Germany, Available Online at: <https://doi.org/10.1145/3211960.3211977>, Jun. 10, 2018, 6 pages.
Lyles Taylor, "Wear OS Smartwatches are Now Sending Reminders to Wash Your Hands", Available Online at: <https://www.theverge.eom/2020/4/14/21221294/google-wear-os-smartwatches-reminders-wash-your-hands>, Apr. 14, 2020, 2 pages.
Peters Jay, "Samsung's Smartwatches Get a Hand-Washing Reminder and Timer App", Available Online at: <https://www.theverge.com/2020/4/17/21225205/samsung-smartwatch-galaxy-active-hand-washing-timer-reminder-app>, Apr. 17, 2020, 2 pages.
Schoon Ben, "Wear OS Now Sends a Reminder to Wash Your Hands Every Few Hours", Available Online at: <https://9to5google.com/2020/04/14/wear-os-wash-hands-Yeminder-coronavirus/>, Apr. 14, 2020, 7 pages.
Final Office Action received for U.S. Appl. No. 16/418,786, dated Jan. 13, 2021, 14 pages.
Notice of Acceptance received for Australian Patent Application No. 2018268972, dated Dec. 18, 2020, 3 pages.
Notice of Allowance received for Japanese Patent Application No. 2018-014096, dated Jan. 5, 2021, 3 pages (1 page of English Translation and 2 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for U.S. Appl. No. 16/556,023, dated Jan. 13, 2021, 8 pages.
Search Report and Opinion received for Danish Patent Application No. PA202070614, dated Jan. 14, 2021, 9 pages.
Supplemental Notice of Allowance received for U.S. Appl. No. 15/925,652, dated Jan. 6, 2021, 2 pages.
Applicant-Initiated Interview Summary received for U.S. Appl. No. 15/627,069, dated Jan. 22, 2021, 4 pages.
Adeniyi Samuel, "How to connect a second PS4 controller to a PlayStation 4 console", Online available on:—https://www.youtube.com/watch?v=mOZX_SrNISE, May 28, 2017, 2 pages.
Allison Conor, "Working out with Fiit's wearable-powered boutique fitness classes", Online available at:—<https://www.wareable.com/wearable-tech/fiit-fitness-classes-review-3849>, May 14, 2018, 8 pages.
Decision to Refuse received for European Patent Application No. 17810749.6, dated Jan. 29, 2021, 24 pages.
Extended European Search Report received for European Patent Application No. 20203526.7, dated Jan. 29, 2021, 13 pages.
Final Office Action received for U.S. Appl. No. 16/377,892, dated Jan. 28, 2021, 11 pages.
Final Office Action received for U.S. Appl. No. 16/378,136, dated Jan. 28, 2021, 9 pages.
Hamilton Jim, "Peloton Tips", Online available on:—<https://www.youtube.com/watch?app=desktop&v=OneXtBOkaD4>, Oct. 22, 2015, 3 pages.
Intention to Grant received for Danish Patent Application No. PA201670656, dated Jan. 18, 2021, 2 pages.
Lovejoy Ben, "Apple Watch blood sugar measurement coming in Series 7, claims report", Available Online at: https://9to5mac.com/2021/01/25/apple-watch-blood-sugar-measurement/, Jan. 25, 2021, 6 pages.
Minutes of the Oral Proceedings received for European Patent Application No. 17810749.6, mailed on Jan. 26, 2021, 8 pages.
Notice of Allowance received for Chinese Patent Application No. 201710439448.7, dated Jan. 26, 2021, 2 pages (1 page of English Translation and 1 page of Official Copy).
Office Action received for European Patent Application No. 16837432.0, dated Jan. 27, 2021, 7 pages.
Office Action received for Japanese Patent Application No. 2020-000492, dated Dec. 11, 2020, 6 pages (3 pages English Translation and 3 pages of Official Copy).
Office Action received for Korean Patent Application No. 10-2019-7033834, dated Jan. 22, 2021, 13 pages (6 pages of English Translation and 7 pages of Official Copy).
Result of Consultation received for European Patent Application No. 17810749.6, mailed on Jan. 18, 2021, 3 pages.
Result of Consultation received for European Patent Application No. 17810749.6, mailed on Jan. 21, 2021, 18 pages.
Supplemental Notice of Allowance received for U.S. Appl. No. 15/925,652, mailed on Jan. 26, 2021, 3 pages.
Supplemental Notice of Allowance received for U.S. Appl. No. 16/556,023, mailed on Feb. 3, 2021, 2 pages.
Vicky's Blog, "How to Log in to PS4 Automatically with Particular User?", Online available on:—https://www.youtube.com/watch?v=kqdlzXAvOkY, May 30, 2018, 3 pages.
Yoyodavid, "How to Use Multiple Accounts on the PlayStation 4", Online available at:—https://www.youtube.com/watch?v=5V21obRMeKE, Jan. 9, 2014, 3 pages.
Applicant-Initiated Interview Summary received for U.S. Appl. No. 16/586,154, dated Dec. 11, 2020, 5 pages.
Applicant-Initiated Interview Summary received for U.S. Appl. No. 16/907,261, dated Dec. 16, 2020, 6 pages.
Board Decision received for Chinese Patent Application No. 201380081349.6, mailed on Nov. 23, 2020, 2 pages (1 page of English Translation and 1 page of Official Copy).
International Search Report and Written Opinion received for PCT Patent Application No. PCT/US2020/035474, dated Nov. 26, 2020, 16 pages.
Non-Final Office Action received for U.S. Appl. No. 16/820,383, dated Dec. 14, 2020, 11 pages.
Non-Final Office Action received for U.S. Appl. No. 17/031,859, dated Dec. 15, 2020, 13 pages.
Notice of Allowance received for U.S. Appl. No. 16/144,753, dated Dec. 4, 2020, 22 pages.
Search Report and Opinion received for Danish Patent Application No. PA202070335, dated Nov. 27, 2020, 10 pages.
Search Report and Opinion received for Danish Patent Application No. PA202070395, dated Nov. 24, 2020, 10 pages.
Gupta Rajat, "Disable High Volume Warning (no root) in Samsung S7, S8 / Android 7.0", Online available at: <https://www.youtube.com/watch?v=9fKwRBtk-x8>, Retrieved on Nov. 26, 2020; esp. 2:04, Aug. 6, 2017, 1 page.
Kalyani Tech.,"I See Some problems in Honor Band 5", Retrieved from https://www.youtube.com/watch?v=5XPnYJFqajl, May 19, 2020, 1 page.
Smartwatch Ticks,"SENBONO S10 IP67 Waterproof Multi-Function Blood Pressure Sports Smartwatch: One Minute Overview", Retrieved from https://www.youtube.com/watch?v=rMxLJvKIVBs, Oct. 30, 2019, 1 page.
Applicant-Initiated Interview Summary received for U.S. Appl. No. 16/888,629, dated Aug. 4, 2021, 5 pages.
Corrected Notice of Allowance received for U.S. Appl. No. 16/377,892, dated Aug. 11, 2021, 3 pages.
Corrected Notice of Allowance received for U.S. Appl. No. 16/378,136, dated Aug. 11, 2021, 2 pages.
Corrected Notice of Allowance received for U.S. Appl. No. 16/820,383, dated Aug. 13, 2021, 2 pages.
Final Office Action received for U.S. Appl. No. 17/192,161, dated Aug. 16, 2021, 22 pages.
Non-Final Office Action received for U.S. Appl. No. 16/994,352, dated Jul. 30, 2021, 11 pages.
Notice of Acceptance received for Australian Patent Application No. 2020256383, dated Aug. 3, 2021, 3 pages.
Notice of Allowance received for U.S. Appl. No. 16/907,261, dated Aug. 13, 2021, 8 pages.

(56) References Cited

OTHER PUBLICATIONS

Office Action received for Chinese Patent Application No. 201780034203.4, dated Jul. 14, 2021, 12 pages (5 pages of English Translation and 7 pages of Official Copy).
Summons to Attend Oral Proceedings received for European Patent Application No. 20180592.6, mailed on Aug. 11, 2021, 16 pages.
Decision on Appeal received for Korean Patent Application No. 10-2019-7025538, mailed on Feb. 24, 2021, 20 pages (4 pages of English Translation and 16 pages of Official Copy).
Notice of Allowance received for Korean Patent Application No. 10-2019-7025538, dated Mar. 10, 2021, 5 pages (2 pages of English Translation and 3 pages of Official Copy).
Advisory Action received for U.S. Appl. No. 16/377,892, dated Apr. 9, 2021, 4 pages.
Advisory Action received for U.S. Appl. No. 16/378,136, dated Apr. 12, 2021, 4 pages.
Applicant Initiated Interview Summary received for U.S. Appl. No. 15/608,848, dated Apr. 13, 2021, 4 pages.
Applicant-Initiated Interview Summary received for U.S. Appl. No. 16/143,997, dated May 3, 2021, 4 pages.
Applicant-Initiated Interview Summary received for U.S. Appl. No. 16/377,892, dated Mar. 26, 2021, 2 pages.
Applicant-Initiated Interview Summary received for U.S. Appl. No. 16/378,136, dated Mar. 26, 2021, 2 pages.
Applicant-Initiated Interview Summary received for U.S. Appl. No. 16/418,786, dated Mar. 30, 2021, 4 pages.
Applicant-Initiated Interview Summary received for U.S. Appl. No. 16/586,154, dated Apr. 14, 2021, 4 pages.
Applicant-Initiated Interview Summary received for U.S. Appl. No. 16/820,383, dated Mar. 11, 2021, 2 pages.
Applicant-Initiated Interview Summary received for U.S. Appl. No. 16/880,552, dated Apr. 21, 2021, 3 pages.
Applicant-Initiated Interview Summary received for U.S. Appl. No. 16/880,714, dated Feb. 26, 2021, 5 pages.
Applicant-Initiated Interview Summary received for U.S. Appl. No. 16/907,261, dated Mar. 25, 2021, 2 pages.
Applicant-Initiated Interview Summary received for U.S. Appl. No. 17/031,859, dated Feb. 26, 2021, 4 pages.
Applicant-Initiated Interview Summary received for U.S. Appl. No. 17/031,874, dated Feb. 26, 2021, 4 pages.
Cook James, "German Period Tracking App Clue Has Over 2.5 Million Active Users—But It's Still Not Sure How It's Going to Make Money", Available online at: https://www.businessinsider.in/tech/german-period-tracking-app-clue-has-over-2-5-million-active-users-but-its-still-not-sure-how-its-going-to-make-money/articleshow/50511307.cms, Jan. 9, 2016, 9 pages.
Corrected Notice of Allowance received for U.S. Appl. No. 16/143,997, dated Jun. 4, 2021, 2 pages.
Corrected Notice of Allowance received for U.S. Appl. No. 16/378,136, dated Jun. 11, 2021, 2 pages.
Decision to Grant received for Danish Patent Application No. PA201670656, dated Jun. 21, 2021, 2 pages.
Decision to Grant received for German Patent Application No. 112015002326.7, dated Jun. 15, 2021, 10 pages (1 page of English Translation and 9 pages of Official Copy).
Decision to Refuse received for European Patent Application No. 18154145.9, dated Feb. 17, 2021, 20 pages.
European Search Report received for European Patent Application No. 21165295.3, dated Jun. 18, 2021, 4 pages.
Final Office Action received for U.S. Appl. No. 16/586,154, dated May 24, 2021, 29 pages.
Final Office Action received for U.S. Appl. No. 16/907,261, dated Mar. 18, 2021, 20 pages.
Final Office Action received for U.S. Appl. No. 17/031,859, dated Apr. 16, 2021, 14 pages.
Final Office Action received for U.S. Appl. No. 17/031,874, dated Apr. 16, 2021, 17 pages.
International Search Report and Written Opinion received for PCT Patent Application No. PCT/US2020/035164, dated Feb. 8, 2021, 26 pages.
International Search Report and Written Opinion received for PCT Patent Application No. PCT/US2020/070280, dated Nov. 30, 2020, 20 pages.
Invitation to Pay Additional Fees received for PCT Patent Application No. PCT/US2020/070280, dated Oct. 7, 2020, 12 pages.
Minutes of the Oral Proceedings received for European Patent Application No. 18154145.9, mailed on Feb. 12, 2021, 8 pages.
Non-Final Office Action received for U.S. Appl. No. 16/880,552, dated Feb. 19, 2021, 11 pages.
Non-Final Office Action received for U.S. Appl. No. 16/888,629, dated Mar. 31, 2021, 14 pages.
Non-Final Office Action received for U.S. Appl. No. 16/990,846, dated May 10, 2021, 16 pages.
Non-Final Office Action received for U.S. Appl. No. 17/192,161, dated May 13, 2021, 28 pages.
Notice of Acceptance received for Australian Patent Application No. 2017277971, dated Feb. 17, 2021, 3 pages.
Notice of Acceptance received for Australian Patent Application No. 2019250251, dated Feb. 18, 2021, 3 pages.
Notice of Acceptance received for Australian Patent Application No. 2021200787, dated Mar. 19, 2021, 3 pages.
Notice of Allowance received for Chinese Patent Application No. 201680047983.1, dated Apr. 28, 2021, 3 pages (1 page of English Translation and 2 pages of Official Copy).
Notice of Allowance received for Korean Patent Application No. 10-2020-7026391, dated May 11, 2021, 3 pages (1 page of English Translation and 2 pages of Official Copy).
Notice of Allowance received for Korean Patent Application No. 10-2020-7026453, dated May 11, 2021, 3 pages (1 page of English Translation and 2 pages of Official Copy).
Notice of Allowance received for U.S. Appl. No. 15/627,069, dated Jun. 17, 2021, 14 pages.
Notice of Allowance received for U.S. Appl. No. 15/925,652, dated Mar. 9, 2021, 9 pages.
Notice of Allowance received for U.S. Appl. No. 16/138,809, dated Apr. 16, 2021, 11 pages.
Notice of Allowance received for U.S. Appl. No. 16/143,997, dated May 13, 2021, 10 pages.
Notice of Allowance received for U.S. Appl. No. 16/144,030, dated Apr. 5, 2021, 8 pages.
Notice of Allowance received for U.S. Appl. No. 16/144,864, dated Mar. 12, 2021, 2 pages.
Notice of Allowance received for U.S. Appl. No. 16/144,864, dated Mar. 30, 2021, 2 pages.
Notice of Allowance received for U.S. Appl. No. 16/377,892, dated May 24, 2021, 9 pages.
Notice of Allowance received for U.S. Appl. No. 16/378,136, dated Jun. 3, 2021, 7 pages.
Notice of Allowance received for U.S. Appl. No. 16/820,383, dated Mar. 31, 2021, 11 pages.
Notice of Allowance received for U.S. Appl. No. 16/880,552, dated May 12, 2021, 7 pages.
Notice of Allowance received for U.S. Appl. No. 16/880,714, dated Jun. 9, 2021, 6 pages.
Notice of Allowance received for U.S. Appl. No. 16/880,714, dated Mar. 19, 2021, 7 pages.
Office Action received for Australian Patent Application No. 2019234289, dated Mar. 16, 2021, 8 pages.
Office Action received for Australian Patent Application No. 2020230340, dated Mar. 2, 2021, 6 pages.
Office Action received for Australian Patent Application No. 2020230340, dated May 27, 2021, 5 pages.
Office Action received for Chinese Patent Application No. 201380081349.6, dated Jan. 5, 2021, 16 pages (7 pages of English Translation and 9 pages of Official Copy).
Office Action received for Chinese Patent Application No. 201680047983.1, dated Feb. 1, 2021, 6 pages (3 pages of English Translation and 3 pages of Official Copy).
Office Action received for Chinese Patent Application No. 202010618240.3, dated Mar. 29, 2021, 21 pages (11 pages of English Translation and 10 pages of Official Copy).

(56) References Cited

OTHER PUBLICATIONS

Office Action received for Chinese Patent Application No. 202010618569.X, dated Mar. 12, 2021, 14 pages (7 pages of English Translation and 7 pages of Official Copy).
Office Action received for Chinese Patent Application No. 202011220489.5, dated Jun. 1, 2021, 12 pages (6 pages of English Translation and 6 pages of Official Copy).
Office Action received for Danish Patent Application No. PA201970534, dated Feb. 16, 2021, 2 pages.
Office Action received for Danish Patent Application No. PA202070335, dated Jun. 11, 2021, 4 pages.
Office Action received for Danish Patent Application No. PA202070620, dated May 10, 2021, 5 pages.
Office Action received for Danish Patent Application No. PA202170113, dated Apr. 15, 2021, 2 pages.
Office Action received for European Patent Application No. 18727543.3, dated Mar. 26, 2021, 7 pages.
Office Action received for European Patent Application No. 19721883.7, dated Jun. 15, 2021, 9 pages.
Office Action received for European Patent Application No. 20180581.9, dated Apr. 1, 2021, 11 pages.
Office Action received for European Patent Application No. 20180592.6, dated Apr. 1, 2021, 11 pages.
Office Action received for Japanese Patent Application No. 2019-563407, dated Feb. 5, 2021, 5 pages (2 pages of English Translation and 3 pages of Official Copy).
Office Action received for Japanese Patent Application No. 2020-115940, dated May 7, 2021, 3 pages (1 page of English Translation and 2 pages of Official Copy).
Office Action received for Japanese Patent Application No. 2020-547369, dated Apr. 9, 2021, 4 pages (2 pages of English Translation and 2 pages of Official Copy).
Result of Consultation received for European Patent Application No. 19726205.8, mailed on Mar. 15, 2021, 19 pages.
Search Report and Opinion received for Danish Patent Application No. PA202070815, dated Mar. 16, 2021, 8 pages.
Summons to Oral Proceedings received for European Patent Application No. 15771747.1, mailed on Apr. 29, 2021, 8 pages.
Supplemental Notice of Allowance received for U.S. Appl. No. 15/925,652, dated Feb. 17, 2021, 3 pages.
Notice of Allowance received for Japanese Patent Application No. 2019-162293, dated Apr. 9, 2021, 4 pages (1 page of English Translation and 3 pages of Official Copy).
Applicant Initiated Interview Summary received for U.S. Appl. No. 17/030,318, dated Jul. 30, 2021, 4 pages.
Applicant Initiated Interview Summary received for U.S. Appl. No. 17/030,321, dated Jul. 30, 2021, 2 pages.
Applicant-Initiated Interview Summary received for U.S. Appl. No. 17/031,704, dated Feb. 9, 2021, 3 pages.
Applicant-Initiated Interview Summary received for U.S. Appl. No. 17/031,704, dated Jun. 25, 2021, 3 pages.
Applicant-Initiated Interview Summary received for U.S. Appl. No. 17/031,717, dated Jan. 29, 2021, 5 pages.
Applicant-Initiated Interview Summary received for U.S. Appl. No. 17/031,717, dated May 17, 2021, 5 pages.
Communication of the Board of Appeal received for European Patent Application No. 15771747.1, mailed on Aug. 25, 2021, 9 pages.
Corrected Notice of Allowance received for U.S. Appl. No. 16/820,383, dated Aug. 19, 2021, 2 pages.
Final Office Action received for U.S. Appl. No. 17/030,321, dated Apr. 2, 2021, 28 pages.
Final Office Action received for U.S. Appl. No. 17/031,704, dated Apr. 1, 2021, 31 pages.
Final Office Action received for U.S. Appl. No. 17/031,717, dated Feb. 24, 2021, 23 pages.
"Gym Book—Strength Training Planner, Logger and Analyzer", GymBookApp, Available Online at: https://web.archive.org/web/20160401104508/https://gymbookapp.com/, Apr. 1, 2016, 10 pages.

Invitation to Pay Additional Fees received for PCT Patent Application No. PCT/US2021/017736, mailed on Jun. 15, 2021, 14 pages.
Non-Final Office Action received for U.S. Appl. No. 17/030,318, dated Apr. 2, 2021, 28 pages.
Non-Final Office Action received for U.S. Appl. No. 17/030,318, dated Dec. 3, 2020, 22 pages.
Non-Final Office Action received for U.S. Appl. No. 17/030,321, dated Dec. 15, 2020, 25 pages.
Non-Final Office Action received for U.S. Appl. No. 17/031,704, dated Dec. 10, 2020, 30 pages.
Non-Final Office Action received for U.S. Appl. No. 17/031,717, dated Nov. 19, 2020, 22 pages.
Notice of Allowance received for Japanese Patent Application No. 2019-563407, dated Aug. 20, 2021, 4 pages (1 page of English Translation and 3 pages of Official Copy).
Notice of Allowance received for U.S. Appl. No. 15/608,848, dated Aug. 25, 2021, 9 pages.
Notice of Allowance received for U.S. Appl. No. 17/031,704, dated Jul. 21, 2021, 10 pages.
Notice of Allowance received for U.S. Appl. No. 17/031,727, dated Dec. 24, 2020, 12 pages.
Notice of Allowance received for U.S. Appl. No. 17/031,727, dated Jun. 25, 2021, 6 pages.
Notice of Allowance received for U.S. Appl. No. 17/031,727, dated Mar. 12, 2021, 7 pages.
Office Action received for Australian Patent Application No. 2020239740, dated Jul. 9, 2021, 4 pages.
Office Action received for Australian Patent Application No. 2020239743, dated Mar. 25, 2021, 8 pages.
Office Action received for Australian Patent Application No. 2020239748, dated Apr. 21, 2021, 6 pages.
Office Action received for Australian Patent Application No. 2020239752, dated Jun. 4, 2021, 8 pages.
Office Action received for European Patent Application No. 21168916.1, dated Aug. 23, 2021, 8 pages.
Search Report and Opinion received for Danish Patent Application No. PA202070612, dated Jun. 7, 2021, 9 pages.
Search Report and Opinion received for Danish Patent Application No. PA202070613, dated Jan. 22, 2021, 9 pages.
Search Report and Opinion received for Danish Patent Application No. PA202070615, dated Jan. 22, 2021, 9 pages.
Search Report and Opinion received for Danish Patent Application No. PA202070616, dated Feb. 3, 2021, 8 pages.
Search Report and Opinion received for Danish Patent Application No. PA202070619, dated Dec. 2, 2020, 11 pages.
Summons to Attend Oral Proceedings received for European Patent Application No. 20180581.9, mailed on Aug. 18, 2021, 15 pages.
Supplemental Notice of Allowance received for U.S. Appl. No. 17/031,727, dated Jan. 15, 2021, 2 pages.
Applicant-Initialed Interview Summary received for U.S. Appl. No. 17/031,859, dated Jun. 30, 2021, 4 pages.
Applicant-Initiated Interview Summary received for U.S. Appl. No. 17/031,874, dated Jun. 30, 2021, 4 pages.
Applicant-Initiated Interview Summary received for U.S. Appl. No. 17/192,161, dated Jun. 29, 2021, 4 pages.
Corrected Notice of Allowance received for U.S. Appl. No. 16/143,997, dated Jul. 2, 2021, 2 pages.
Corrected Notice of Allowance received for U.S. Appl. No. 16/880,552, dated Jul. 7, 2021, 2 pages.
Notice of Allowance received for Korean Patent Application No. 10-2019-7025781, dated Jun. 29, 2021, 5 pages (2 pages of English Translation and 3 pages of Official Copy).
Notice of Allowance received for Korean Patent Application No. 10-2019-7033834, dated Jul. 3, 2021, 4 pages (2 page of English Translation and 2 pages of Official Copy).
Office Action received for Chinese Patent Application No. 202010606407.4, dated Jun. 2, 2021, 12 pages (5 pages of English Translation and 7 pages of Official Copy).
Office Action received for European Patent Application No. 21165295.3, dated Jul. 1, 2021, 10 pages.

(56) References Cited

OTHER PUBLICATIONS

Office Action received for Japanese Patent Application No. 2020-153166, dated May 31, 2021, 6 pages (3 pages of English Translation and 3 pages of Official Copy).
Supplemental Notice of Allowance received for U.S. Appl. No. 15/627,069, dated Jul. 12, 2021, 2 pages.
Office Action received for Korean Patent Application No. 10-2020-7026035, dated Feb. 19, 2021, 13 pages (6 pages of English Translation and 7 pages of Official Copy).
Office Action received for Japanese Patent Application No. 2018-184532, dated Mar. 1, 2021, 11 pages (6 pages of English Translation and 5 pages of Official Copy).
Office Action received for European Patent Application No. 20182116.2, dated May 25, 2021, 9 pages.
Office Action received for Australian Patent Application No. 2020256383, dated Jun. 4, 2021, 3 pages.
Office Action received for Chinese Patent Application No. 202010606407.4, dated Jan. 27, 2021, 16 pages (7 pages of English Translation and 9 pages of Official Copy).
Corrected Notice of Allowance received for U.S. Appl. No. 16/820,383, dated Oct. 5, 2021, 2 pages.
Final Office Action received for U.S. Appl. No. 17/030,318, dated Sep. 30, 2021, 28 pages.
Non-Final Office Action received for U.S. Appl. No. 16/418,786, dated Oct. 4, 2021, 10 pages.
Notice of Allowance received for U.S. Appl. No. 16/143,997, dated Sep. 30, 2021, 8 pages.
Office Action received for Australian Patent Application No. 2020239740, dated Sep. 28, 2021, 5 pages.
Office Action received for Danish Patent Application No. PA202070613, dated Sep. 30, 2021, 4 pages.
Office Action received for Danish Patent Application No. PA202070614, dated Sep. 28, 2021, 4 pages.
Corrected Notice of Allowance received for U.S. Appl. No. 16/143,997, dated Oct. 21, 2021, 2 pages.
Corrected Notice of Allowance received for U.S. Appl. No. 16/586,154, dated Oct. 27, 2021, 2 pages.
Final Office Action received for U.S. Appl. No. 17/192,161, dated Oct. 18, 2021, 22 pages.
International Search Report and Written Opinion received for PCT Patent Application No. PCT/US2021/035227, dated Oct. 6, 2021, 17 pages.
Non-Final Office Action received for U.S. Appl. No. 17/030,321, dated Oct. 18, 2021, 28 pages.
Notice of Allowance received for U.S. Appl. No. 16/586,154, dated Oct. 15, 2021, 8 pages.
Office Action received for Australian Patent Application No. 2020230340, dated Oct. 11, 2021, 4 pages.
Office Action received for Danish Patent Application No. PA202070619, dated Oct. 14, 2021, 3 pages.
Office Action received for Danish Patent Application No. PA202070815, dated Oct. 18, 2021, 2 pages.
Applicant-Initiated Interview Summary received for U.S. Appl. No. 16/586,154, dated Sep. 3, 2021, 4 pages.
Non-Final Office Action received for U.S. Appl. No. 17/031,717, dated Sep. 14, 2021, 35 pages.
Notice of Allowance received for Korean Patent Application No. 10-2020-7026035, dated Aug. 23, 2021, 4 pages (2 pages of English Translation and 2 pages of Official Copy).
Notice of Allowance received for U.S. Appl. No. 16/377,892, dated Sep. 9, 2021, 9 pages.
Notice of Allowance received for U.S. Appl. No. 16/921,312, dated Sep. 14, 2021, 9 pages.
Office Action received for Australian Patent Application No. 2020239743, dated Sep. 3, 2021, 4 pages.
Office Action received for Australian Patent Application No. 2020239748, dated Sep. 1, 2021, 4 pages.
Office Action received for Danish Patent Application No. PA202070619, dated Aug. 27, 2021, 12 pages.
Office Action received for Japanese Patent Application No. 2019-044107, dated Jul. 30, 2021, 9 pages (5 pages of English Translation and 4 pages of Official Copy).
Office Action received for Korean Patent Application No. 10-2021-7026284, dated Aug. 31, 2021, 10 pages (4 pages of English Translation and 6 pages of Official Copy).
Applicant-Initiated Interview Summary received for U.S. Appl. No. 17/192,161, dated Sep. 29, 2021, 3 pages.
Corrected Notice of Allowance received for U.S. Appl. No. 16/921,312, dated Sep. 24, 2021, 2 pages.
International Search Report and Written Opinion received for PCT Patent Application No. PCT/US2021/017736, dated Sep. 2, 2021, 25 pages.
Notice of Allowance received for Japanese Patent Application No. 2020-153166, dated Sep. 13, 2021, 4 pages (1 page of English Translation and 3 pages of Official Copy).
Notice of Allowance received for U.S. Appl. No. 16/378,136, dated Sep. 22, 2021, 7 pages.
Notice of Allowance received for U.S. Appl. No. 16/907,261, dated Sep. 28, 2021, 6 pages.
Notice of Allowance received for U.S. Appl. No. 16/990,846, dated Sep. 22, 2021, 9 pages.
Office Action received for Chinese Patent Application No. 202010618569.X, dated Sep. 7, 2021, 7 pages (4 pages of English Translation and 3 pages of Official Copy).
Supplemental Notice of Allowance received for U.S. Appl. No. 16/880,714, dated Sep. 16, 2021, 2 pages.
Applicant-Initiated Interview Summary received for U.S. Appl. No. 16/907,261, dated Jul. 16, 2021, 10 pages.
European Search Report received for European Patent Application No. 21168916.1, dated Jul. 14, 2021, 5 pages.
Notice of Allowance received for Japanese Patent Application No. 2020-000492, dated Jul. 16, 2021, 4 pages (1 page of English Translation and 3 pages of Official Copy).
Notice of Allowance received for Japanese Patent Application No. 2020-547369, dated Jul. 16, 2021, 4 pages (1 page of English Translation and 3 pages of Official Copy).
Notice of Allowance received for U.S. Appl. No. 16/138,809, dated Jul. 20, 2021, 6 pages.
Notice of Allowance received for U.S. Appl. No. 16/820,383, dated Jul. 21, 2021, 11 pages.
Notice of Allowance received for U.S. Appl. No. 16/880,552, dated Jul. 23, 2021, 5 pages.
Office Action received for Australian Patent Application No. 2019234289, dated Jul. 20, 2021, 4 pages.
Office Action received for Australian Patent Application No. 2020239692, dated Jul. 20, 2021, 5 pages.
Office Action received for Chinese Patent Application No. 201380081349.6, dated Jun. 2, 2021, 17 pages (8 pages of English Translation and 9 pages of Official Copy).
Office Action received for Chinese Patent Application No. 201910858933.7, dated Jun. 29, 2021, 8 pages (3 pages of English Translation and 5 pages of Official Copy).
Office Action received for European Patent Application No. 20203526.7, dated Nov. 23, 2021, 9 pages.
Notice of Allowance received for Korean Patent Application No. 10-2021-7038005, dated Dec. 14, 2021, 4 pages (2 pages of English Translation and 2 pages of Official Copy).
Office Action received for Chinese Patent Application No. 202010606407.4, dated Nov. 18, 2021, 6 pages (3 pages of English Translation and 3 pages of Official Copy).
Summons to Attend Oral Proceedings received for European Patent Application No. 20182116.2, dated Dec. 21, 2021, 7 pages.
Applicant-Initiated Interview Summary received for U.S. Appl. No. 16/987,275, dated Feb. 3, 2022, 4 pages.
Applicant-Initiated Interview Summary received for U.S. Appl. No. 17/157,728, dated Feb. 3, 2022, 5 pages.
Brief Communication Regarding Oral Proceedings received for European Patent Application No. 20180581.9, dated Jan. 26, 2022, 1 page.
Brief Communication regarding Oral Proceedings received for European Patent Application No. 20180592.6, dated Jan. 26, 2022, 2 pages.

(56) References Cited

OTHER PUBLICATIONS

Corrected Notice of Allowance received for U.S. Appl. No. 16/888,629, dated Jan. 21, 2022, 2 pages.
Corrected Notice of Allowance received for U.S. Appl. No. 17/030,318, dated Jan. 24, 2022, 2 pages.
Intention to Grant received for Danish Patent Application No. PA202070619, dated Jan. 17, 2022, 2 pages.
International Preliminary Report on Patentability received for PCT Patent Application No. PCT/US2020/042439, dated Jan. 27, 2022, 10 pages.
Non-Final Office Action received for U.S. Appl. No. 17/031,723, dated Jan. 24, 2022, 17 pages.
Non-Final Office Action received for U.S. Appl. No. 17/031,874, dated Jan. 24, 2022, 18 pages.
Notice of Acceptance received for Australian Patent Application No. 2020239743, dated Jan. 13, 2022, 3 pages.
Notice of Allowance received for Chinese Patent Application No. 201780034203.4, dated Jan. 17, 2022, 2 pages (1 page of English Translation and 1 page of Official Copy).
Notice of Allowance received for Chinese Patent Application No. 202010606407.4, dated Jan. 24, 2022, 2 pages (1 page of English Translation and 1 page of Official Copy).
Notice of Allowance received for Japanese Patent Application No. 2018-184532, dated Jan. 17, 2022, 4 pages (1 page of English Translation and 3 pages of Official Copy).
Notice of Allowance received for Korean Patent Application No. 10-2021-7042504, dated Jan. 17, 2022, 6 pages (1 page of English Translation and 5 pages of Official Copy).
Notice of Allowance received for U.S. Appl. No. 16/990,846, dated Jan. 20, 2022, 6 pages.
Office Action received for Japanese Patent Application No. 2020-160023, dated Jan. 17, 2022, 11 pages (06 pages of English Translation and 05 pages of Official Copy).
Office Action received for Japanese Patent Application No. 2020-160054, dated Jan. 21, 2022, 8 pages (4 pages of English Translation and 4 pages of Official Copy).
Result of Consultation received for European Patent Application No. 20180581.9, dated Jan. 21, 2022, 14 pages.
Result of Consultation received for European Patent Application No. 20180592.6, dated Jan. 26, 2022, 18 pages.
Applicant Initiated Interview Summary received for U.S. Appl. No. 16/994,352, dated Nov. 2, 2021, 4 pages.
Applicant-Initiated Interview Summary received for U.S. Appl. No. 17/031,717, dated Nov. 4, 2021, 5 pages.
Applicant-Initiated Interview Summary received for U.S. Appl. No. 17/192,161, dated Dec. 24, 2021, 4 pages.
Brief Communication Regarding Oral Proceedings received for European Patent Application No. 20180581.9, dated Nov. 30, 2021, 1 page.
Brief Communication regarding Oral Proceedings received for European Patent Application No. 20180592.6, dated Dec. 21, 2021, 1 page.
Corrected Notice of Allowance received for U.S. Appl. No. 16/143,997, dated Nov. 16, 2021, 2 pages.
Corrected Notice of Allowance received for U.S. Appl. No. 16/418,786, dated Jan. 5, 2022, 3 pages.
Corrected Notice of Allowance received for U.S. Appl. No. 16/880,552, dated Dec. 22, 2021, 2 pages.
Corrected Notice of Allowance received for U.S. Appl. No. 16/921,312, dated Dec. 7, 2021, 2 pages.
Corrected Notice of Allowance received for U.S. Appl. No. 17/031,704, dated Nov. 2, 2021, 7 pages.
Decision of Appeal received for European Patent Application No. 15771747.1, dated Dec. 14, 2021, 21 pages.
Final Office Action received for U.S. Appl. No. 16/994,352, dated Dec. 6, 2021, 14 pages.
International Preliminary Report on Patentability received for PCT Patent Application No. PCT/US2020/035164, dated Dec. 16, 2021, 19 pages.
International Preliminary Report on Patentability received for PCT Patent Application No. PCT/US2020/035199, dated Dec. 16, 2021, 14 pages.
International Preliminary Report on Patentability received for PCT Patent Application No. PCT/US2020/035462, dated Dec. 16, 2021, 16 pages.
International Preliminary Report on Patentability received for PCT Patent Application No. PCT/US2020/025768, dated Dec. 16, 2021, 8 pages.
International Preliminary Report on Patentability received for PCT Patent Application No. PCT/US2020/025997, dated Nov. 18, 2021, 10 pages.
International Preliminary Report on Patentability received for PCT Patent Application No. PCT/US2020/035474, dated Dec. 16, 2021, 11 pages.
International Search Report and Written Opinion received for PCT Patent Application No. PCT/US2021/035504, dated Sep. 16, 2021, 12 pages.
Minutes of the Oral Proceedings received for European Patent Application No. 15771747.1, dated Dec. 1, 2021, 4 pages.
Non-Final Office Action received for U.S. Appl. No. 16/820,383, dated Jan. 10, 2022, 18 pages.
Non-Final Office Action received for U.S. Appl. No. 16/987,275, dated Nov. 23, 2021, 17 pages.
Non-Final Office Action received for U.S. Appl. No. 17/031,854, dated Dec. 27, 2021, 13 pages.
Non-Final Office Action received for U.S. Appl. No. 17/031,859, dated Dec. 24, 2021, 16 pages.
Non-Final Office Action received for U.S. Appl. No. 17/157,728, dated Nov. 26, 2021, 18 pages.
Notice of Acceptance received for Australian Patent Application No. 2020288147, dated Dec. 22, 2021, 3 pages.
Notice of Allowance received for Chinese Patent Application No. 201380081349.6, dated Dec. 17, 2021, 2 pages (1 page of English Translation and 1 page of Official Copy).
Notice of Allowance received for Chinese Patent Application No. 202010618569.X, dated Jan. 7, 2022, 2 pages (1 page of English Translation and 1 page of Official Copy).
Notice of Allowance received for Japanese Patent Application No. 2020-115940, dated Oct. 22, 2021, 4 pages (1 page of English Translation and 3 pages of Official Copy).
Notice of Allowance received for U.S. Appl. No. 15/608,848, dated Oct. 29, 2021, 7 pages.
Notice of Allowance received for U.S. Appl. No. 16/418,786, dated Dec. 9, 2021, 9 pages.
Notice of Allowance received for U.S. Appl. No. 16/880,552, dated Nov. 24, 2021, 5 pages.
Notice of Allowance received for U.S. Appl. No. 16/888,629, dated Nov. 9, 2021, 11 pages.
Notice of Allowance received for U.S. Appl. No. 16/921,312, dated Nov. 29, 2021, 5 pages.
Notice of Allowance received for U.S. Appl. No. 17/030,318, dated Jan. 5, 2022, 8 pages.
Office Action received for Australian Patent Application No. 2019234289, dated Nov. 1, 2021, 4 pages.
Office Action received for Australian Patent Application No. 2020239752, dated Oct. 25, 2021, 5 pages.
Office Action received for Chinese Patent Application No. 201780034203.4, dated Sep. 24, 2021, 7 pages (3 pages of English Translation and 4 pages of Official Copy).
Office Action received for Chinese Patent Application No. 202010618240.3, dated Dec. 3, 2021, 23 pages (14 pages of English Translation and 9 pages of Official Copy).
Office Action received for Chinese Patent Application No. 202011220489.5, dated Dec. 1, 2021, 19 pages (11 pages of English Translation and 8 pages of Official Copy).
Office Action received for Chinese Patent Application No. 202110363565.6, dated Nov. 16, 2021, 16 pages (9 pages of English Translation and 7 pages of Official Copy).
Office Action received for Danish Patent Application No. PA202070335, dated Nov. 17, 2021, 6 pages.
Office Action received for Danish Patent Application No. PA202070395, dated Dec. 15, 2021, 5 pages.

(56) References Cited

OTHER PUBLICATIONS

Office Action received for Danish Patent Application No. PA202070615, dated Nov. 16, 2021, 4 pages.
Office Action received for Danish Patent Application No. PA202070620, dated Nov. 19, 2021, 2 pages.
Office Action received for European Patent Application No. 20721342.2, dated Nov. 4, 2021, 9 pages.
Office Action received for Indian Patent Application No. 202014041484, dated Dec. 8, 2021, 8 pages.
Office Action received for Indian Patent Application No. 202014041563, dated Dec. 30, 2021, 6 pages.
Office Action received for Indian Patent Application No. 202014041571, dated Dec. 17, 2021, 5 pages.
Office Action received for Japanese Patent Application No. 2020-160052, dated Dec. 17, 2021, 10 pages (5 pages of English Translation and 5 pages of Official Copy).
Office Action received for Japanese Patent Application No. 2020-551585, dated Jan. 6, 2022, 11 pages (5 pages of English Translation and 6 pages of Official Copy).
Office Action received for Korean Patent Application No. 10-2021-7031939, dated Oct. 19, 2021, 11 pages (5 pages of English Translation and 6 pages of Official Copy).
Search Report and Opinion received for Danish Patent Application No. PA202170113, dated Nov. 30, 2021, 9 pages.

* cited by examiner

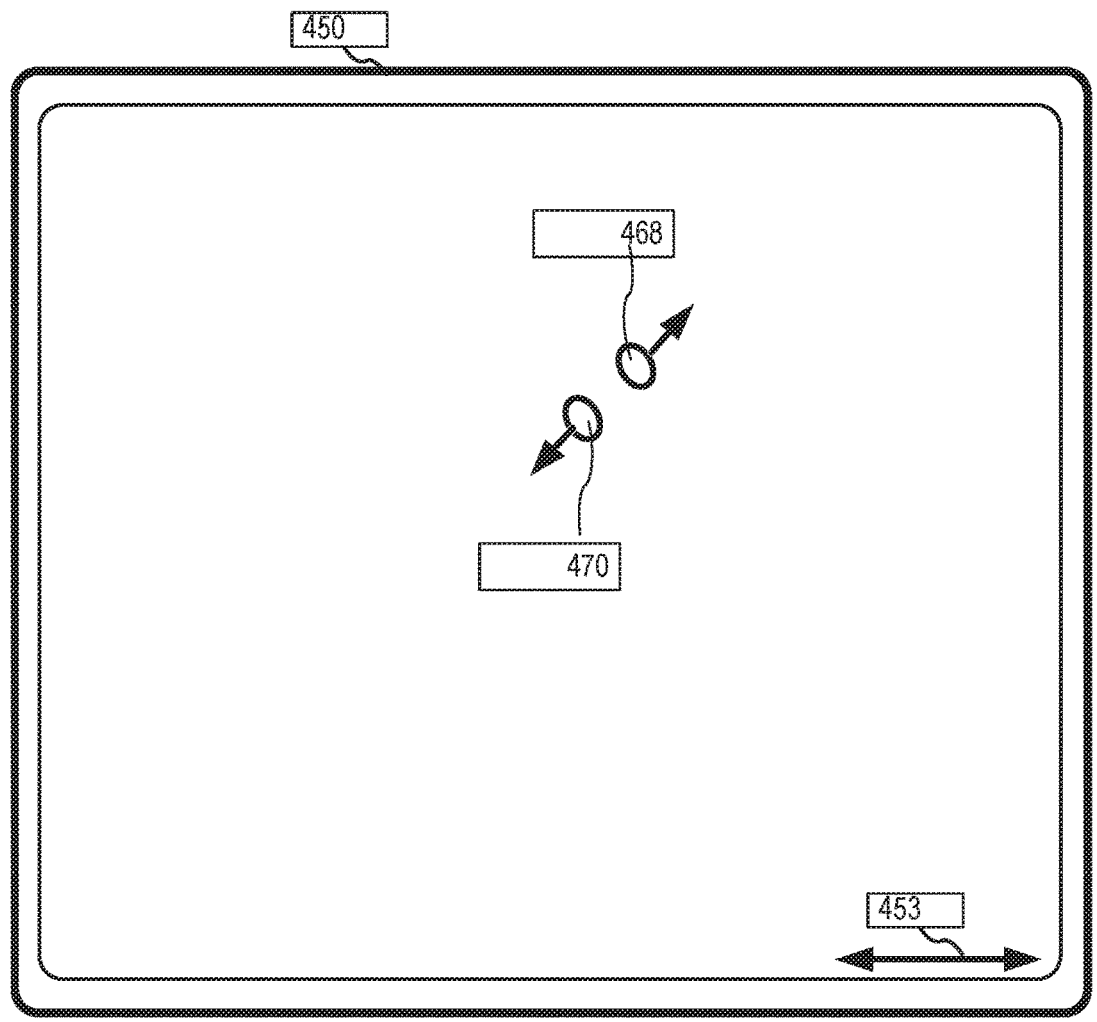
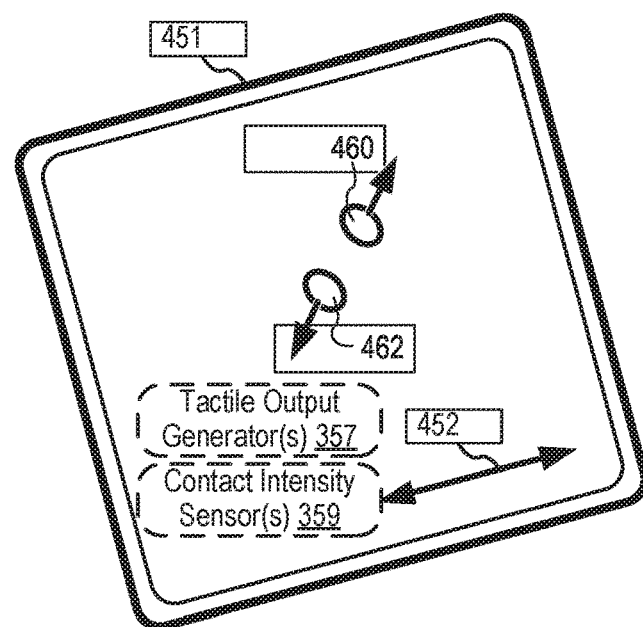
FIG. 4B

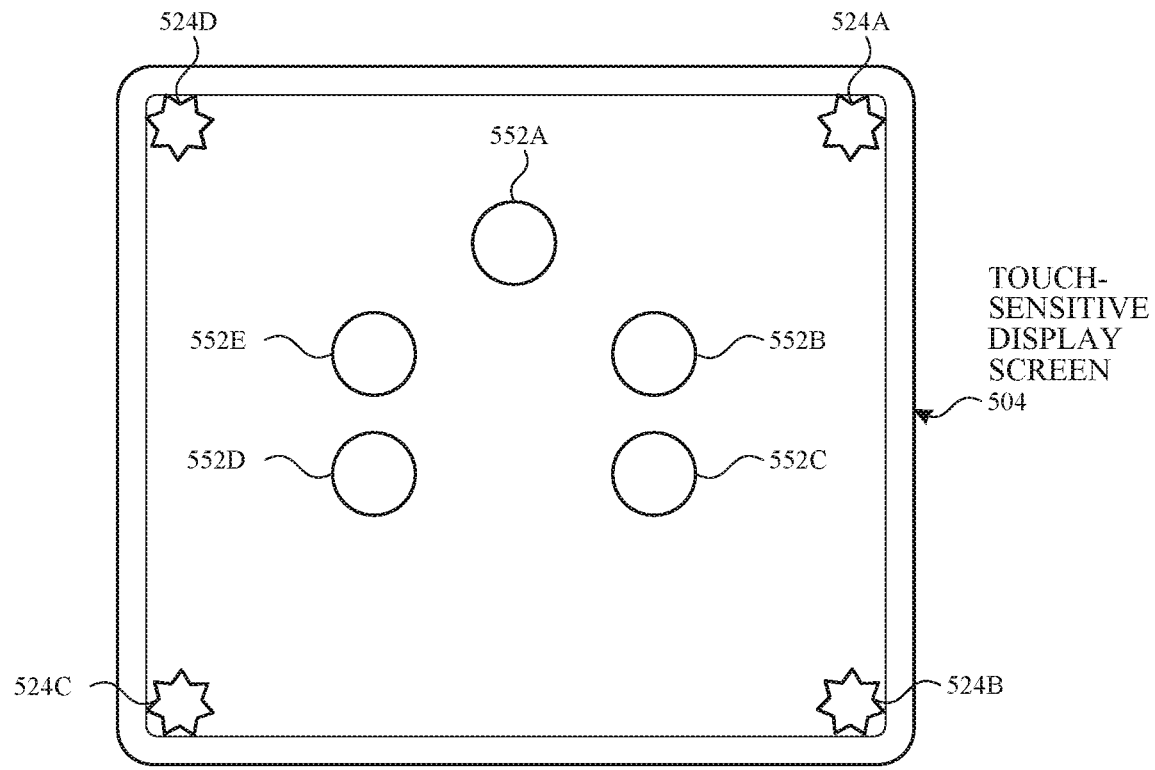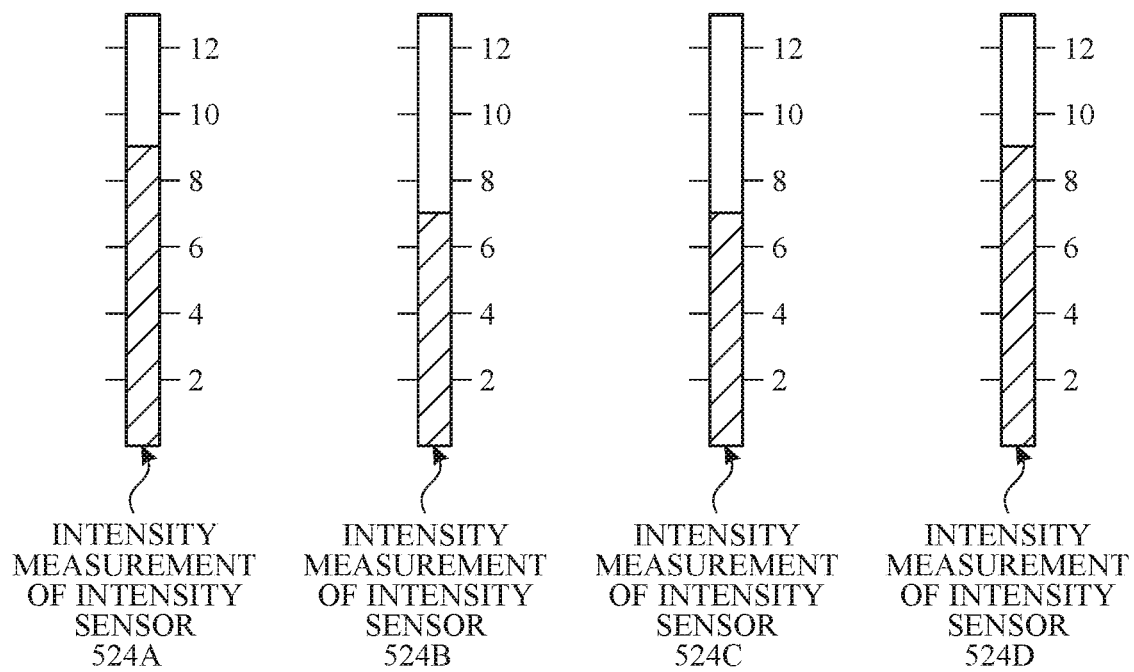
FIG. 5C

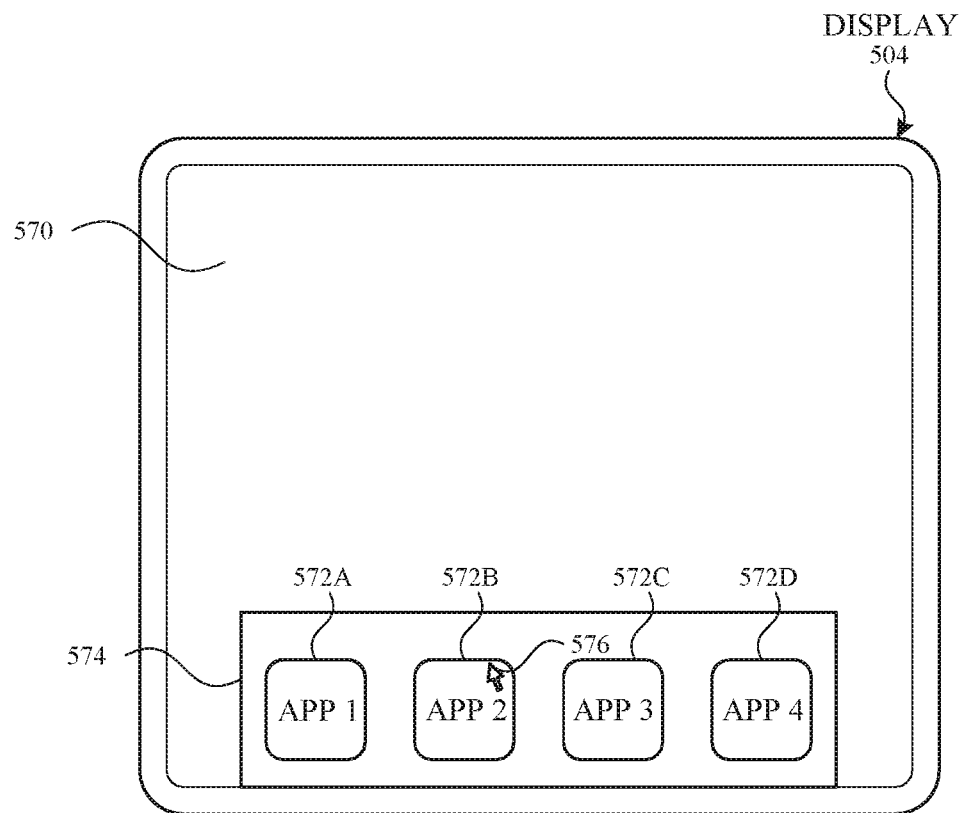
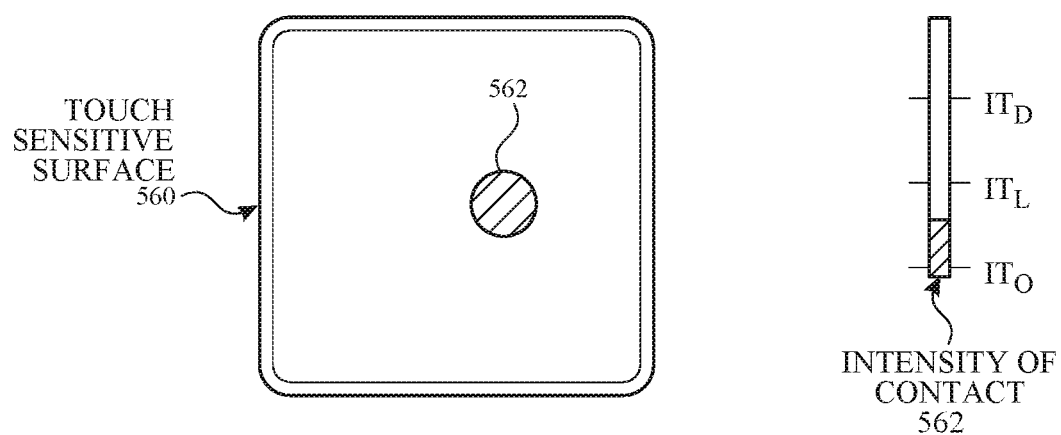
FIG. 5E

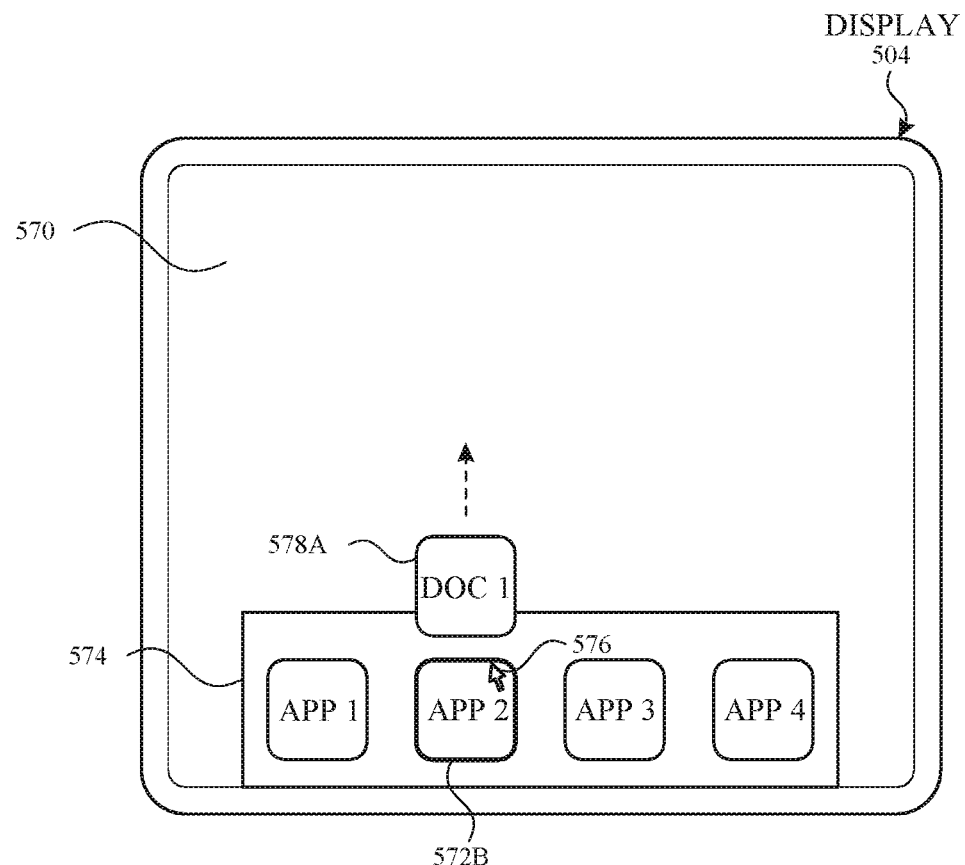
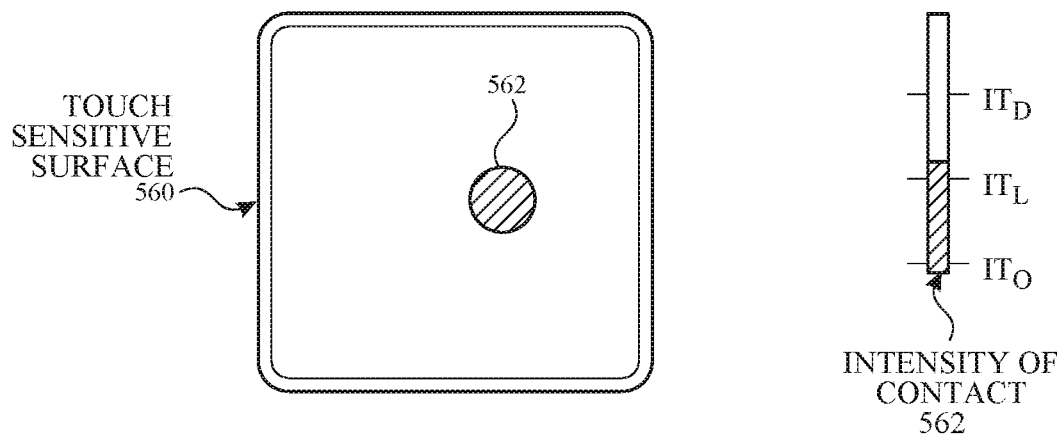
FIG. 5F

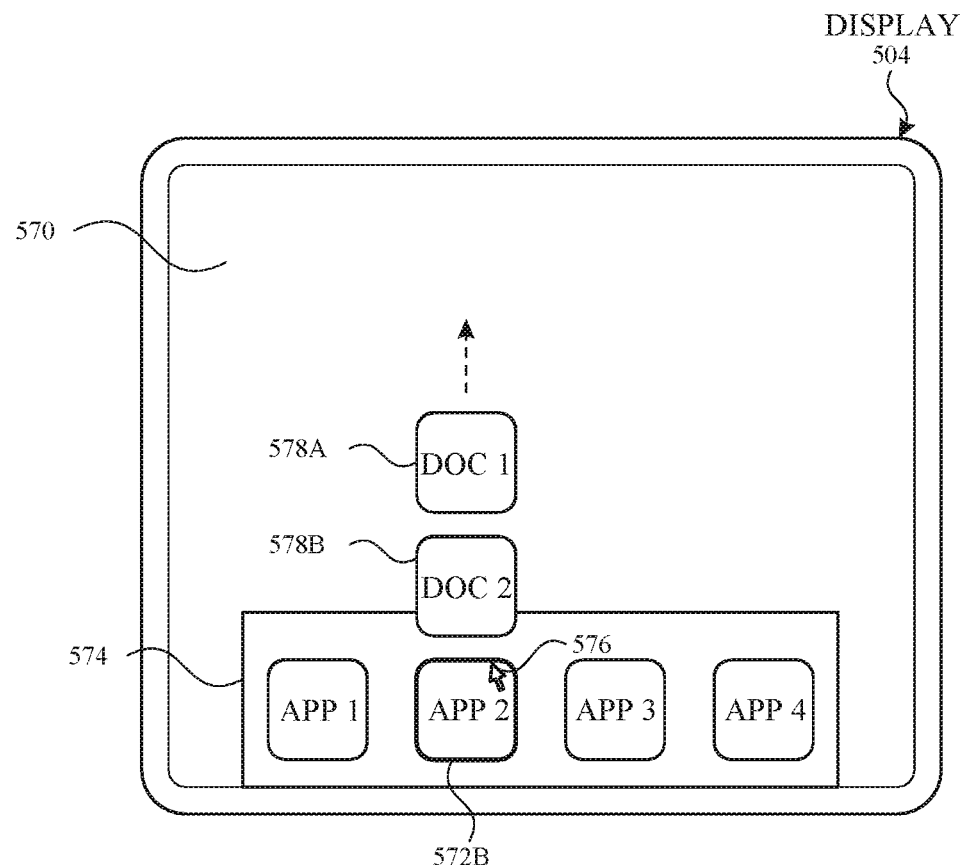
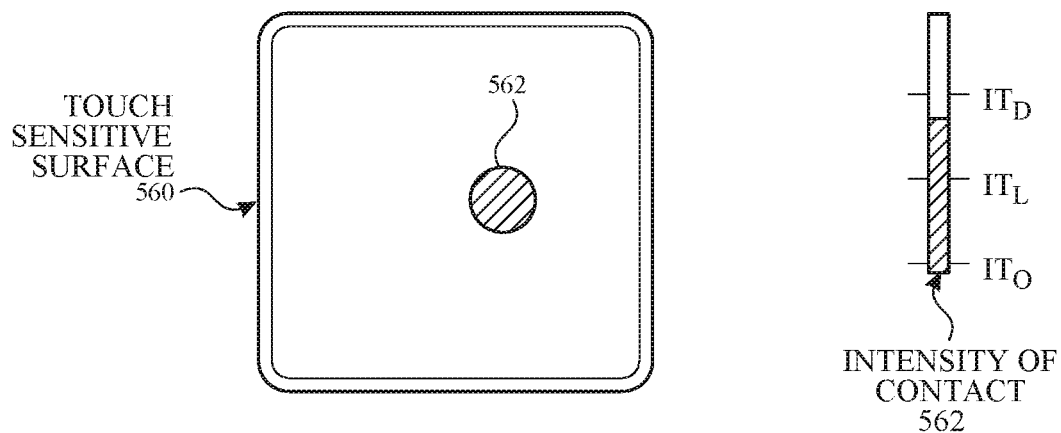
FIG. 5G

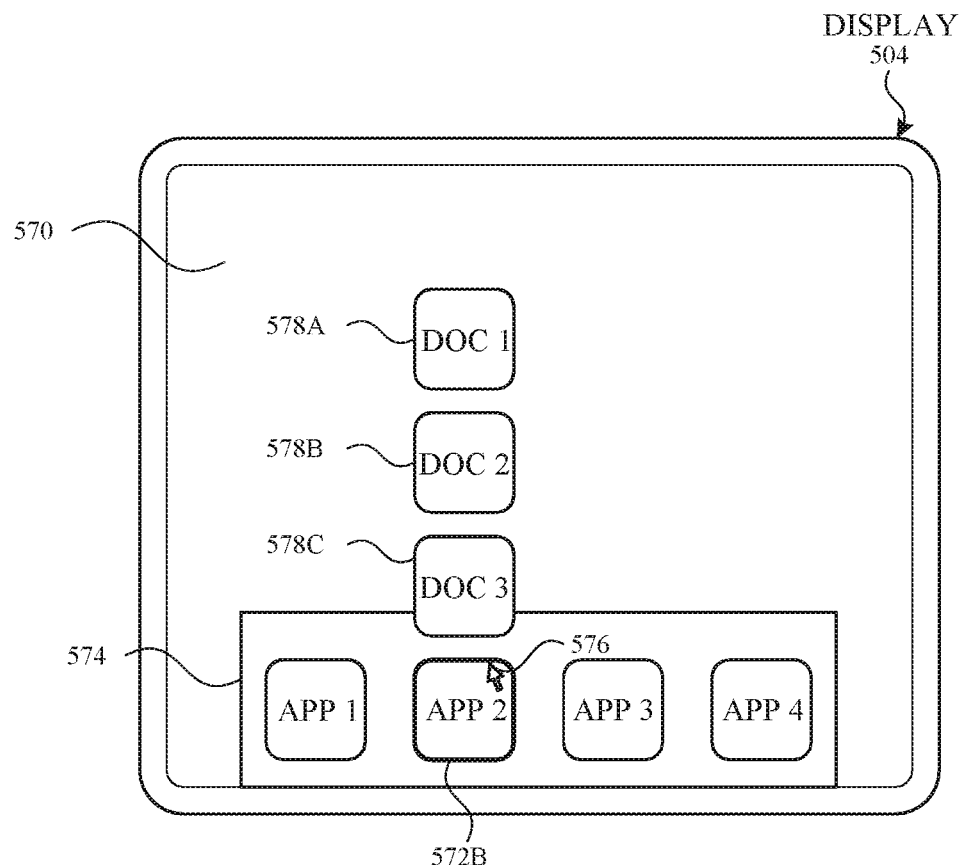
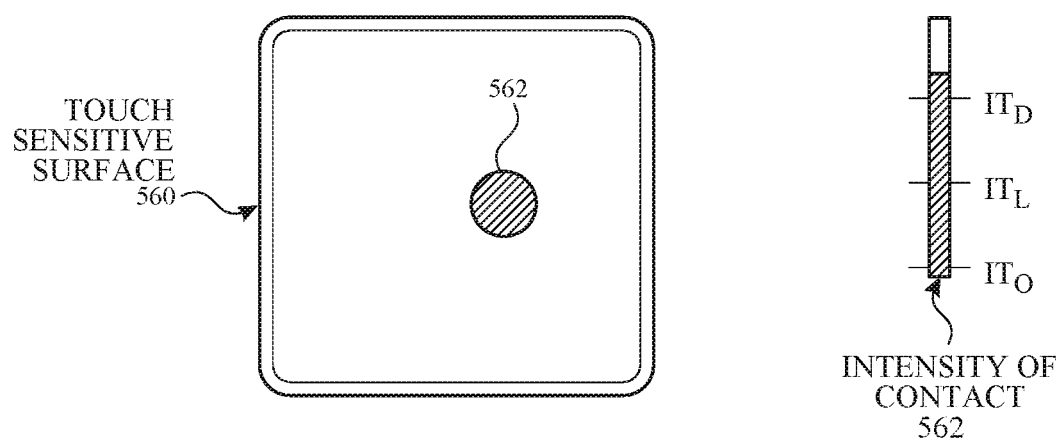
FIG. 5H

DISPLAYING USER INTERFACES ASSOCIATED WITH PHYSICAL ACTIVITIES

CROSS-REFERENCE TO RELATED APPLICATIONS

This application is a continuation of U.S. patent application Ser. No. 16/144,849, entitled "DISPLAYING USER INTERFACES ASSOCIATED WITH PHYSICAL ACTIVITIES", filed on Sep. 27, 2018, which claims priority to U.S. provisional patent application 62/668,159, entitled "DISPLAYING USER INTERFACES ASSOCIATED WITH PHYSICAL ACTIVITIES", filed on May 7, 2018, and U.S. provisional patent application 62/679,906, entitled "DISPLAYING USER INTERFACES ASSOCIATED WITH PHYSICAL ACTIVITIES", filed on Jun. 3, 2018, the entire contents of which are hereby incorporated by reference.

FIELD

The present disclosure relates generally to user interfaces and more specifically to techniques for displaying user interfaces associated with physical activities.

BACKGROUND

Many modern electronic devices provide the capability of tracking physical activities by a user. Such electronic devices often display information associated with the physical activities to the user. Some techniques provide the ability to compare the physical activities of the user with physical activities of other users. Other techniques provide the ability to begin and end tracking of a physical activity. Other techniques provide the ability to set pace alerts for a physical activity. However, such techniques can be cumbersome and inefficient.

SUMMARY

Some techniques for displaying user interfaces associated with physical activities using electronic devices are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for displaying user interfaces associated with physical activities. Such methods and interfaces optionally complement or replace other methods for displaying user interfaces associated with physical activities. Such methods and interfaces reduce the cognitive burden on a user and produce a more efficient human-machine interface. For battery-operated computing devices, such methods and interfaces conserve power and increase the time between battery charges.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a method performed at an electronic device including a display. The method includes receiving first user activity data for a time period, the first user activity data including at least first user activity data for a first time subset and first user activity data for a second time subset. The method further includes receiving second user activity data for the time period, the second user activity data including at least second user activity data for the first time subset and second user activity data for the second time subset. The method further includes displaying, on the display, a user interface including: (1) a representation of the first user activity data for the first time subset; (2) a representation of the first user activity data for the second time subset; (3) a cumulative representation of the first user activity data for the time period, where the cumulative representation of the first user activity data for the time period is based on at least the first user activity data for a first time subset and the first user activity data for a second time subset; (4) a representation of the second user activity data for the first time subset; (5) a representation of the second user activity data for the second time subset; and (6) a cumulative representation of the second user activity data for the time period, where the cumulative representation of the second user activity data for the time period is based on at least the second user activity data for a first time subset and the second user activity data for a second time subset. Other examples of this aspect include corresponding computer systems, apparatus, and computer programs recorded on one or more computer storage devices, each configured to perform the actions of the methods.

One general aspect includes a method performed at an electronic device including a display. The method includes receiving first user activity data for a first user, where the first user activity data corresponds to a first time period and a second time period. The method further includes receiving second user activity data for a second user, where the second user activity data corresponds to the first time period, and where the first time period includes a first elapsed sub-period and a first unelapsed sub-period for an activity competition between the first user and the second user. The method further includes receiving third user activity data for the third user, where the third user activity data corresponds to the second time period, and where the second time period includes a second elapsed sub-period and a second unelapsed sub-period for an activity competition between the first user and the third user. The method further includes displaying, on the display, a user interface including: (1) a representation of the first user activity data and the second user activity data during the first elapsed sub-period for the activity competition between the first user and the second user; (2) an indication of an amount of time in the first unelapsed sub-period for the activity competition between the first user and the second user; (3) a representation of the first activity data and the third activity data during the second elapsed sub-period for the activity competition between the first user and the third user; and (4) an indication of an amount of time in the second unelapsed sub-period for the activity competition between the first user and the third user. Other examples of this aspect include corresponding computer systems, apparatus, and computer programs recorded on one or more computer storage devices, each configured to perform the actions of the methods.

One general aspect includes a method performed at an electronic device including a display and one or more sensors. The method includes detecting, via the one or more sensors, activity data. The method further includes, in response to detecting the activity data and in accordance with a determination that the activity data satisfies activity boundary alert criteria, displaying an activity boundary alert. The method further includes, in further response to detecting the activity data and in accordance with a determination that the activity data does not satisfy the activity boundary alert criteria, forgoing display of the activity boundary alert. Other examples of this aspect include corresponding computer systems, apparatus, and computer programs recorded on one or more computer storage devices, each configured to perform the actions of the methods.

One general aspect includes a method performed at an electronic device. The method includes displaying a physical activity rate user interface including a first setting affordance and a second setting affordance. The method further includes. while displaying the physical activity rate user interface, receiving a first user input. The method further includes, in response to receiving the first user input and in accordance with the first user input corresponding to selection of the first setting affordance, configuring a physical activity rate calculation to use a first portion of a dataset. The method further includes, in response to receiving the first user input and in accordance with the first user input corresponding to selection of the second setting affordance, configuring a physical activity rate calculation to use a second portion of the dataset different from the first portion. Other examples of this aspect include corresponding computer systems, apparatus, and computer programs recorded on one or more computer storage devices, each configured to perform the actions of the methods.

One general aspect includes a non-transitory computer-readable storage medium storing one or more programs configured to be executed by one or more processors of an electronic device with a display, the one or more programs including instructions for any of the methods described above.

One general aspect includes a transitory computer-readable storage medium storing one or more programs configured to be executed by one or more processors of an electronic device with a display, the one or more programs including instructions for any of the methods described above.

One general aspect includes an electronic device, including a display. The electronic device also includes one or more processors. The electronic device also includes memory storing one or more programs configured to be executed by the one or more processors, the one or more programs including instructions for performing any of the methods described above.

One general aspect includes an electronic device, including a display. The electronic device also includes means for receiving first user activity data for a time period, the first user activity data including at least first user activity data for a first time subset and first user activity data for a second time subset. The electronic device also includes means for receiving second user activity data for the time period, the second user activity data including at least second user activity data for the first time subset and second user activity data for the second time subset. The electronic device also includes means for displaying, on the display, a user interface including: (1) a representation of the first user activity data for the first time subset; (2) a representation of the first user activity data for the second time subset; (3) a cumulative representation of the first user activity data for the time period, where the cumulative representation of the first user activity data for the time period is based on at least the first user activity data for a first time subset and the first user activity data for a second time subset; (4) a representation of the second user activity data for the first time subset; (5) a representation of the second user activity data for the second time subset; (6) and a cumulative representation of the second user activity data for the time period, where the cumulative representation of the second user activity data for the time period is based on at least the second user activity data for a first time subset and the second user activity data for a second time subset.

One general aspect includes an electronic device, including a display. The electronic device also includes means for receiving first user activity data for a first user, where the first user activity data corresponds to a first time period and a second time period. The electronic device also includes means for receiving second user activity data for a second user, where the second user activity data corresponds to the first time period, and where the first time period includes a first elapsed sub-period and a first unelapsed sub-period for an activity competition between the first user and the second user. The electronic device also includes means for receiving third user activity data for the third user, where the third user activity data corresponds to the second time period, and where the second time period includes a second elapsed sub-period and a second unelapsed sub-period for an activity competition between the first user and the third user. The electronic device also includes means for displaying, on the display, a user interface including: (1) a representation of the first user activity data and the second user activity data during the first elapsed sub-period for the activity competition between the first user and the second user; (2) an indication of an amount of time in the first unelapsed sub-period for the activity competition between the first user and the second user; (3) a representation of the first activity data and the third activity data during the second elapsed sub-period for the activity competition between the first user and the third user; and (4) an indication of an amount of time in the second unelapsed sub-period for the activity competition between the first user and the third user.

One general aspect includes an electronic device, including a display. The electronic device also includes means for detecting, via the one or more sensors, activity data. The electronic device also includes a means for, in response to detecting the activity data and in accordance with a determination that the activity data satisfies activity boundary alert criteria, displaying an activity boundary alert. The electronic device also includes a means for, in response to detecting the activity data and in accordance with a determination that the activity data does not satisfy the activity boundary alert criteria, forgoing display of the activity boundary alert.

One general aspect includes an electronic device, including a display. The electronic device also includes means for displaying a physical activity rate user interface including a first setting affordance and a second setting affordance. The electronic device also includes means for, while displaying the physical activity rate user interface, receiving a first user input. The electronic device also includes means for, in response to receiving the first user input and in accordance with the first user input corresponding to selection of the first setting affordance, configuring a physical activity rate calculation to use a first portion of a dataset. The electronic device also includes means for, in response to receiving the first user input and in accordance with the first user input corresponding to selection of the second setting affordance, configuring a physical activity rate calculation to use a second portion of the dataset different from the first portion.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for displaying user interfaces associated with physical activities, thereby increasing the effectiveness, efficiency, and user satisfaction with such devices. Such methods and interfaces may complement or replace other methods for displaying user interfaces associated with physical activities.

DESCRIPTION OF THE FIGURES

For a better understanding of the various described examples, reference should be made to the Description of Examples below, in conjunction with the following drawings in which like reference numerals refer to corresponding parts throughout the figures.

FIG. 4B illustrates an exemplary user interface for a multifunction device with a touch-sensitive surface that is separate from the display in accordance with some examples.

FIGS. 5C-5D illustrate exemplary components of a personal electronic device having a touch-sensitive display and intensity sensors in accordance with some examples.

FIGS. 5E-5H illustrate exemplary components and user interfaces of a personal electronic device in accordance with some examples.

DESCRIPTION OF EXAMPLES

The following description sets forth exemplary methods, parameters, and the like. It should be recognized, however, that such description is not intended as a limitation on the scope of the present disclosure but is instead provided as a description of exemplary examples.

There is a need for electronic devices that provide efficient methods and interfaces for displaying user interfaces associated with physical activities. Such techniques can reduce the cognitive burden on a user who accesses user interfaces associated with physical activities, thereby enhancing productivity. Further, such techniques can reduce processor and battery power otherwise wasted on redundant user inputs.

Figure 6A:
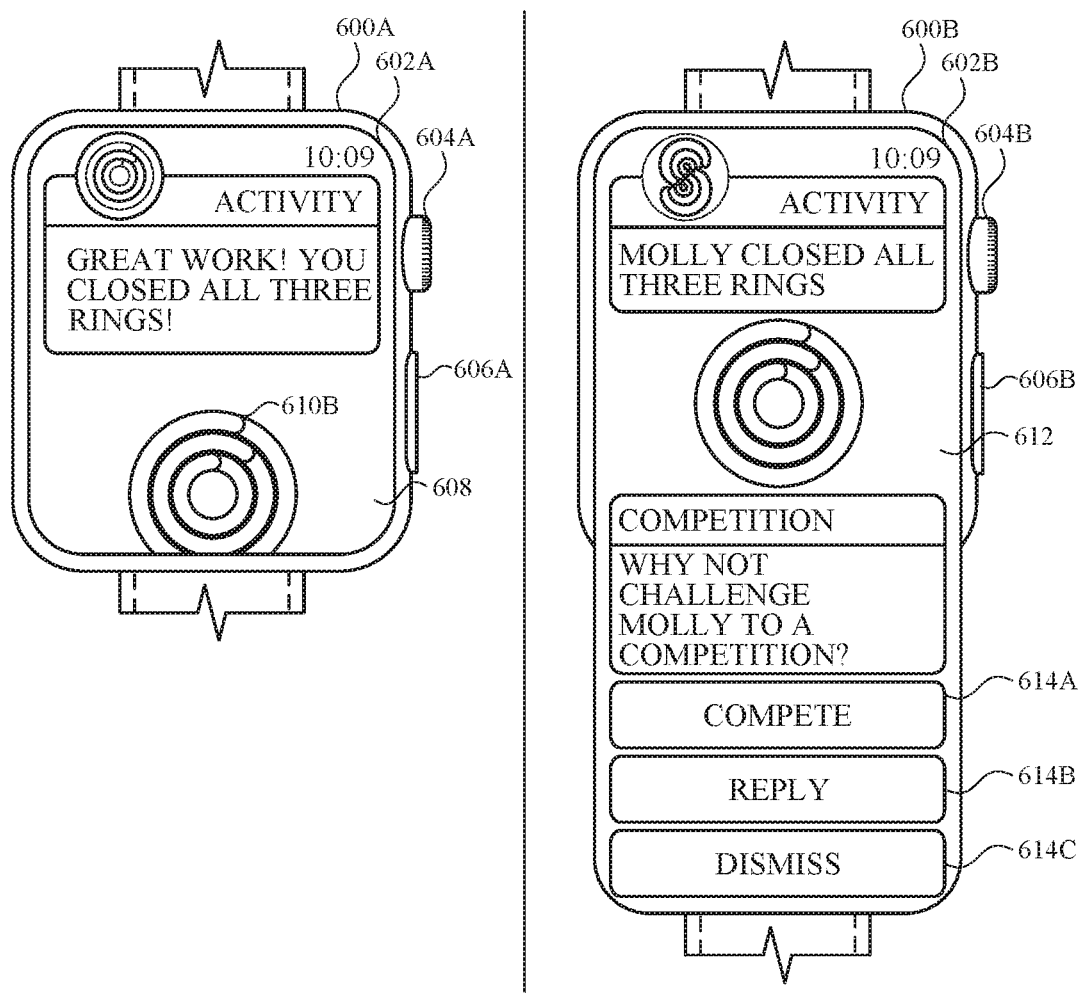
FIGS. 6A-6T illustrate exemplary user interfaces related to activity competitions in accordance with some examples.
Figure 6T:
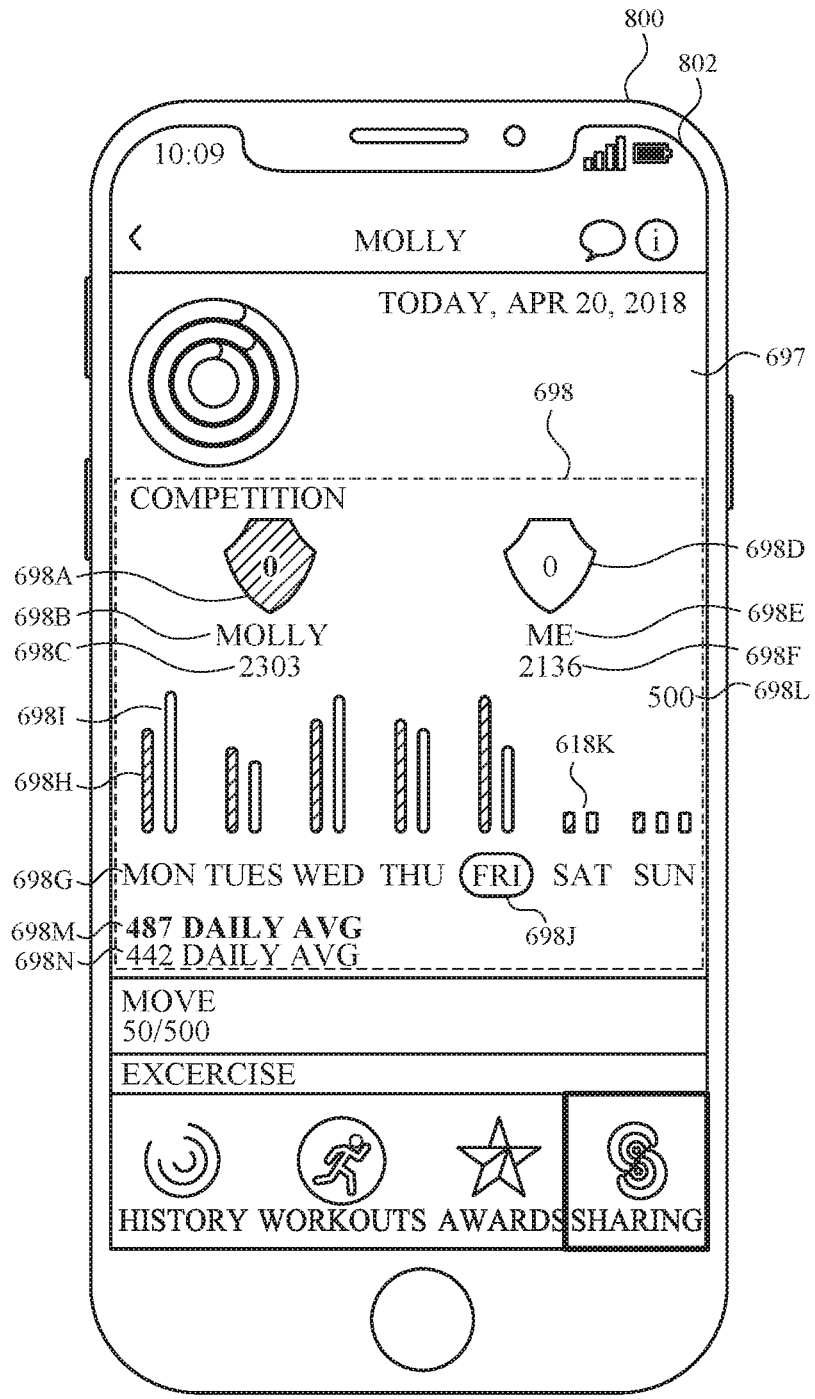
Figure 7A:
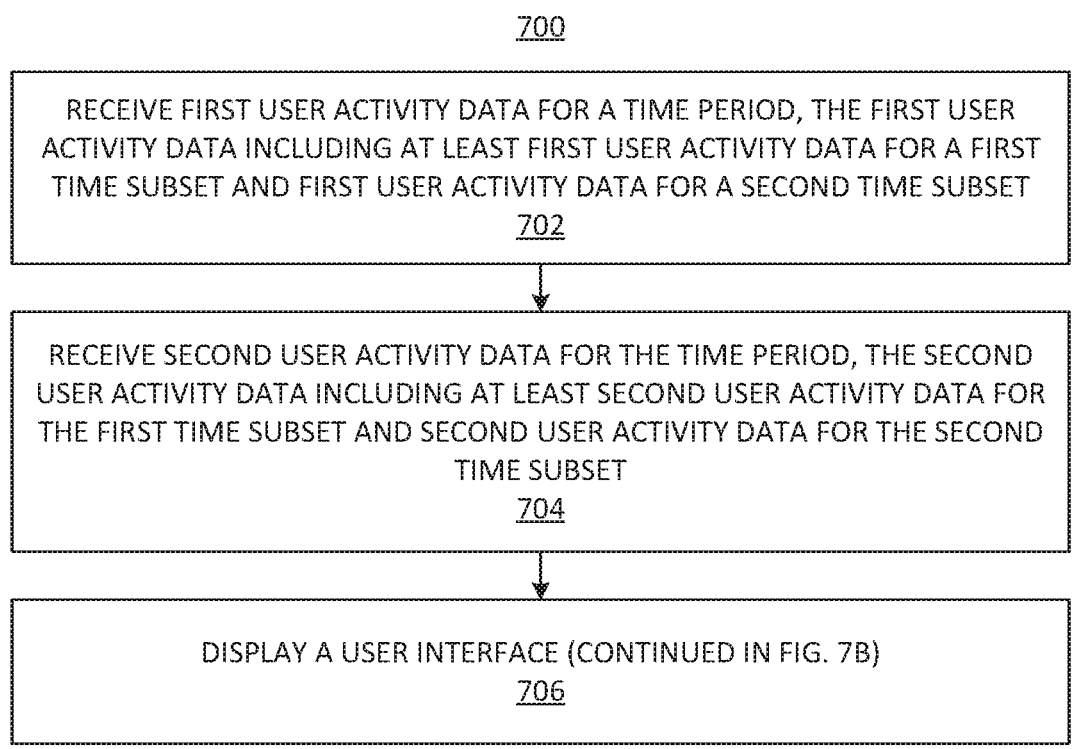
FIGS. 7A-7B is a flow diagram illustrating a method for displaying an activity competition representation using an electronic device in accordance with some examples.
Figure 7B:
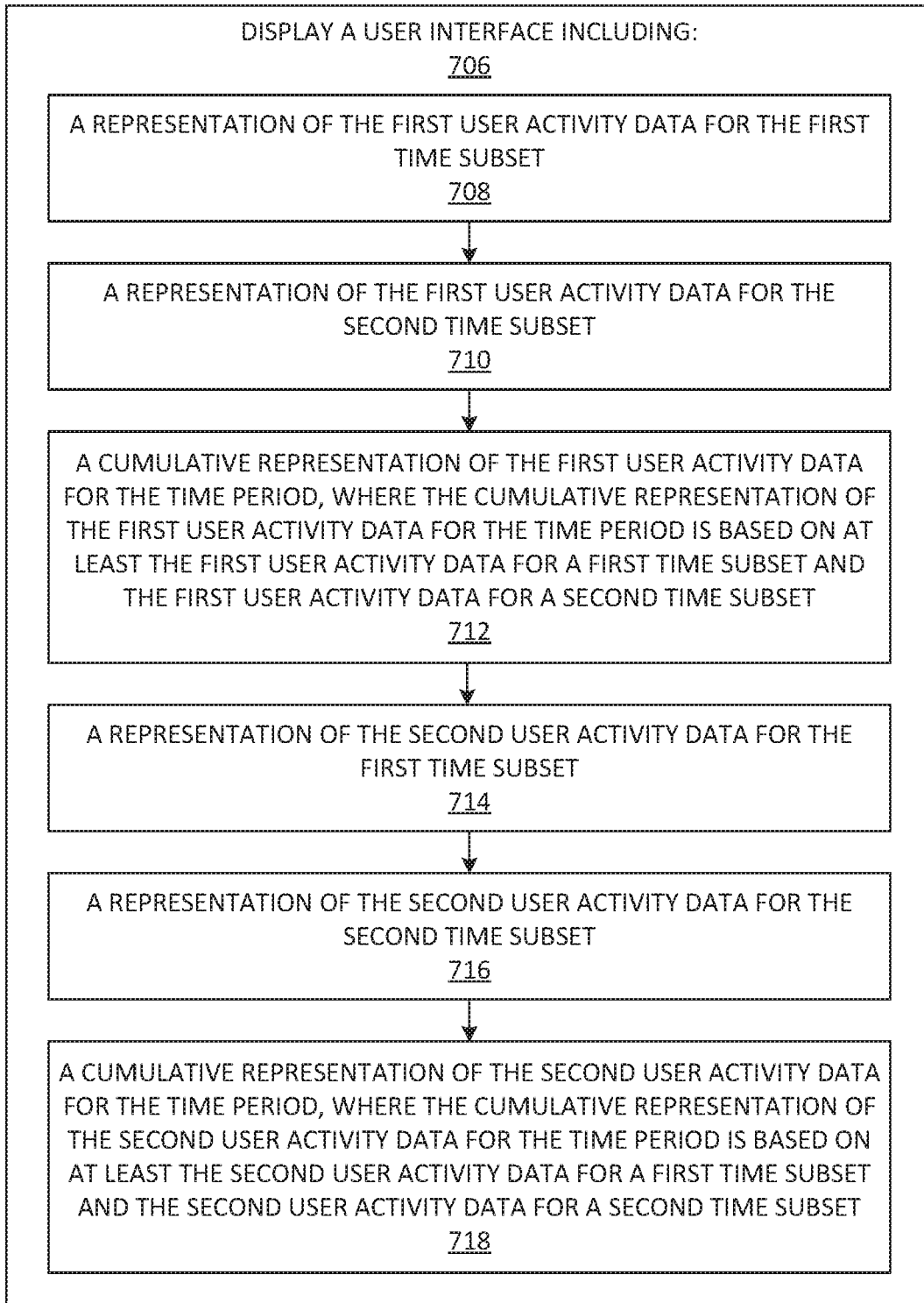
Figure 8A:
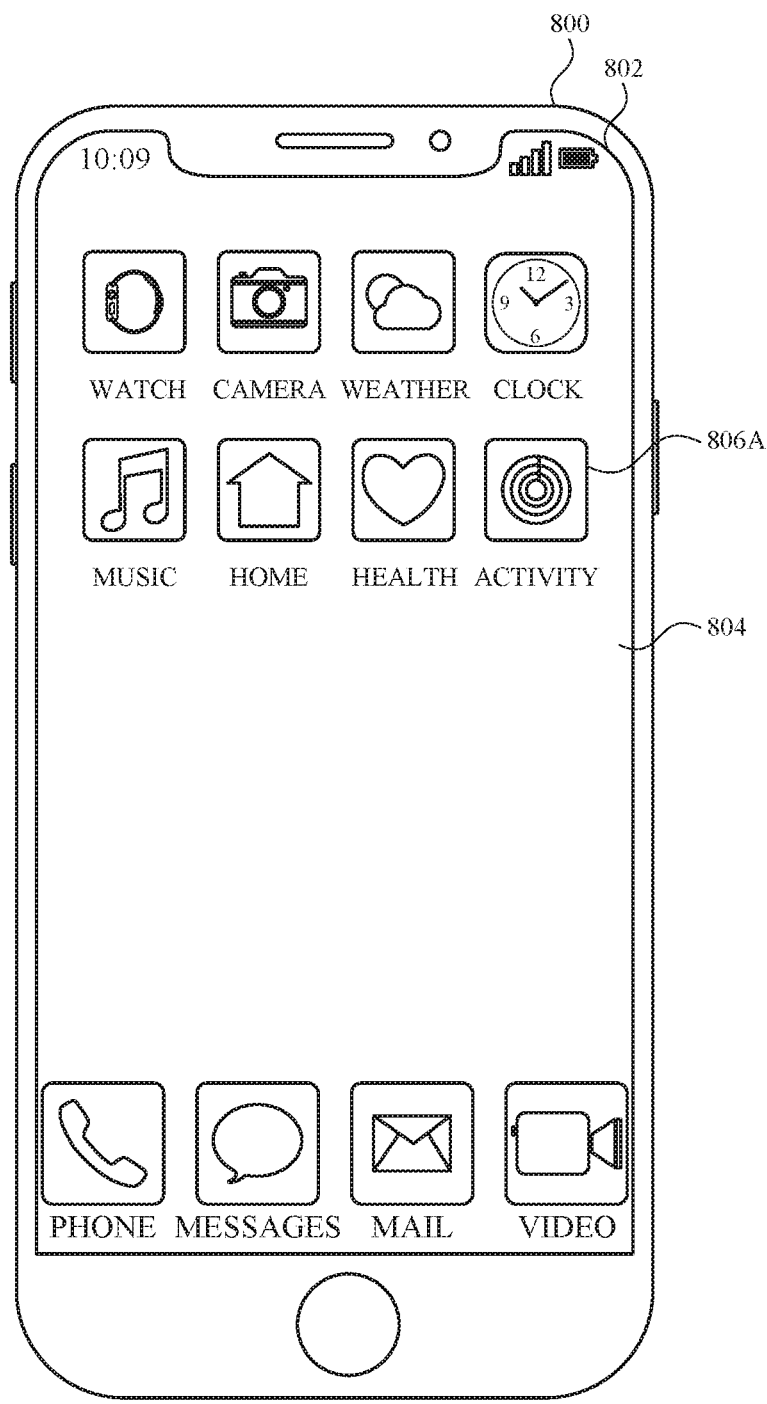
FIGS. 8A-8Y illustrate exemplary user interfaces related to a friends list for activity sharing in accordance with some examples.
Figure 8B:
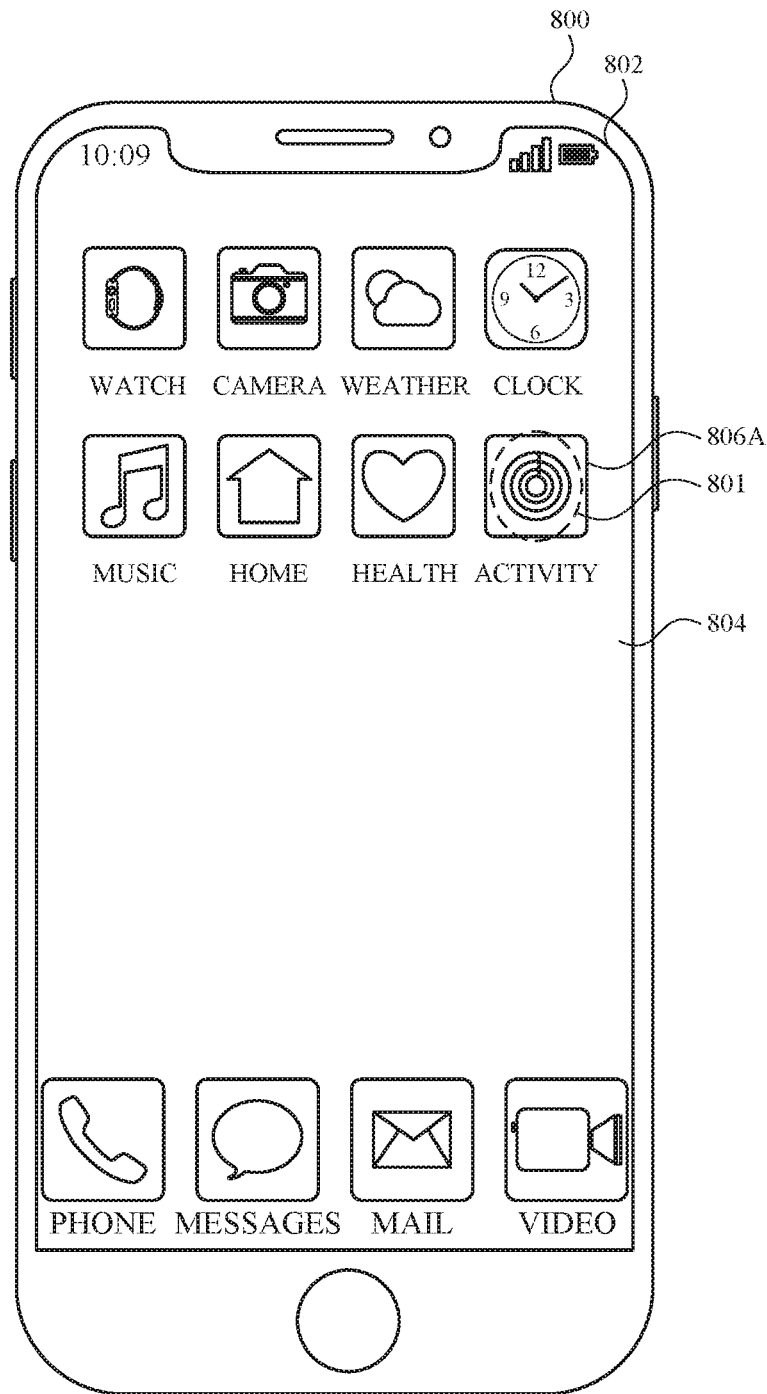
Figure 8Y:
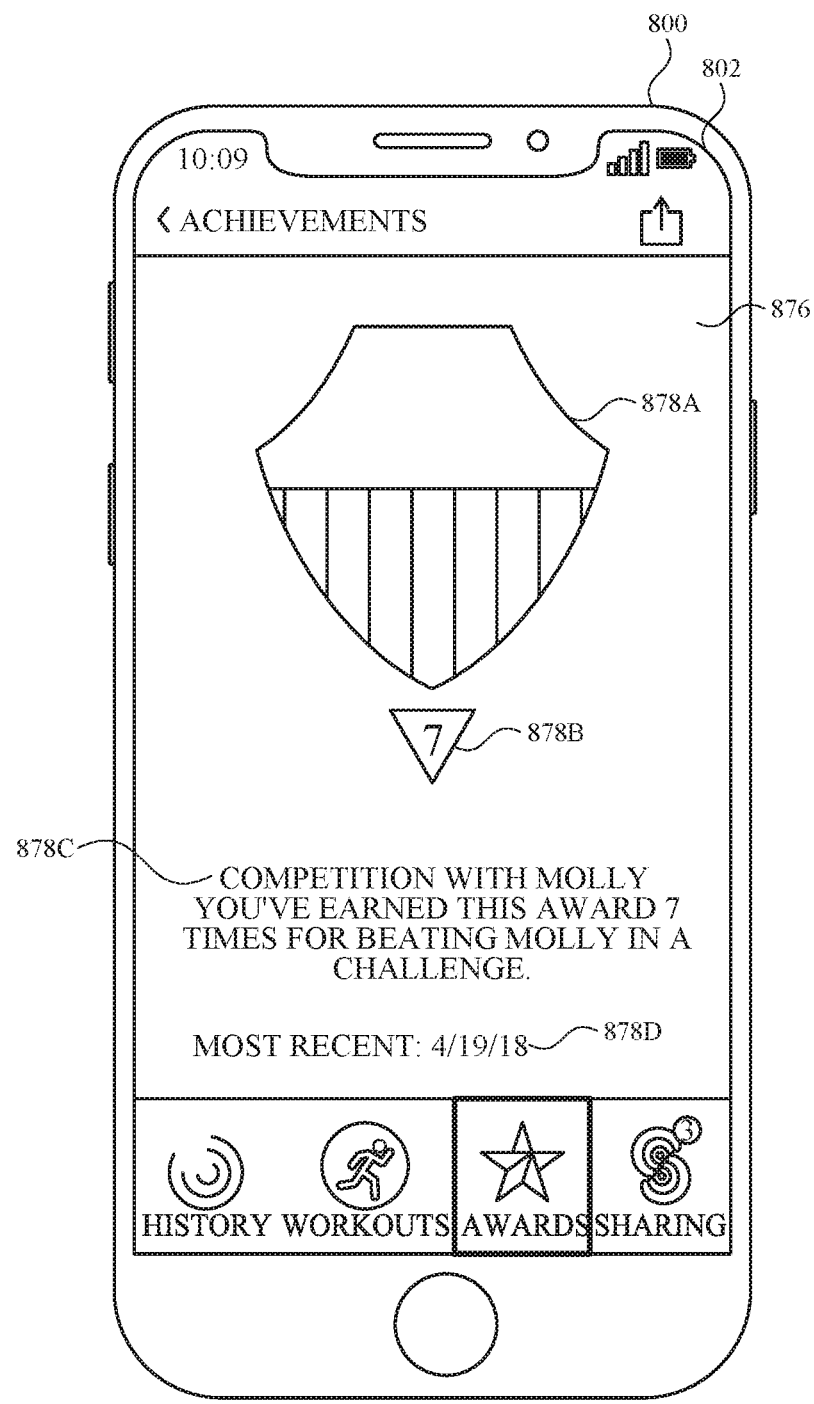
Figure 9A:
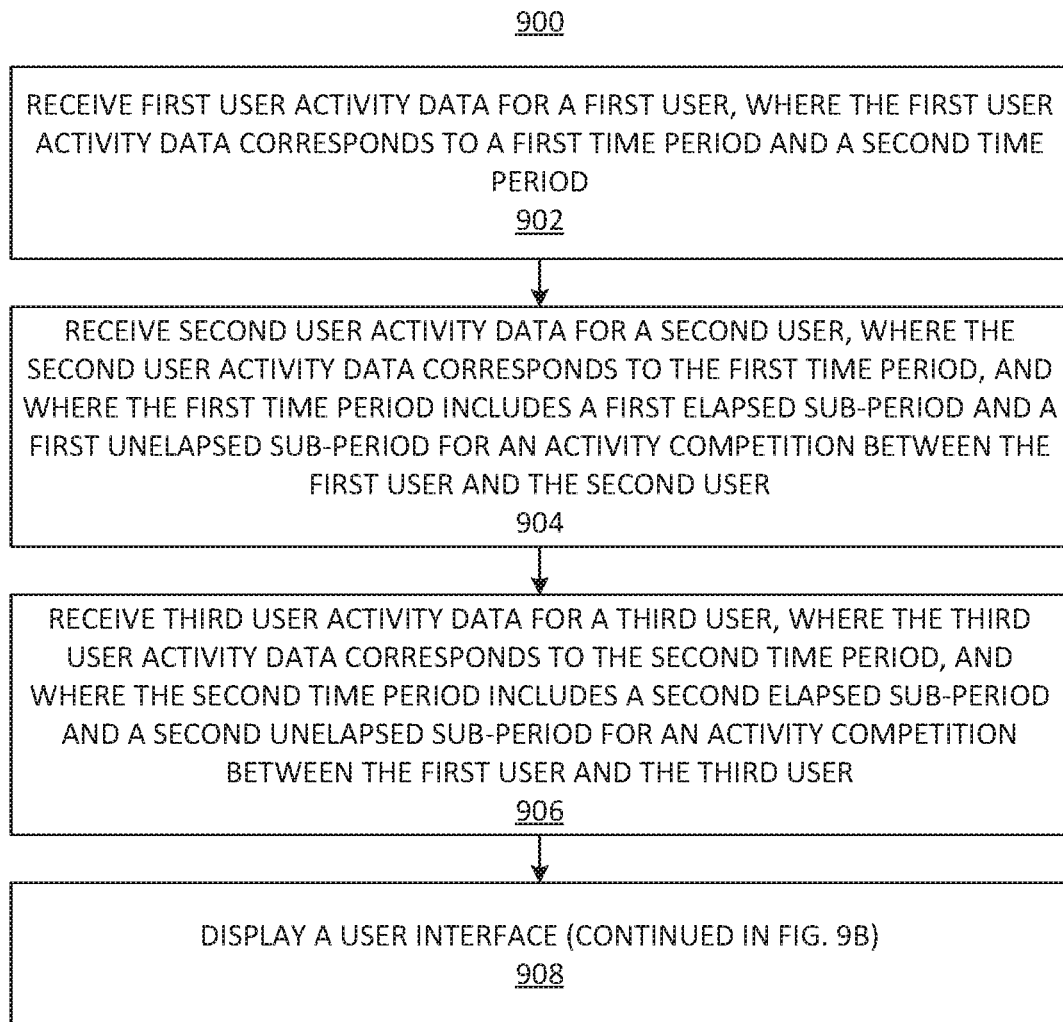
FIGS. 9A-9B is a flow diagram illustrating a method for displaying a friends list representation using an electronic device in accordance with some examples.
Figure 9B:
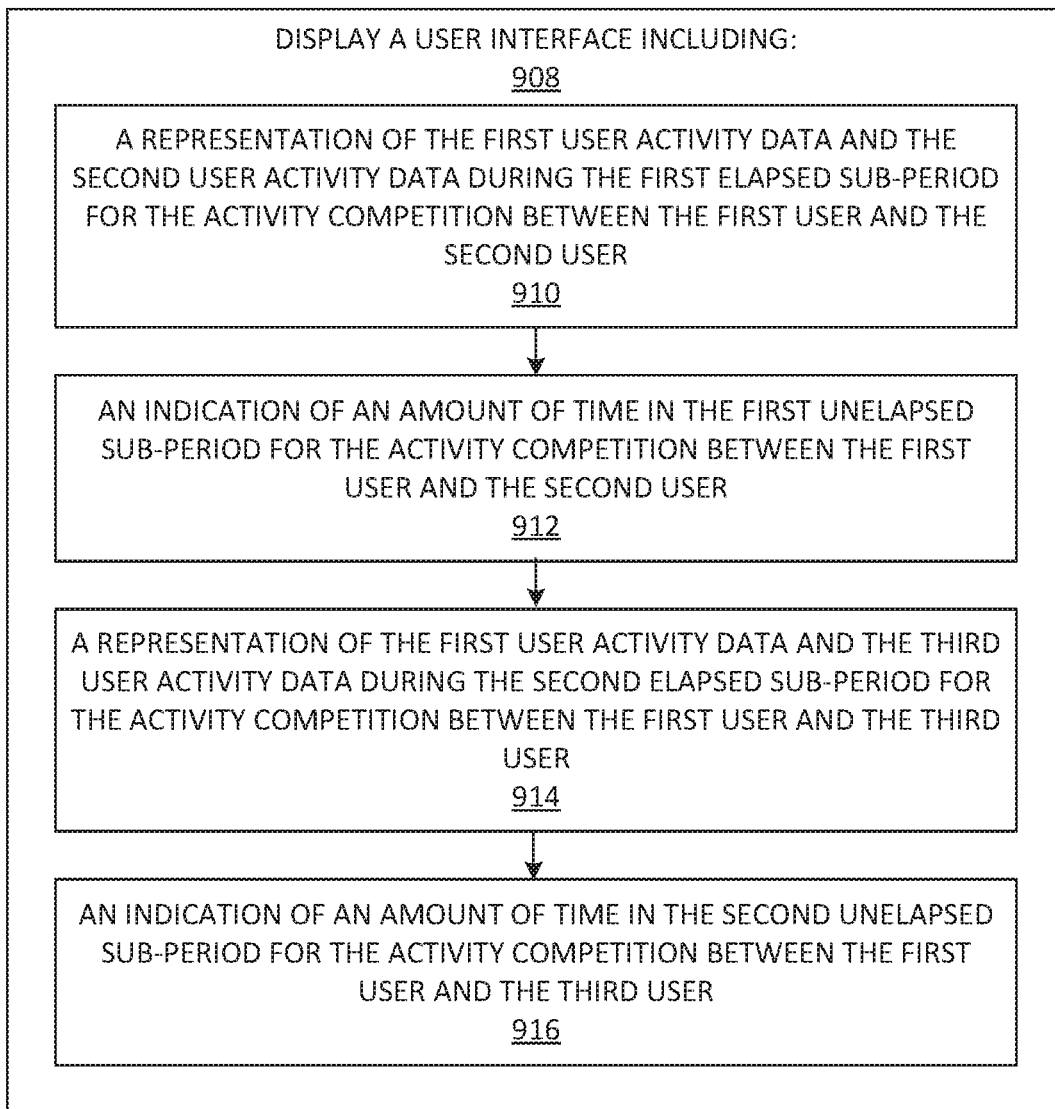
Figure 10A:
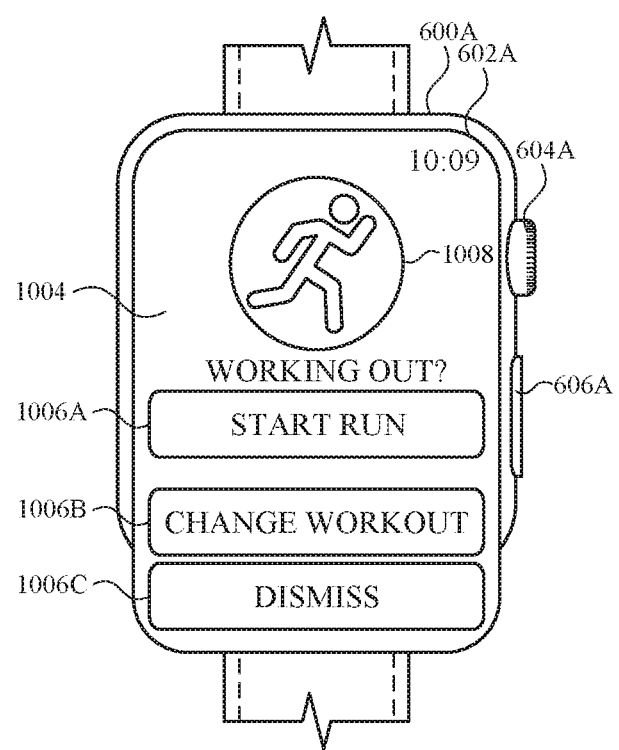
FIGS. 10A-10Q illustrate exemplary user interfaces associated with alerts presented to a user in response to automatically determining a boundary of a workout in accordance with some examples.
Figure 10B:
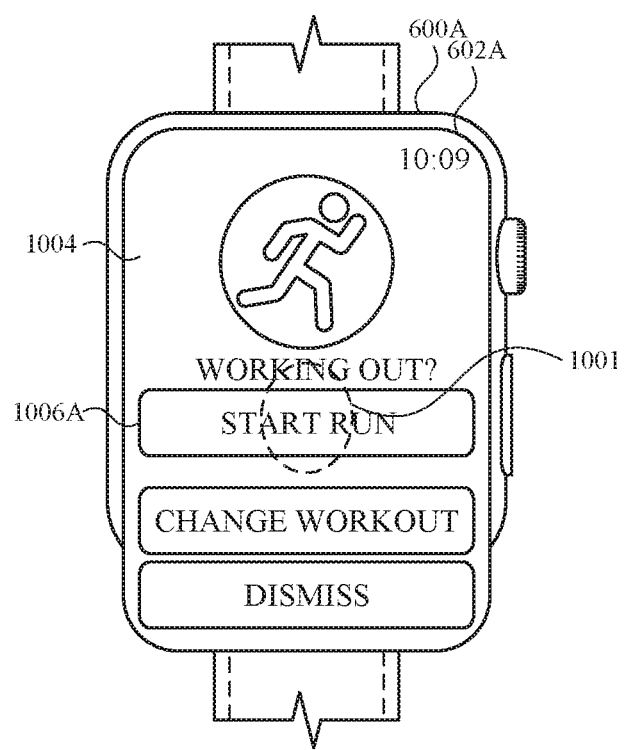
Figure 10C:
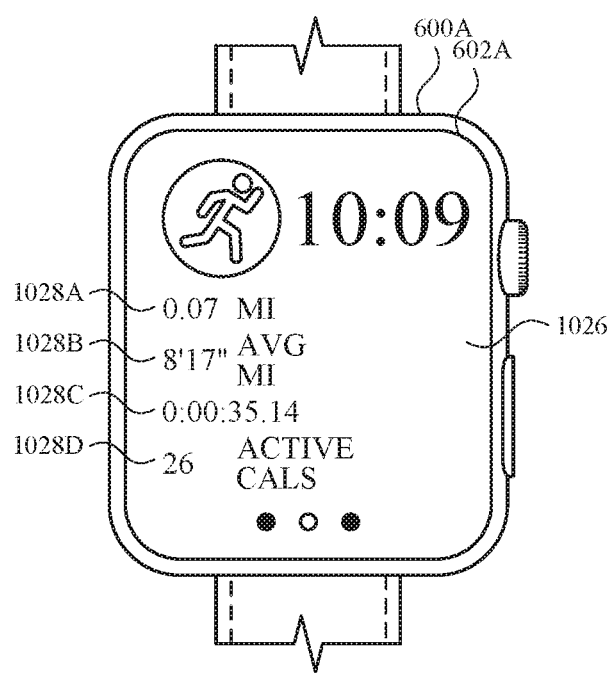
Figure 10D:
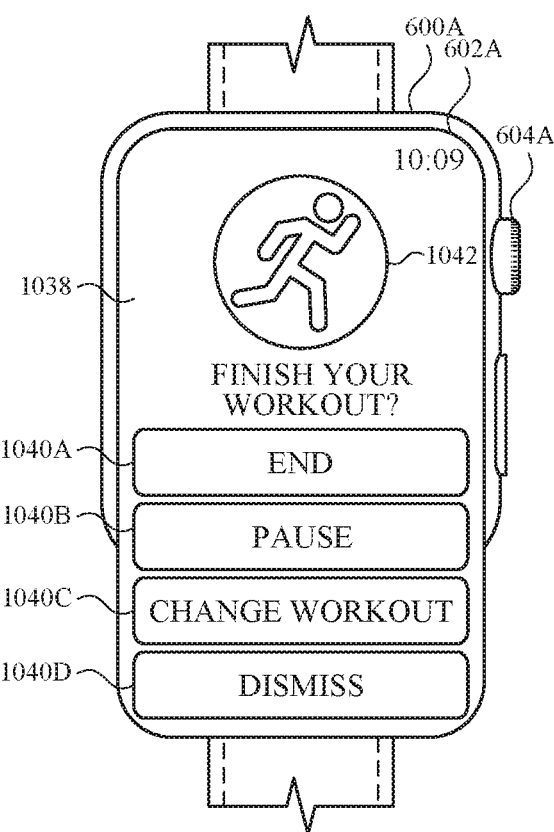
Figure 10E:
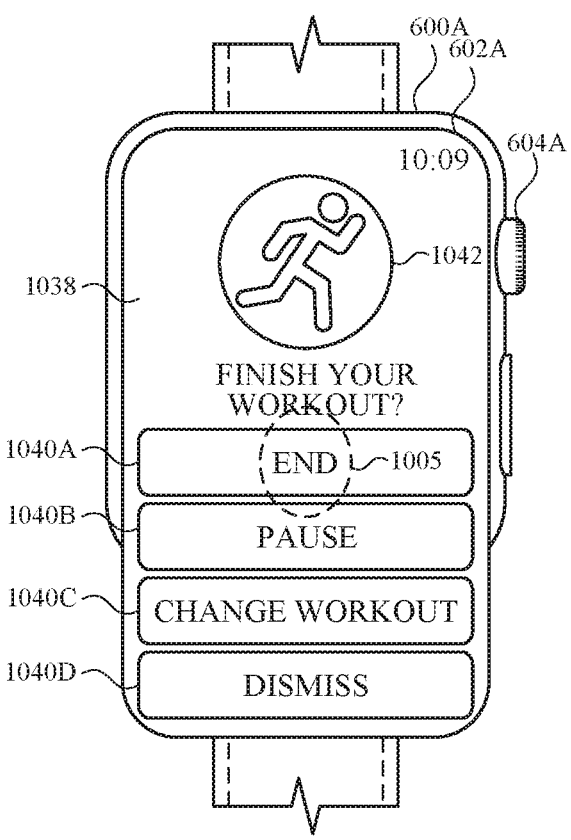
Figure 10F:
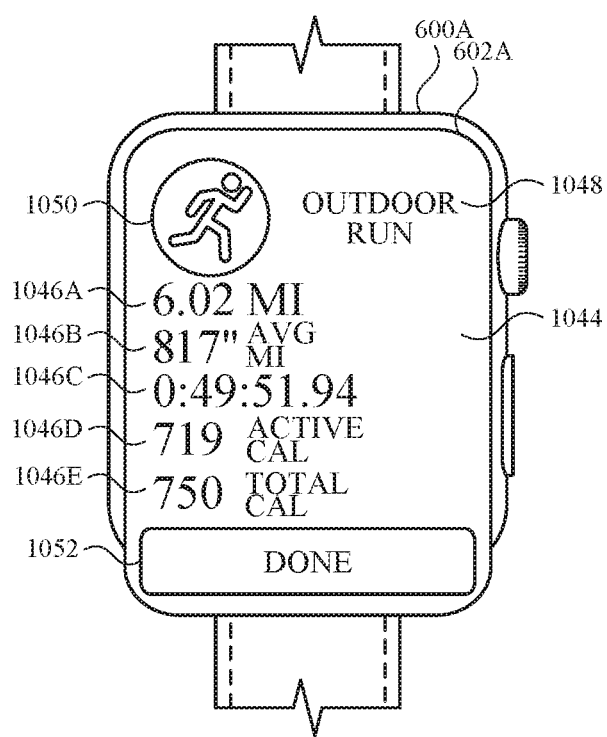
Figure 10G:
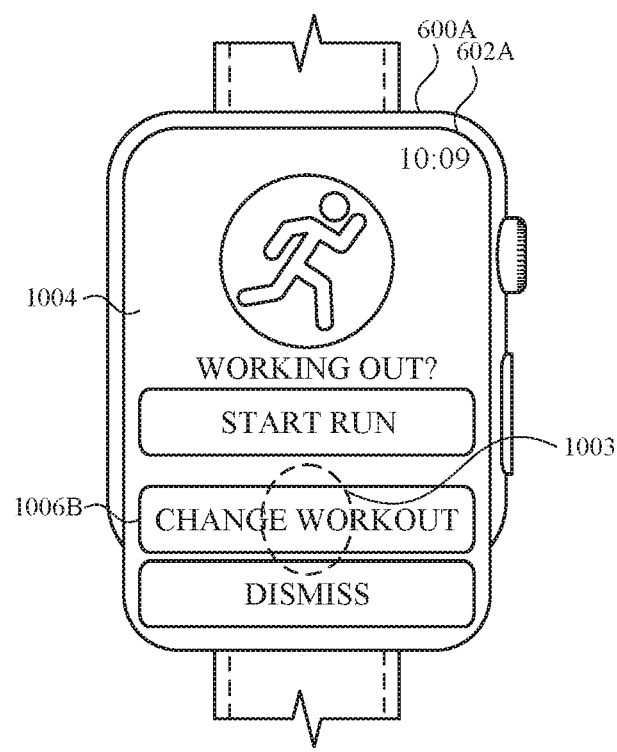
Figure 10H:
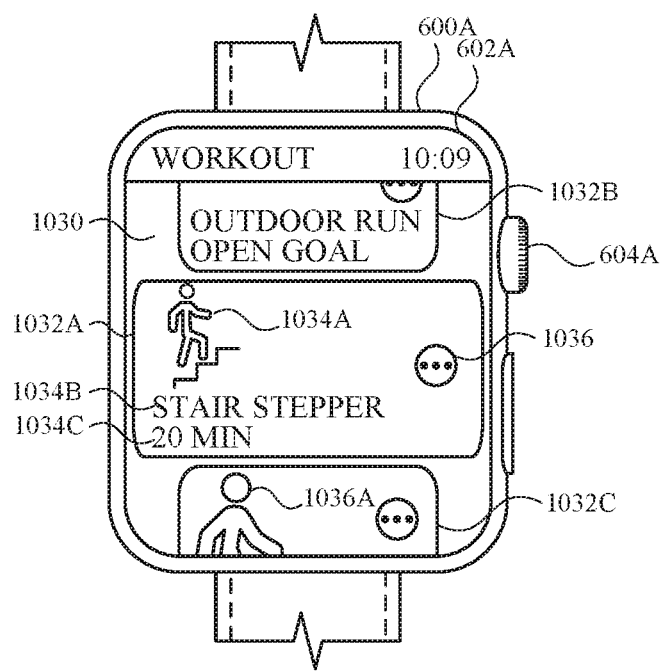
Figure 10I:
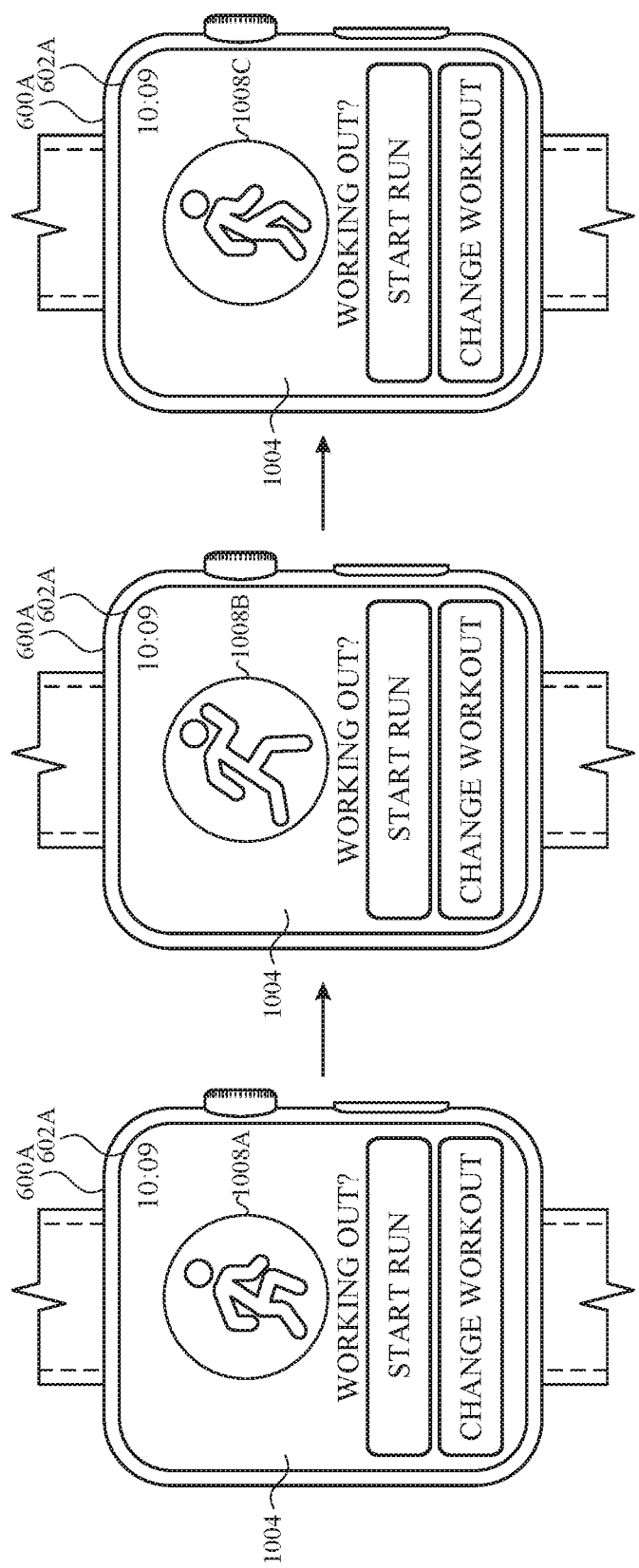
Figure 10J:
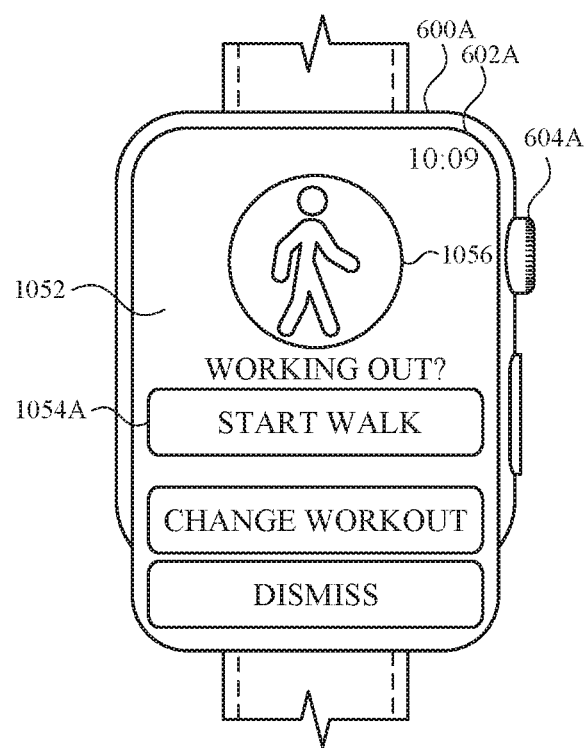
Figure 10K:
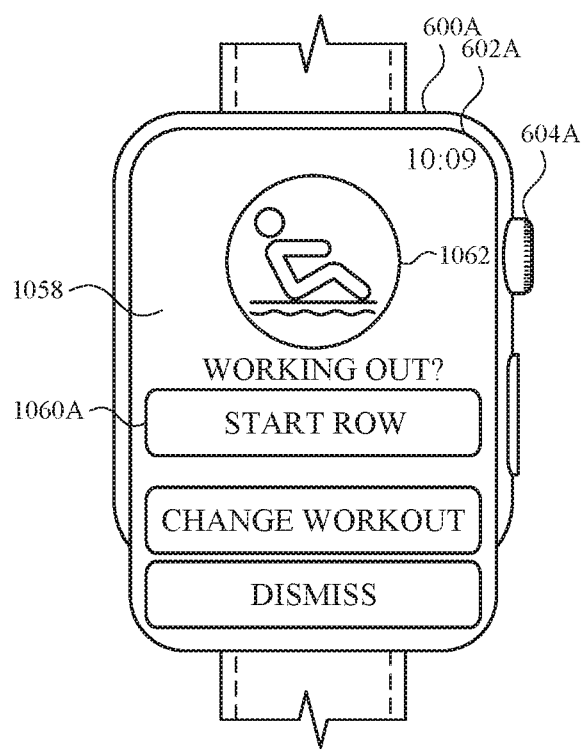
Figure 11:
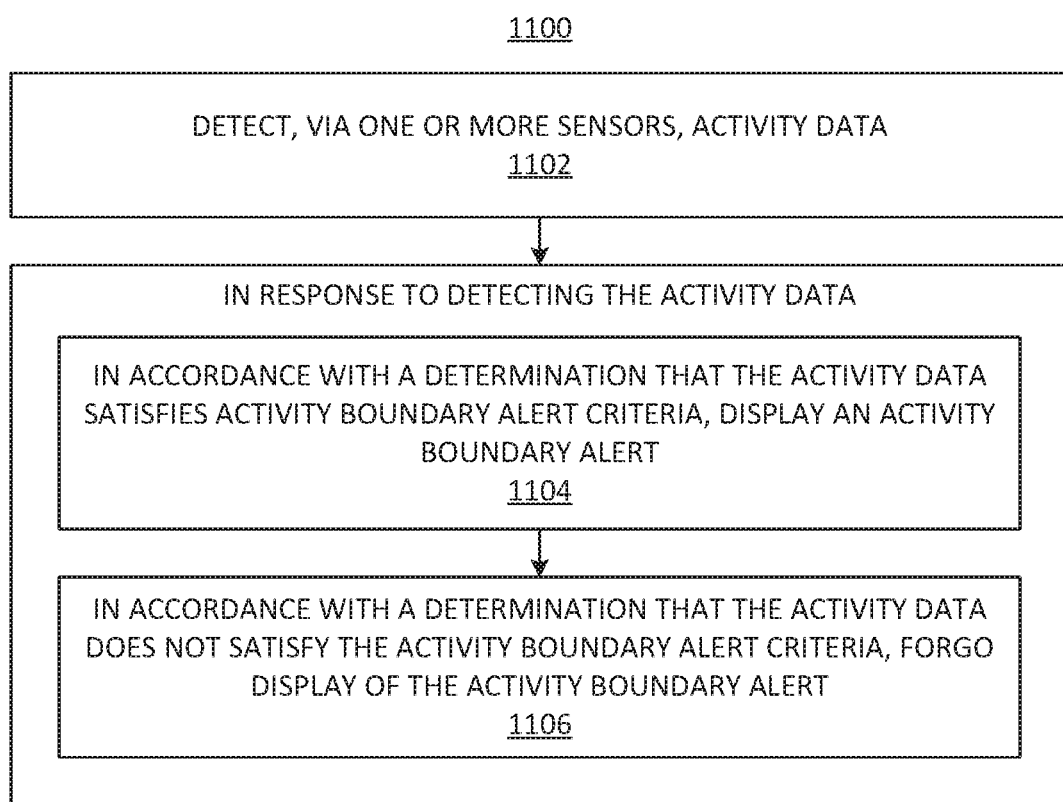
FIG. 11 is a flow diagram illustrating a method for displaying an alert in response to automatically determining a boundary of physical activity using an electronic device in accordance with some examples.
Figure 12A:
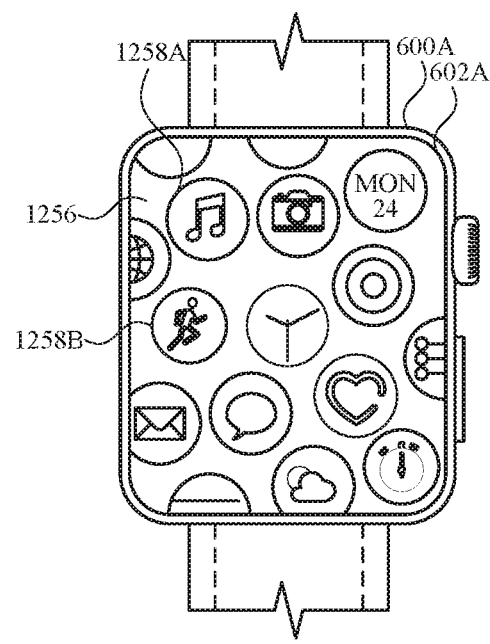
FIGS. 12A-12AK illustrate exemplary user interfaces associated with configuring a pace alert for a workout application in accordance with some examples.
Figure 13:
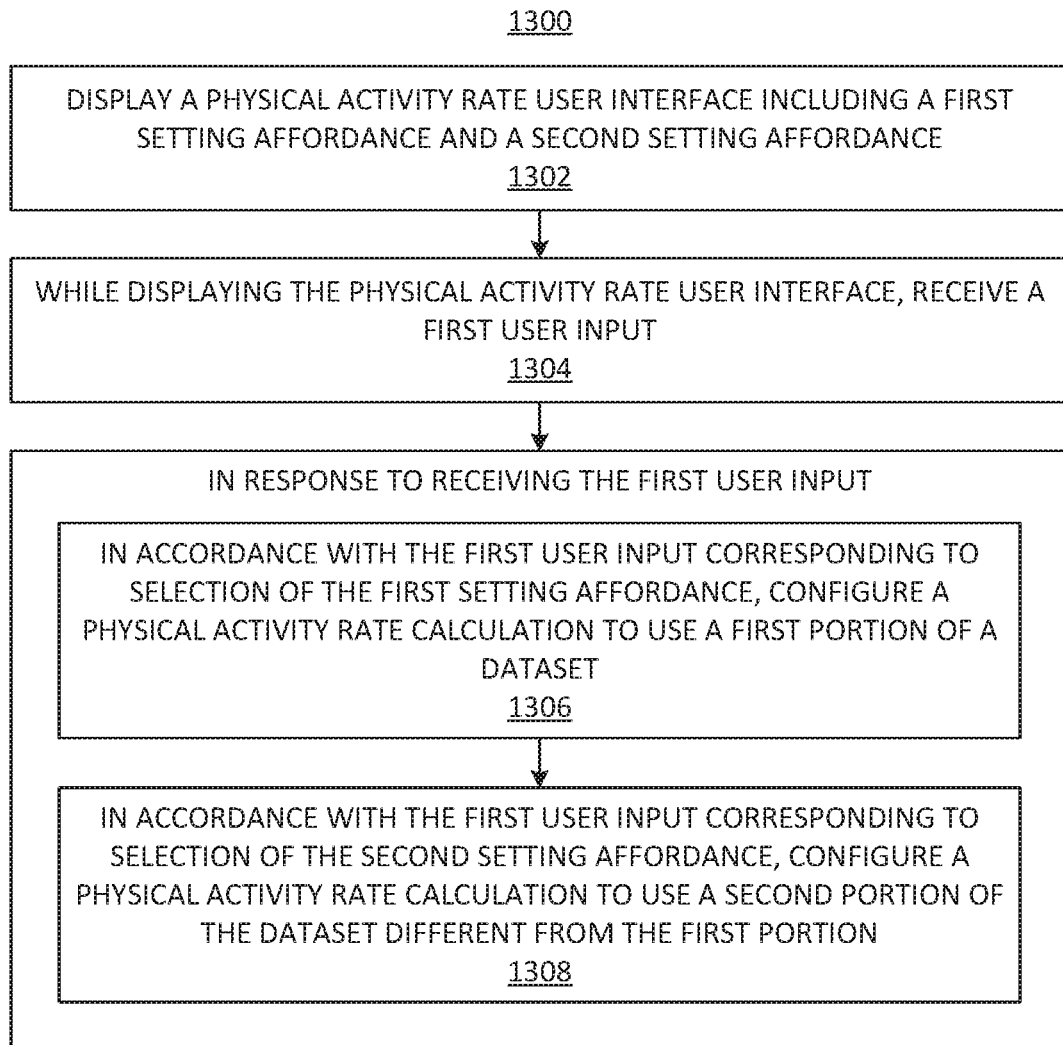
FIG. 13 is a flow diagram illustrating a method for displaying a user interface to configure a dataset that is used to calculate a pace using an electronic device in accordance with some examples.

Below, FIGS. 1A-1B, 2, 3, 4A-4B, and 5A-5H provide a description of exemplary devices for performing the techniques for managing event notifications. FIGS. 6A-6T illustrate exemplary user interfaces related to activity competitions in accordance with some examples. FIGS. 7A-7B is a flow diagram illustrating a method for displaying an activity competition representation using an electronic device in accordance with some examples. The user interfaces in FIGS. 6A-6T are used to illustrate the processes described below, including the process in FIGS. 7A-7B. FIGS. 8A-8Y illustrate exemplary user interfaces related to a friends list for activity sharing in accordance with some examples. FIGS. 9A-9B is a flow diagram illustrating a method for displaying a friends list representation using an electronic device in accordance with some examples. The user interfaces in FIGS. 8A-8Y are used to illustrate the processes described below, including the process in FIGS. 9A-9B. FIGS. 10A-10Q illustrate exemplary user interfaces associated with alerts presented to a user in response to automatically determining a boundary of a workout in accordance with some examples. FIG. 11 is a flow diagram illustrating a method for displaying an alert in response to automatically determining a boundary of physical activity using an electronic device in accordance with some examples. The user interfaces in FIGS. 10A-10Q are used to illustrate the processes described below, including the process in FIG. 11. FIGS. 12A-12AK illustrate exemplary user interfaces associated with configuring a pace alert for a workout application in accordance with some examples. FIG. 13 is a flow diagram illustrating a method for displaying a user interface to configure a dataset that is used to calculate a pace using an electronic device in accordance with some examples. The user interfaces in FIGS. 12A-12AK are used to illustrate the processes described below, including the process in FIG. 13.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described examples. The first touch and the second touch are both touches, but they are not the same touch.

The terminology used in the description of the various described examples herein is for the purpose of describing particular examples only and is not intended to be limiting. As used in the description of the various described examples and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Examples of electronic devices, user interfaces for such devices, and associated processes for using such devices are described. In some examples, the device is a portable communications device, such as a mobile telephone, that also contains other functions, such as PDA and/or music player functions. Exemplary examples of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some examples, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
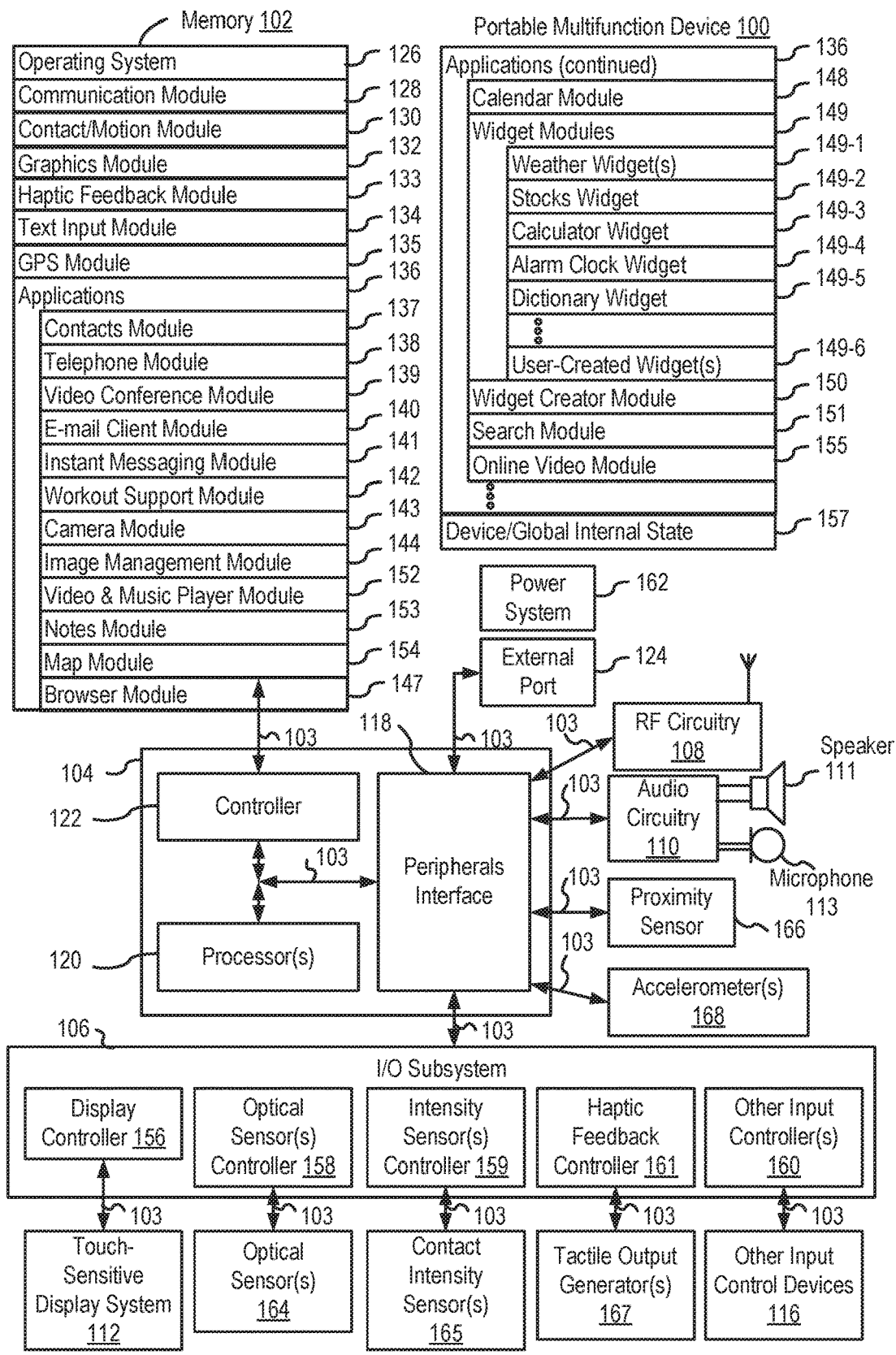
FIG. 1A is a block diagram illustrating a portable multifunction device with a touch-sensitive display in accordance with some examples.

Attention is now directed toward examples of portable devices with touch-sensitive displays. FIG. 1A is a block diagram illustrating portable multifunction device 100 with touch-sensitive display system 112 in accordance with some examples. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some examples, peripherals interface 118, CPU 120, and memory controller 122 are, optionally, implemented on a single chip, such as chip 104. In some other examples, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some examples, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate examples, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some examples, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary example, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other examples. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary example, projected mutual capacitance sensing technology is used, such as that found in the iPhone® and iPod Touch® from Apple Inc. of Cupertino, Calif.

A touch-sensitive display in some examples of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some examples of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some examples, the touch screen has a video resolution of approximately 160 dpi. The user optionally makes contact with touch screen 112 using any suitable object or appendage, such as a stylus, a finger, and so forth. In some examples, the user interface is designed to work primarily with finger-based contacts and gestures, which can be less precise than stylus-based input due to the larger area of contact of a finger on the touch screen. In some examples, the device translates the rough finger-based input into a precise pointer/cursor position or command for performing the actions desired by the user.

In some examples, in addition to the touch screen, device 100 optionally includes a touchpad (not shown) for activating or deactivating particular functions. In some examples, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some examples, an optical sensor is located on the back of device 100, opposite touch screen display 112 on the front of the device so that the touch screen display is enabled for use as a viewfinder for still and/or video image acquisition. In some examples, an optical sensor is located on the front of the device so that the user's image is, optionally, obtained for video conferencing while the user views the other video conference participants on the touch screen display. In some examples, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some examples, at least one contact intensity sensor is collocated with, or proximate to, a touch-sensitive surface (e.g., touch-sensitive display system 112). In some examples, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some examples, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some examples, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some examples, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some examples, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
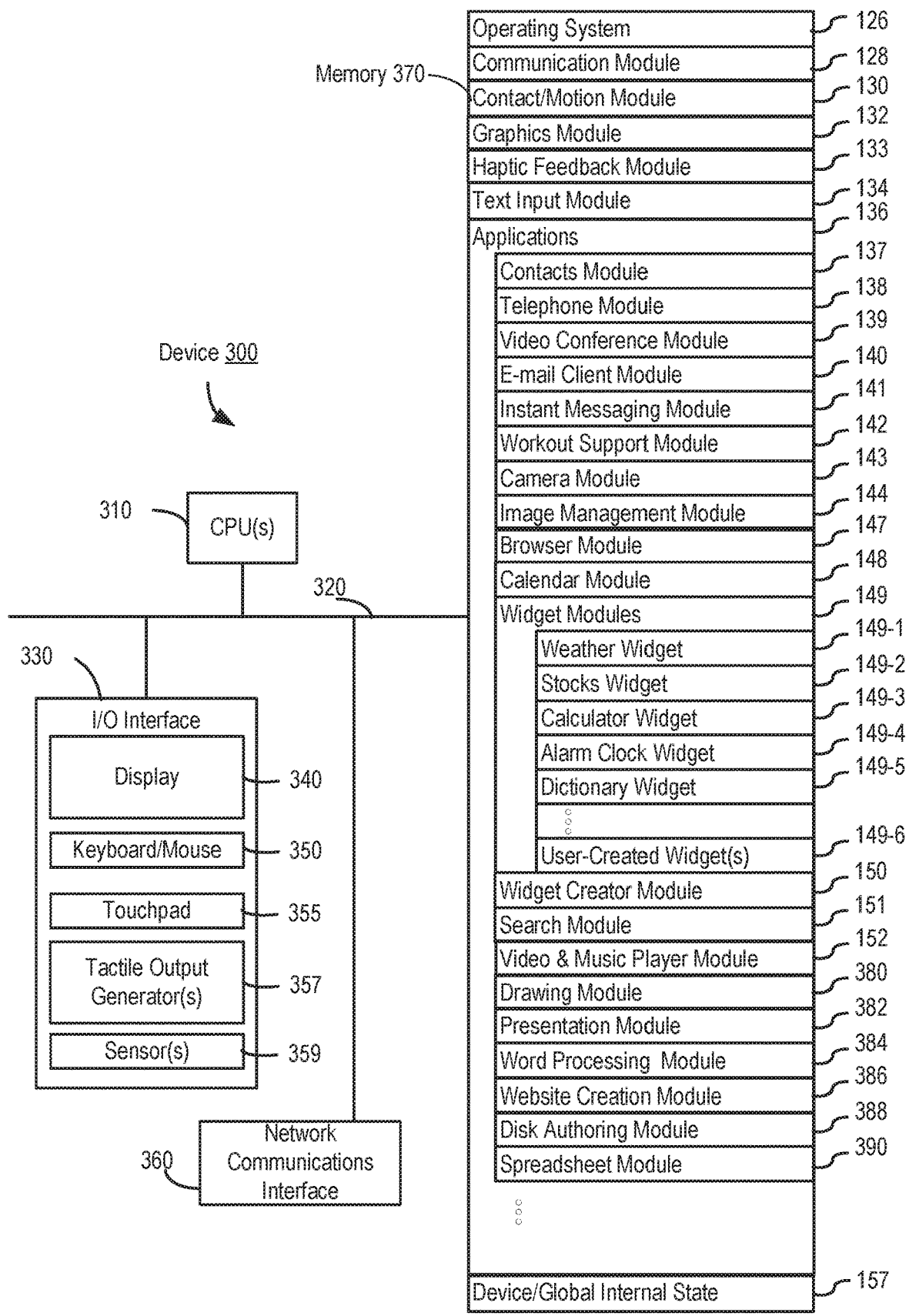
FIG. 3 is a block diagram of an exemplary multifunction device with a display and a touch-sensitive surface in accordance with some examples.

In some examples, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some examples, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some examples, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some examples, contact/motion module 130 and display controller 156 detect contact on a touchpad.

In some examples, contact/motion module 130 uses a set of one or more intensity thresholds to determine whether an operation has been performed by a user (e.g., to determine whether a user has "clicked" on an icon). In some examples, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some examples, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some examples, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some examples, a widget includes an HTML (Hypertext Markup Language) file, a CSS (Cascading Style Sheets) file, and a JavaScript file. In some examples, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some examples, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some examples, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various examples. For example, video player module is, optionally, combined with music player module into a single module (e.g., video and music player module 152, FIG. 1A). In some examples, memory 102 optionally stores a subset of the modules and data structures identified above. Furthermore, memory 102 optionally stores additional modules and data structures not described above.

In some examples, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some examples, the touchpad, when touched by the user, navigates device 100 to a main, home, or root menu from any user interface that is displayed on device 100. In such examples, a "menu button" is implemented using a touchpad. In some other examples, the menu button is a physical push button or other physical input control device instead of a touchpad.

Figure 1B:
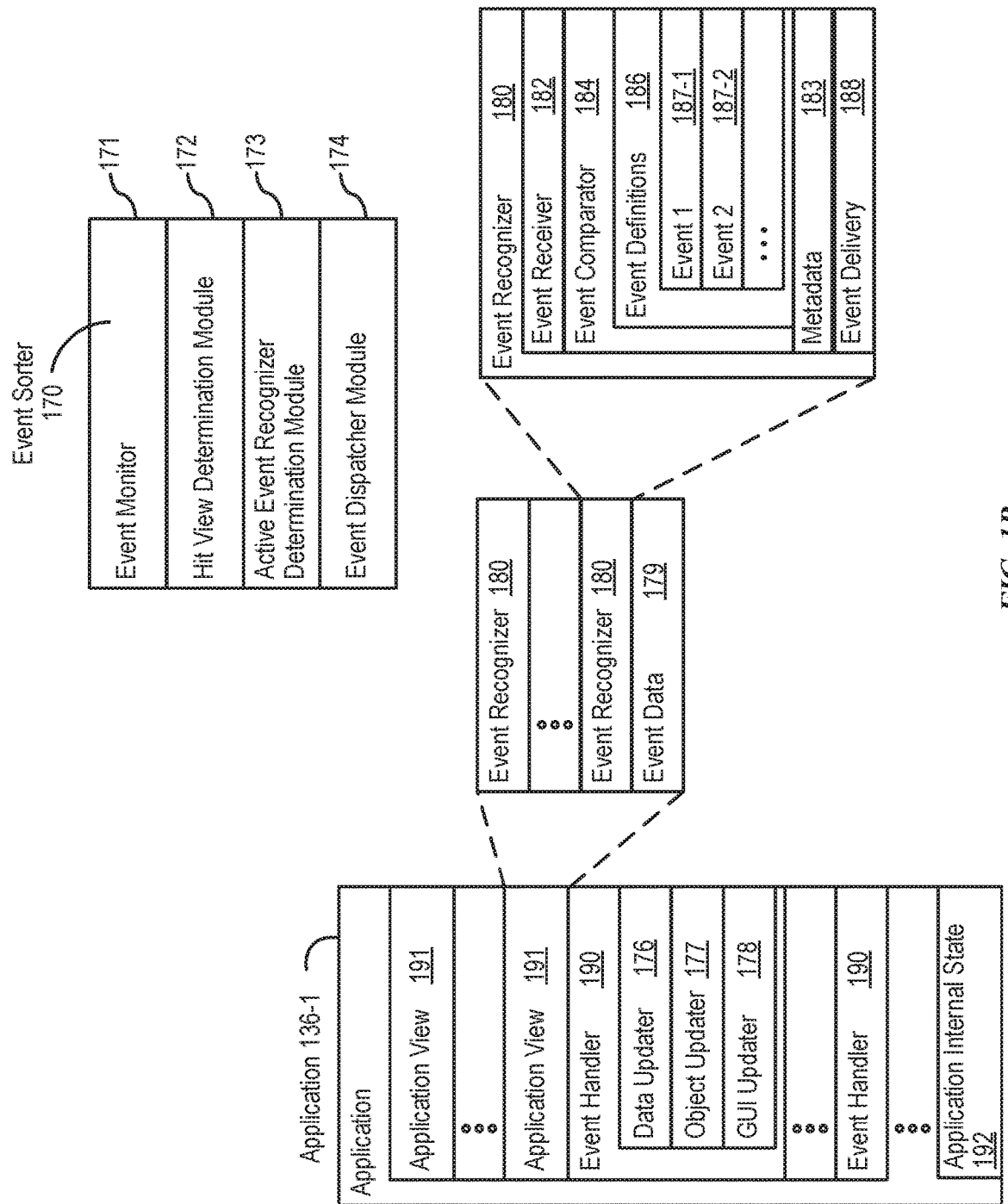
FIG. 1B is a block diagram illustrating exemplary components for event handling in accordance with some examples.

FIG. 1B is a block diagram illustrating exemplary components for event handling in accordance with some examples. In some examples, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some examples, application 136-1 includes application internal state 192, which indicates the current application view(s) displayed on touch-sensitive display 112 when the application is active or executing. In some examples, device/global internal state 157 is used by event sorter 170 to determine which application(s) is (are) currently active, and application internal state 192 is used by event sorter 170 to determine application views 191 to which to deliver event information.

In some examples, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some examples, event monitor 171 sends requests to the peripherals interface 118 at predetermined intervals. In response, peripherals interface 118 transmits event information. In other examples, peripherals interface 118 transmits event information only when there is a significant event (e.g., receiving an input above a predetermined noise threshold and/or for more than a predetermined duration).

In some examples, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some examples, active event recognizer determination module 173 determines that only the hit view should receive a particular sequence of sub-events. In other examples, active event recognizer determination module 173 determines that all views that include the physical location of a sub-event are actively involved views, and therefore determines that all actively involved views should receive a particular sequence of sub-events. In other examples, even if touch sub-events were entirely confined to the area associated with one particular view, views higher in the hierarchy would still remain as actively involved views.

Event dispatcher module 174 dispatches the event information to an event recognizer (e.g., event recognizer 180). In examples including active event recognizer determination module 173, event dispatcher module 174 delivers the event information to an event recognizer determined by active event recognizer determination module 173. In some examples, event dispatcher module 174 stores in an event queue the event information, which is retrieved by a respective event receiver 182.

In some examples, operating system 126 includes event sorter 170. Alternatively, application 136-1 includes event sorter 170. In yet other examples, event sorter 170 is a stand-alone module, or a part of another module stored in memory 102, such as contact/motion module 130.

In some examples, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other examples, one or more of event recognizers 180 are part of a separate module, such as a user interface kit (not shown) or a higher level object from which application 136-1 inherits methods and other properties. In some examples, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some examples, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some examples, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some examples, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some examples, event comparator 184 includes event definitions 186. Event definitions 186 contain definitions of events (e.g., predefined sequences of sub-events), for example, event 1 (187-1), event 2 (187-2), and others. In some examples, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some examples, the event also includes information for one or more associated event handlers 190.

In some examples, event definition 187 includes a definition of an event for a respective user-interface object. In some examples, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some examples, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some examples, a respective event recognizer 180 includes metadata 183 with configurable properties, flags, and/or lists that indicate how the event delivery system should perform sub-event delivery to actively involved event recognizers. In some examples, metadata 183 includes configurable properties, flags, and/or lists that indicate how event recognizers interact, or are enabled to interact, with one another. In some examples, metadata 183 includes configurable properties, flags, and/or lists that indicate whether sub-events are delivered to varying levels in the view or programmatic hierarchy.

In some examples, a respective event recognizer 180 activates event handler 190 associated with an event when one or more particular sub-events of an event are recognized. In some examples, a respective event recognizer 180 delivers event information associated with the event to event handler 190. Activating an event handler 190 is distinct from sending (and deferred sending) sub-events to a respective hit view. In some examples, event recognizer 180 throws a flag associated with the recognized event, and event handler 190 associated with the flag catches the flag and performs a predefined process.

In some examples, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some examples, data updater 176 creates and updates data used in application 136-1. For example, data updater 176 updates the telephone number used in contacts module 137, or stores a video file used in video player module. In some examples, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some examples, event handler(s) 190 includes or has access to data updater 176, object updater 177, and GUI updater 178. In some examples, data updater 176, object updater 177, and GUI updater 178 are included in a single module of a respective application 136-1 or application view 191. In other examples, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
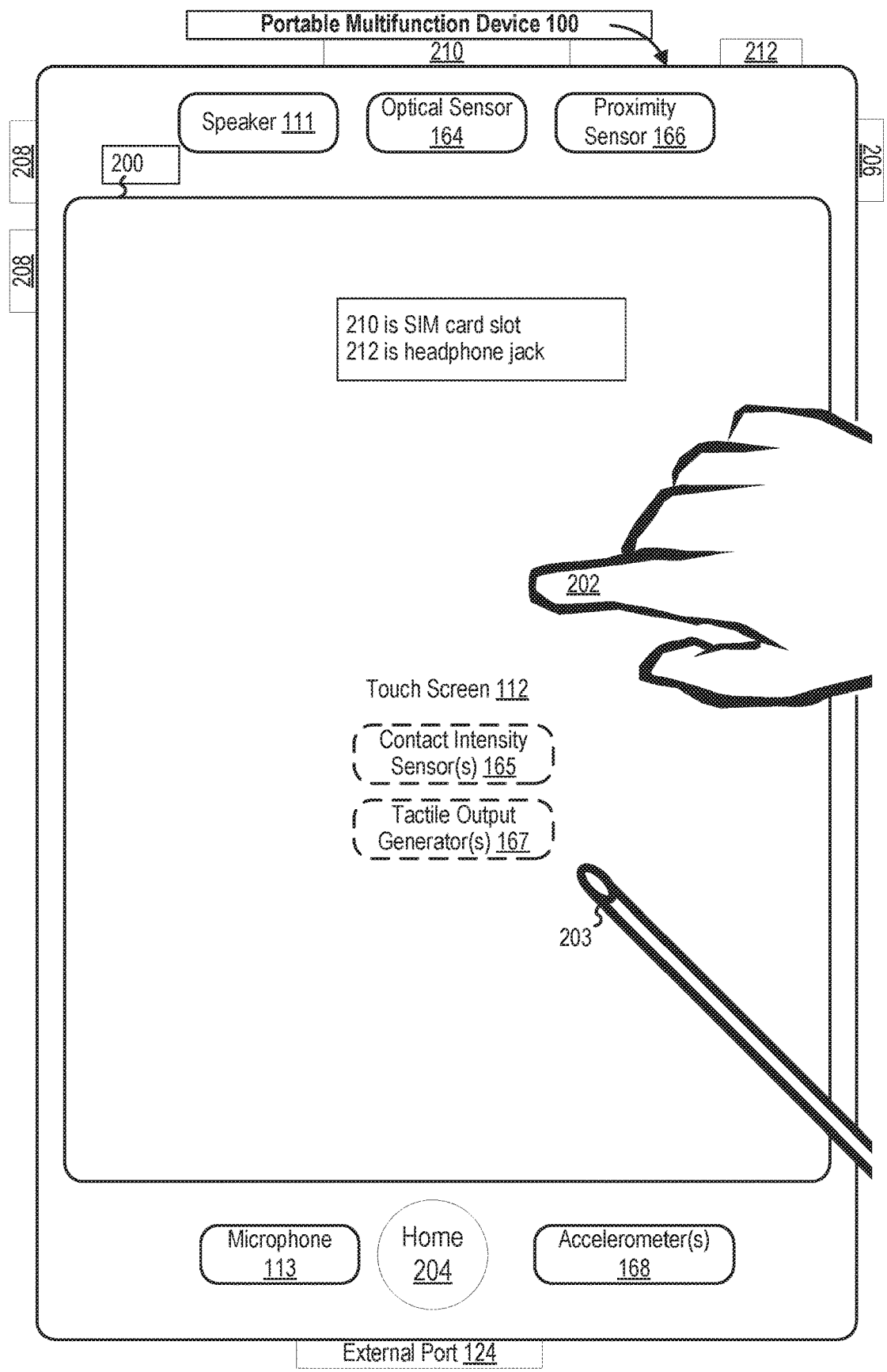
FIG. 2 illustrates a portable multifunction device having a touch screen in accordance with some examples.

FIG. 2 illustrates a portable multifunction device 100 having a touch screen 112 in accordance with some examples. The touch screen optionally displays one or more graphics within user interface (UI) 200. In this example, as well as others described below, a user is enabled to select one or more of the graphics by making a gesture on the graphics, for example, with one or more fingers 202 (not drawn to scale in the figure) or one or more styluses 203 (not drawn to scale in the figure). In some examples, selection of one or more graphics occurs when the user breaks contact with the one or more graphics. In some examples, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some examples, the menu button is implemented as a soft key in a GUI displayed on touch screen 112.

In some examples, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative example, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some examples. Device 300 need not be portable. In some examples, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some examples, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various examples. In some examples, memory 370 optionally stores a subset of the modules and data structures identified above. Furthermore, memory 370 optionally stores additional modules and data structures not described above.

Attention is now directed towards examples of user interfaces that are, optionally, implemented on, for example, portable multifunction device 100.

Figure 4A:
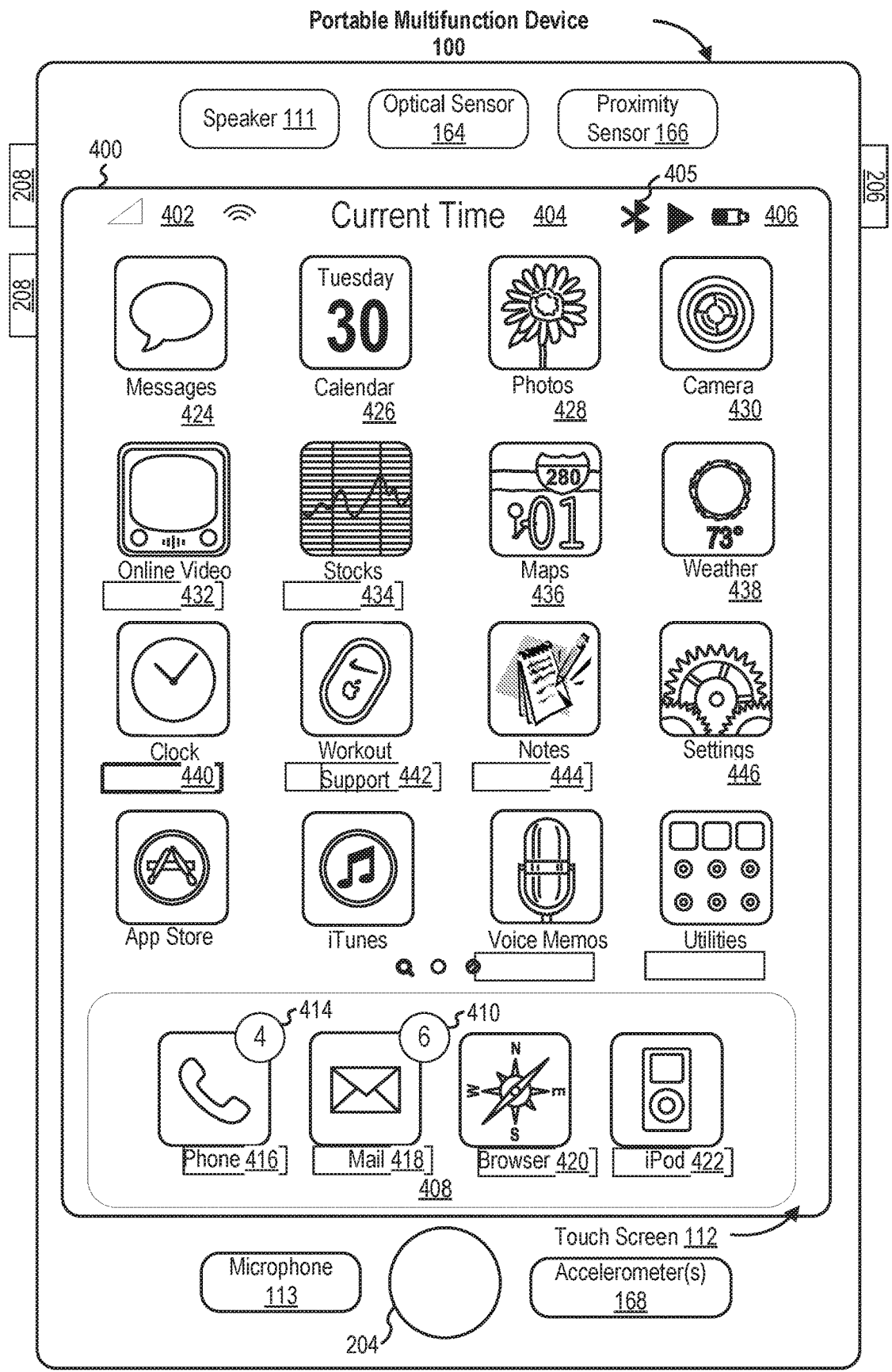
FIG. 4A illustrates an exemplary user interface for a menu of applications on a portable multifunction device in accordance with some examples.

FIG. 4A illustrates an exemplary user interface for a menu of applications on portable multifunction device 100 in accordance with some examples. Similar user interfaces are, optionally, implemented on device 300. In some examples, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some examples, a label for a respective application icon includes a name of an application corresponding to the respective application icon. In some examples, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some examples, the device detects inputs on a touch-sensitive surface that is separate from the display, as shown in FIG. 4B. In some examples, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these examples, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some examples, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
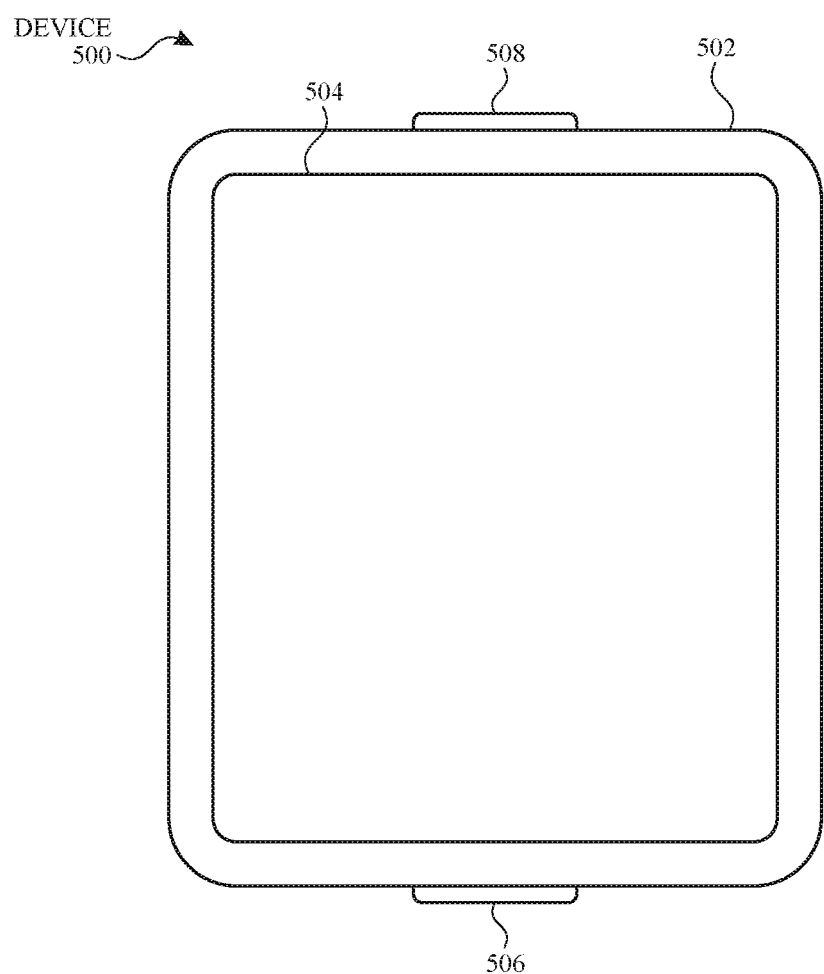
FIG. 5A illustrates a personal electronic device in accordance with some examples.
Figure 6B:
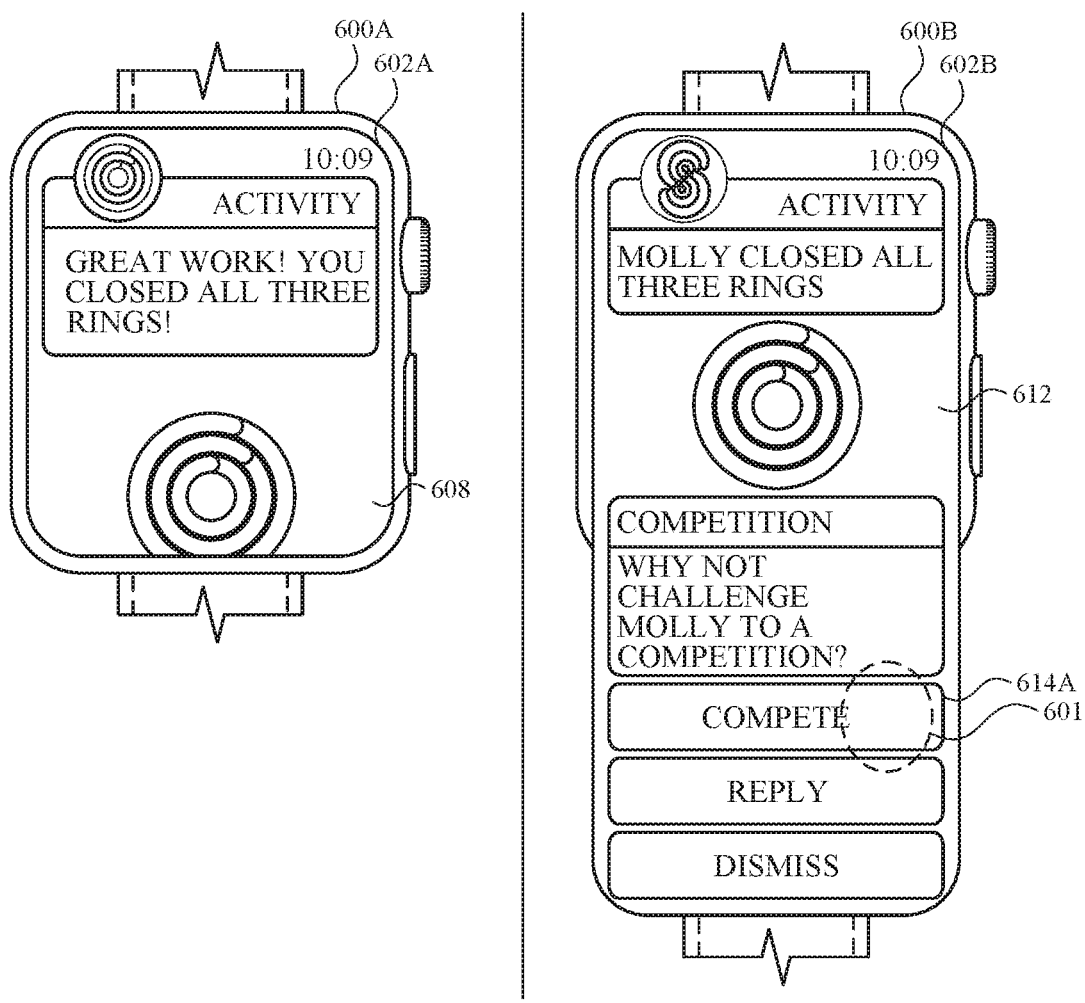

FIG. 5A illustrates exemplary personal electronic device 500. Device 500 includes body 502. In some examples, device 500 can include some or all of the features described with respect to devices 100 and 300 (e.g., FIGS. 1A-4B). In some examples, device 500 has touch-sensitive display screen 504, hereafter touch screen 504. Alternatively, or in addition to touch screen 504, device 500 has a display and a touch-sensitive surface. As with devices 100 and 300, in some examples, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some examples, device 500 has one or more input mechanisms 506 and 508. Input mechanisms 506 and 508, if included, can be physical. Examples of physical input mechanisms include push buttons and rotatable mechanisms. In some examples, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
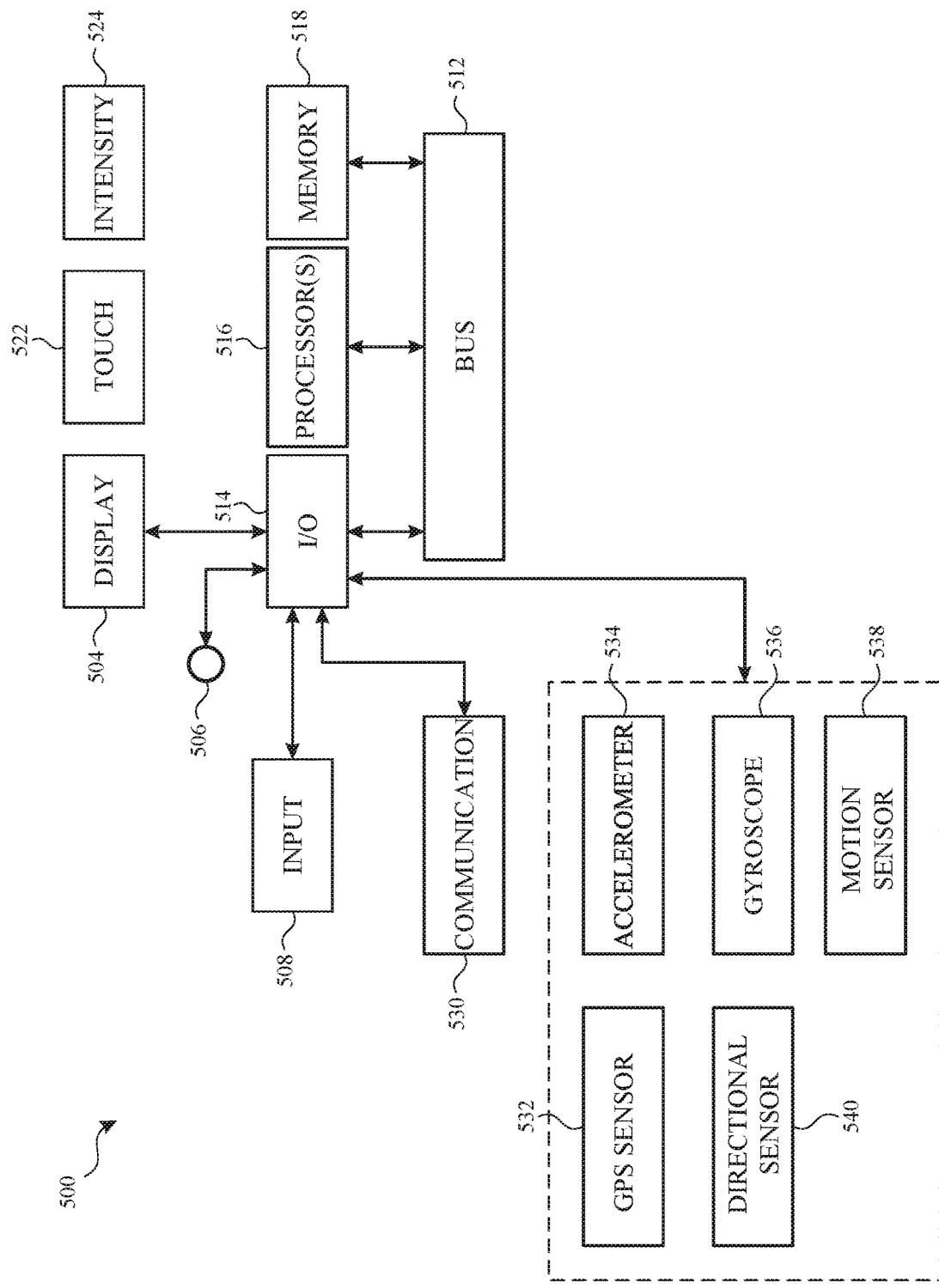
FIG. 5B is a block diagram illustrating a personal electronic device in accordance with some examples.

FIG. 5B depicts exemplary personal electronic device 500. In some examples, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700 (FIGS. 7A-7B), 900 (FIGS. 9A-9B), 1100 (FIG. 11), and 1300 (FIG. 13). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some examples, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some examples, the duration of the contact is used in determining the characteristic intensity (e.g., when the characteristic intensity is an average of the intensity of the contact over time). In some examples, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some examples, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Figure 5D:
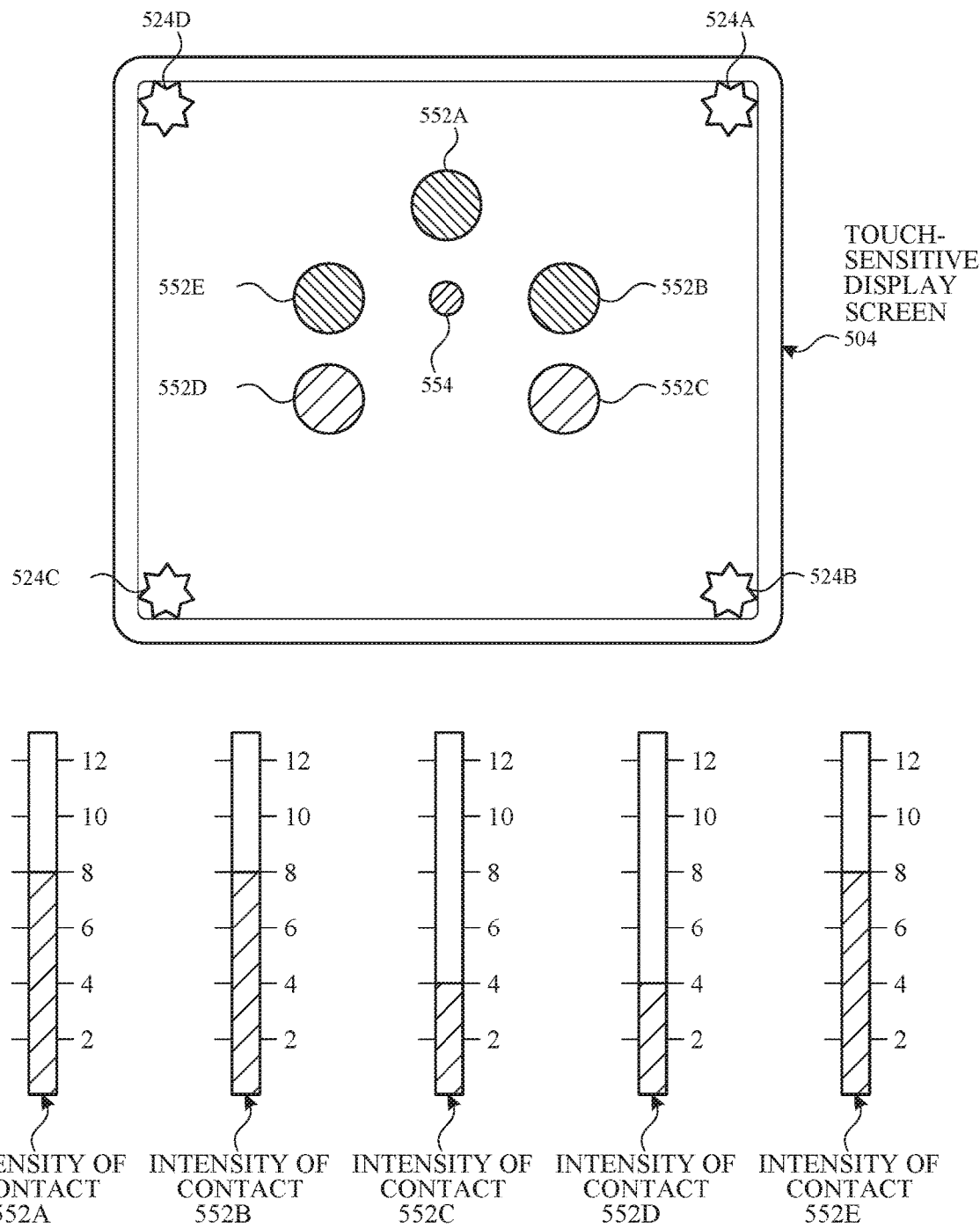

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some examples, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity Ij that is a portion of the aggregate intensity, A, in accordance with a predefined mathematical function, $Ij=A \cdot (Dj/\Sigma Di)$, where Dj is the distance of the respective contact j to the center of force, and $\Sigma Di$ is the sum of the distances of all the respective contacts (e.g., i=1 to last) to the center of force. The operations described with reference to FIGS. 5C-5D can be performed using an electronic device similar or identical to device 100, 300, or 500. In some examples, a characteristic intensity of a contact is based on one or more intensities of the contact. In some examples, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some examples, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some examples, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some examples, the light press intensity threshold corresponds to an intensity at which the device will perform operations typically associated with clicking a button of a physical mouse or a trackpad. In some examples, the deep press intensity threshold corresponds to an intensity at which the device will perform operations that are different from operations typically associated with clicking a button of a physical mouse or a trackpad. In some examples, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some examples, the contact-detection intensity threshold is zero. In some examples, the contact-detection intensity threshold is greater than zero.

In some examples described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some examples, the respective operation is performed in response to detecting the increase in intensity of the respective contact above the press-input intensity threshold (e.g., a "down stroke" of the respective press input). In some examples, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

FIGS. 5E-5H illustrate detection of a gesture that includes a press input that corresponds to an increase in intensity of a contact 562 from an intensity below a light press intensity threshold (e.g., "IT$_L$") in FIG. 5E, to an intensity above a deep press intensity threshold (e.g., "IT$_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some examples, the gesture is detected on touch-sensitive display 504. The intensity sensors detect the intensity of contacts on touch-sensitive surface 560. The device determines that the intensity of contact 562 peaked above the deep press intensity threshold (e.g., "IT$_D$"). Contact 562 is maintained on touch-sensitive surface 560. In response to the detection of the gesture, and in accordance with contact 562 having an intensity that goes above the deep press intensity threshold (e.g., "IT$_D$") during the gesture, reduced-scale representations 578A-578C (e.g., thumbnails) of recently opened documents for App 2 are displayed, as shown in FIGS. 5F-5H. In some examples, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some examples, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some examples, the animation progresses in accordance with an intensity of contact 562, as shown in FIGS. 5F-5G, where the representations 578A-578C appear and move upwards as the intensity of contact 562 increases toward the deep press intensity threshold (e.g., "IT$_D$"). In some examples, the intensity, on which the progress of the animation is based, is the characteristic intensity of the contact. The operations described with reference to FIGS. 5E-5H can be performed using an electronic device similar or identical to device 100, 300, or 500.

In some examples, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some examples, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some examples, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some examples, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;

a background application (or background processes), which is not currently displayed, but one or more processes for the application are being processed by one or more processors; and a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards examples of user interfaces ("UP") and associated processes that are implemented on an electronic device, such as portable multifunction device 100, device 300, or device 500.

FIGS. 6A-6T illustrate exemplary user interfaces related to activity competitions in accordance with some examples. Such activity competitions allow participants of the activity competitions to compete for a set time period using physical activity detected by their respective devices. For example, an activity competitions can be configured to last for a week. During the week, devices of participants can detect physical activity performed by the participants. By the end of the week, the participant with the most detected physical activity can win the activity competition. In some examples, an activity competition can be between two participants. In other examples, an activity competition can be between more than two participants.

FIG. 6A depicts two electronic devices (i.e., device 600A and device 600B). For explanatory purposes, device 600A will belong to Molly and device 600B will belong to Aled; the two devices are in electronic communication (e.g., wireless communication). Each of the two electronic devices can include a touch-sensitive display (e.g., touch-sensitive display 602A and touch-sensitive display 602B) for displaying user interfaces that can be interacted with by touching the touch-sensitive display. It should be recognized that other input mechanisms (other than touch) can be used to interact with the user interfaces displayed by the two electronic devices. For example, each electronic device includes a rotatable input mechanism (e.g., rotatable input mechanism 604A and rotatable input mechanism 604B that can each rotate with respect to the housings of the respective devices) and a push button (e.g., push button 606A and push button 606B). In some examples, devices 600A and 600B may include one or more features of devices 100, 300, or 500, as described above. When multiple electronic devices are illustrated in a single figure, it should be recognized that the user interfaces depicted in the figure can be synced in time (e.g., while device 600A displays a first user interface in a figure, device 600B displays a second user interface in the figure).

Referring to device 600A in FIG. 6A, user interface 608 is displayed on touch-sensitive display 602A. User interface 608 is a notification that is displayed in response to a determination that a participant of the activity competition (e.g., Molly) associated with device 600A has completed three different physical activity goals (referred to as rings). A representation of the three different physical activity goals completed is illustrated at representation 610B.

Referring to device 600B in FIG. 6A, user interface 612 is displayed in response to receiving data, transmitted from device 600A, indicating that Molly completed her three different physical activity goals. For example, user interface 612 can be informing Aled that Molly completed her three different physical activity goals (as illustrated at representation 610A). It should be recognized that user interface 612 can be displayed in response to other physical activity performed by Molly, such as Molly completing a workout.

User interface 612 can include a scrollable list of affordances 614, where each affordance is associated with a different operation. For example, the scrollable list of affordances 614 includes first affordance 614A, second affordance 614B, and third affordance 614C. Selection of first affordance 614A can initiate a sequence to begin an activity competition between Aled and Molly. Selection of second affordance 614B can cause a messaging interface to be displayed (as depicted in FIG. 6J and discussed below) to allow Aled to send a message to Molly in response to her completing her three physical activity goals. Selection of third affordance 614 can cause device 600B to cease to display user interface 612. In FIG. 6A, the full content of user interface 612 is shown, including portions that would not initially fit on the display (e.g., portions accessed via scrolling), for ease of explanation. Throughout the disclosure, additional user interfaces are shown in this manner for ease of explanation.

FIG. 6B again illustrates the user interfaces depicted in FIG. 6A. While device 600A is continuing to display user interface 608 in FIG. 6B, it should be recognized that device 600A can display a different user interface. As described above, user interface 612 on device 600B includes first affordance 614A. Referring to FIG. 6B, user input (e.g., tap input) 601 is received, where user input 601 corresponds to selection of first affordance 614A. In accordance with a determination that user input 601 is detected at first affordance 614A, a user interface related to initiating an activity competition is displayed (e.g., user interface 616 depicted in FIG. 6C).

Figure 6C:
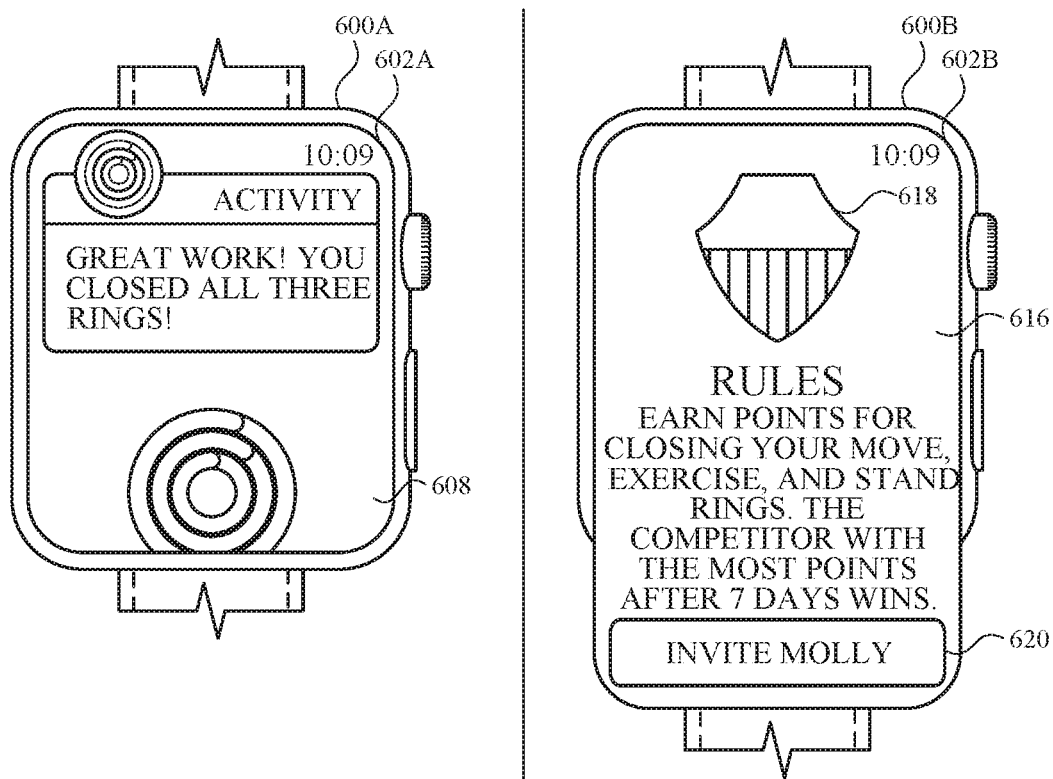

Referring to FIG. 6C, user interface 616 is displayed on touch-sensitive display 602B in response to selection of first affordance 614A. User interface 616 describes rules for an activity competition. It should be recognized that, in some examples, user interface 616 might not be displayed in response to selection of first affordance 614A (as depicted in FIG. 6B). For example, Aled might have already initiated a particular number of activity competitions such that a user interface describing rules for an activity competition is not necessary. In some examples, user interface 616 can be displayed in response to selection of first affordance 614A for a particular number of times per participant. For example, user interface 616 can be displayed to Aled 2 times before it is no longer displayed to Aled.

User interface 616 includes icon 618. Icon 618 can represent activity competitions between Molly and Aled, such that all activity competitions (e.g., past activity competitions) between Molly and Aled are associated with icon 618. In some examples, activity competitions between different participants (such as Molly and Steve) can be represented by different icons with different visual themes than icon 618. It should be recognized that, in some examples, icons can be assigned to activity competitions prior to display of user interface 616. User interface 616 further includes affordance 620 for indicating an acceptance of the terms in user interface 616 and causing an invitation to begin an activity competition to be sent to Molly (e.g., to device 600A).

Figure 6D:
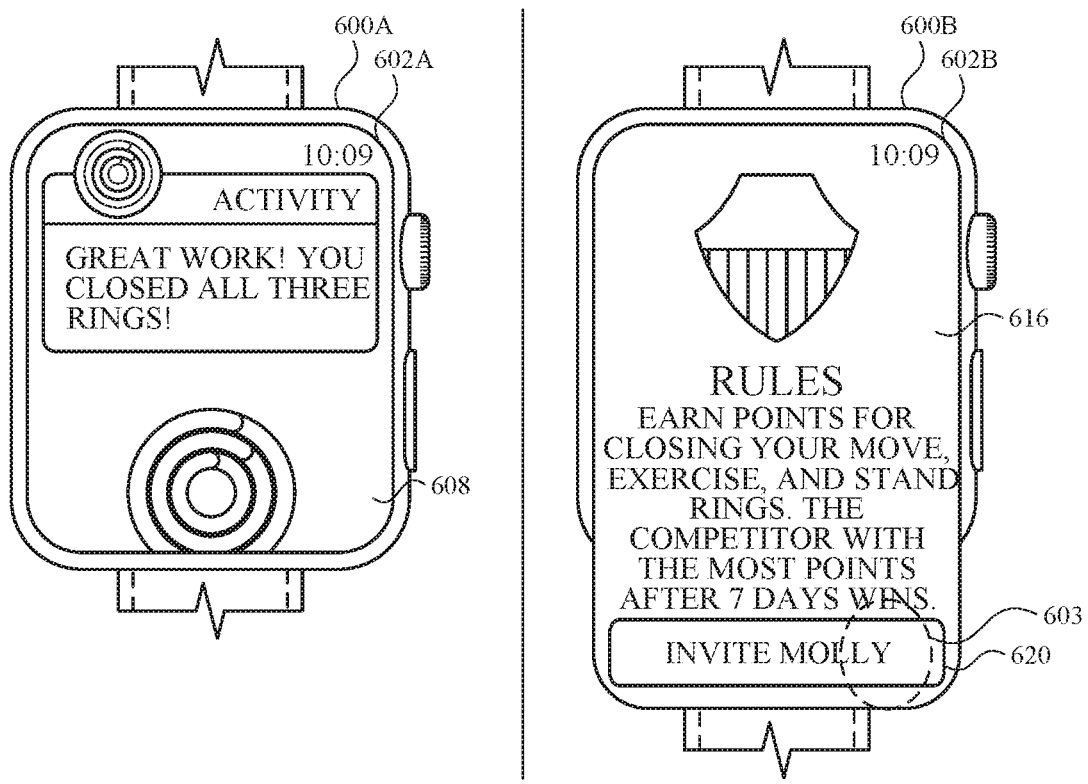

FIG. 6D again illustrates the user interfaces depicted in FIG. 6C. While device 600A is continuing to display user interface 608 in FIG. 6D, it should be recognized that device 600A can display a different user interface. As described above, user interface 616 includes an affordance 620A. Referring to FIG. 6D, user input (e.g., tap input) 603 is received, where user input 603 corresponds to selection of affordance 620. In accordance with a determination that user input 603 is detected at affordance 620, an invitation for an activity competition between Aled and Molly can be sent to device 600A (as depicted in FIG. 6E).

Figure 6E:
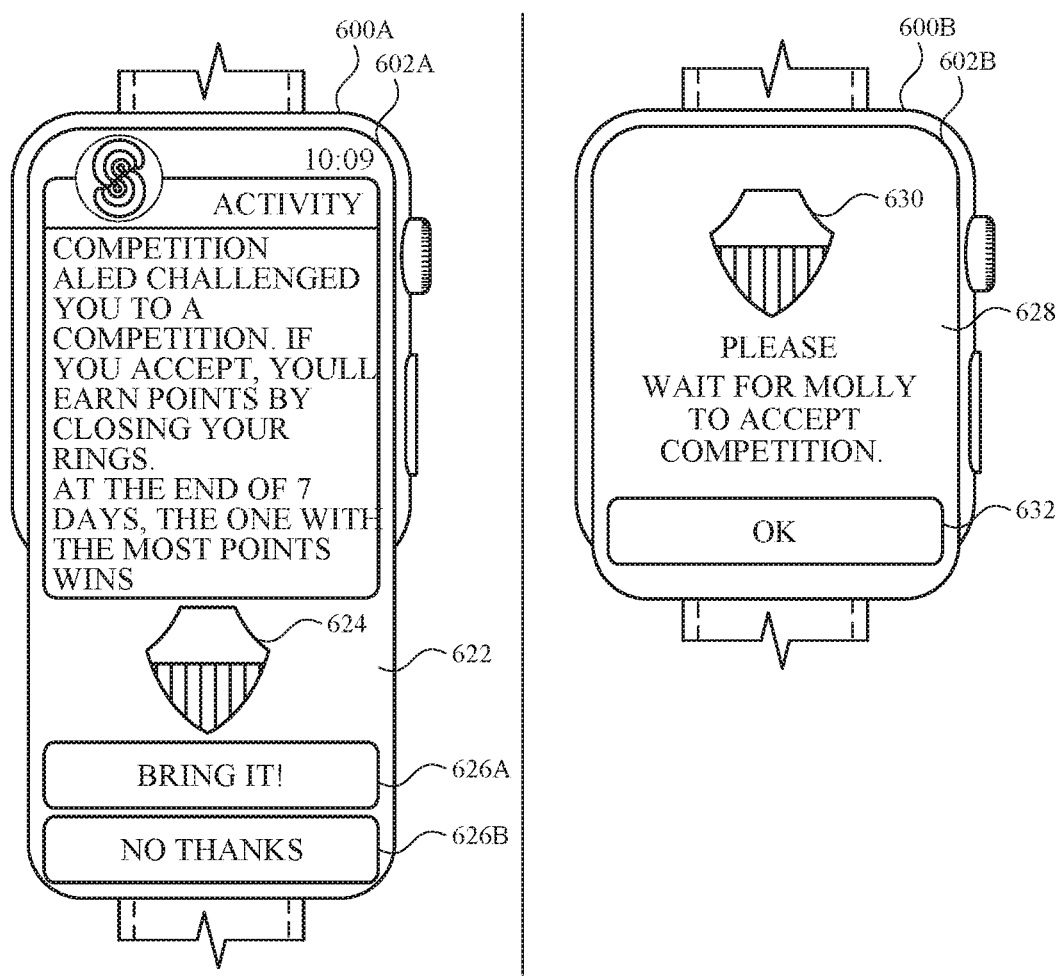

Referring to FIG. 6E, in response to Molly selecting affordance 620 in user interface 616 (as depicted in FIG. 6D), user interface 628 can be displayed on device 600B and user interface 622 can be displayed on device 600A. User interface 628 indicates that Aled must wait for Molly to accept the invitation sent by Aled, before the activity competition will start. User interface 628 includes icon 630 (which can have the same theme as icon 618, as depicted in FIG. 6C) and affordance 632, to cease to display user interface 628.

User interface 622 of device 600A describes rules for an activity competition, similar to user interface 616. User interface 622 includes icon 624 (which can have the same theme as icon 618, as depicted in FIG. 6C). User interface 622 further includes a scrollable list of affordances 626, where each affordance is associated with a different operation. For example, the scrollable list of affordances 626 includes first affordance 626A and second affordance 626B.

Selection of first affordance 626A can accept the invitation for the activity competition sent by Aled. Acceptance of the invitation can cause the activity competition to begin at a predefined time after the selection (e.g., midnight of the current day), as further described below. Selection of second affordance 626B can cause device 600B to reject the invitation (e.g., cause the activity competition to not begin) and cease to display user interface 612.

Figure 6F:
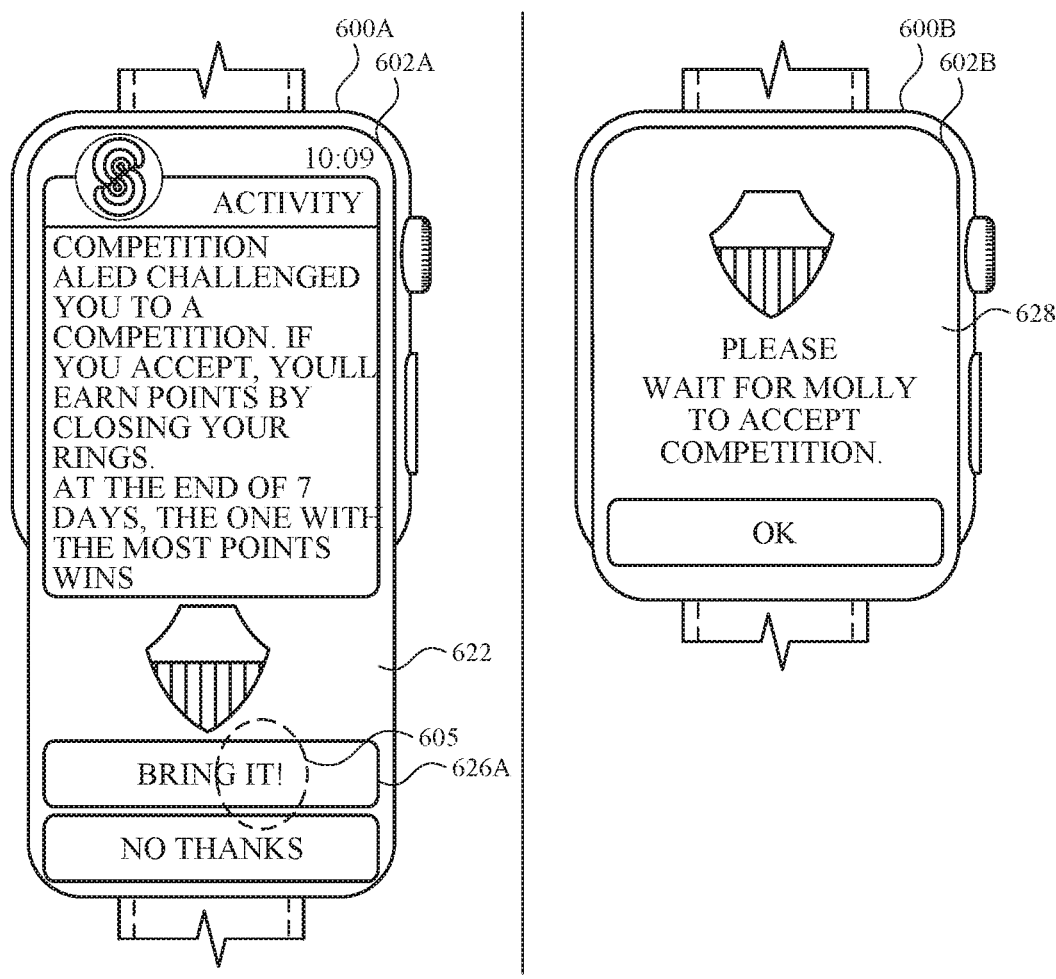

FIG. 6F again illustrates the user interfaces depicted in FIG. 6E. While device 600B is continuing to display user interface 628 in FIG. 6F, it should be recognized that device 600B can display a different user interface. As described above, user interface 622 on device 600A includes first affordance 626A. Referring to FIG. 6F, user input (e.g., tap input) 605 is received, where user input 605 corresponds to selection of first affordance 626A. In accordance with a determination that user input 605 is detected at first affordance 626A, an activity competition between Molly and Aled can be set to initiate at a predefined time in the future.

Figure 6G:
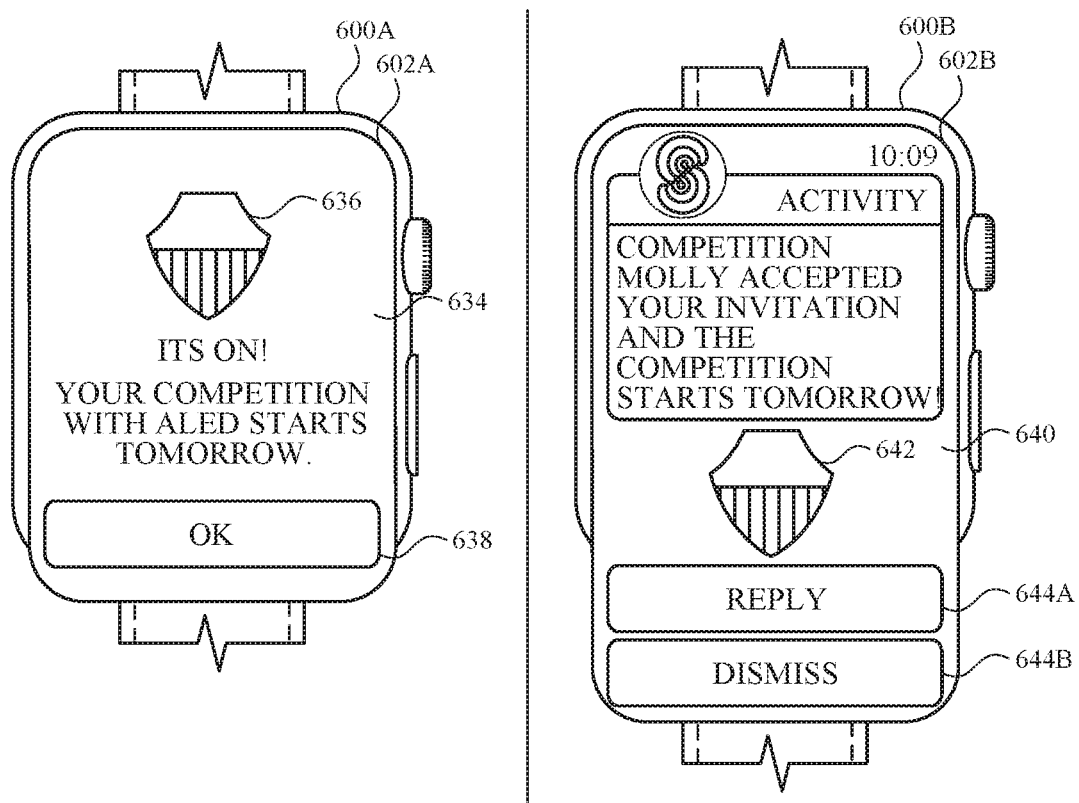

Referring to FIG. 6G, in response to receiving the selection (e.g., by Molly) of affordance 605 in user interface 622 (as depicted in FIG. 6F), user interface 634 can be displayed on device 600A and user interface 640 can be displayed on device 600B. User interface 634 indicates that the activity competition with Aled will start tomorrow. User interface 634 includes icon 636 (which can have the same theme as icon 618, as depicted in FIG. 6C) and affordance 638, to cease to display user interface 638.

User interface 640 indicates that the invitation that Aled sent was accepted and that the activity competition with Molly will start tomorrow. User interface 640 includes icon 642 (which can have the same theme as icon 618, as depicted in FIG. 6C). User interface 622 further includes a scrollable list of affordances 644, where each affordance is associated with a different operation. For example, the scrollable list of affordances 626 includes first affordance 626A for displaying a messaging user interface (as depicted in FIG. 6I) and second affordance 626B for ceasing to display user interface 640.

Figure 6H:
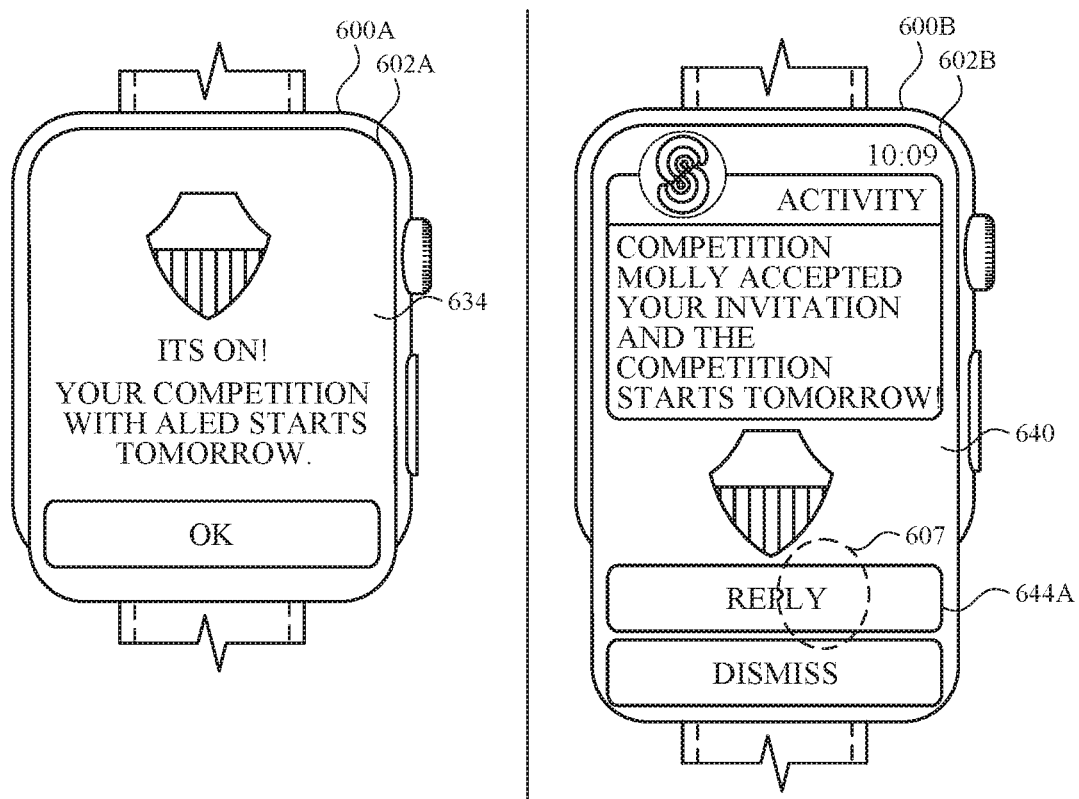

FIG. 6H again illustrates the user interfaces depicted in FIG. 6G. While device 600A is continuing to display user interface 634 in FIG. 6H, it should be recognized that device 600A can display a different user interface. As described above, user interface 640 on device 600B includes first affordance 644A. Referring to FIG. 6H, user input (e.g., tap input) 607 is received, where user input 607 corresponds to selection of first affordance 644A. In accordance with a determination that user input 607 is detected at first affordance 644A, a messaging user interface is displayed (as depicted in FIG. 6I).

Figure 6I:
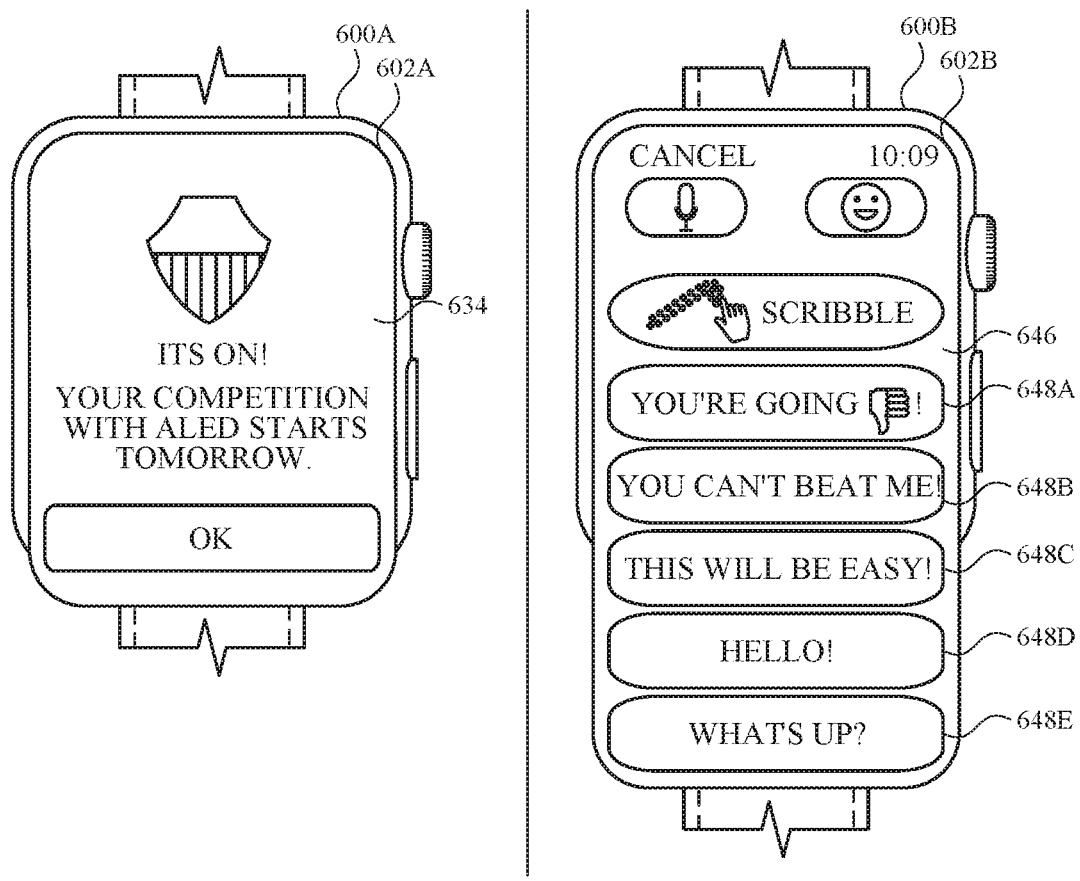
Figure 6J:
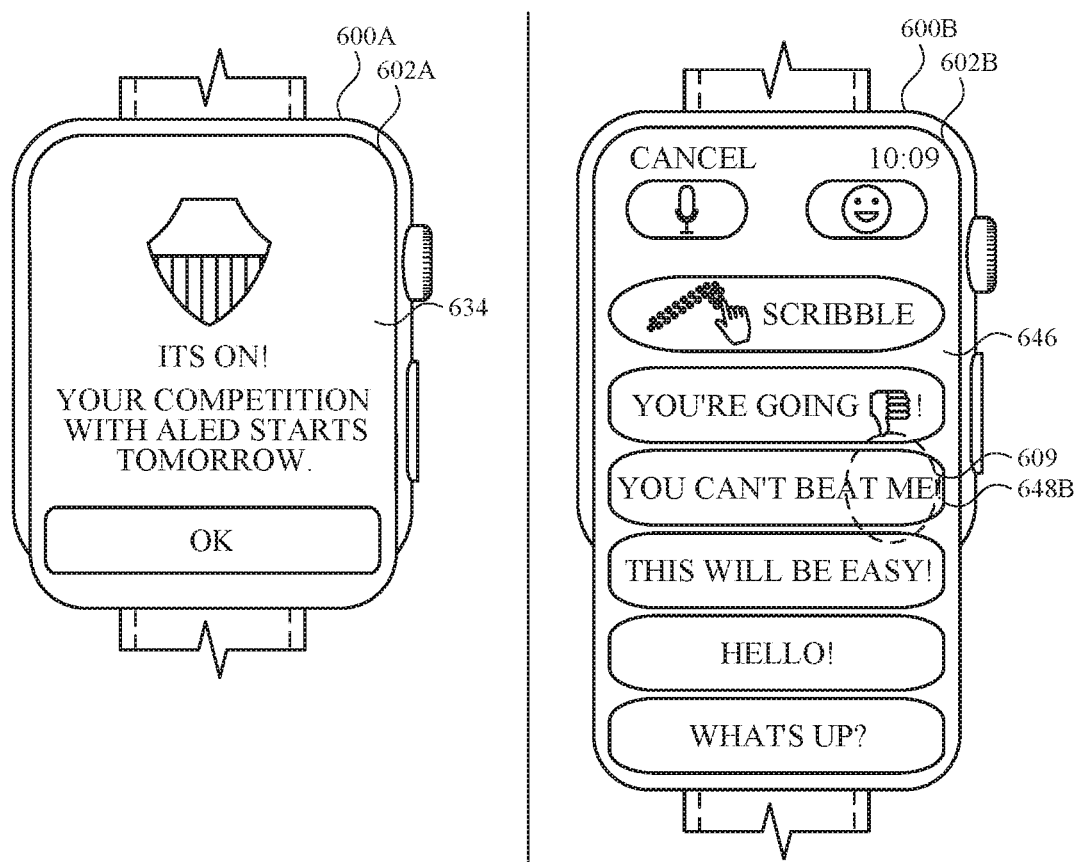

Referring to FIG. 6I, device 600B displays user interface 646 in response to selection of first affordance 644A in user interface 640 (as depicted in FIG. 6H). User interface 646 includes a scrollable list of affordances 648, where each affordance is associated with a different predefined message. Selection of an affordance in the scrollable list of affordance 648 can cause a communication (sometimes referred to as a message) to be generated with the corresponding predefined message and sent to Molly. For example, selection of second affordance 648B can cause a communication with the text "YOU CAN'T BEAT ME!" to be sent to Molly.

FIG. 6J again illustrates the user interfaces depicted in FIG. 6I. While device 600A is continuing to display user interface 634 in FIG. 6J, it should be recognized that device 600A can display a different user interface. As described above, user interface 646 on device 600B includes second affordance 648B. Referring to FIG. 6J, user input (e.g., tap input) 609 is received, where user input 609 corresponds to selection of second affordance 648B. In accordance with a determination that user input 609 is detected at second affordance 648B, a communication can be generated with text corresponding to second affordance 648B and sent to Molly.

Figure 6K:
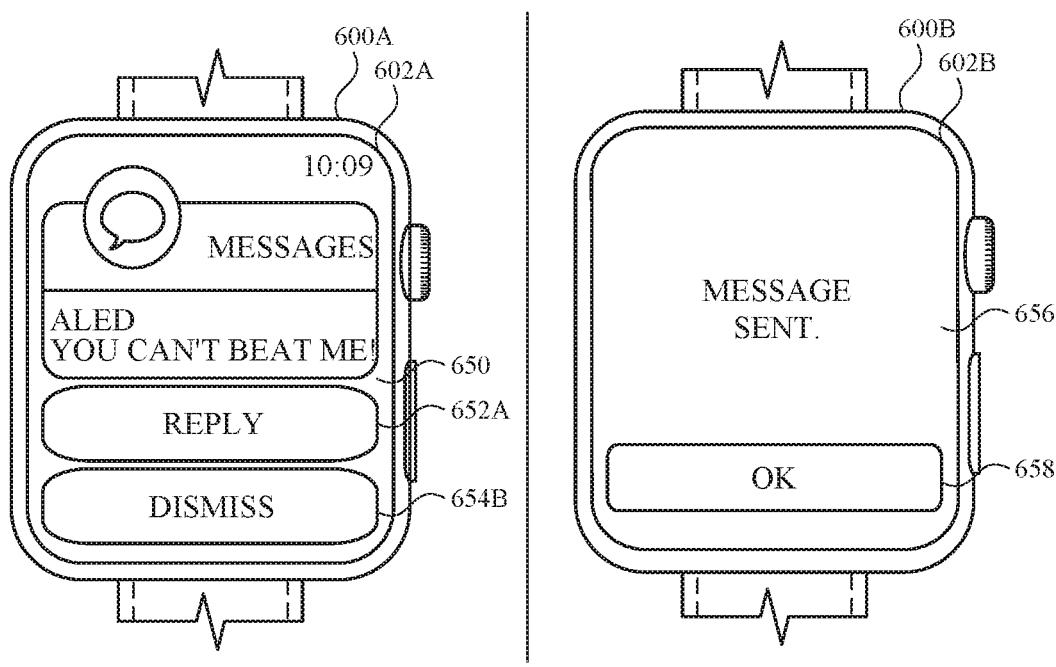

Referring to FIG. 6K, device 600B displays user interface 656 in response to selection of second affordance 648B in user interface 646 (as depicted in FIG. 6J). User interface 656 indicates that a message has been sent and includes affordance 658 for causing user interface 656 to cease to display.

Also in response to selection of second affordance 648B in user interface 646 (as depicted in FIG. 6J), device 600A displays user interface 650 in touch-sensitive display 602A, as depicted in FIG. 6K. User interface 650 includes a representation of the predefined message sent by Aled, as discussed above. User interface 650 also includes a scrollable list of affordances 652, where each affordance is associated with a different operation. For example, the scrollable list of affordances 626 includes first affordance 626A for displaying a messaging user interface (as depicted in FIG. 6I) and second affordance 626B for ceasing to display user interface 650.

While an activity competition is active, participants in the activity competition can receive notifications including a status of the activity competition. For example, in response to the activity competition beginning, a notification can be displayed to each of the participants in the activity competition, as depicted in FIG. 6L.

Figure 6L:
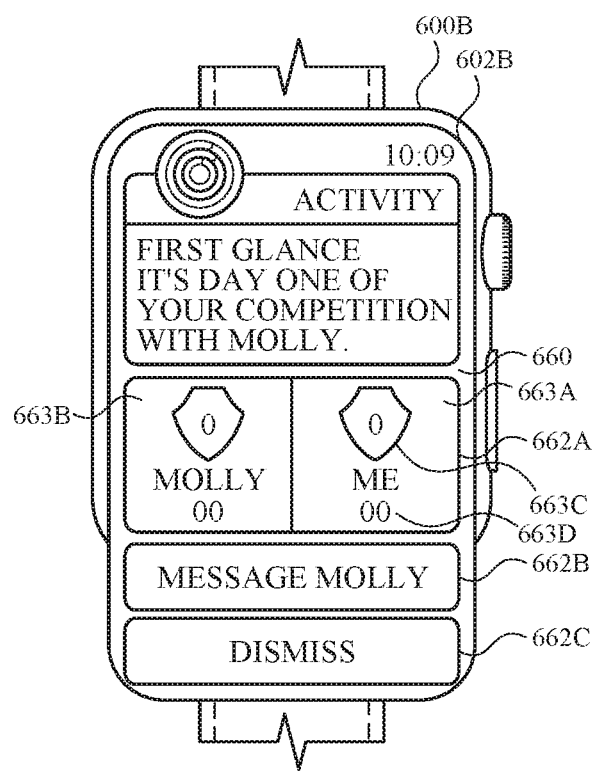

Referring to FIG. 6L, user interface 660 is displayed on touch-sensitive display 602B of device 600B. While not illustrated, a similar user interface can be displayed on touch-sensitive display 602A of device 600A.

User interface 660 indicates that the activity competition with Molly has begun. User interface 600 includes a scrollable list of affordances 662, where each affordance is associated with a different operation. For example, the scrollable list of affordances 626 includes (1) first affordance 662A for displaying information related to the activity competition, (2) second affordance 662B for displaying a messaging user interface (as depicted in FIG. 6I), and (3) third affordance 662C for ceasing to display user interface 660.

As depicted in FIG. 6L, first affordance 662A includes first portion 663A with information related to Aled for the activity competition and second portion 663B with information related to Molly for the activity competition. The information related to Aled includes icon 663C with a number indicating a number of times that Aled has won an activity competition against Molly. The information related to Aled further includes score 663D for Aled for the activity competition so far. It should be recognized that the information included within first affordance 662A can be different than illustrated, such as the information can include graph 670, as depicted in FIG. 6M and discussed below).

Selection of first affordance 662A can cause a user interface with additional information regarding the activity competition to be displayed. For example, the additional information can include graph 670, as depicted in FIG. 6M and discussed below.

In addition to a notification being displayed when the activity competition begins, notifications can be displayed at predefined times during the activity competition. For example, a predefined time can be an absolute time during the activity competition (e.g., each day at 10 AM) or as a result of an event occurring on a device where the notification is displayed (e.g., a participant completing a goal, performing a workout, or accessing a particular application on the device). Such notifications can include information related to one or more active activity competitions.

Figure 6M:
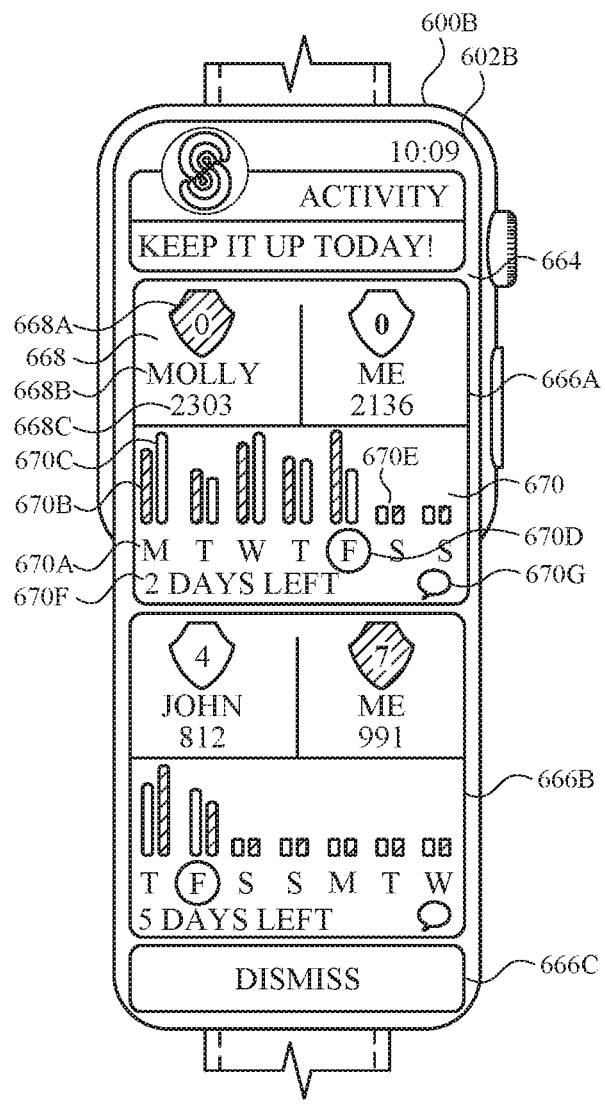

Referring to FIG. 6M, user interface 664 is displayed on touch-sensitive display 602B in response to a trigger being activated at a predefined time. For example, the predefined time can be at 10 PM on Friday, causing user interface 644 to be displayed.

User interface 644 includes a scrollable list of affordances 666, where each affordance is associated with a different operation. For example, the scrollable list of affordances 666 includes first affordance 666A for a first activity competition, second affordance 666B for a second activity competition, and third affordance 666C for ceasing to display user interface 660. In some examples, the order of affordances for activity competitions can be based upon when the activity competitions are finishing. For example, activity competitions finishing sooner can be included in the scrollable list before activity competitions finishing later.

First affordance 666A includes information related to the first activity competition. As depicted in FIG. 6M, first affordance 666A includes information similar to first affordance 662A (as depicted in FIG. 6L). For example, first affordance 666A (as depicted in FIG. 6M) includes icon 668A with a number indicating a number of times that Molly has won an activity competition against Aled. First affordance 666A further includes an identification of Molly (e.g., element 668B) and a score for Molly for the first activity competition so far (e.g., element 668C) (sometimes referred to as a cumulative score).

As depicted in FIG. 6M, first affordance 666A further includes graph 670 for the first activity competition, where graph 670 includes information regarding the first activity competition for multiple subsets (e.g., days). Graph 670 can include more granular information than included in element 668. The x-axis of graph 670 includes identifications of multiple subsets of the first activity competition. As depicted in FIG. 6M, each subset is a day of the week (e.g., reference 670A points to "M" for Monday). It should be noted that "M" is located first to indicate that the first activity competition began on Monday. In addition, it should be noted that "F" (e.g., reference 670D) is visually highlighted (e.g., circled) in FIG. 6M to indicate that Friday is the current day.

The y-axis of graph 670 includes representations of physical activity detected for each participant in the first activity competition for each subset. For example, representation 670B indicates an amount of physical activity detected for Molly (e.g., detected by device 600A and transmitted to device 600B) on Monday and representation 670C indicates an amount of physical activity detected for Aled on Monday. By having representation 670B adjacent to representation 670C, physical activity for each participant for Monday can easily be compared. It should be noted that representations for Molly are provided to the left of representations for Aled in graph 670. The configuration is such because 600B corresponds to Aled's device. When a subset has not occurred yet (e.g., Saturday as depicted in FIG. 6M), representations corresponding to the subset (e.g., reference 670E) can be displayed as zero.

In some examples, representations for subsets can be normalized across the time period such that the highest representation for a subset of the time period can be displayed a certain size, with other representations normalized based upon the highest representation. For example, if Molly scored the most points for the time period on Friday, a representation for Molly on Friday will be the biggest representation. In such an example, a representation for either Molly or Aled with half the score will be represented as half the size of the representation for Molly on Friday.

It should be noted that representations associated with Molly are illustrated as being visually distinct from representations associated with Aled in FIG. 6M. For example, icon 668A for Molly is visually distinct from the icon for Aled. In addition, representations for subsets for Molly are visually distinct from representations for subsets for Aled.

In some examples, representations associated with a participant that is winning an activity competition can be highlighted as compared to a participant that is losing the activity competition. For example, because Molly's cumulative score is higher than Aled's cumulative score, representations associated with Molly visually appear to be highlighted as compared to representations associated with Aled. Visually highlighting representations associated with a participant that is winning can allow a participant to quickly assess how they are doing in the activity competition.

Graph 670 also includes a number of subsets remaining in the first activity competition (e.g., reference 670F). For example, as depicted in FIG. 6M, there are two days left in the first activity competition.

Representation 670 also includes icon 670G. Icon 670G can either indicate that selection of affordance 666A or icon 670G (depending upon configuration of icon 670G) will cause a messaging interface to be displayed (as depicted in FIG. 6J).

As depicted in FIG. 6M, second affordance 666B includes information related to the second activity competition between John and Aled. Second affordance 666B indicates that John and Aled have competed 11 times, where John has won 4 times and Aled has won 7 times. It should be noted that second affordance 666B illustrates that different activity competitions can begin on different days. For example, the first activity competition began on Monday and the second activity competition began on Thursday. It should also be noted that second affordance 666B illustrates that time periods (e.g., 7 days) can be the same across different activity competitions.

In addition to a notification being displayed when the activity competition begins and at a predefined time, notifications can be displayed in response to activity by another participant. For example, a notification can be displayed for Aled in response to physical activity by Molly, such as Molly reaching a goal for a day (such as closing three activity rings) or performing a workout. Such notifications can include information related to an activity competition with the other participant.

Figure 6N:
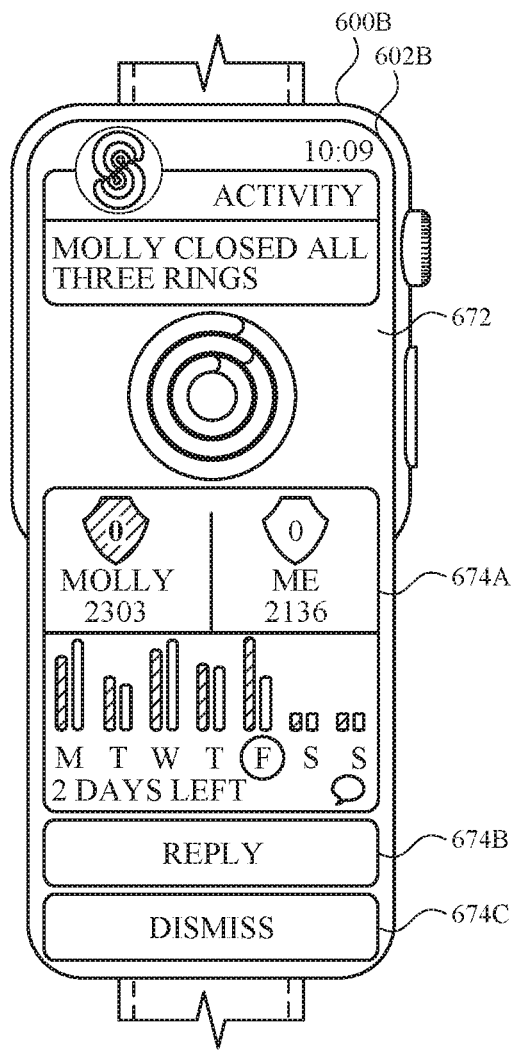

Referring to FIG. 6N, user interface 672 is displayed on touch-sensitive display 602B in response to Molly reaching her three ring goal for the day. User interface 672 includes a scrollable list of affordances 674, where each affordance is associated with a different operation. For example, the scrollable list of affordances 674 includes first affordance 674A for an activity competition between Molly and Aled, second affordance 674B for displaying a messaging user interface (as depicted FIG. 6I), and third affordance 674C for ceasing to display user interface 672. First affordance 674A is similar to that discussed above for first affordance 666A in FIG. 6M.

Notifications can be sent (e.g., displayed on respective devices of participants) to participants of an activity competition when the activity competition ends. Such notifications can provide results of the activity competition, including an award of a medal for the winner, and include an option to begin a new activity competition, as depicted in FIG. 6O.

Figure 6O:
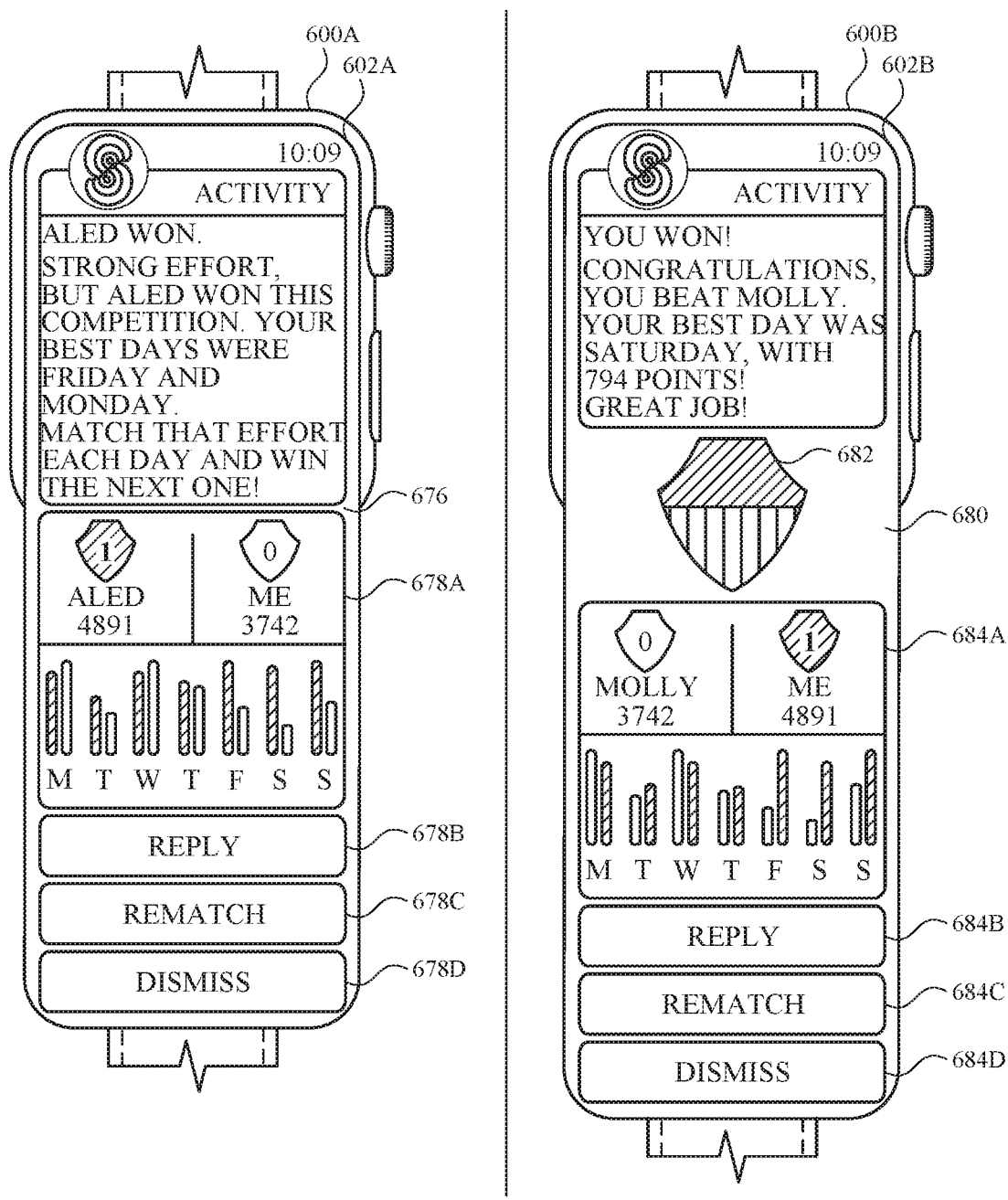

Referring to FIG. 6O, user interface 676 is displayed on touch-sensitive display 602A in response to an activity competition between Molly and Aled ending. User interface 676 can include text catered to Molly and the outcome of the activity competition. For example, user interface 676 states that "ALED WON." and includes information that Molly's best days during the activity competition were Friday and Monday.

User interface 676 includes a scrollable list of affordances 678, where each affordance is associated with a different operation. For example, the scrollable list of affordances 678 includes first affordance 678A for the activity competition between Molly and Aled, second affordance 678B for displaying a messaging user interface (as depicted FIG. 6I), third affordance 678C for initiating a process to start a new activity competition (as further discussed below), and fourth affordance 678D for ceasing to display user interface 672.

Also in response to the activity competition between Molly and Aled ending, user interface 680 is displayed on touch-sensitive display 602B. User interface 680 can include text catered to Aled and the outcome of the activity competition. For example, user interface 676 states that "YOU WON." and includes information that Aled's best day during the activity competition was Saturday with 794 points.

User interface 680 includes icon 682, representing that Aled won icon 682 in response to winning the activity competition. In response to winning icon 682, icon 682 can be placed in a trophy case for Aled, as further discussed below for FIG. 8V.

User interface 680 also includes a scrollable list of affordances 684, where each affordance is associated with a different operation. For example, the scrollable list of affordances 684 includes first affordance 684A for the activity competition between Molly and Aled, second affordance 684B for displaying a messaging user interface (as depicted FIG. 6I), third affordance 684C for initiating a process to start a new activity competition (as further discussed below), and fourth affordance 684D for ceasing to display user interface 680.

Having user interface 676 and user interface 680 side-by-side, it should be recognized that representations in a graph (e.g., the graph included in first affordance 678A and the graph included in first affordance 684A) can be swapped depending upon where the graph is being displayed. For example, when the graph is being displayed on Aled's device, representations associated with Aled are generally on the right of representations associated with Molly. Likewise, when the graph is being displayed on Molly's device, representations associated with Molly are generally on the right of representations associated with Alex. It should also be noted that FIG. 6O illustrates that highlighted representations have been changed (e.g., swapped) from Molly to Aled (relative to FIG. 6M) because Aled is winning the activity competition depicted in FIG. 6O. Such swapping can occur anytime a lead for the activity competition changes.

Figure 6P:
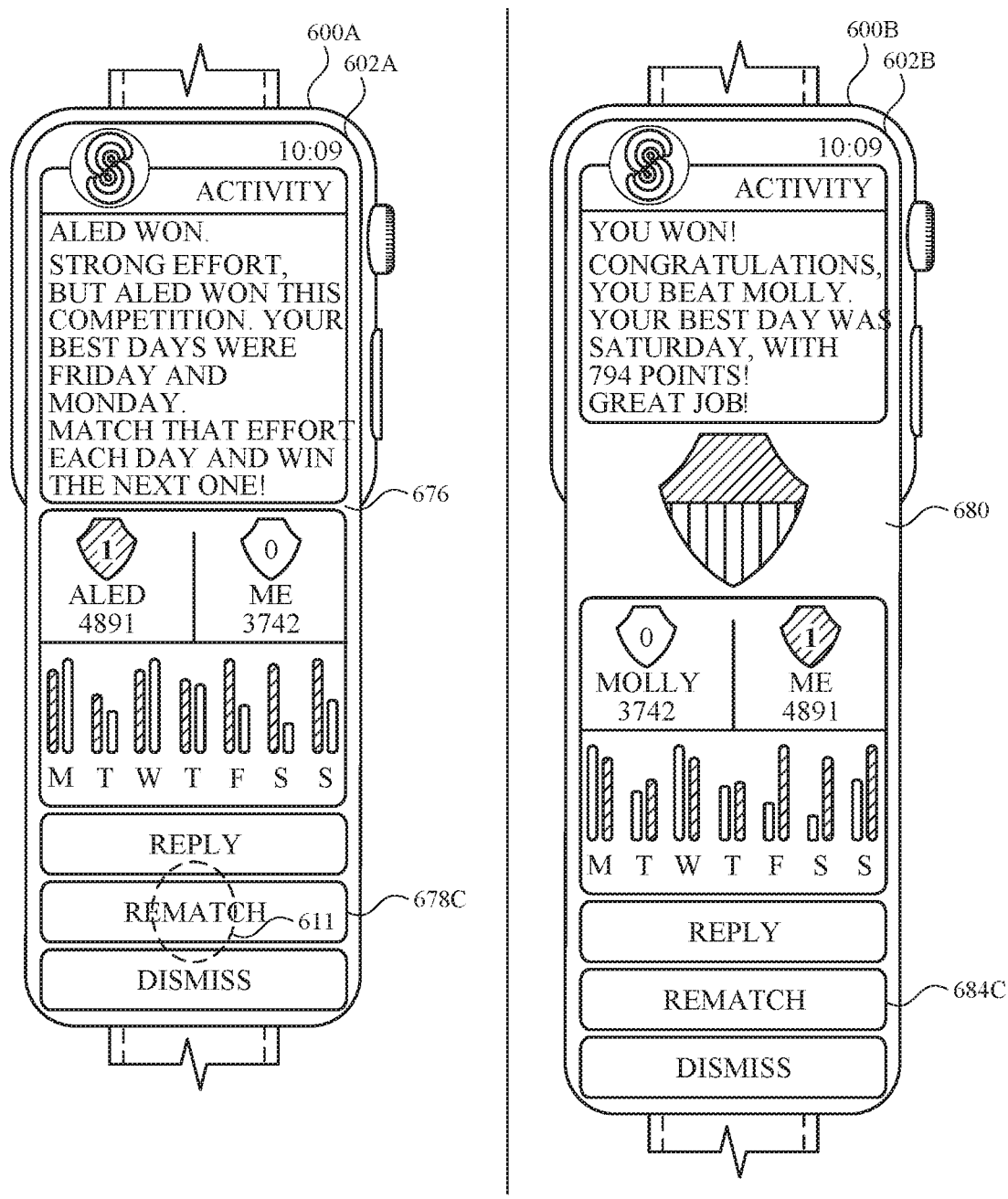
Figure 6Q:
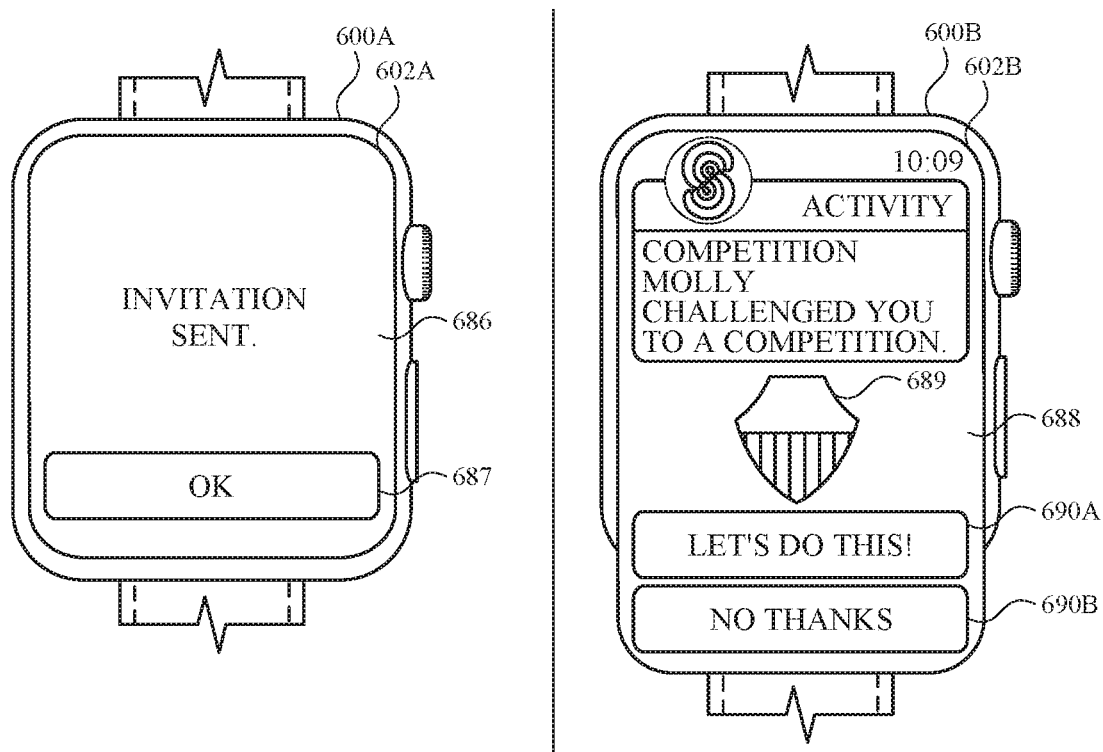

FIG. 6P again illustrates the user interfaces depicted in FIG. 6O. As described above, user interface 676 on device 600A includes third affordance 678C. Referring to FIG. 6P, user input (e.g., tap input) 611 is received, where user input 611 corresponds to selection of third affordance 678C. In accordance with a determination that user input 611 is detected at third affordance 678C, a user interface related to initiating an activity competition is displayed (e.g., user interface 686 as depicted in FIG. 6Q), an invitation for a new activity competition is sent to Aled, and a user interface related to the invitation is displayed (e.g., user interface 688 as depicted in FIG. 6Q). While device 600A is depicted as receiving user input 611, it should be recognized that device 600B can receive a similar user input on third affordance 684C, causing similar functionality to be performed.

Referring to FIG. 6Q, user interface 686 is displayed on touch-sensitive display 602A in response to selection of third affordance 678C (as depicted in FIG. 6P). User interface 686 indicates that an invitation for an new activity competition has been sent to Aled. User interface 686 includes affordance 687 for ceasing to display user interface 686.

Also referring to FIG. 6Q, user interface 688 is displayed on touch-sensitive display 602B in response to selection of third affordance 678C (as depicted in FIG. 6P). User interface 688 indicates that Molly has invited Aled to a new activity competition. User interface 688 includes icon 689, representing activity competitions between Molly and Aled. User interface 688 further includes a scrollable list of affordances 690, where each affordance is associated with a different operation. For example, the scrollable list of affordances 690 includes first affordance 690A and second affordance 690B.

Similar to as described above for FIG. 6E, selection of first affordance 690A accepts the invitation sent by Molly, causing the new activity competition between Molly and Aled to begin at a predefined time (e.g., midnight of the current day) after selection of first affordance 690A. Selection of second affordance 626B can cause device 600B to reject the invitation (e.g., cause the new activity competition to not begin) and cease to display user interface 688.

Figure 6R:
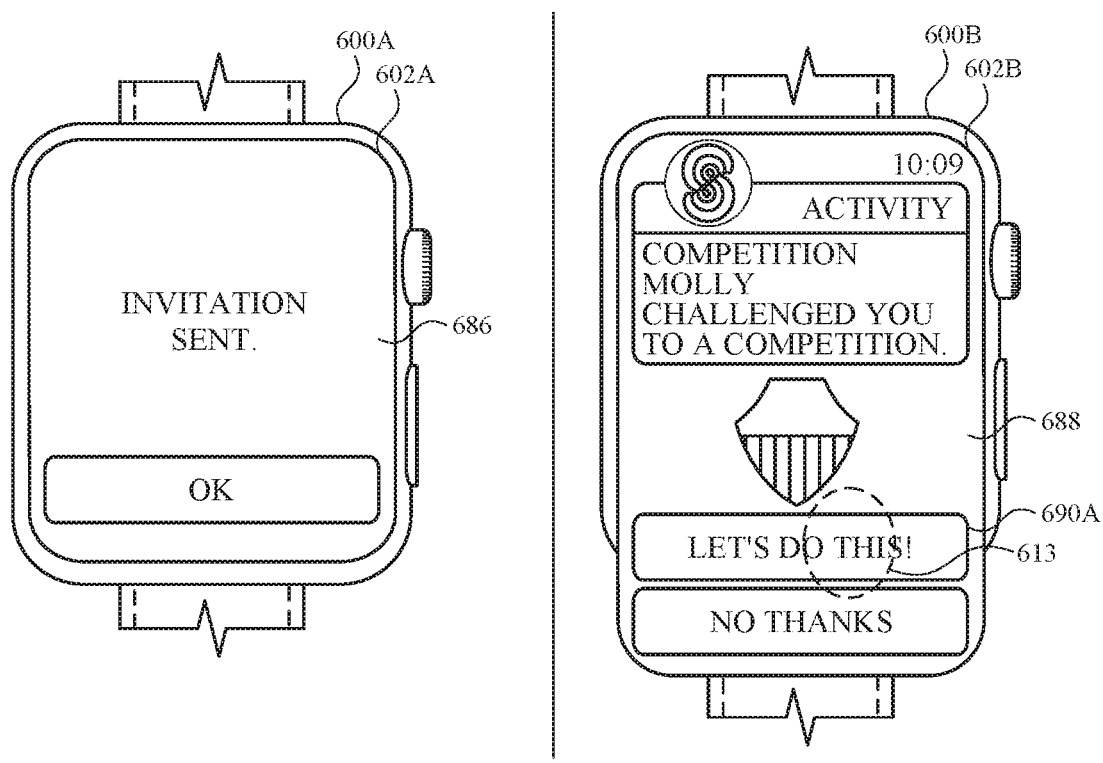

FIG. 6R again illustrates the user interfaces depicted in FIG. 6Q. While device 600A is continuing to display user interface 686 in FIG. 6R, it should be recognized that device 600A can display a different user interface. As described above, user interface 688 on device 600B includes first affordance 690A. Referring to FIG. 6R, user input (e.g., tap input) 613 is received, where user input 613 corresponds to selection of first affordance 690A. In accordance with a determination that user input 613 is detected at first affordance 690A, a new activity competition between Molly and Aled can be set to initiate at a predefined time in the future.

Figure 6S:
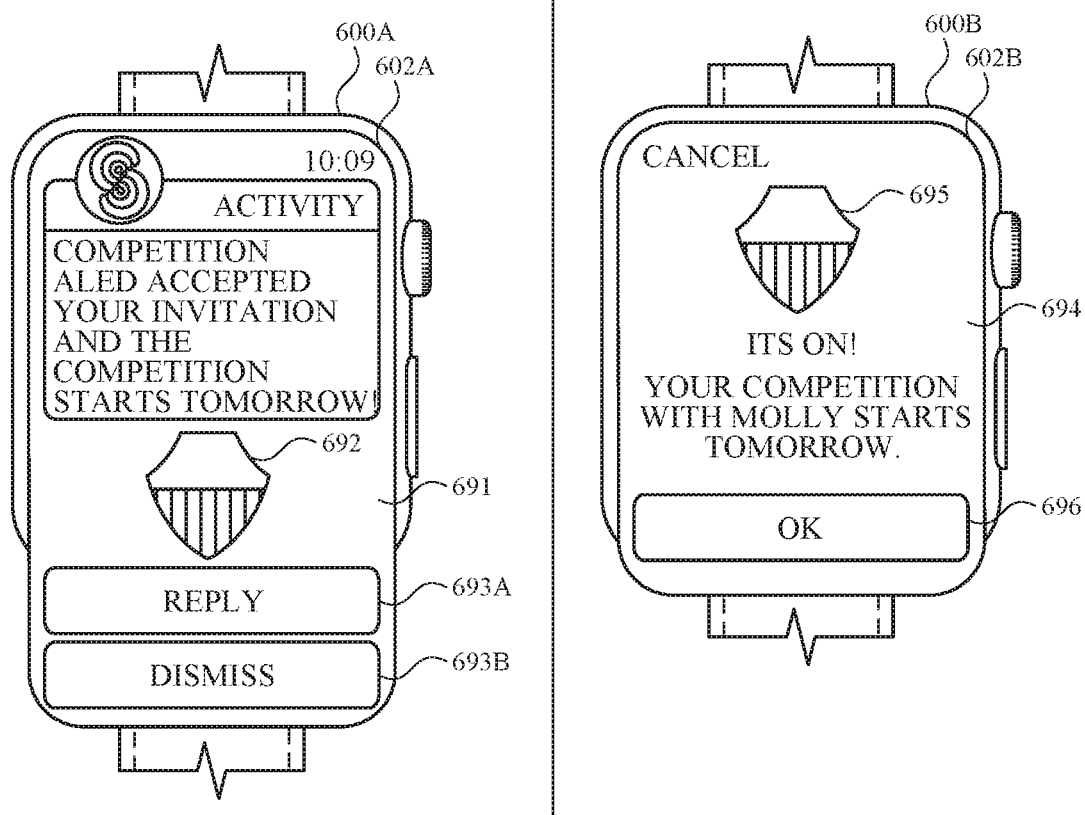

Referring to FIG. 6S, in response to receiving Aled's selection of affordance 690A in user interface 688 (as depicted in FIG. 6R), user interface 694 is displayed on device 600B and user interface 691 is displayed on device 600A. User interface 694 indicates that the new activity competition with Molly will start tomorrow. User interface 694 includes icon 695 (which can have the same theme as icon 618, as depicted in FIG. 6C) and affordance 696, to cease to display user interface 694.

User interface 691 indicates that the invitation that Molly sent was accepted and that the activity competition with Aled will start tomorrow. User interface 691 includes icon 692 (which can have the same theme as icon 618, as depicted in FIG. 6C). User interface 691 further includes a scrollable list of affordances 693, where each affordance is associated with a different operation. For example, the scrollable list of affordances 693 includes first affordance 693A for displaying a messaging user interface (as depicted in FIG. 6I) and second affordance 693B for ceasing to display user interface 691.

While the figures described above depict an electronic device in the form of a smart watch, it should be recognized that any of the user interfaces discussed above can be displayed on different electronic devices, such as a smart phone. In some examples, display of the user interfaces discussed above on an electronic device with a larger display area can include further detail (as depicted in FIG. 6T) not shown on electronic devices with a smaller display.

Referring to FIG. 6T, user interface 697 is displayed on touch-sensitive display 802 of device 800. In some examples, device 800 includes one or more features of device 100, 300, 500, or 600. User interface 697 includes affordance 698, which includes information related to an activity competition between Molly and Aled. Similar to as described above for FIG. 6M, affordance 698 includes icon 698A with a number indicating a number of times that Molly has won an activity competition against Aled. Affordance 698 further includes an identification of Molly (e.g., element 698B) and a score for Molly for the activity competition so far (e.g., element 698C) (sometimes referred to as a cumulative score).

Also similar to as described above for FIG. 6M, affordance 698 further includes a graph for the activity competition, where the graph includes information regarding the activity competition for multiple subsets (e.g., days). The x-axis of the graph includes identifications of multiple subsets of the activity competition. As depicted in FIG. 6T, each subset is a day of the week (e.g., reference 698G points to "Mon" for Monday). It should be noted that "Mon" is located first to indicate that the activity competition began on Monday. In addition, it should be noted that "Fri" (e.g., reference 698J) is visually highlighted (e.g., circled) in FIG. 6T to indicate that Friday is the current day.

The y-axis of the graph includes representations of physical activity detected for each participant in the activity competition for each subset. For example, representation 698H indicates an amount of physical activity received for Molly (e.g., detected by device 600A and transmitted to device 800) on Monday and representation 698I indicates an amount of physical activity detected for Aled on Monday. By having representation 698H adjacent to representation 698I, physical activity for each participant for Monday can easily be compared. When a subset has not occurred yet (e.g., Saturday as depicted in FIG. 6T), representations corresponding to the subset (e.g., reference 618K) can be displayed as zero.

In some examples, representations for subsets can be normalized across the time period such that the highest representation for a subset of the time period can be displayed a certain size, with other representations normalized based upon the highest representation. For example, if Aled scored the most points for the time period on Monday, a representation for Aled on Monday will be the biggest representation. In such an example, a representation for either Molly or Aled with half the score will be represented as half the size of the representation for Aled on Monday. As depicted in FIG. 6T, the graph further includes value 698L for indicating a scale of the graph. The scale can allow a participant to better understand a number of points for each representation in the graph.

It should be noted that representations associated with Molly are illustrated as being visually distinct from representations associated with Aled in FIG. 6T. For example, icon 698A for Molly is visually distinct from icon 698D for Aled. In addition, representations for subsets for Molly are visually distinct from representations for subsets for Aled.

In some examples, representations associated with a participant that is winning an activity competition can be highlighted as compared to a participant that is losing the activity competition. For example, because Molly's cumulative score is higher than Aled's cumulative score, representations associated with Molly visually appear to be highlighted as compared to representations associated with Aled. Visually highlighting representations associated with a participant that is winning can allow a participant to quickly assess how they are doing in the activity competition.

Unlike graph 670 depicted in FIG. 6M, the graph depicted in FIG. 6T further includes additional information regarding the activity competition. For example, the graph includes a daily average number of points for each participant during the activity competition (e.g., reference 698M and 698N). In particular, the graph states that Molly has a daily average of 487 points and Aled has a daily average of 442 points. In the example depicted in FIG. 6T, the daily average for Molly is highlighted (e.g., bolded) because Molly is currently winning the activity competition. It should be recognized that other additional information not included in graph 670 (as depicted in FIG. 6M) can be included in the graph depicted in FIG. 6T.

In some examples, points provided to a participant in an activity competition are based upon a percentage of a goal reached by the participant. For example, a goal can correspond to an amount of walking for each day. Such a goal can be set by the participant either before the activity begins (in some examples) or at any time during the activity competition (in other examples). In some examples, different participants in an activity competition can have different goals. In some examples, points provided to a participant in an activity completion are based upon a two-tier scoring system, where scoring changes when a participant reaches a threshold (e.g., bonus points after the threshold).

FIGS. 7A-7B include a flow diagram illustrating a method for displaying an activity competition representation using an electronic device in accordance with some examples. Method 700 is performed at a device (e.g., 100, 300, 500, 600A, 600B, 800) with a display. Some operations in method 700 are, optionally, combined, the orders of some operations are, optionally, changed, and some operations are, optionally, omitted.

As described below, method 700 provides an intuitive way for displaying a user interface on a device corresponding to a first user, where the user interface includes an activity competition graph (associated with the first user and a second user) having (1) a score comparison for each day of an activity competition between the first user and the second user and (2) a total sum over the activity competition. The user interface permits a user viewing the user interface to readily access physical activity data corresponding to the second user. The method reduces the cognitive burden on a user for accessing physical activity data corresponding to another user, thereby creating a more efficient human-machine interface. For battery-operated computing devices, enabling a user to access physical activity data corresponding to another user faster and more efficiently conserves power and increases the time between battery charges.

At block 702, the device (e.g., FIG. 6M, 600B, and FIG. 6T, 800) receives first user activity data (e.g., FIG. 6M, data represented by top right portion of 666A and representations for Aled, and FIG. 6T, data represented by 698D, 698E, 698F, 698I, and other representations for Aled) for a time period (e.g., a day, a week, a month) (e.g., FIG. 6M, Monday through Sunday for first activity competition and Thursday through Wednesday for second activity competition, and FIG. 6T, Monday through Sunday). The first user activity data includes at least first user activity data (e.g., FIG. 6M, data represented by representation 670C, and FIG. 6T, data represented by representation 698I) for a first time subset (e.g., an hour, a day, a week) (e.g., FIG. 6M, Monday for first activity competition and Thursday for second activity competition, and FIG. 6T, Monday) and first user activity data (e.g., FIG. 6M, data represented by Aled's representation for Tuesday, and FIG. 6T, data represented by Aled's representation for Tuesday) for a second time subset (e.g., FIG. 6M, Tuesday for first activity competition and Wednesday for second activity competition, and FIG. 6T, Tuesday).

In some examples, the first user activity data is received (e.g., via one or more antennas of the device) by the device (e.g., FIG. 6M, 600B, and FIG. 6T, 800) from a second device (e.g., FIG. 6A, 600A). For example, receiving the first user activity data can include detecting, using one or more sensors of the device, the first user activity data. In some examples, the one or more sensors include a heart rate monitor, a GPS locating device, a gyroscope, or the like.

At block 704, the device (e.g., FIG. 6M, 600B, and FIG. 6T, 800) receives second user activity data (e.g., FIG. 6M, data represented by top left portion of 666A and representations for Molly, and FIG. 6T, data represented by 698A, 698B, 698C, 698H, and other representations for Molly) for the time period. The second user activity data includes at least second user activity data (e.g., FIG. 6M, data represented by representation 670B, and FIG. 6T, data represented by representation 698H) for the first time subset and second user activity data (e.g., FIG. 6M, data represented by Molly's representation for Tuesday, and FIG. 6T, data represented by Molly's representation for Tuesday) for the second time subset.

In some examples, the second user activity data is received (e.g., via one or more antennas of the device) by the device from a second device (e.g., FIG. 6A, 600A). For example, receiving the second user activity data can include receiving the second user activity data from an external device (e.g., via a transmission from the external device) (e.g., FIG. 6A, 600A).

In some examples, in response to receiving the second user activity data from an external device (e.g., FIG. 6A, 600A), the device (e.g., FIG. 6M, 600B, and FIG. 6T, 800) can output an activity notification (e.g., visual, haptic, or audio alert) (FIG. 6A, 612).

At 712, the device (e.g., FIG. 6M, 600B, and FIG. 6T, 800) displays, on the display (e.g., FIG. 6M, 602B, and FIG. 6T, 802), a user interface (e.g., FIG. 6M, 664, and FIG. 6T, 697). In some examples, the activity notification (e.g., FIG. 6M, 612) described above is outputted prior to displaying the user interface.

In some examples, prior to displaying the user interface (e.g., FIG. 6M, 664, and FIG. 6T, 697), the device (e.g., FIG. 6M, 600B, and FIG. 6T, 800) displays an activity summary notification (e.g., FIG. 6M, 664 when the user interface is FIG. 6N, 672). The activity summary notification can include: (1) a first notification element (e.g., information relating to an activity competition between the first and second user) (e.g., FIG. 6M, 666A) based on the first user activity data and/or the second user activity data; and (2) a second notification element (e.g., information relating to an activity competition between the third user and the first user) (e.g., FIG. 6M, 666B) based on at least third user activity data, different from the first user activity data and different than the second user activity data.

At 714, the user interface (e.g., FIG. 6M, 664, and FIG. 6T, 697) includes a representation (e.g., graphical or textual indication of a value) (e.g., FIG. 6M, 670C) of the first user activity data for the first time subset.

At 716, the user interface (e.g., FIG. 6M, 664, and FIG. 6T, 697) further includes a representation (e.g., graphical or textual indication of a value) (e.g., FIG. 6M, Aled's representation for Tuesday) of the first user activity data for the second time subset.

At 718, the user interface (e.g., FIG. 6M, 664, and FIG. 6T, 697) further includes a cumulative representation (e.g., a graphical or textual summary of activity data for the entire time period) (e.g., FIG. 6M, top right portion) of the first user activity data for the time period. The cumulative representation of the first user activity data for the time period is based on at least the first user activity data for a first time subset and the first user activity data for a second time subset. In some examples, the cumulative representation is presented in the same units as (or different units than) the representations of the activity data for the time subsets.

At 720, the user interface (e.g., FIG. 6M, 664, and FIG. 6T, 697) further includes a representation (e.g., FIG. 6M, 670B) of the second user activity data for the first time subset. Displaying scores for different users for a day provides feedback as to activity data received by the device for the day. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. The scores also provide an improved man-machine interface by reducing the number of interactions to display activity data information for multiple users.

In some examples, the representation of the second user activity data for the first time subset is displayed adjacent to (e.g., next to or in a first region of the user interface) the representation (e.g., FIG. 6M, 670C) of the first user activity data for the first time subset. In some examples, the representation of the first user activity data for the first time subset is adjacent (e.g., without any interceding representations of activity data for other time subsets) to the representation of the second user activity data for the first time subset. Displaying a score for a first user adjacent to a score for a second user provides comparative feedback to physical activity being detected by the device. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

At 722, the user interface (e.g., FIG. 6M, 664, and FIG. 6T, 697) further includes a representation (e.g., FIG. 6M, Molly's representation for Tuesday) of the second user activity data for the second time subset. Displaying scores for different days provides feedback as to activity data received by the device for different days. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. The scores also provide an improved man-machine interface by reducing the number of interactions to display activity data information for separate time subsets.

In some examples, the representation of the second user activity data for the second time subset is displayed adjacent to (e.g., next to or in a second region of the user interface) the representation (e.g., FIG. 6M, Aled's representation for Tuesday) of the first user activity data for the second time subset and is not displayed adjacent to representations of second user activity data for any other time subsets.

At 724, the user interface (e.g., FIG. 6M, 664, and FIG. 6T, 697) further includes a cumulative representation (e.g., FIGS. 6M, 668A, 668B, and 669C) of the second user activity data for the time period. The cumulative representation of the second user activity data for the time period can be based on at least the second user activity data for a first time subset and the second user activity data for a second time subset. Displaying total scores for users provides feedback as to activity data being received by the device for the first user and the second user. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. Displaying total scores for users provides feedback as to activity data being received by the device for the first user and the second user. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, the first time subset of the first user activity data corresponds to the first time subset of the second user activity data.

In some examples, the user interface (e.g., FIG. 6M, 664, and FIG. 6T, 697) can further include a representation (e.g., a textual representation; a graphical representation) (e.g., FIG. 6M, 670F) of the number of remaining time subsets in the time period.

In some examples, the user interface (e.g., FIG. 6M, 664, and FIG. 6T, 697) includes an identification of a current time subset (e.g., FIG. 6M, "F" in first activity competition), where the identification of the current time subset is visually emphasized (e.g., FIG. 6M, circle around "F").

In some examples, a length of the first time subset is equal to a length of the second time subset (e.g., FIG. 6M, Monday through Sunday).

In some examples, displaying the user interface (e.g., FIG. 6M, 664, and FIG. 6T, 697) can further include: (1) in accordance with a determination that a first value (e.g., FIG. 6M, "2136") corresponding to the cumulative representation of the first user activity data exceeds a second value (e.g., FIG. 6M, "2303") corresponding to the cumulative representation of the second user activity data, visually emphasizing (e.g., highlighting) the cumulative representation of the first user activity data for the time period; and (2) in accordance with a determination that the second value exceeds the first value, visually emphasizing (e.g., FIG. 6M, 668A) the cumulative representation of the second user activity data for the time period.

In some examples, the representations can be normalized.

In some examples, the representations can be based upon percentage completion of one or more goals. Optionally, the one or more goals are user defined.

In some examples, the first user activity data corresponds to a first user and the second user activity data corresponds to a second user. In such examples, prior to displaying the user interface (e.g., FIG. 6M, 664, and FIG. 6T, 697), the device displays a competition completion user interface (e.g., an interface showing details of a previously completed competition) (e.g., FIG. 6P, 680). The competition completion user interface can include a representation (e.g., FIG. 6P, Aled's portion of graph) of activity data for the first user for a preceding time period (e.g., FIG. 6P, Monday through Sunday), a representation (e.g., FIG. 6P, Molly's portion of graph) of activity data for the second user for the preceding time period, and a new competition initiation affordance (e.g., FIG. 6P, 684C). The competition completion user interface can also include content (e.g., FIG. 6P, text at top of 680) based upon whether the first user or the second user had more activity data for the preceding time period. In such examples, the device receives a first user input (e.g., FIG. 6P, 611 but on wrong device) corresponding to selection of the new competition initiation affordance and, in response to receiving the first user input, initiates a process for an activity competition between the first user and the second user (e.g., sending an invitation to the second user to accept/start a competition between the first and second user). In such examples, the user interface is displayed after (e.g., in response to the second user accepting the invitation to start the competition) initiating the process for an activity competition between the first user and the second user. Providing different entry points to activity competitions provides increased interaction with the device by allowing the initiation of activity competitions to be available in an intuitive manner and in multiple locations. Providing entry points as described herein increases user participation in activity competitions, enhances the operability of the device, and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, while displaying the user interface, the device receives a second user input corresponding to a request to display additional information corresponding to the first user activity data and/or the second user activity data. In such examples, in response to receiving the second user input, the device displays a second user interface including additional information corresponding to the first user activity data and/or the second user activity data. In such examples, the additional information was not included in the user interface. In some examples, the additional information includes contact information, daily average, actual number of points corresponding to activity data for particular days, or the like. In some examples, the additional information functionality occurs when the affordance is included in an alert rather than a notification, where an alert must be dismissed before looking at other content using the device and a notification is available for a user to view in the background.

In some examples, while displaying the user interface, the device receives a third user input corresponding to a request to display a messaging user interface (e.g., FIG. 6I, 646) for sending a message to an external device (e.g., FIG. 6I, 600A). In such examples, in response to receiving the third user input, the device displays the messaging user interface. In some examples, the messaging interface functionality occurs when the affordance is included in a notification rather than an alert. In some examples, the messaging user interface includes one or more predefined replies (e.g., FIG. 6I, 648).

In some examples, in response to user input at a location corresponding to a representation, the device displays a messaging user interface (e.g., FIG. 6I, 646). In other examples, in response to user input at a location corresponding to a representation, the device displays additional information regarding a second user corresponding to the second user activity data.

In some examples, the first user activity data includes standing data, moving data, and exercise data.

In some examples, the first user activity data corresponds to a first user and the second user activity data corresponds to a second user. In such examples, the user interface further can include a representation (e.g., FIG. 6M, 668A) based on a comparison of activity data for the first user and the second user for one or more previous time periods, preceding the time period.

Note that details of the processes described above with respect to method 700 (e.g., FIGS. 7A-7B) are also applicable in an analogous manner to the methods described below. For example, method 700 optionally includes one or more of the characteristics of the various methods described below with reference to method 900, method 1100, or method 1300. For example, the user interface of method 700 can be included in an affordance for an activity competition of method 900. For another example, the user interface of method 700 can be based upon activity data detected based upon the alert of method 1100. For another example, the user interface of method 700 can include pace information detected based upon a pace configured as described in method 1300. For brevity, these details are not repeated below.

FIGS. 8A-8Y illustrate exemplary user interfaces related to a friends list for activity sharing in accordance with some examples. The activity sharing can include representations for activity competitions (as discussed above in FIGS. 6A-6T and 7A-7B). The friends list can also include affordances for initiating activity competitions in an intuitive manner, as further described below.

Referring to FIG. 8A, user interface 804 (referred to as a home screen) is displayed on touch-sensitive display 802 of device 800. For explanatory purposes, device 800 belongs to a first user, Aled. User interface 804 includes multiple affordances 806 for different applications, including affordance 806A for an activity application. In FIG. 8B, device 800 receives selection of affordance 806A and, in response, causes a user interface (e.g., user interface 808 as depicted in FIG. 8C) corresponding to the activity application to be displayed.

Figure 8C:
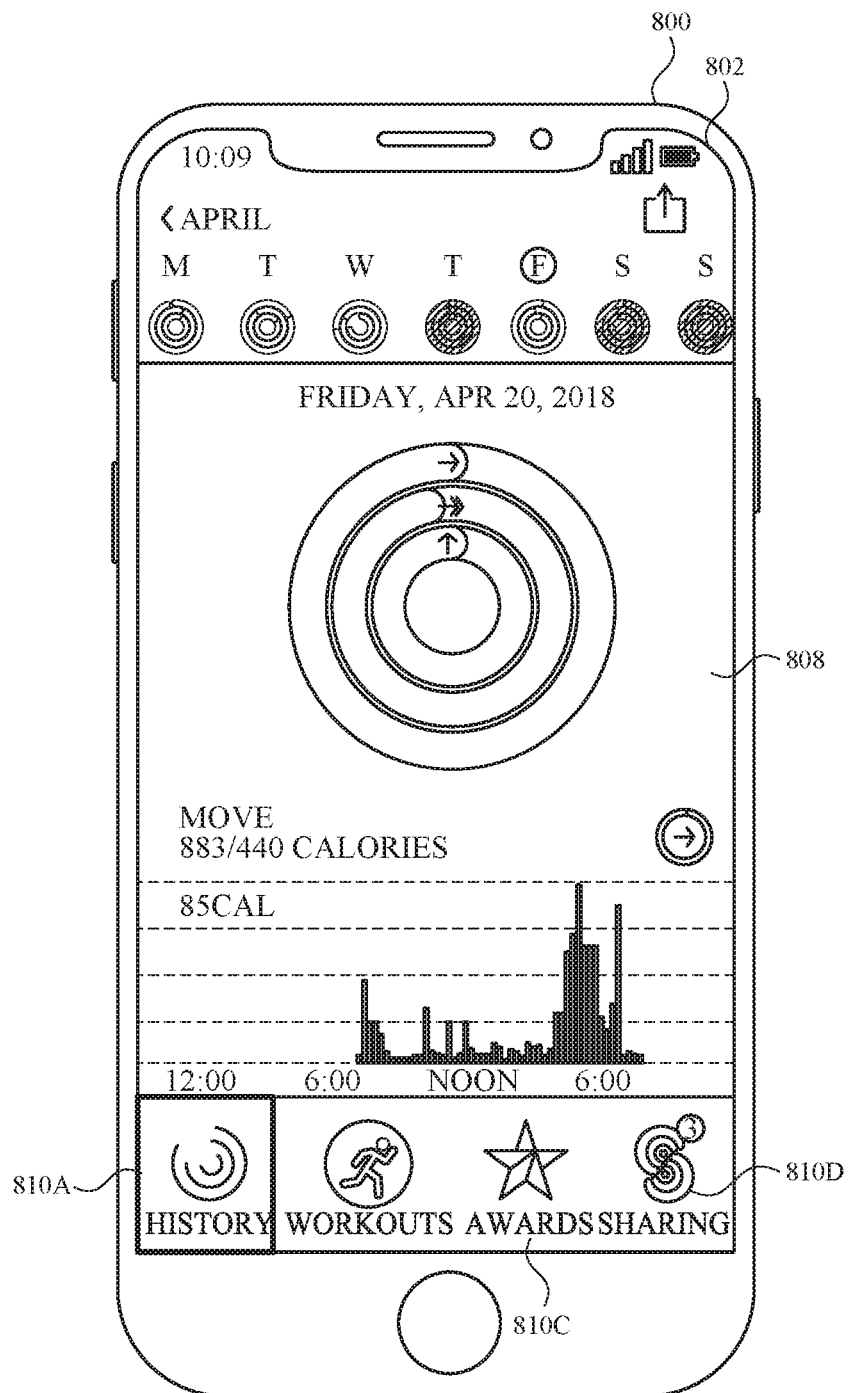
Figure 8D:
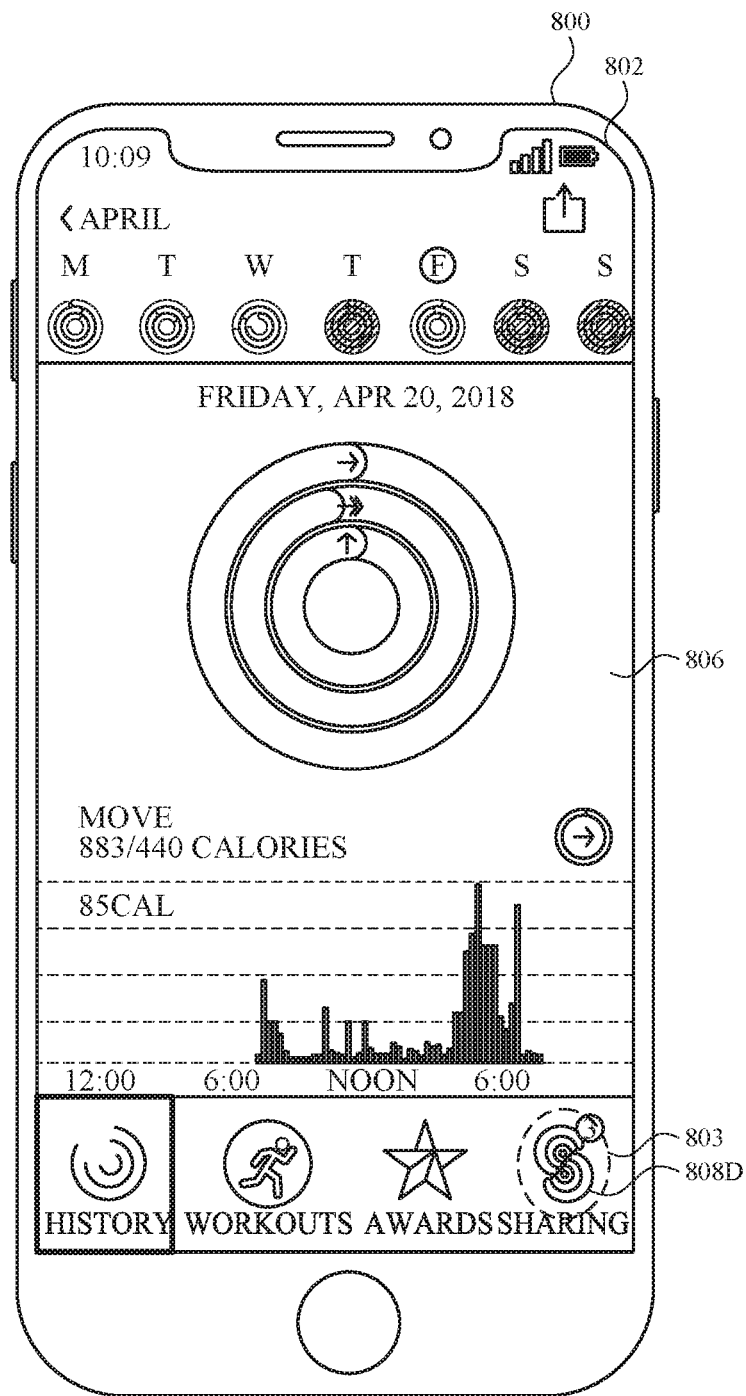

Referring to FIG. 8C, user interface 808 includes affordance 810D for displaying a user interface corresponding to sharing activity data. As depicted in FIG. 8C, affordance 810D includes an indication that three notifications related to the user interface corresponding to sharing activity data are pending. In FIG. 8D, device 800 receives selection of affordance 810D and, in response, causes a user interface (e.g., user interface 812 as depicted in FIG. 8E) corresponding to sharing activity data to be displayed.

Figure 8E:
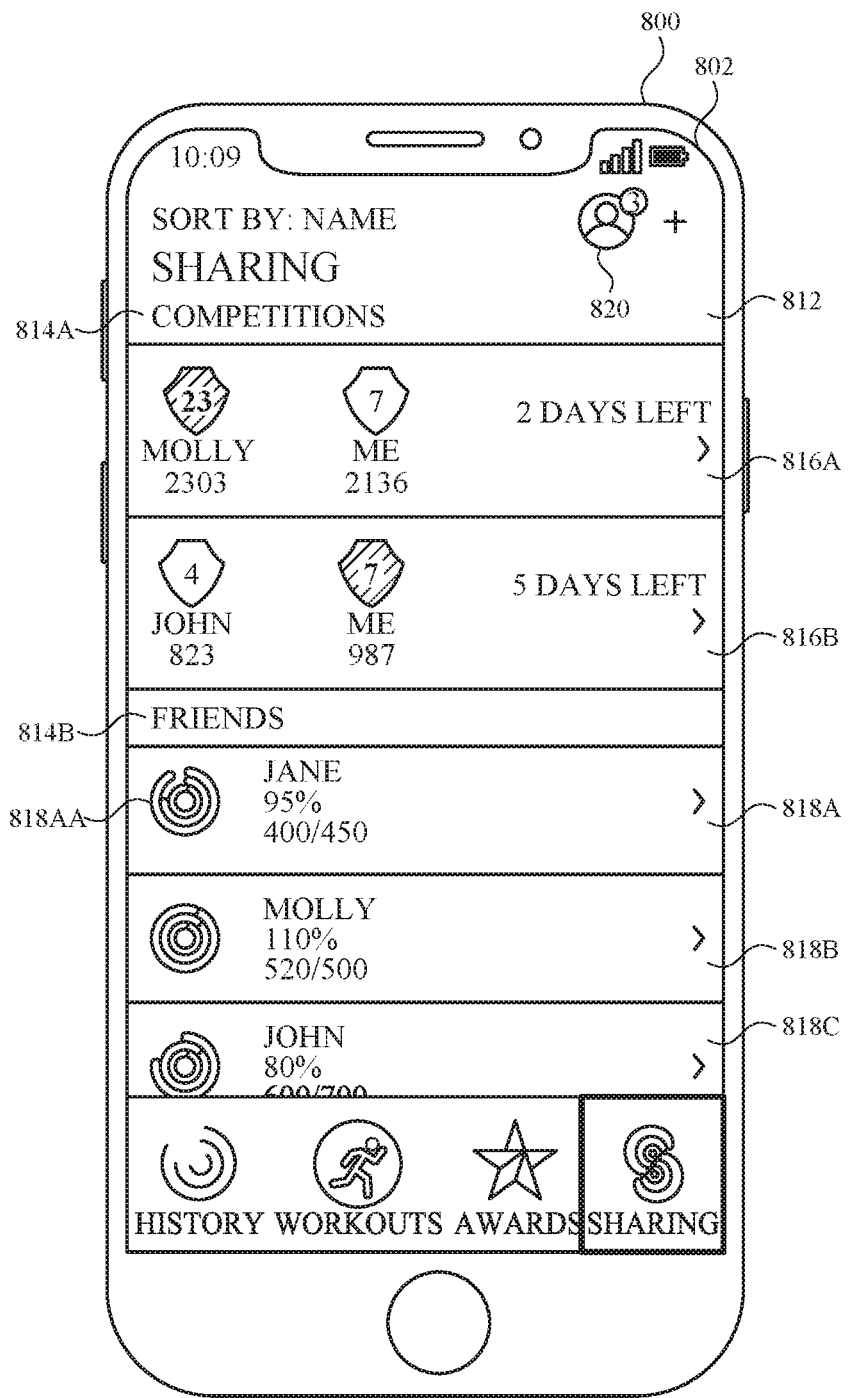

FIG. 8E illustrates device 800 displaying user interface 812 (sometimes referred to as a friends list). User interface 812 includes first portion 814A for information related to activity competitions and second portion 814B for information related to friends.

As depicted in FIG. 8E, first portion 814A is above second portion 814B such that first portion 814A is displayed before (when scrolling through the interface) second portion 814B. Displaying first portion 814A before second portion 814B can affect what is displayed when first portion 814A and second portion 814B include too much content to be displayed on touch-sensitive display 802. For example, first portion 814A will be displayed in its entirety before any of second portion 814B when first portion 814A is before second portion 814B in user interface 812. In such an example, content not included in touch-sensitive display 802 can be displayed by in response to a scrolling input.

First portion 812 includes a scrollable list of affordances 816, where each affordance is associated with a different activity competition. For example, the scrollable list of affordances 816 includes first affordance 816A for a first activity competition (between Molly and Aled) and second affordance 816B for a second activity competition (between John and Aled). In some examples, the order of affordances for activity competitions can be based upon when the activity competitions are finishing. For example, activity competitions finishing sooner can be included in the scrollable list of affordances 816 before activity competitions finishing later.

First affordance 816A includes information related to the first activity competition, such as a cumulative score for Molly (i.e., 2303) and Aled (i.e., 2136, labeled "ME"), a number of times Molly has won a past activity competition between Molly and Aled (i.e., 23 times), a number of times Aled has won a past activity competition between Molly and Aled (i.e., 7 times), and an amount of time left in the first activity competition (i.e., 2 days left). Second affordance 616B includes information related to the second activity competition, which can be similar to the information related to the first activity competition described above. It should be noted that, in some examples, affordances in the scrollable list of affordances 816 can include more or less information than depicted in FIG. 8E, including an affordance including more information than another affordance.

Second portion 814B includes a scrollable list of affordances 818, where each affordance is associated with a different friend of a user (e.g., Aled) logged into device 800. For example, the scrollable list of affordances 818 includes first affordance 818A for a first friend (i.e., Jane), second affordance 818B for a second friend (i.e., Molly), and third affordance 818C for a third friend (i.e., John). It should be noted that, in some examples, friends included in second portion 814B can also be included in an activity competition in first portion 814A. For example, Molly is a participant of the first activity competition (e.g., first affordance 816A) and included in the scrollable list of affordances 818 (e.g., second affordance 818B). In other examples, friends included in first portion 814A are not included in second portion 814B.

Each affordance in the scrollable list of affordances 818 includes information related to the corresponding friend. For example, first affordance 818A corresponds to Jane and includes an identification of Jane (e.g., "Jane"), a percent of goals for Jane that Jane has completed (e.g., "95%"), an absolute amount of a goal that Joan has completed with the absolute amount of the goal (e.g., "400/450"), and icon 818AA visually depicting an amount of multiple goals that Joan has completed.

User interface 812 further includes sharing affordance 820. Selection of sharing affordance 820 causes device 800 to display a user interface (e.g., user interface 834 as depicted in FIG. 8O) with sharing details, as further described below with respect to FIG. 8O. Sharing affordance 820 includes an indication that three notifications related to sharing data are pending.

Figure 8F:
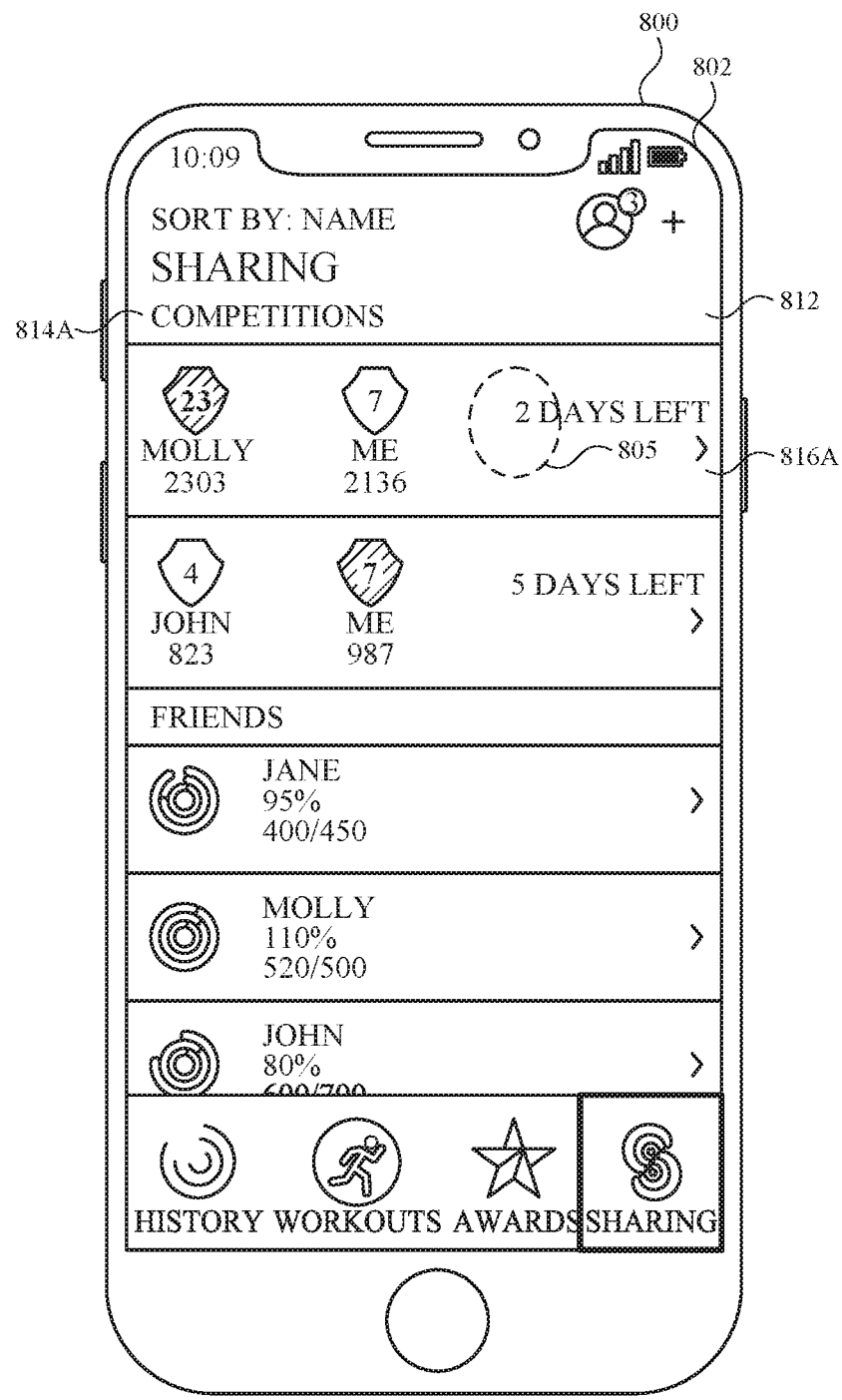

FIG. 8F again illustrates user interface 812 (as depicted in FIG. 8E). As described above, user interface 810 includes first affordance 816A. Referring to FIG. 8F, user input (e.g., tap input) 805 is received by device 800, where user input 805 corresponds to selection of first affordance 816A in first portion 814A. In accordance with a determination that user input 805 is detected at first affordance 816A in the scrollable list of affordances 816, a user interface (e.g., user interface 822 as depicted in FIG. 8G) with additional information related to the first activity competition (not included in first affordance 816A) is displayed.

Figure 8G:
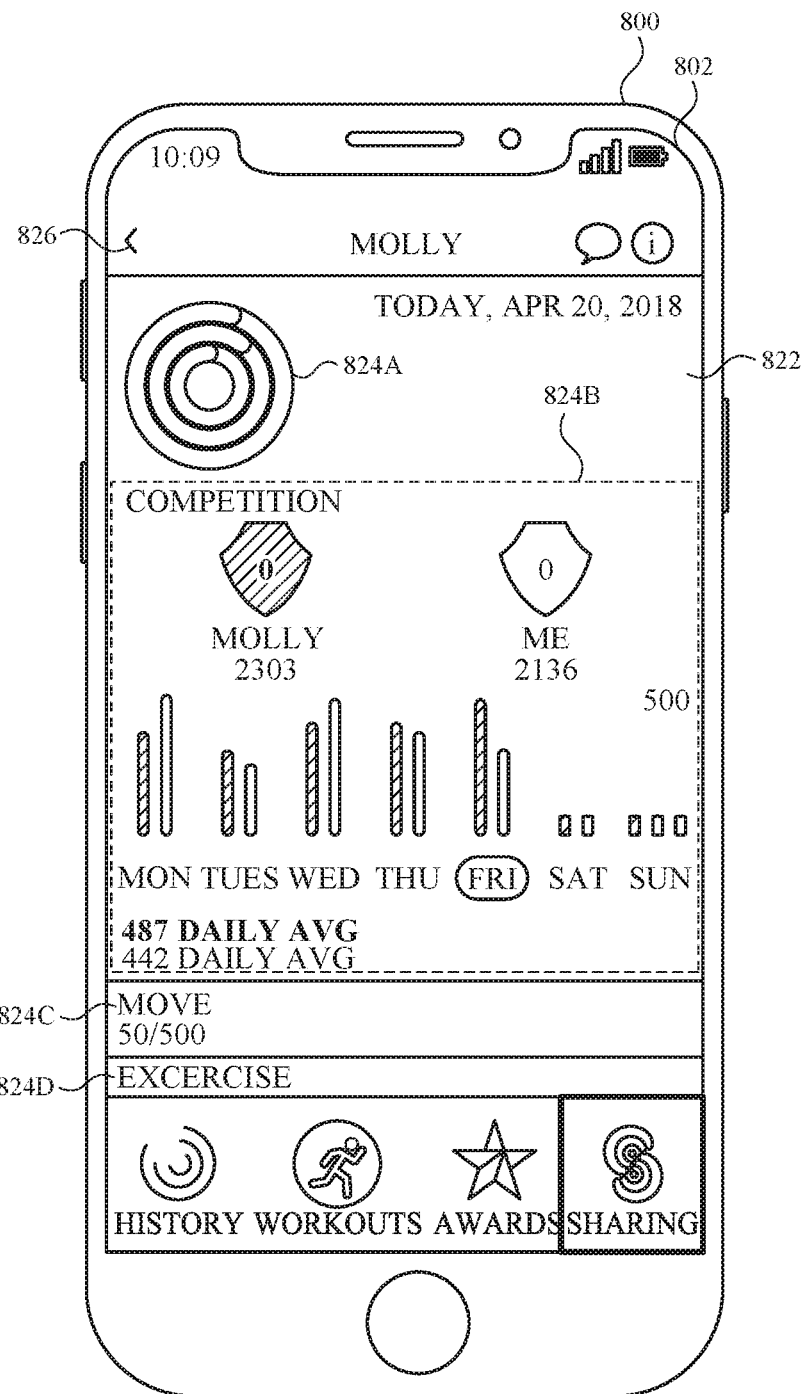

Referring to FIG. 8G, device 800 displays user interface 822 on touch-sensitive display 802 in response to selection of first affordance 816A in first portion 814A (as depicted in FIG. 8F). User interface 822 includes multiple representations 824 of information related to the first activity competition. For example, representation 824A is a visual representation of Molly's current completion of activity goals for the current day. The visual representation includes three circles, each circle corresponding to a different goal. Representation 824B includes information for the first activity competition, as discussed above in FIG. 6T. Representation 824C includes a current status (e.g., 50/500) for Molly completing a first goal (e.g., move goal). Representation 824D includes a current status for Molly completing a second goal (e.g., exercise goal). It should be recognized that user interface 816 can include more or fewer representations of information related to the first activity competition than depicted in FIG. 8G.

Figure 8H:
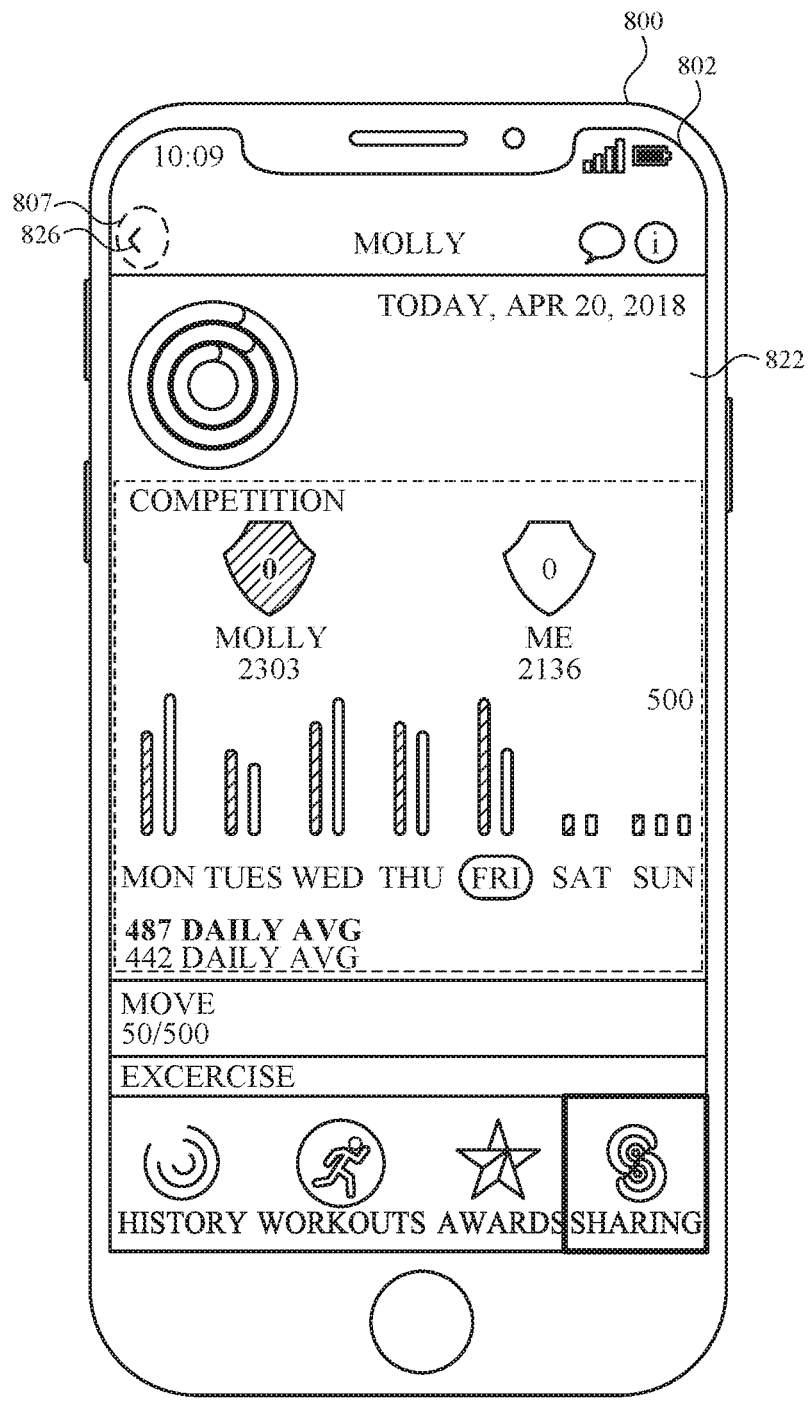

User interface 822 also includes back affordance 826 to cause a previous user interface (e.g., user interface 812 as depicted in FIG. 8E) to be displayed. Referring to FIG. 8H, user input (e.g., tap input) 807 is received, where user input 807 corresponds to selection of back affordance 826. In accordance with a determination that user input 807 is detected at back affordance 826, a user interface (e.g., user interface 812 as depicted in FIG. 8I) is displayed.

Figure 8I:
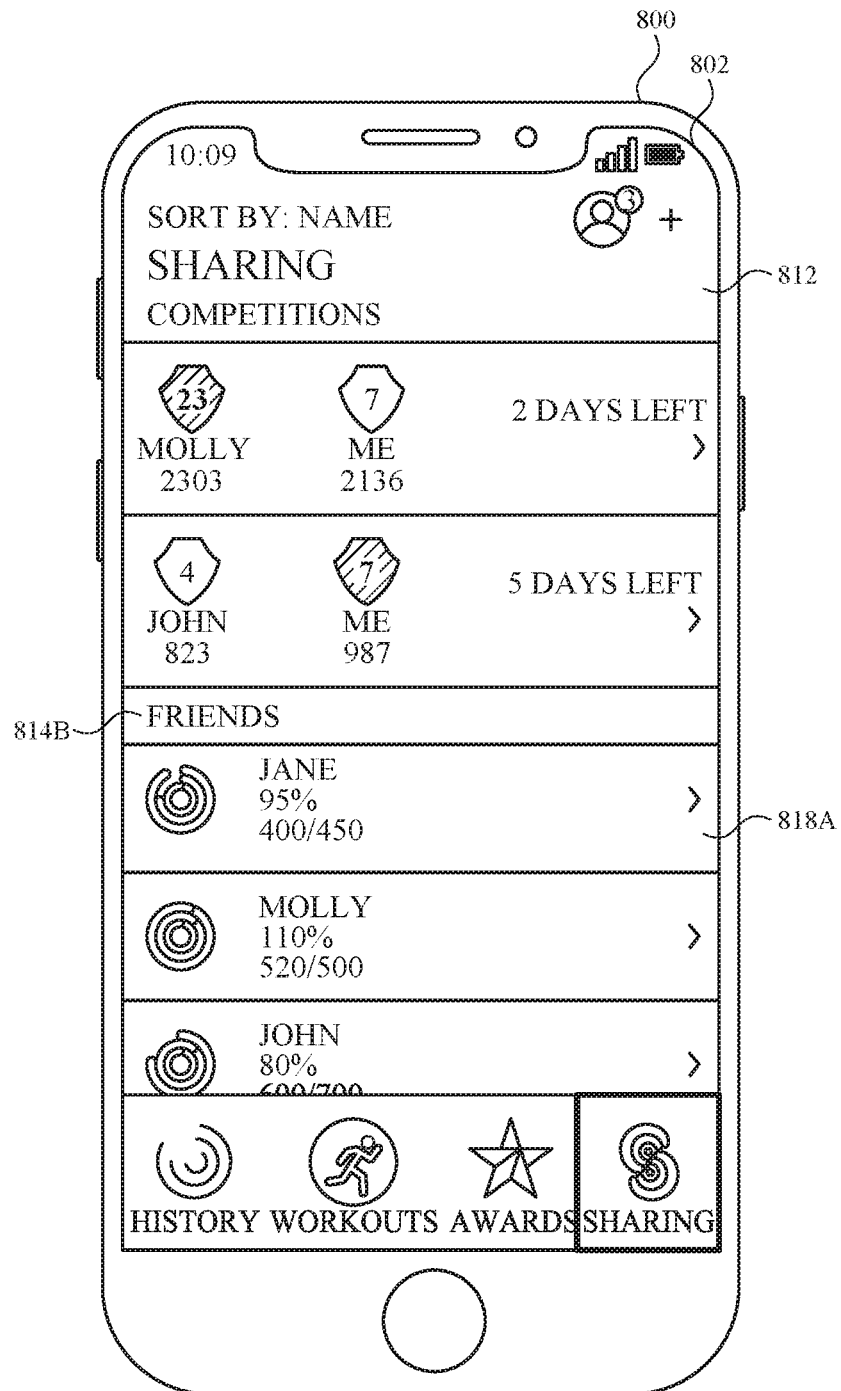
Figure 8J:
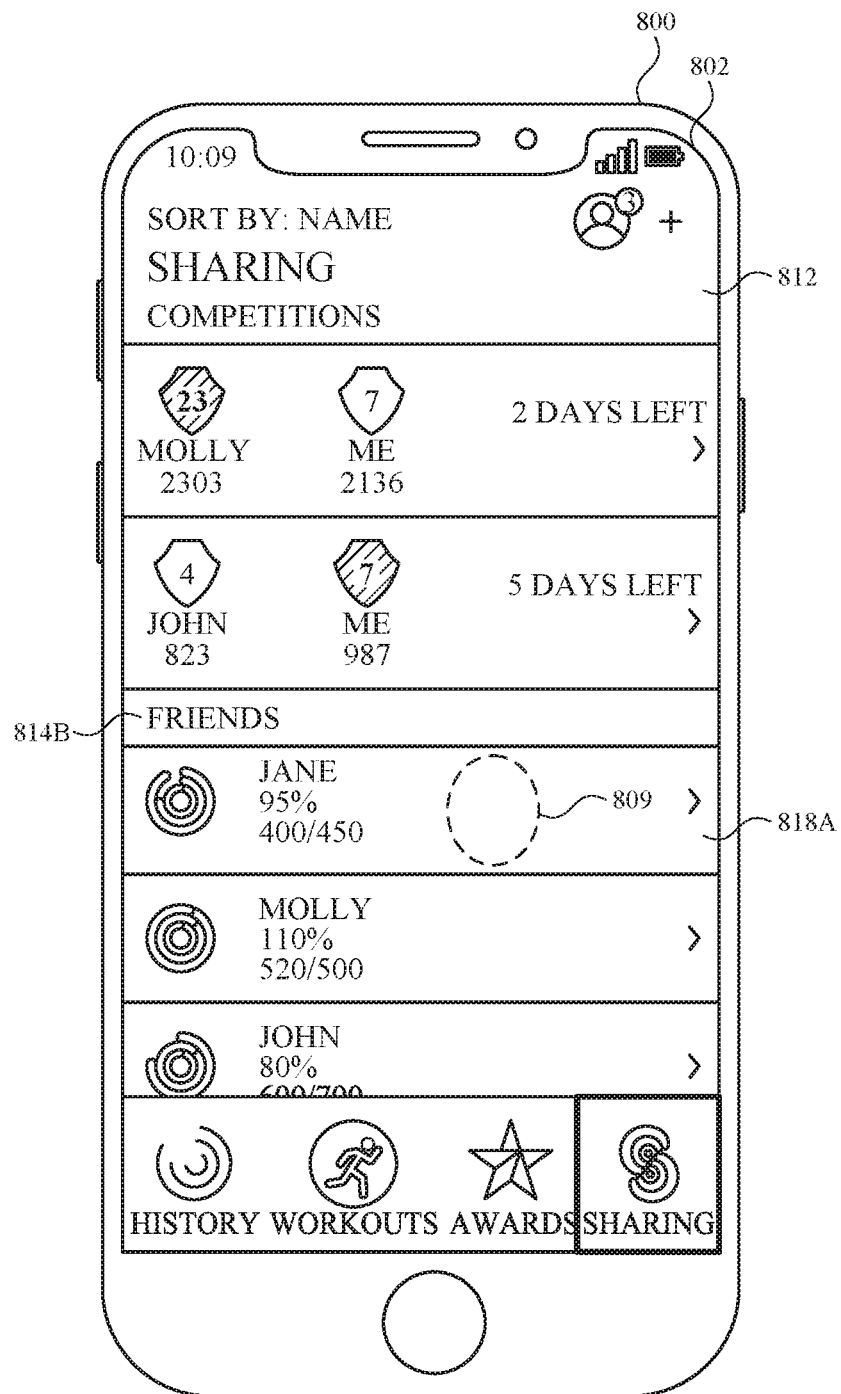

FIG. 8I illustrates device 800 displaying user interface 812 in response to selection of back affordance 826 (as depicted in FIG. 8H). As described above, user interface 812 includes first affordance 818A in second portion 814B. Referring to FIG. 8J, user input (e.g., tap input) 809 is received, where user input 809 corresponds to selection of first affordance 818A. In accordance with a determination that user input 809 is detected at first affordance 818A, a user interface (e.g., user interface 812 as depicted in FIG. 8I) with information related to a friend (e.g., Jane) corresponding to first affordance 818A is displayed.

Figure 8K:
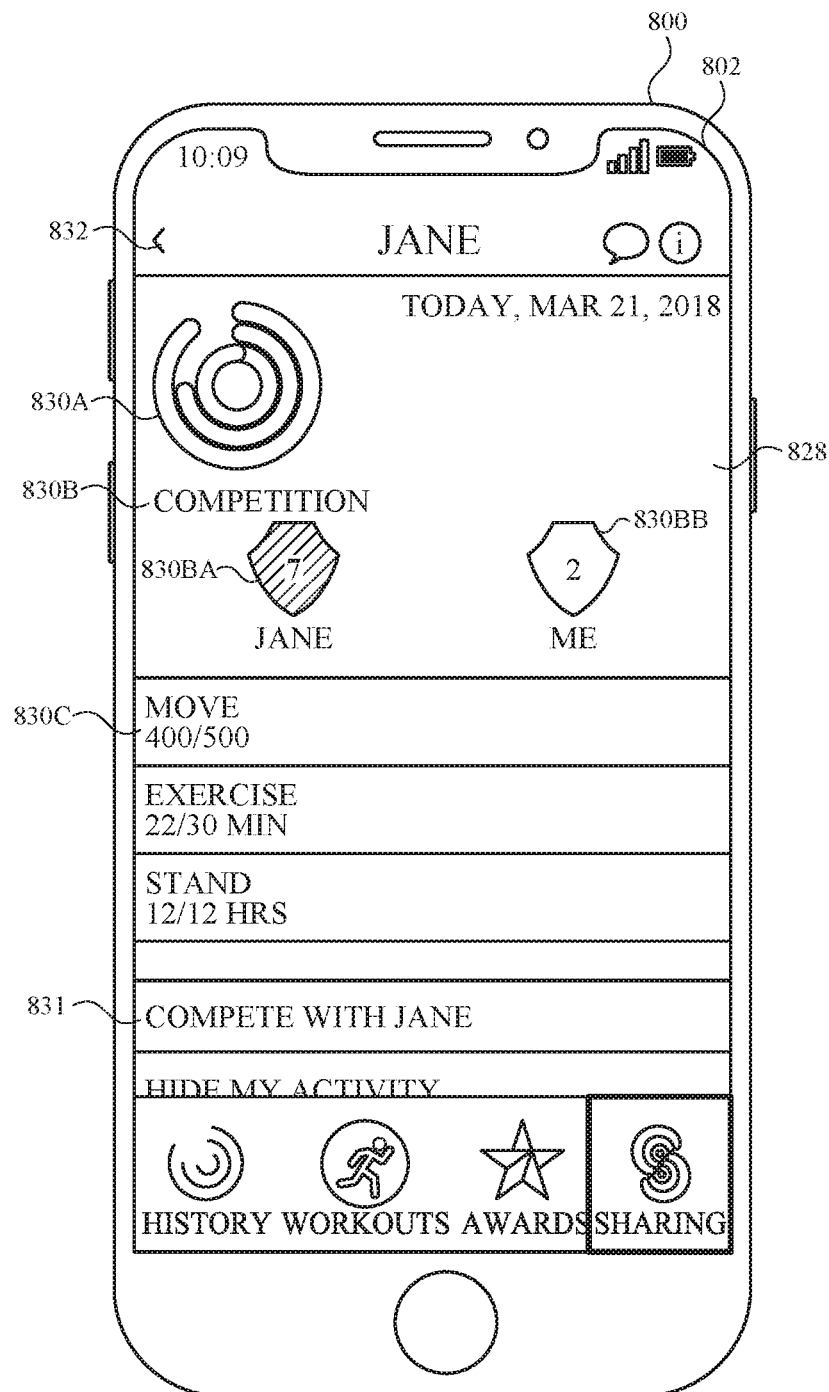

Referring to FIG. 8K, device 800 displays user interface 828 on touch-sensitive display 802 in response to selection of first affordance 818A in second portion 814B (as depicted in FIG. 8J). User interface 828 includes multiple representations 830 of information related to Jane. For example, representation 830A is a visual representation of Jane's current completion of activity goals for the current day. The visual representation includes three circles, each circle corresponding to a different goal. Representation 830B includes information related to past activity competitions between Jane and Aled. For example, icon 830BA indicates a number (e.g., 7) of past activity competitions that Jane beat Aled (e.g., "ME") and icon 830BB indicates a number (e.g., 2) of past activity competitions that Aled beat Jane. Representation 830C includes a current status (e.g., 400/500) for Jane completing a first goal (e.g., move goal).

User interface 828 also includes invite affordance 831 to initiate a process for beginning an activity competition between Jane and Aled. For explanatory purposes, selection of invite affordance 831 can cause user interface 616 (as depicted in FIG. 6C) or user interface 686 (as depicted in FIG. 6Q) to be displayed on touch-sensitive display 802.

Figure 8L:
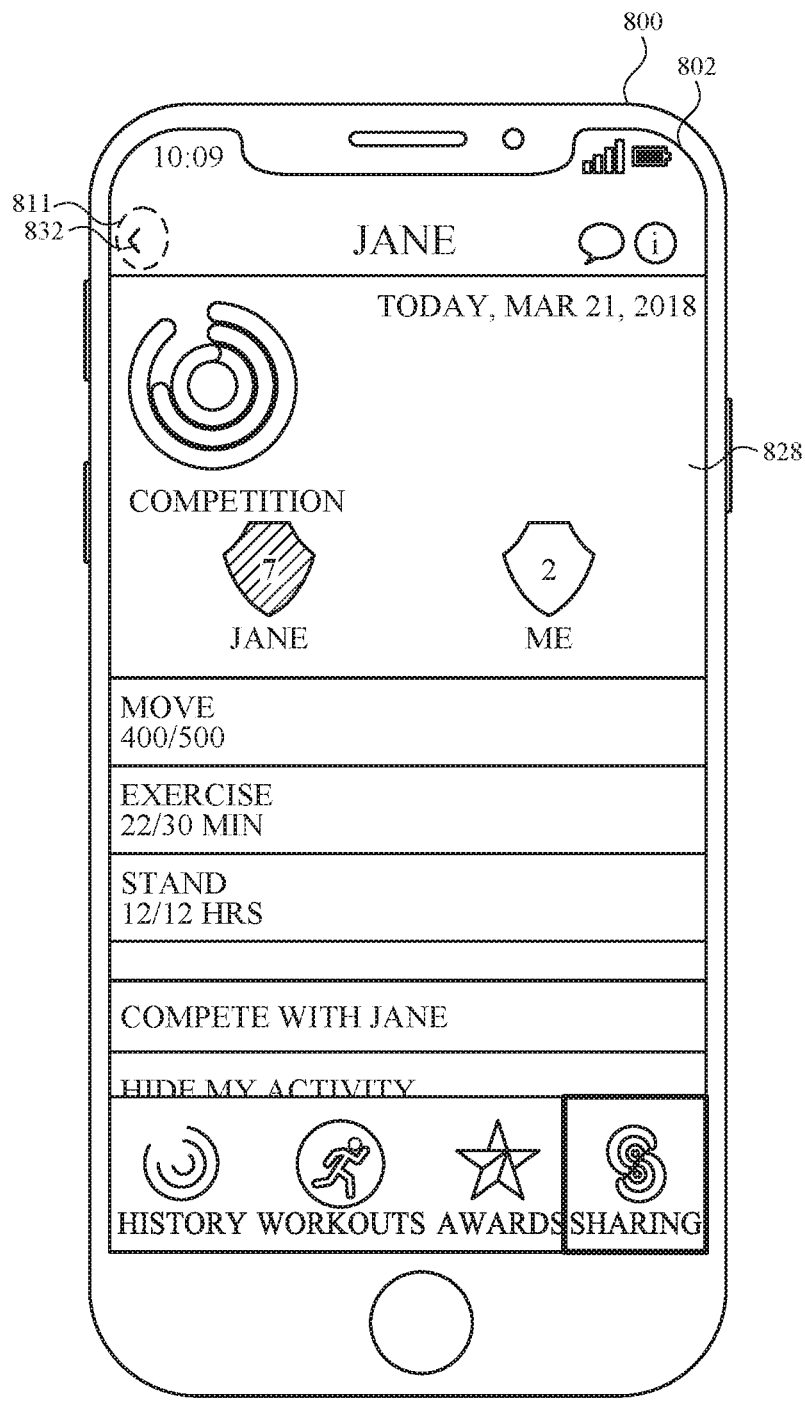

Referring to FIG. 8K, user interface 828 also includes back affordance 832 to cause a previous user interface (e.g., user interface 812 as depicted in FIG. 8J) to be displayed. Referring to FIG. 8L, user input (e.g., tap input) 811 is received, where user input 811 corresponds to selection of back affordance 832. In accordance with a determination that user input 811 is detected at back affordance 832, a user interface (e.g., user interface 812 as depicted in FIG. 8M) is displayed.

Figure 8M:
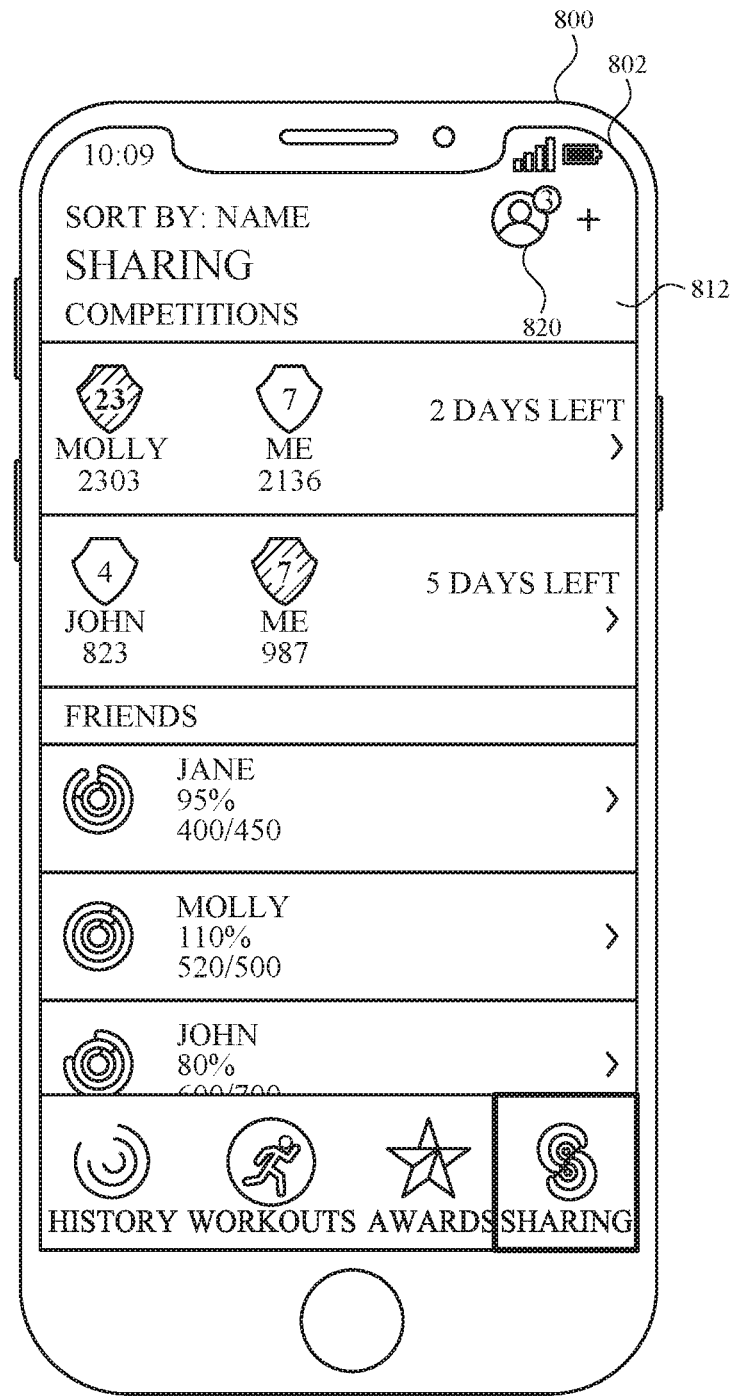
Figure 8N:
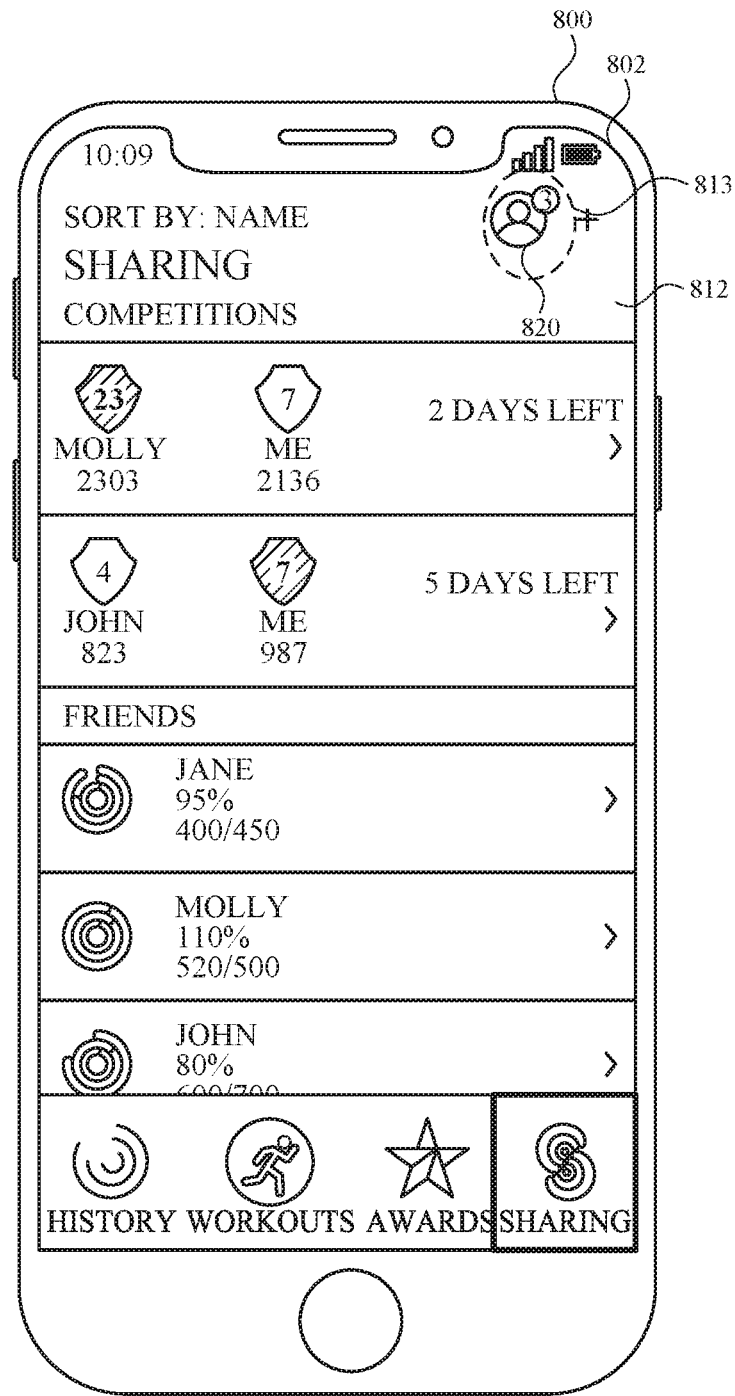
Figure 80:
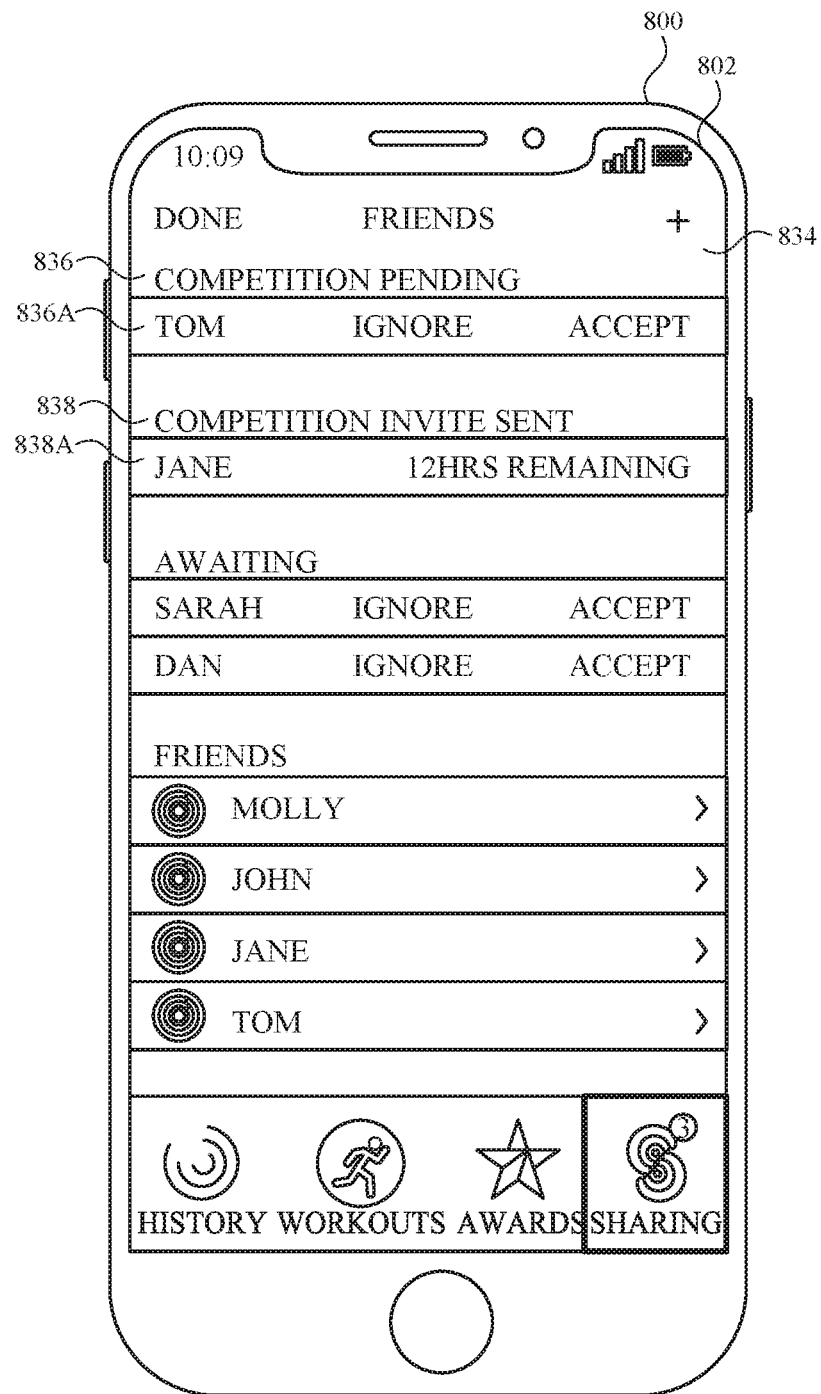

FIG. 8M illustrates device 800 displaying user interface 812 in response to selection of back affordance 832 (as depicted in FIG. 8L). As described above, user interface 812 includes sharing affordance 820. Referring to FIG. 8N, user input (e.g., tap input) 813 is received, where user input 813 corresponds to selection of sharing affordance 820. In accordance with a determination that user input 813 is detected at sharing affordance 820, a user interface (e.g., user interface 834 as depicted in FIG. 8O) is displayed.

Referring to FIG. 8O, device 800 displays user interface 834 on touch-sensitive display 802 in response to selection of sharing affordance 820 (as depicted in FIG. 8N). User interface 834 is divided into multiple portions (e.g., first portion 836 and second portion 838), each portion including a different type of information.

First portion 836 includes information related to invitations for activity competitions received by device 800. For example, first portion 836 includes invitation 836A. Invitation 836A indicates that Tom has sent an invitation to begin an activity competition to Aled (e.g., to one or more devices (e.g., device 800) associated with Aled). Invitation 836A includes an accept affordance and an ignore affordance in order to respond to the invitation from Tom. Selection of the accept affordance initiates a process to begin an activity competition between Tom and Aled. Selection of the ignore affordance removes invitation 836A from first portion 836.

Second portion 838 includes information related to invitations for activity competitions sent by device 800. For example, second portion 838 includes invitation 838A. Invitation 838A indicates that Aled has sent an invitation to begin an activity competition to Jane. Invitation 838A includes a representation of the amount of time that remains for Jane to accept the invitation.

Figure 8P:
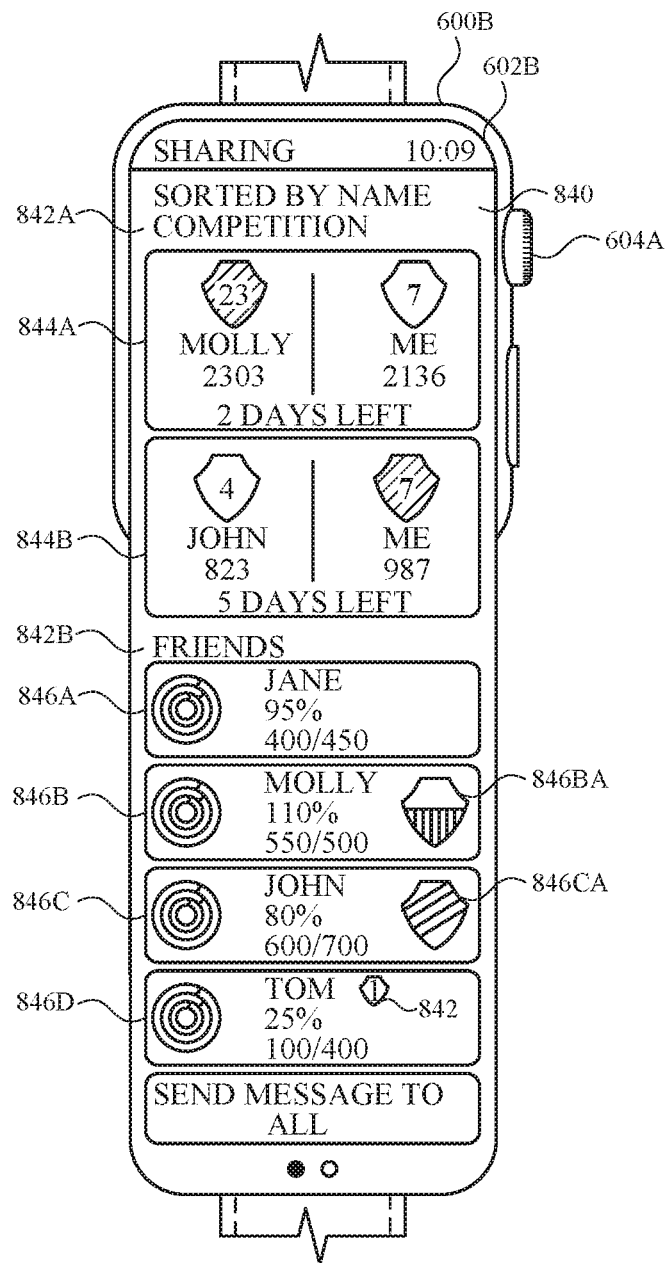

FIG. 8P illustrates device 600B (e.g., a second device associated with the same user, Aled) displaying user interface 840 on touch-sensitive display 602B. User interface 840, like user interface 812 (as depicted in FIG. 8E), corresponds to a friends list. However, unlike user interface 812, user interface 840 is configured to be used on an electronic device with a smaller display area than device 800.

Similar to user interface 812, user interface 830 includes first portion 842A and second portion 842B. As depicted in FIG. 8P, first portion 842A is above second portion 842B such that first portion 842A is displayed before second portion 842B. Displaying first portion 842A before second portion 842B can affect what is displayed when first portion 842A and second portion 842B include too much content to be displayed on touch-sensitive display 602B. For example, first portion 842A will be displayed in its entirety before any of second portion 842B when first portion 842A is before second portion 842B in user interface 812. In such an example, content not included in touch-sensitive display 802 can be displayed by in response to a scrolling input (e.g., rotation of rotatable input mechanism 604A).

Referring to FIG. 8P, first portion 842A includes a scrollable list of affordances 844, where each affordance is associated with a different activity competition. For example, the scrollable list of affordances 844 includes first affordance 844A for a first activity competition (between Molly and Aled) and second affordance 816B for a second activity competition (between John and Aled). In some examples, the order of affordances for activity competitions can be based upon when the activity competitions are finishing. For example, activity competitions finishing sooner can be included in the scrollable list of affordances 844 before activity competitions finishing later.

First affordance 844A includes information related to the first activity competition, such as a cumulative score for Molly (i.e., 2303) and Aled (i.e., 2136), a number of times Molly has won a past activity competition between Molly and Aled (i.e., 23 times), a number of times Aled has won a past activity competition between Molly and Aled (i.e., 7 times), and an amount of time left in the first activity competition (i.e., 2 days left). Second affordance 616B includes information related to the second activity competition, which can be similar to the information related to the first activity competition described above. It should be noted that, in some examples, affordances in the scrollable list of affordances 816 can include more or less information than depicted in FIG. 8E, including an affordance including more information than another affordance.

It should also be noted that while user interface 840 is depicted as having the same information in first portion 842A as user interface 812 in first portion 814A, an organization of the information in user interface 840 is different than an organization of the information in user interface 812. The difference in organization can be because of touch-sensitive display 602B having a smaller display area than touch-sensitive display 802.

Second portion 842B includes a scrollable list of affordances 846, where each affordance is associated with a different friend of a user (e.g., Aled) logged into device 800. For example, the scrollable list of affordances 846 includes first affordance 846A for a first friend (i.e., Jane), second affordance 846B for a second friend (i.e., Molly), third affordance 846C for a third friend (i.e., John), and fourth affordance 846D for a fourth friend (i.e., Tom). It should be noted that, in some examples, friends included in second portion 842B can also be included in an activity competition in first portion 842A. For example, Molly is a participant of the first activity competition (e.g., first affordance 842A) and included in the scrollable list of affordances 846 (e.g., second affordance 846B). In other examples, friends included in first portion 842A are not included in second portion 842B.

Each affordance in the scrollable list of affordances 846 includes information related to the corresponding friend. For example, first affordance 846A corresponds to Jane and includes an identification of Jane (e.g., "Jane"), a percent of goals for Jane that Jane has completed (e.g., "95%"), an absolute amount of a goal that Joan has completed with the absolute amount of the goal (e.g., "400/450"), and an icon visually depicting an amount of multiple goals that Joan has completed.

FIG. 8P depicts some information related to a friend not illustrated in FIG. 8E. Such information can also be included in FIG. 8E. For example, second affordance 846B in second portion 842B includes icon 846BA. Icon 846BA indicates that Aled has won an activity competition between Aled and Molly. Icon 846BA can be a unique identification of activity competitions between Aled and Molly such that other icons for other activity competitions between other participants have a different theme (as depicted for icon 846CA).

FIG. 8P also depicts invitation icon 842 included in third affordance 846D in second portion 842B. Invitation icon 842 indicates that a friend corresponding to third affordance 846D (e.g., Tom) has sent an invitation to compete in an activity competition with Aled. Invitation icon 842 also includes a number indicating how many invitations from Tom have been received.

Figure 8Q:
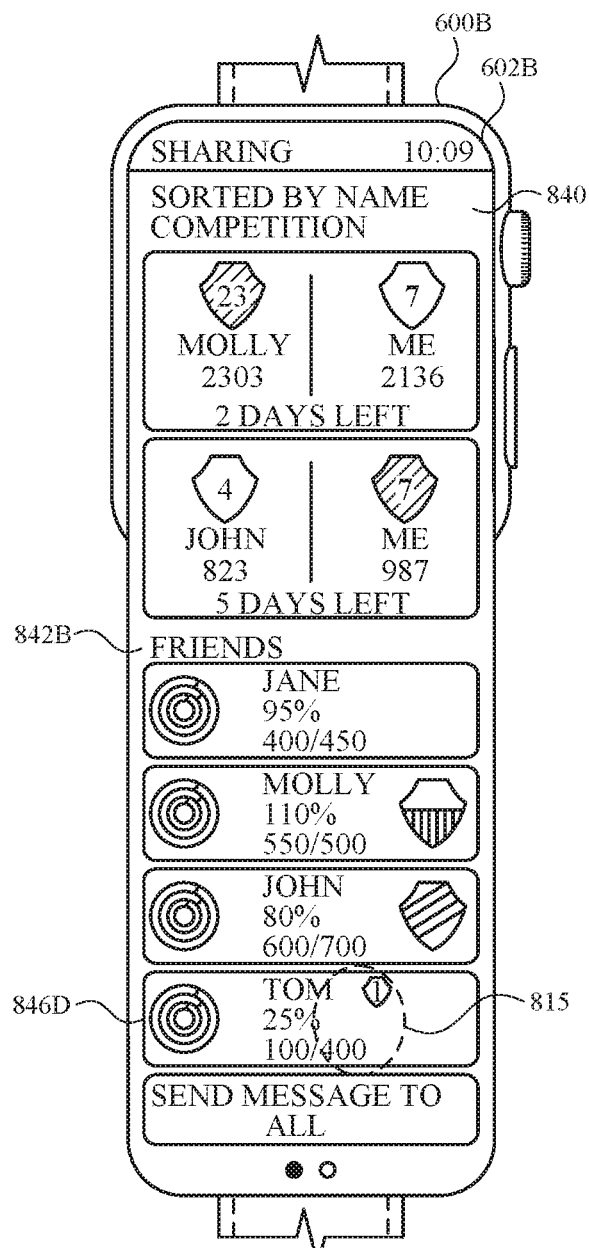

FIG. 8Q again illustrates user interface 840 (as depicted in FIG. 8P). As described above, user interface 810 includes fourth affordance 846D with invitation icon 842. Referring to FIG. 8Q, user input (e.g., tap input) 815 is received, where user input 815 corresponds to selection of invitation icon 842 or fourth affordance 846D (depending upon how user interface 840 is configured). In accordance with a determination that user input 815 is detected at invitation icon 842 (or fourth affordance 846D), a user interface (e.g., user interface 848 as depicted in FIG. 8R) is displayed.

Figure 8R:
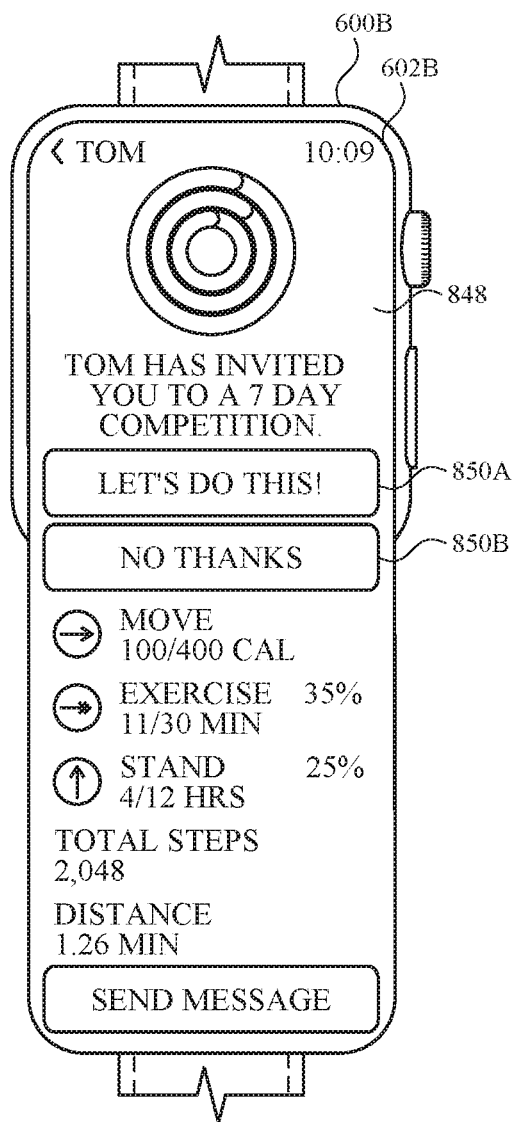

Referring to FIG. 8R, device 800 is displaying user interface 848 in response to selection of invitation icon 842 (or fourth affordance 846D) (as depicted in FIG. 8Q). User interface 848 indicates that Tom has invited Aled to a 7 day activity competition. User interface 848 includes activity data for Tom for a current day. User interface 848 further includes a scrollable list of affordances 850, where each affordance is associated with a different operation. For example, the scrollable list of affordances 850 includes first affordance 850A and second affordance 850B.

Selection of first affordance 850A can accept the invitation for the activity competition sent by Tom. Acceptance of the invitation can cause the activity competition to begin at a predefined time after the selection (e.g., midnight of the current day), as further described below. Selection of second affordance 850B can cause device 600B to reject the invitation (e.g., cause the activity competition to not begin) and cease to display user interface 848. Selection of second affordance 850B can further cause invitation icon 842 to be removed from fourth affordance 846D.

Figure 8S:
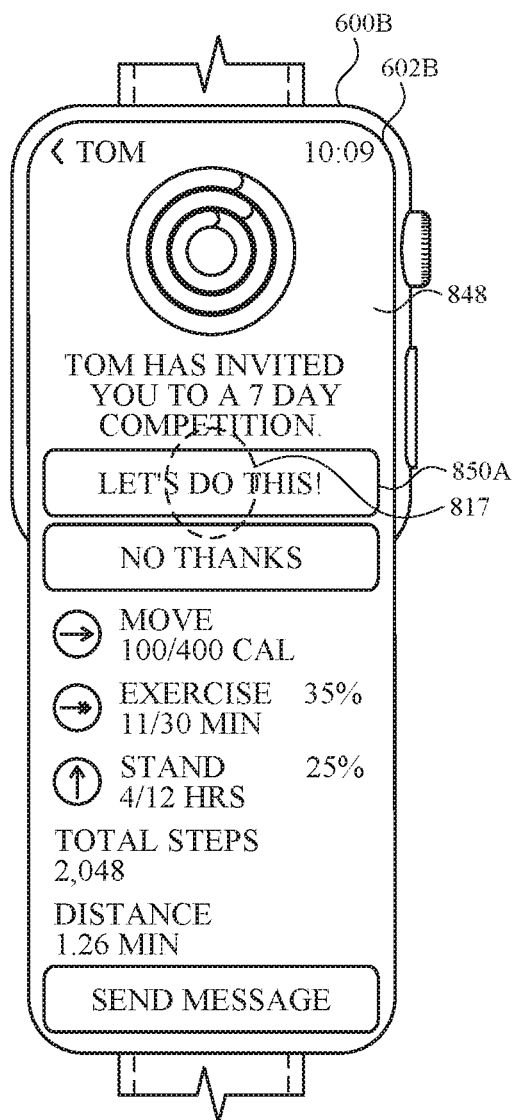

FIG. 8S again illustrates user interface 848 (as depicted in FIG. 8R). As described above, user interface 810 includes first affordance 850A. Referring to FIG. 8S, user input (e.g., tap input) 817 is received, where user input 817 corresponds to selection of first affordance 850A. In accordance with a determination that user input 817 is detected at first affordance 850A, a user interface (e.g., user interface 852 as depicted in FIG. 8T) is displayed.

Figure 8T:
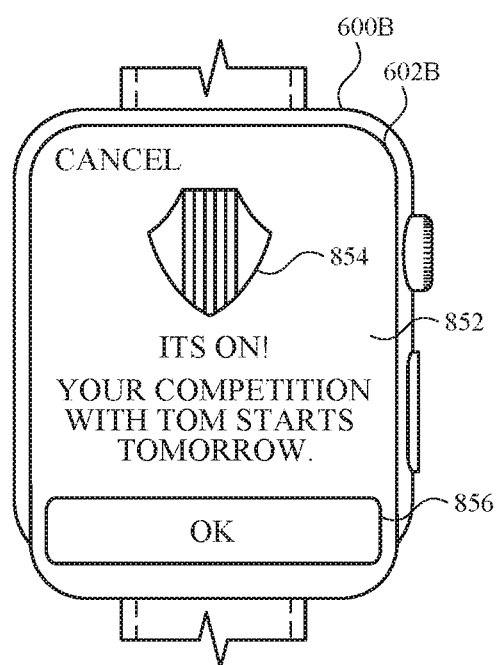

Referring to FIG. 8T, device 600B displays user interface 852 in response to selection of first affordance 850A in user interface 848 (as depicted in FIG. 8S). User interface 852 indicates that an activity competition between Tom and Aled starts tomorrow. User interface 852 includes icon 854, which represents activity competitions between Tom and Aled. User interface also includes affordance 856. Selection of affordance 856 causes device 600B to cease to display user interface 852.

Figure 8U:
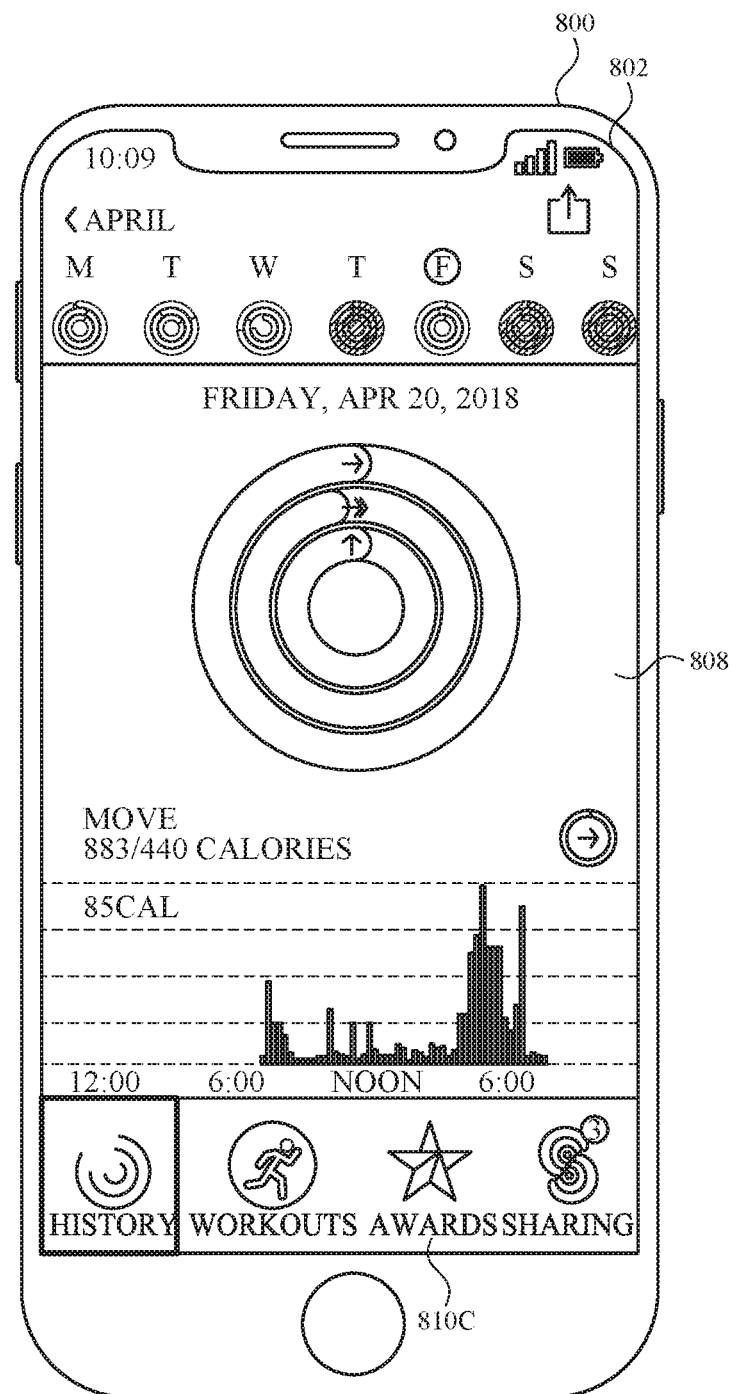
Figure 8V:
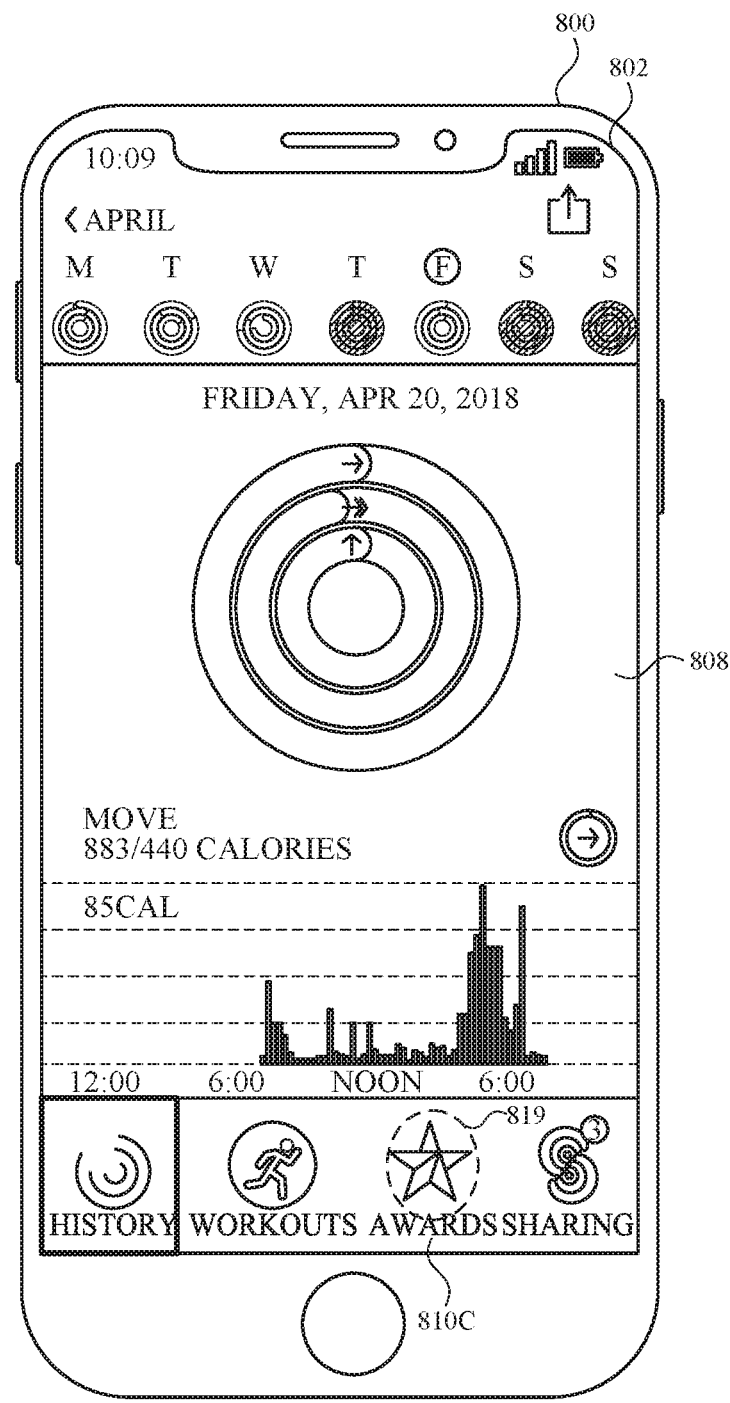

FIG. 8U again illustrates user interface 808 (as depicted in FIG. 8C). User interface 810 includes third affordance 810C. In response to selection of third affordance 810C (as depicted in FIG. 8V), device 800 displays user interface 858 (as depicted in FIG. 8W).

Figure 8W:
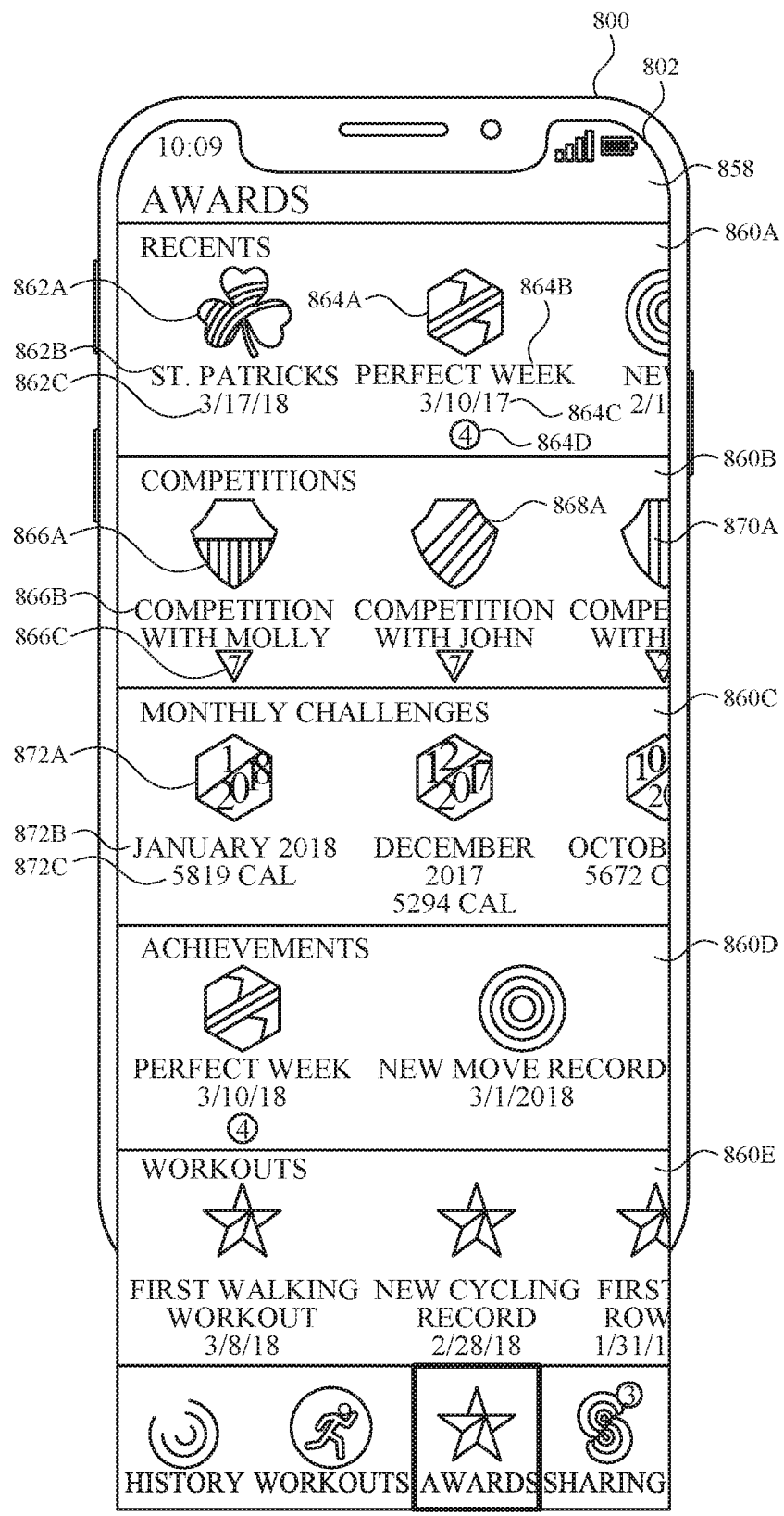

Referring to FIG. 8W, user interface 858 (sometimes referred to as a trophy case) relates to awards that have been given to Aled. User interface 858 is divided into multiple portions 860, where each portion includes a different type of award. For example, portions 860 includes recents 860A, competitions 860B, monthly challenges 860C, achievements 860D, and workouts 860E.

Each portion can include one or more awards associated with a corresponding type of award. For example, recents 860 can include awards that have been awarded within a particular amount of time from a current time. In some examples, awards in recents 860 can be larger than awards in other portions. Competitions 860B can include awards that have been awarded for activity competitions. Monthly challenges 860C can include awards that have been predefined as a monthly challenge. Achievements 860D can include awards that have been predefined as an achievement. Workouts 860E can include awards that have been awarded using a workout application (as described herein).

In some examples, some awards in a portion might not be visible. In such examples, the awards can be navigated by side scrolling through them.

Display of awards in user interface 858 can differ based upon the particular award. For example, a representation for an award that is received only once on a particular day can include an icon (e.g., icon 862A), an identification of the award (e.g., identification 862B), and a date that the award was received (e.g., date 862C). In some examples, a representation for an award that is received only once on a particular day can include an icon (e.g., icon 862A), an identification of the award (e.g., identification 862B), and further information related to achieving the award, such as a number of calories burned which satisfied at least a minimum amount for the award (e.g., calories 872C). In such examples, the representation might not include a date that the award was received because the identification indicates the date.

For another example, a representation for an award that is received multiple times can include an icon (e.g., icon 864A or 866A), an identification of the award (e.g., identification 864B or 866B), and a number of times that the award has been received (e.g., number 864D or 866C). In some examples, the representation for an award that is received multiple times can also include a date that the award has last been received (e.g., date 864C). In such examples, the representation can also include the date when the award is predefined as hard to receive or the award has been received below a particular number of times.

It should be noted that each icon for each award in competitions 860B (e.g., icons 866A, 868A, and 870A) is different. This can be due to each activity competition being assigned a different representation, as discussed herein.

Figure 8X:
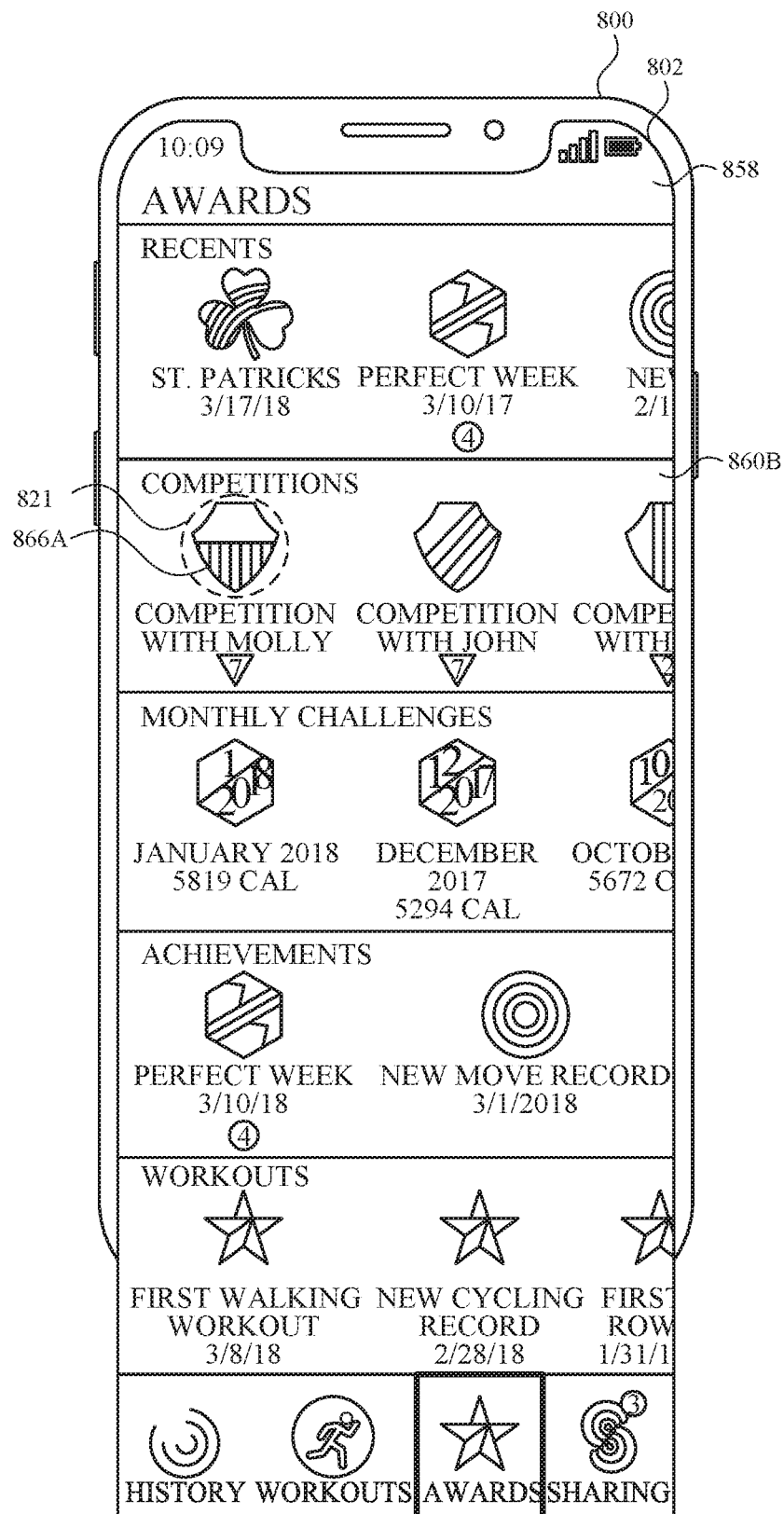

FIG. 8X again illustrates user interface 858 (as depicted in FIG. 8W). User interface 810 includes icon 866A of representation 866. In response to selection of icon 866A (or representation 866) (as depicted in FIG. 8X), device 800 displays user interface 876 (as depicted in FIG. 8X). Referring to FIG. 8X, user interface 876 includes icon 878A (which corresponds to icon 866A (as depicted in FIG. 8W), identification 873B of an award corresponding to icon 878 (which corresponds to identification 866B), and further information not included in representation 866 (as depicted in FIG. 8W). The further information includes a description of the award (reference 878C) and a date that the award was last received (reference 878D).

FIGS. 9A-9B include a flow diagram illustrating a method for displaying a friends list representation using an electronic device in accordance with some examples. Method 900 is performed at a device (e.g., 100, 300, 500, 600A, 600B, 800) with a display. Some operations in method 900 are, optionally, combined, the orders of some operations are, optionally, changed, and some operations are, optionally, omitted.

As described below, method 900 provides an intuitive way for displaying a user interface on a device corresponding to a first user, where the user interface includes affordances for multiple activity competitions, where each activity competition (1) is between the first user and another user and (2) is represented by current scores for the activity competition and a number of days remaining in the activity competition. The user interface permits a user viewing the user interface to readily access physical activity data corresponding to multiple users. The method reduces the cognitive burden on a user for accessing physical activity data corresponding to multiple user, thereby creating a more efficient human-machine interface. For battery-operated computing devices, enabling a user to access physical activity data corresponding to multiple users faster and more efficiently conserves power and increases the time between battery charges.

At 902, the device (e.g., FIG. 8A, 800) receives first user activity data (e.g., FIG. 8C, data represented in FIG. 8C) for a first user (e.g., Aled), where the first user activity data corresponds to a first time period (e.g., a day, a week, a month, a duration of an activity competition between the first user and a second user) (e.g., FIG. 8I, Monday through Sunday for activity competition with Molly) and a second time period (e.g., a day, a week, a month, a duration of an activity competition between the first user and a user; a time period different than the first time period) (e.g., FIG. 8I, Thursday through Wednesday for activity competition with John). In some examples, the first user activity data is received via one or more sensors of the device.

In some examples, a length (e.g., FIG. 8I, 7 days for activity competition with Molly) of the first time period is the same as a length (e.g., FIG. 8I, 7 days for activity competition with John) of the second time period. In some examples, a length of the first time period is different from a length of the second time period. In some examples, the first time period and the second time period overlap (e.g., FIG. 8I, activity competition with Molly and activity competition with John).

At 904, the device (e.g., FIG. 8A, 800) receives second user activity data (e.g., FIG. 8H, data represented by representations for Molly) for a second user (e.g., FIG. 8I, Molly), where the second user activity data corresponds to the first time period, and where the first time period includes a first elapsed (e.g., completed) sub-period (e.g., FIG. 8H, Monday through Friday) and a first unelapsed (e.g., remaining) sub-period (e.g., FIG. 8H, Saturday through Sunday) for an activity competition (e.g., FIG. 8H) between the first user and the second user. In some examples, the second user activity data is received (e.g., via one or more antennas of the device) by the device from a second device (e.g., a device associated with Molly).

At 906, the device (e.g., FIG. 8A, 800) receives third user activity data (e.g., FIG. 8I, data represented by representations for John) for the third user (e.g., FIG. 8I, John), where the third user activity data corresponds to the second time period, and where the second time period includes a second elapsed sub-period (e.g., FIG. 8I, Thursday through Friday) and a second unelapsed sub-period (e.g., FIG. 8I, Saturday through Wednesday) for an activity competition (e.g., FIG. 8I, activity competition with John) between the first user and the third user. In some examples, the third user activity data is received (e.g., via one or more antennas of the device) by the device from a third electronic device (e.g., a device associated with John).

In some examples, the activity competition between the first user and the second user began at a first time (e.g., FIG. 8I, Monday), and where the activity competition between the first user and the third user began at a second time (e.g., FIG. 8I, Thursday) different from the first time.

At 908, the device (e.g., FIG. 8A, 800) displays, on the display (e.g., FIG. 8A, 802), a user interface (e.g., FIG. 8E, 812). In some examples, the user interface is for a friends list.

At 910, the user interface (e.g., FIG. 8E, 812) includes a representation (e.g., FIG. 8E, 816A) of the first user activity data and the second user activity data during the first elapsed sub-period for the activity competition between the first user and the second user. In some examples, the representation of the first activity data and the second activity data is a score for each of the first user and the second user.

At 912, the user interface (e.g., FIG. 8E, 812) includes an indication of an amount of time in the first unelapsed sub-period (e.g., FIG. 8E, 816A with "2 days left") for the activity competition between the first user and the second user. In some examples, the indication is a remaining amount of time in the activity competition.

At 914, the user interface (e.g., FIG. 8E, 812) includes a representation (e.g., FIG. 8E, 816B) of the first activity data and the third activity data during the second elapsed sub-period for the activity competition between the first user and the third user. In some examples, the representation of the first activity data and the third activity data is a score for each of the first user and the third user. Displaying information for multiple activity competitions provides feedback as to activity data being received by the device for multiple different users. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. The information for multiple activity competitions also provides an improved man-machine interface by reducing number of interactions to display information for different activity competitions.

At 916, the user interface (e.g., FIG. 8E, 812) includes an indication of an amount of time in the second unelapsed sub-period (e.g., FIG. 8E, 816B with "5 days left") for the activity competition between the first user and the third user. Displaying remaining time in activity competitions provides feedback as to activity data to be received in the future. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. The remaining time also provides an improved man-machine interface by increasing an amount of sustained interaction with the device based upon an amount of the remaining time.

In some examples, the user interface (e.g., FIG. 8E, 812) further comprises: (1) a first portion (e.g., FIG. 8E, 814A) including the representations and the indications; and (2) a second portion (e.g., FIG. 8E, 814B) visually distinct from the first portion, the second portion including: (1) a first affordance (e.g., FIG. 8E, 818A) with an identification (e.g., FIG. 8E, "Jane) of the second user; (2) a second affordance (e.g., FIG. 8E, 818B) with an identification (e.g., FIG. 8E, "Molly") of the third user; and (3) a third affordance (e.g., FIG. 8E, 818C) with an identification (e.g., FIG. 8E, "John") of a fourth user not in an active activity competition with the first user. Displaying competing friends different than non-competing friends provides feedback as to data received by the device (e.g., where the data is coming from). Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. Displaying a first set of friends differently from a second set of friends also provides an improved man-machine interface by emphasizing one set of friends over another.

In some examples, the third affordance includes a notification (e.g., FIG. 8P, 842) that the fourth user has requested to initiate an activity competition between the first user and the fourth user. In such examples, the device receives a first user input (e.g., FIG. 8Q, 815) corresponding to selection of the third affordance. In response to receiving the first user input, the device initiates a process for starting an activity competition between the first user and the fourth user, where the activity competition between the first user and the fourth user causes first user activity data and fourth user activity data to be received during a time period (e.g., 7 days starting from when the activity competition between Tom and Aled begins). Displaying an additional entry point for an activity competition next to a friend's name in a friends list provides feedback as to pending requests from user's in an intuitive location. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, the notification is removed from the third affordance after an amount of time (e.g., 48 hours) has passed since the fourth user sent a corresponding request to initiate the activity competition between the first user and the fourth user.

In some examples, while displaying the user interface (e.g., FIG. 8E, 812), the device (e.g., FIG. 8A, 800) receives a second user input (e.g., an input corresponding to the representation of the first user activity data and the second user activity data) (e.g., FIG. 8F, 805) corresponding to a request to display additional information regarding the activity competition between the first user and the second user. In response to receiving the second user input, the device displays a second user interface (e.g., FIG. 8G, 822) including the additional information. In some examples, the additional information includes (1) a representation (e.g., FIG. 8E, "Me") of the first user activity data during a portion of the first elapsed sub-period for the activity competition between the first user and the second user and (2) a representation (e.g., FIG. 8G, 824B) of the second user activity data during the portion of the first elapsed sub-period for the activity competition between the first user and the second user.

In some examples, the representation of the first user activity data and the second user activity data includes: an identification of the first user (e.g., FIG. 8E, "Me"); an identification of the second user (e.g., FIG. 8E, "Molly"); and a representation based on a comparison of activity data for the first user and the second user for one or more previous time periods, preceding the time period (e.g., FIG. 8E, "23" in 816A)

In some examples, the third affordance (e.g., FIG. 8P, 846C) includes a first icon (e.g., a graphical element) (e.g., FIG. 8P, 846CA) indicating previous (e.g., assigned to) activity competitions between the first user and the fourth user.

In some examples, selection of the fourth affordance (e.g., FIG. 8J, 809) causes a user interface (e.g., FIG. 8K, 828) to be displayed with a representation (e.g., FIG. 8K, 830BA) indicating previous activity competitions between the first user and the fourth user.

In some examples, the second affordance includes a second icon indicating previous activity competitions between the first user and the third user, where the first icon has a first visual theme (e.g., a shape, a background color or pattern, and where the second icon with a second visual theme different from the first visual theme. In some examples, two graphical indications may share a common visual theme, while differing in non-thematic visual elements (e.g., such as a number or initials that are not part of the visual theme. In some examples, unique visual themes are assigned to each other user (e.g., a second user, a third user) that has been, or is currently, in a competition with the user of the electronic device (e.g., the first user).

In some examples, icons for different activity competitions between the same two participants are the same.

In some examples, while displaying the user interface, receiving a third user input (e.g., FIG. 8V, 819) corresponding to a request to display an awards user interface (e.g., FIG. 8W, 858); in response to receiving the third user input, the device displays, on the display, a third user interface (e.g., FIG. 8W, 858) including: a first portion (e.g., FIG. 8W, 860B) corresponding to a first type of icons, where the first type of icons relates to activity competitions, where the first portion includes the first icon (e.g., FIG. 8W, 866A) and the second icon (e.g., FIG. 8W, 868A); and a second portion (e.g., FIG. 8W, 860E) corresponding to a second type of icons, where the second portion includes a third icon (e.g., FIG. 8W, star icon). In some examples, the third user interface is a trophy case. In some examples, the first portion includes icons related to activity competitions. In some examples, the second portion includes icons related to workouts. In some examples, the third user interface further includes a third portion (e.g., FIG. 8W, 860A) corresponding to icons recently received, where icons included in the third portion are visually distinct (e.g., bigger) than icons in other portions. In some examples, icons in a portion are configured to be side scrolled.

In some examples, the third user interface, for an icon (e.g., FIG. 8W, 864) included in the third user interface, includes one or more of the following adjacent to the icon: an identification of the icon (e.g., FIG. 8W, 864B) and a number of times the icon has been earned (e.g., FIG. 8W, 864D).

In some examples, the device receives a fourth user input (e.g., FIG. 8Q, 815) corresponding to selection of the third affordance. In response to receiving the fourth user input, the device displays a third user interface (e.g., FIG. 8R, 848) comprising a competition initiation affordance (e.g., FIG. 8R, 850A). The device receives a fifth user input (e.g., FIG. 8S, 817) corresponding to the competition initiation affordance. In response to receiving the fifth user input, the device initiates an activity competition between the first user and the fourth user, where the activity competition between the first user and the fourth user causes first user activity data and fourth user activity data to be received during a third time period.

In some examples, the representation of the first user activity data and the second user activity data during the first elapsed sub-period for the activity competition between the first user and the second user is based upon a two-tier scoring system, where scoring changes when a user reaches a threshold (e.g., bonus points).

In some examples, while displaying the user interface, the device receives, using a rotatable input mechanism (e.g., an input mechanism that can rotate relative to a housing of the device) (e.g., FIG. 8P, 604A) of the device, a sixth user input. In response to receiving the sixth user input, the device updates the user interface to display a fourth affordance for a fifth user, where the fourth affordance is not visible prior to receiving the sixth user input.

Note that details of the processes described above with respect to method 900 (e.g., FIGS. 9A-9B) are also applicable in an analogous manner to the methods described below/above. For example, method 900 optionally includes one or more of the characteristics of the various methods described below with reference to method 700, method 1100, or method 1300. For example, the user interface of method 900 can lead to (e.g., by selecting an affordance in first portion) to the user interface of method 700. For another example, the user interface of method 1100 can generate activity data that is represented in the user interface of method 900. For another example, the user interface of method 1300 can generate activity data that is represented in the user interface of method 900. For brevity, these details are not repeated below.

FIGS. 10A-10Q illustrate exemplary user interfaces associated with alerts presented to a user in response to automatically determining a boundary of a workout in accordance with some examples. For example, FIG. 10A depicts an alert presented in response to automatically determining a beginning of a workout and FIG. 10D depicts an alert presented in response to automatically determining an end of a workout. Such alerts reduce the need for a user to remember to start and/or end a workout. The user interfaces in these figures are used to illustrate the processes described below, including the processes in FIG. 11.

Referring to FIG. 10A, user interface 1004 of a workout application is displayed on touch-sensitive display 602A of device 600A. In some examples, user interface 1004 is displayed in response to a determination that a user wearing device 600A has begun an outdoor run. The determination can be based upon data detected by one or more sensors associated with device 600A. For example, device 600A can include or be paired with a heart-rate monitor and a GPS sensor. In response to heart-rate information detected by the heart-rate monitor and GPS information detected by the GPS sensor, device 600A (or a device connected to device 600A) can determine that the user is likely running outside.

User interface 1004 includes a scrollable list of affordances 1006, where each affordance is associated with a different operation. For example, the scrollable list of affordances 1006 includes start affordance 1006A, change affordance 1006B, and dismiss affordance 1006C. Start affordance 1006A causes a physical activity tracking function configured for outdoor runs to be launched. Change affordance 1006B allows a user to pick a different type of workout such that a physical tracking function configured for the different type of workout is launched. Dismiss affordance 1006C causes user interface 1004 to cease to display.

User interface 1004 further includes physical activity icon 1008 corresponding to the outdoor run. Physical activity icon 1008 is an icon of a runner. In various examples, physical activity icon 1008 is displayed in an animated state, as further illustrated in FIG. 10I.

In some examples, content included in user interface 1004 might not fit within touch-sensitive display 602A; in which case content not displayed can be displayed in response to a scrolling input (e.g., rotation of rotatable input mechanism 604A).

In some examples, an alert (e.g., user interface 1004) is reissued (e.g., re-displayed or a new alert corresponding to the alert is displayed) after an amount of time (e.g., a predetermined amount of time) has passed without causing the alert to be dismissed (e.g., selecting an affordance in the scrollable list of affordances 1006). For example, if a user does not select an affordance in the scrollable list of affordances 1006 within 3 minutes, a new user interface that is the same or similar to user interface 1004 is displayed on touch-sensitive display 602A of device 600A. In some examples, if the user does select an affordance (e.g., dismiss affordance 1006A) within three minutes of user interface 1004 being displayed, user interface 1004 is not reissued after 3 minutes. While 3 minutes is used as an example, it should be recognized that a different amount of time may be used.

In some examples, the alert is only reissued when the alert has been interrupted (e.g., user interface 1004 is no longer being displayed due to another alert). In some examples, if the alert has not been interrupted, the alert remains (e.g., continues to be displayed and/or is displayed whenever touch-sensitive display 602A transitions from an inactive state to an active state) for a particular amount of time. In some examples, the particular amount of time is based on a type of workout corresponding to the alert. For example, if the alert corresponds to swimming, the alert can remain for 60 minutes; and if the alert corresponds to running or some other type of workout other than swimming, the alert can remain for 30 minutes. In some examples, a notification corresponding to user interface 1004 can be sent to a notification center such that a user is able to view the notification after user interface 1004 ceases to display.

Figure 10L:
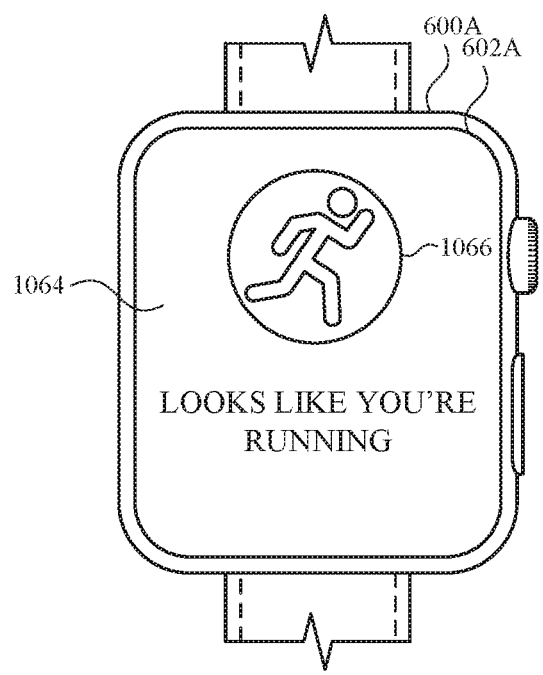

In some examples, prior to displaying user interface 1004, user interface 1064 is displayed on touch-sensitive display 602A of device 600A, as depicted in FIG. 10L. In such examples: user interface 1064 is displayed in response to the determination that a user wearing device 600A has begun an outdoor run, and user interface 1004 is displayed after displaying user interface 1064 (e.g., in response to user interface 1004 being displayed for a particular amount of time). In some examples, when user interface 1064 is displayed, user interface 1004 is displayed in response to a determination that a set of one or more short-look criteria has been met and user interface 1064 is displayed in response to a determination that a set of one or more long-look criteria has been met, as discussed below.

As depicted in FIG. 10L, user interface 1064 includes physical activity icon 1066 corresponding to the outdoor run. In various examples, physical activity icon 1064 is displayed in an animated state, as further illustrated in FIG. 10I. In some examples, content such as physical activity icon 1064 is included in both user interface 1064 and user interface 1004 (where it is referred to as physical activity icon 1008). In such examples, user interface 1004 includes additional content that is not included in user interface 1064, such as the scrollable list of affordances 1006. User interface 1064 further includes text to indicate that user interface 1064 is being displayed because it has been determined that the user is running (e.g., "Looks like you're running").

In some examples, user interface 1064 is displayed in response to detecting a user input within a first time interval following a perceptual output (e.g., thereby satisfying short-look criteria). Information in user interface 1064 may be referred to as first portion of information. In such examples, after raising a user's wrist to view user interface 1064, the user may then wish to view more information associated with user interface 1064. If device 600A determines that the user continues to maintain device 600A in a viewing position for a predetermined time interval (e.g., thereby satisfying a long-look criteria) after displaying user interface 1064, device 600A displays user interface 1004, which may be referred to as a second portion of the information. That is, in some examples, device 600A can automatically transition from displaying user interface 1064 to displaying user interface 1004 when the user holds device 600A in a viewing position and waits.

FIG. 10B again illustrates user interface 1004 (as depicted in FIG. 10A). As described above, user interface 1004 includes start affordance 1006A. Referring to FIG. 10B, user input (e.g., tap input) 1001 is received, where user input 1001 corresponds to selection of start affordance 1006A. In accordance with a determination that user input 1001 is detected at start affordance 1006A in the scrollable list of affordances 1006, a physical activity tracking function configured for outdoor runs is launched.

In response to selection of start affordance 1006A, user interface 1026 (which is depicted in FIG. 10C) is displayed. User interface 1026 displays (e.g., provide feedback regarding) data detected by device 600A for the outdoor run. In some examples, the displayed data can be based upon data detected prior to selection of start affordance 1006A and/or prior to display of user interface 1004. For example, a preliminary determination that the user is performing the outdoor run can be made. At some time after the preliminary determination, a final determination that the user is performing the outdoor run can be made, the final determination causing user interface 1004 to be displayed. In such an example, all data since the preliminary determination can be used when calculating data to display in user interface 1026. For another example, in response to selection of start affordance 1006A, an amount of data prior to the selection can be determined to likely (e.g., above a threshold) be associated with the outdoor run, where the amount of data is used when calculating data to display in user interface 1026.

To display the data detected by device 600A, user interface 1026 includes representations 1028. In FIG. 10C, representations 1028 include total mileage 1028A (e.g., an indication of a number of miles traveled during the outdoor run), average pace per mile 1028B (e.g., an indication of an average amount of time it has taken for device 600A to travel a mile during the outdoor run), total time 1028C (e.g., an indication of a duration of the outdoor run), and total calories 1028D (e.g., an indication of an amount of calories determined to be burned by the user during the outdoor run). It should be recognized that, in some examples, user interface 1026 can include more or fewer representations.

User interface 1026 also includes a current time, a physical activity icon (as discussed above), or other information determinable by device 600A. The physical activity icon depicted in user interface 1026 can be animated. While FIG. 10C depicts a particular visual appearance of representations 1028, it should be recognized that representations 1028 can appear differently.

At some point after a workout has started (e.g., after selection of start affordance 1006A), it can be determined that the user is likely (e.g., above a threshold criteria) no longer running outside. The determination can be based upon similar data as described above for beginning the outdoor run, such as data detected by one or more sensors associated with device 600A. In response to the determination that the user is likely no longer running outside, user interface 1038 (as depicted in FIG. 10D) is displayed on touch-sensitive display 602A.

User interface 1038 includes a scrollable list of affordances 1040, which are associated with different operations. For example, the scrollable list of affordances 1040 includes end affordance 1040A, pause affordance 1040B, change affordance 1040C, and dismiss affordance 1006D. End affordance 1040A causes the physical activity tracking function corresponding to the outdoor run to stop and data generated by the physical tracking function to be stored as a previous workout. Pause affordance 1040B causes the physical activity tracking function corresponding to the outdoor run to pause. Change affordance 1040C allows a user to choose a different type of workout so that a different physical activity tracking function corresponding to the different type of workout can be launched. Dismiss affordance 1006D causes user interface 1038 to cease to display and the physical activity tracking function for the outdoor run to continue to execute.

User interface 1038 further includes physical activity icon 1042 corresponding to the outdoor run. Physical activity icon 1042 is an icon of a runner. In various examples, physical activity icon 1042 is displayed in a static state.

In some examples, content included in user interface 1038 might not fit within touch-sensitive display 602A; in which case content not displayed can be displayed in response to a scrolling input (e.g., rotation of rotatable input mechanism 604A).

Referring to FIG. 10E, user input (e.g., tap input) 1005 is received, where user input 1005 corresponds to selection of end affordance 1040A. In accordance with a determination that user input 1005 is detected at end affordance 1040A in the scrollable list of affordances 1040, the physical activity tracking function for the outdoor run is discontinued. That is, execution of the physical activity tracking function for the outdoor run is stopped in accordance to the selection of end affordance 1040A. The selection can cause data to be stored for the outdoor run as a previous workout. It should be recognized that data can be stored for the outdoor run as the data is detected.

Referring to FIG. 10F, user interface 1044 is displayed in response to selection of end affordance 1040A. User interface 1044 can provide feedback regarding data detected by device 600A for the outdoor run. For example, user interface 1044 includes representations 1046 of different types of data detected by device 600A for the outdoor run. In FIG. 10F, representations 1046 include total mileage 1046A (e.g., an indication of a number of miles traveled during the outdoor run), average pace per mile 1046B (e.g., an indication of an average amount of time it has taken for device 600A to travel a mile during the outdoor run), total time 1046C (e.g., an indication of a duration of the outdoor run), total active calories 1046D (e.g., an indication of an amount of calories determined to be burned by the user wearing device 600A during an active state for the outdoor run), and total calories 1046E (e.g., an indication of an amount of calories determined to be burned by the user wearing device 600A during the outdoor run). It should be recognized that, in some examples, user interface 1044 can include more or fewer representations.

User interface 1044 also includes an identification of the outdoor run (e.g., representation 1048), a physical activity icon (e.g., physical activity icon 1050), or other information known by device 600A. While FIG. 10F depicts a particular visual appearance of representations 1046, it should be recognized that representations can appear differently.

FIG. 10G again illustrates user interface 1004 (as depicted in FIG. 10A and under circumstances as described with respect to FIG. 10A). As described above, user interface 1004 includes change affordance 1006B. Referring to FIG. 10G, user input (e.g., tap input) 1003 is received, where user input 1003 corresponds to selection of change affordance 1006B. In some examples, when selecting to change a type of workout, data detected prior to selecting change affordance 1006B is not configured to be associated with the new type of workout. For example, changing the workout causes a new workout to begin after the new workout is selected, unlike what occurs (in some examples) when selecting to start a workout using affordance 1006A) (e.g., data detected prior to starting the workout using affordance 1006A can be configured to be associated with the workout). In other words, start affordance 1006A causes data detected prior to selection of start affordance 1006A to be used and change affordance 1006B causes data detected prior to selection of change affordance 1006B to not be used. In accordance with a determination that user input 1003 is detected at change affordance 1006B in the scrollable list of affordances 1006, user interface 1030 illustrated in FIG. 10H is displayed.

User interface 1030 allows a user to select a different type of workout for a current workout. For example, when it is determined that the user is running outside, the user can change the outdoor run to a second type of workout, indicating that the determination of the outdoor run was incorrect. When a different type of workout is selected, a physical activity tracking function corresponding to the different type of workout launches automatically.

User interface 1030 includes a scrollable list of affordances 1032, which are associated with respective physical activity tracking functions for a physical activity. For example, the scrollable list of affordances 1032 includes affordance 1032A (which corresponds to a physical activity tracking function for climbing stairs (referred to as stair stepping)), affordance 1032B (which corresponds to a physical activity tracking function for an outdoor run), and affordance 1032C (which corresponds to a physical activity tracking function for a walk). It is noted that the scrollable list of affordances 1032 can include additional affordances corresponding to other physical activity tracking functions that are not currently displayed but can be displayed in response to a scrolling input (e.g., rotation of rotatable input mechanism 604A).

In some examples, each of one or more affordances in the scrollable list of affordances 1032 includes representations 1034 corresponding to a physical activity associated with the affordance. Representations 1034 includes a physical activity icon corresponding to the physical activity associated with the affordance. For example, affordance 1032A includes physical activity icon 1034A (e.g., icon of a person climbing stairs). Similarly, affordance 1032C includes physical activity icon 1034D (e.g., icon of a person walking). In various examples, physical activity icons are displayed in a first state (e.g., static state).

Representations 1034 further includes a workout identifier. For example, affordance 1032A includes workout identifier 1034B that indicates that affordance 1032A is associated with a stair stepper workout. Similarly, affordance 1032B includes a workout identifier that indicates that affordance 1032B is associated with an outdoor run workout.

In some examples, one or more affordances in the scrollable list of affordances 1032 includes workout goal information. For example, affordance 1032A includes workout goal information 1034C that indicates that the stair stepper workout associated with affordance 1032A has a predetermined goal of twenty minutes. That is, when affordance 1032A is selected, the associated physical activity tracking function will automatically track information for the stair stepper workout with a preset goal of twenty minutes. Affordance 1032B includes a goal workout affordance that indicates that the outdoor run associated with affordance 1032B is an "open goal." An open goal indication indicates to the user that the associated workout does not currently have any preset goals. Accordingly, when affordance 1032B is selected, various metrics will be tracked by the associated physical activity tracking function, wherein the metrics do not include any preset goal values.

FIG. 10I illustrates a series of states of device 600A with touch-sensitive display 602A. The series of states depict user interface 1004 (which is also depicted in FIG. 10A) over time.

By depicting user interface 1004 over time, it is illustrated how physical activity icon 1008 can be animated. For example, physical activity icon 1008A depicts physical activity icon 1008 in a first state, physical activity icon 1008B depicts physical activity icon 1008 in a second state subsequent to the first state, and physical activity icon 1008C depicts physical activity icon 1008 in a third state subsequent to the second state.

The animation can give the impression that a person is running. Animating physical activity icon 1008 can provide feedback to a user that device 600A has determined (e.g., detected) that a workout has begun.

FIGS. 10J and 10K illustrate user interfaces displayed in response to determinations that different types of workouts have begun. For example, different types of workouts can be associated with different sets of one or more criteria. When a set of one or more criteria for a particular type of workout is satisfied, a user interface for beginning a workout corresponding to the particular type of workout can be displayed.

Referring to FIG. 10J, user interface 1052 of a workout application is displayed on touch-sensitive display 602A. User interface 1052 includes a scrollable list of affordances 1054, which is similar (e.g., functions in a similar manner) to the scrollable list of affordances 1006. For example, the scrollable list of affordances 1054 includes start affordance 1054A (which corresponds to a physical activity tracking function for a walk). It is noted that the scrollable list of affordances 1054 might not fit within touch-sensitive display 602A; in which case one or more affordances not displayed can be displayed in response to a scrolling input (e.g., rotation of rotatable input mechanism 604A).

User interface 1054 further includes physical activity icon 1056 corresponding to a physical activity associated with start affordance 1054A. Physical activity icon 1056 is an icon of a person walking. In various examples, physical activity icon 1056 is displayed in an animated state.

Referring to FIG. 10K, user interface 1058 of a workout application is displayed on touch-sensitive display 602A. User interface 1058 includes a scrollable list of affordances 1060, which is similar (e.g., functions in a similar manner) to the scrollable list of affordances 1006. For example, the scrollable list of affordances 1060 includes start affordance 1060A (which corresponds to a physical activity tracking function for a rowing exercise). It is noted that the scrollable list of affordances 1060 might not fit within touch-sensitive display 602A; in which case one or more affordances not displayed can be displayed in response to a scrolling input (e.g., rotation of rotatable input mechanism 604A).

User interface 1058 further includes physical activity icon 1062 corresponding to a physical activity associated with start affordance 1060A. Physical activity icon 1062 is an icon of a person rowing. In various examples, physical activity icon 1062 is displayed in an animated state.

Figure 10M:
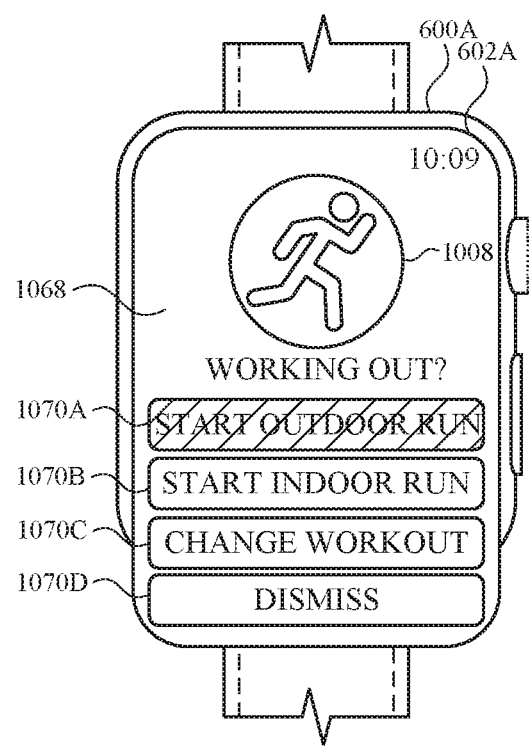

In some examples, instead of displaying user interface 1004, user interface 1068 is displayed, as depicted in FIG. 10M. In such examples, user interface 1068 is displayed when a determination is made that there are multiple types of workouts that have potentially begun. User interface 1068 includes a scrollable list of affordances 1070, where each affordance is associated with a different operation. For example, the scrollable list of affordances 1070 includes start outdoor run affordance 1070A, start indoor run affordance 1070B, change affordance 1070C, and dismiss affordance 1070D. Start outdoor run affordance 1070A causes a physical activity tracking function configured for outdoor runs to be launched (similar to start affordance 1006A). Start indoor run affordance 1070B causes a physical activity tracking function configured for indoor runs to be launched. Change affordance 1070C allows a user to pick a different type of workout such that a physical tracking function configured for the different type of workout is launched (similar to start affordance 1006B). Dismiss affordance 1070D causes user interface 1068 to cease to display (similar to start affordance 1006C).

In some examples, start indoor run affordance 1070B is related to a type of workout that is an alternative to a type of workout corresponding to start outdoor run affordance 1070A (in some examples, types of workouts are related when tracking data used for one can be used for the other). In such examples, start outdoor run affordance 1070A is visually highlighted (e.g., a different color and/or a different size) as compared to start indoor run affordance 1070B (and in comparison to the other affordances 1070C and 1070D). In some examples, start outdoor run affordance 1070A is visually highlighted because a determination, based on sensor data, has been made that it is more likely that a user is running outdoor than indoors. In some examples, start indoor run affordance 1070B is not visually highlighted as compared to change affordance 1070C and dismiss affordance 1070D. In other words, start indoor run affordance 1070B, change affordance 1070C, and dismiss affordance 1070D can appear similar while start outdoor run affordance 1070A is visually distinct from all three. Examples of types of workouts that might commonly be paired together as a main workout and an alternative workout include outdoor/indoor run, outdoor/indoor walk, and pool swim/open water swim. While only a single alternative is illustrated in FIG. 10M, it should be recognized that more than one alternative may be included in the scrollable list of affordances 1070.

Figure 10N:
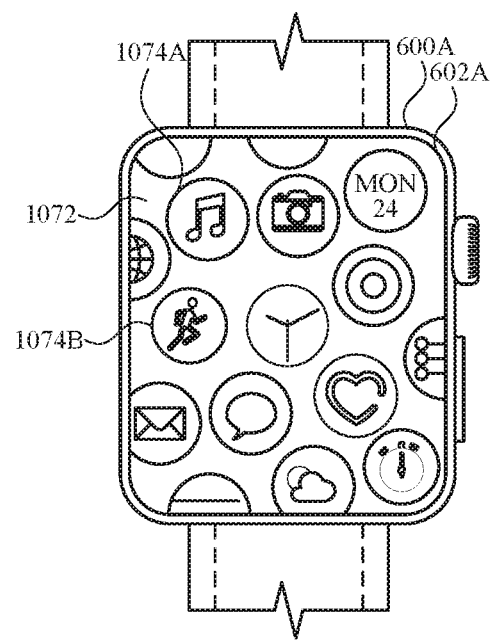
Figure 10O:
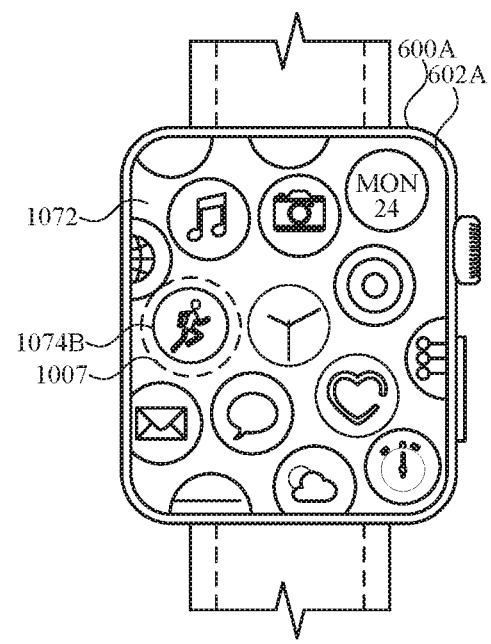
Figure 10P:
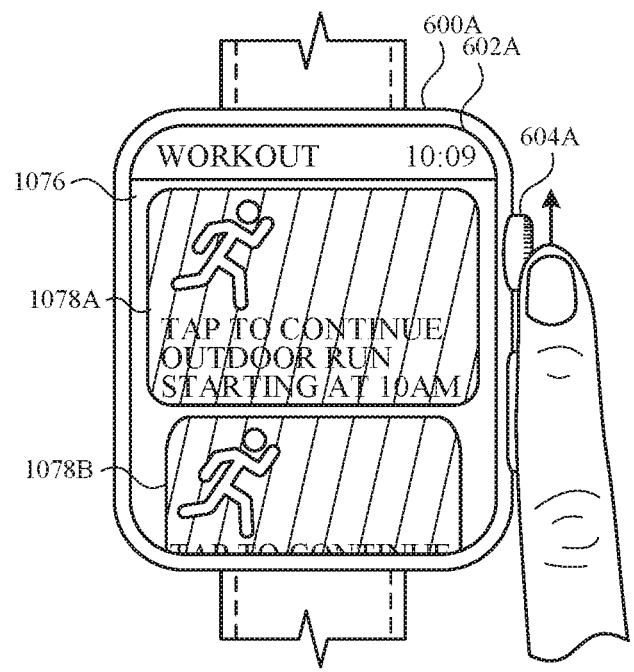
Figure 10Q:
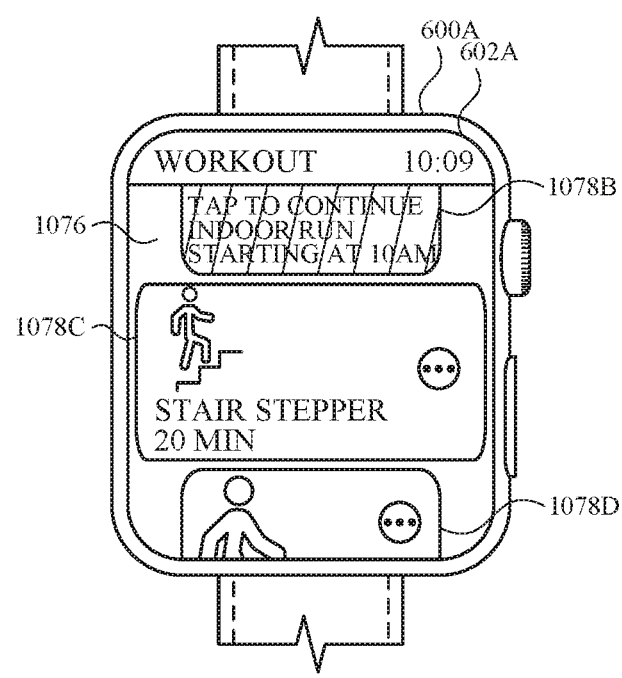

In some examples, after an alert is issued (e.g., user interface 1004), a user interface (e.g., user interface 1076) for selecting to start a workout from a list of workouts includes one or more representations corresponding to the alert, as depicted in FIGS. 10P-10Q and discussed below. Such a user interface can be navigated to as depicted in FIGS. 10N-10O and discussed below.

FIG. 10N illustrates user interface 1072 displayed on touch-sensitive display 602A of device 600A. User interface 1072 includes multiple application affordances 1074 associated with applications. For example, affordance 1074A is associated with an audio application and affordance 1074B is associated with a workout application. In some examples, user interface 1072 can be displayed to present which application can be launched using device 600A. Selection of an affordance included in user interface 1072 can cause a corresponding application to be launched.

FIG. 10O again illustrates user interface 1072 (as depicted in FIG. 10N). As described above, user interface 1072 includes affordance 1074B. Referring to FIG. 10O, user input (e.g., tap input) 1007 is received, where user input 1007 corresponds to selection of affordance 1074B. In accordance with a determination that user input 1007 is detected at affordance 1074B, the workout application that corresponds to affordance 1074B is launched and user interface 1076 (which is discussed below and depicted in FIG. 10P) is displayed.

Referring to FIG. 10P, user interface 1076 includes a scrollable list of affordances 1078, which are associated with respective physical activity tracking functions for respective physical activities. In some examples, the scrollable list of affordances 1078 includes at least two types of affordances: a first type of affordance associated with physical activity tracking functions corresponding to an alert (e.g., user interface 1004) issued by device 600A; and a second type of affordance (e.g., 1078C) associated with physical activities that are track-able by device 600A (but do not correspond to an alert (e.g., 1004) issued by device 600A). In some examples, physical activities are represented in both the first type and the second type such that the scrollable list of affordances 1078 includes (1) a first affordance (of a first type of affordance) associated with a particular type of physical activity and (2) a second affordance (of a second type of affordance different from the first type of affordance) associated with the particular type of physical activity. In other examples, physical activities represented by the first type of affordance are not represented by the second type of affordance.

As depicted in FIG. 10P, the scrollable list of affordances 1078 includes multiple affordances of the first type of affordance: affordance 1078A (which corresponds to continuing a physical activity tracking function for an outdoor run that began at 10 AM) and affordance 1078B (which corresponds to continuing a physical activity tracking function for an indoor run that began at 10 AM). The scrollable list of affordances 1078 includes multiple affordances of the first type of affordance in response to either (1) multiple different alerts (e.g., user interface 1004) have been issued without initiating a physical activity tracking function corresponding to one of the multiple different alerts or (2) an alert with multiple types of workouts (e.g., user interface 1068) has been issued without initiating a physical activity tracking function corresponding to one of the multiple types of workouts.

It should be noted that user interface 1076 includes a clock indicating that the time is "10:09" and affordance 1078A indicates a workout starting at 10 AM. This illustrates that selection of affordance 1078A causes data tracked since 10 AM to be recorded for a current outdoor running workout even though a user did not indicate to begin an outdoor running workout at 10 AM.

In some examples, the scrollable list of affordances 1078 can include additional affordances corresponding to other physical activity tracking functions that are not currently displayed but can be displayed in response to a scrolling input (e.g., rotation of rotatable input mechanism 604A). FIG. 10Q depicts user interface 1076 in response to a scrolling input. User interface 1076 in FIG. 10Q again includes the scrollable list of affordances 1078.

As depicted in FIG. 10Q, the scrollable list of affordances 1078 includes an affordance of the first type of affordance (i.e., affordance 1078B) and multiple affordances of the second type of affordance, the multiple affordances including: affordance 1078C (which corresponds to a physical activity tracking function for a stair stepping workout) and affordance 1078D (which corresponds to a physical activity tracking function for a walk). The scrollable list of affordances 1206 is configured such that a type of physical activity can be selected for a current workout. In some examples, when an affordance of the first type of affordance is selected, a workout is started using data detected before selection of the affordance. In such examples, when a affordance of the second type of affordance is selected, a workout is started that does not use data detect before selection of the affordance (only data detected after selection of the affordance). In some examples, affordances of the first type of affordance (e.g., affordance 1078A and affordance 1078B) are visually highlighted as compared to affordances of the second type of affordance (e.g., affordance 1078C and affordance 1078D).

FIG. 11 is a flow diagram illustrating a method for displaying an alert in response to automatically determining a boundary of physical activity using an electronic device in accordance with some examples. Method 1100 is performed at a device (e.g., 100, 300, 500, 600A, 600B, 800) with a display and one or more sensors (e.g., a gyroscope, a camera, an accelerometer, GPS sensor, heart rate monitor, clock, the like, or any combination thereof. Some operations in method 1100 are, optionally, combined, the orders of some operations are, optionally, changed, and some operations are, optionally, omitted.

As described below, method 1100 provides an intuitive way for displaying an alert in response to automatically determining a boundary of physical activity (e.g., a workout). The method reduces the cognitive burden on a user for starting and stopping a physical activity tracking function, thereby creating a more efficient human-machine interface. For battery-operated computing devices, enabling a user to track activity data faster and more efficiently conserves power and increases the time between battery charges.

At 1102, the device (e.g., 600A) detects, via the one or more sensors, activity data (e.g., heart rate data, GPS data, movement data, or the like) (e.g., FIG. 10A, data detected to cause user interface 1004 to be displayed). In some examples, the one or more sensors used to detect the activity data are a subset of sensors included with the electronic device (e.g., some sensors may not be used to detect the activity data).

In some examples, the activity data is detected before a physical activity tracking function is active (e.g., a tracking function corresponding to 1026). In such examples the activity data is used to determine whether to initiate a physical activity tracking function (e.g., the boundary condition is a start of a workout).

At 1102, in response to detecting the activity data, in accordance with a determination that the activity data satisfies activity boundary alert criteria (e.g., criteria for categorizing activity data as corresponding to a boundary (e.g., a start, an end, a transition from one type of activity to another) of user activity (e.g., a user workout)), the device (e.g., 600A) displays an activity boundary alert (e.g., a user interface including a confirmation affordance and an indication of the type of activity boundary detected) (e.g., 1004 or 1038). Displaying an activity boundary alert provides feedback as to when a device detects an activity boundary. Providing improved feedback and performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, the activity boundary alert (e.g., 1004) includes a first affordance (e.g., 1006A). In such examples, the device (e.g., 600A) receives a first user input (e.g., 1001) corresponding to selection of the first affordance. In response to receiving the first user input, the device initiates a physical activity tracking function (e.g., user interface 1026 can be displayed with information from physical activity tracking function) corresponding to a type of physical activity (e.g., running, HIIT, yoga, or the like) corresponding to the activity boundary alert (e.g., the physical tracking functions corresponds to the first affordance). In some examples, the activity boundary alert includes a third affordance (e.g., 1006C). In such examples, selection of the third affordance causes the device to forgo initiating the physical activity tracking function corresponding to a type of physical activity corresponding to the activity boundary alert. In such examples, the device continues to determine when a workout begins.

In some examples, the physical activity tracking function corresponding to the activity boundary alert (e.g., 1004) tracks activity data detected prior to displaying the activity boundary alert.

In some examples, the activity boundary alert (e.g., 1004) corresponds to a first physical activity tracking function (e.g., an activity tracking function corresponding to a predicted type of activity (e.g., running, swimming, rowing)). In such examples, the activity boundary alert includes a second affordance (e.g., 1006). In such examples, the device receives a second user input (e.g., 1003) corresponding to selection of the second affordance in the activity boundary alert. In response to receiving the second user input, the device displays a first user interface (e.g., 1030) including: a third affordance (e.g., 1032A) corresponding to a second physical activity tracking function different than the first physical activity tracking function; and a fourth affordance (e.g., 1032C) corresponding to a third physical activity tracking function different than the first physical activity tracking function. While displaying the first user interface the device receives a third user input. In accordance with the third user input corresponding to selection of the third affordance in the first user interface, the device configures the electronic device to track activity data detected after selection of the third affordance using the second physical activity tracking function. In accordance with the third user input corresponding to selection of the fourth affordance in the second user interface, the device configures the electronic device to track activity data detected after selection of the fourth affordance using the third physical activity tracking function. In some examples, the activity boundary alert includes an animated affordance (e.g., FIG. 10I) representing a type of workout associated with the activity boundary alert.

In some examples, the activity data was detected via a first sensor of the one or more sensors. In such examples, initiating the physical activity tracking function corresponding to the type of physical activity corresponding to the activity boundary alert (e.g., the physical tracking functions corresponds to the first affordance) includes detecting second activity data via a second sensor, different than the first sensor (e.g., the first sensor is an accelerometer and the second sensor is a GPS sensor), of the one or more sensors. In some examples, the second sensor is activated, from an inactive state.

In some examples, the activity data is detected while an existing physical activity tracking function is active (e.g., a tracking function corresponding to 1026).

In some examples, the activity data is detected while an existing physical activity tracking function is active. For example, the device is already tracking a workout. In such examples, the activity boundary alert (e.g., 1038) includes a fifth affordance (e.g., 1040A). In such examples, the device receives a fourth input (e.g., 1005) corresponding to selection of the fifth affordance. In response to receiving the fourth user input, the device ends the current physical activity tracking function. In further response to receiving the fourth user input, the device stores activity data (e.g., including the activity data) detected prior to receiving the fourth user input as a previous workout.

In some examples, the activity boundary alert (e.g., 1038) includes a sixth affordance (e.g., 1040B). In such examples, the device receives a fifth user input corresponding to selection of the sixth affordance. In response to receiving the fifth user input, the device pauses execution of a physical activity tracking function. In some examples, the activity boundary alert includes a dismiss affordance (e.g., 1040D) to not stop recording a workout.

In some examples, the activity boundary alert (e.g., 1038) corresponds to a first physical activity tracking function. In such examples, the activity boundary alert includes a seventh affordance (e.g., 1040C). In such examples, the device receives a sixth user input (e.g., similar to 1003) corresponding to selection of the seventh affordance. In response to receiving the sixth input, the device initiates a process for ceasing execution of a first physical activity tracking function. In further response to receiving the sixth input, the device displays a second user interface (e.g., 1030) including: a eighth affordance (e.g., 1032A) corresponding to a second physical activity tracking function different than the first physical activity tracking function, and a ninth affordance (e.g., 1032C) corresponding to a third physical activity tracking function different than the first physical activity tracking function. In such examples, the device receives a seventh user input. In accordance with the seventh user input corresponding to selection of the eighth affordance in the second user interface, the device initiates the second physical activity tracking function. In accordance with the seventh user input corresponding to selection of the ninth affordance in the second user interface, the device initiates the third physical activity tracking function.

In some examples, the activity boundary alert includes a static affordance (e.g., FIG. 10G, icon of running man) representing a type of workout associated with the activity boundary alert.

In some examples, the determination that the activity data satisfies activity boundary alert criteria can update over time based upon user interactions.

In some examples, the activity boundary alert (e.g., 1068) includes a tenth affordance (e.g., 1070B) (in some examples, the tenth affordance is an affordance for an alternative type of workout as compared to the first affordance (e.g., 1070A)), and wherein the physical activity tracking function corresponding to the activity boundary alert is a first physical activity tracking function. In such examples, the electronic device receives an eighth user input corresponding to selection of the tenth affordance and, in response to receiving the eighth user input, initiates a second physical activity tracking function corresponding to the activity boundary alert, wherein the second physical activity tracking function is different from the first physical activity tracking function (in some examples, each of the first physical activity tracking function and the second physical activity tracking function uses the activity data in a first manner (e.g., tracking number of miles) while a third physical activity tracking function that does not correspond to the activity boundary alert criteria uses the activity data in a second manner different from the first manner (e.g., tracking number of laps)).

In some examples, the first affordance (e.g., 1070A) and the tenth affordance (e.g., 1070B) are ordered based upon which respective workout is determined to be more likely the type of workout being performed. For example, if a determination is made that it is more likely that a user is performing an outdoor run than an indoor run, an affordance associated with an outdoor run precedes an affordance associated with an indoor run, as illustrated in FIG. 10M.

In some examples, the first affordance is highlighted as compared to the tenth affordance, to highlight that a workout corresponding to the first affordance has been determined to be more likely being performed than a workout corresponding to the tenth affordance.

In some examples, wherein the activity boundary alert is a first activity boundary alert (e.g., 1064) including (in some examples, the activity boundary alert is displayed in response to a short look) first content, after displaying the first activity boundary alert, the electronic device displays a second activity boundary alert (e.g., 1004) (in some examples, the second activity boundary alert is displayed in response to a long look) including second content, wherein the second content is different from the first content (e.g., the second content includes the first content and additional content) (in some examples, the second activity boundary alert is displayed in accordance with a determination that look criteria have been satisfied).

At 1106, in further response to detecting the activity data and in accordance with a determination that the activity data does not satisfy the activity boundary alert criteria, the device forgoes display of the activity boundary alert (e.g., forgoes displaying 1004).

In some examples, further in response to detecting the activity data and in accordance with a determination that the activity data satisfies second activity boundary alert criteria, the device displays a second activity boundary alert (e.g., alert 1058), where the activity boundary alert criteria and the activity boundary alert (e.g., alert 1004) relate to a first type of physical activity (e.g., running), and where the second activity boundary alert criteria and the second activity boundary alert relate to a second type of physical activity (e.g., rowing) different than the first type. In accordance with a determination that the activity data does not satisfy the second activity boundary alert criteria, the device forgoes display of the second activity boundary alert (e.g., forgoes displaying 1004).

In some examples, where the activity boundary alert is a first activity boundary alert, after a predetermined time (e.g., 3 minutes) has lapsed without initiating a physical activity tracking function corresponding to the first activity boundary alert, the electronic device displays a second activity boundary alert (e.g., 1004), wherein a physical activity tracking function corresponding to the second activity boundary alert tracks activity data detected prior to displaying the first activity boundary alert.

In some examples, after displaying the activity boundary alert and before a physical activity tracking function is active, the electronic device displays a third user interface (e.g., 1076) (in some examples, the third user interface is the first user interface) including a scrollable list of affordances (e.g., 1078) associated with physical activities. In some examples, the electronic device receives a ninth user input. In some examples, in accordance with a determination that the ninth user input is detected at an eleventh affordance (e.g., 1078A) in the scrollable list of affordances, the electronic device launches a physical activity tracking function corresponding to the activity boundary alert (in some examples, the physical activity tracking function associated corresponding to the activity boundary alert tracks activity data detected prior to displaying the third user interface) (in some examples, the physical activity tracking function corresponding to the activity boundary alert tracks activity data detected prior to displaying the activity boundary alert). In some examples, in accordance with a determination that the ninth user input is detected at a twelfth affordance (e.g., 1078C) in the scrollable list of affordances, the electronic device launches a physical activity tracking function (1) not corresponding to the activity boundary alert and (2) different from the physical activity tracking function corresponding to the activity boundary alert. In some examples, wherein the physical activity tracking function corresponding to the activity boundary alert is a first the physical activity tracking function, in accordance with a determination that the ninth user input is detected at a thirteenth affordance (e.g., 1078B) in the scrollable list of affordances, the electronic device launches a second physical activity tracking function corresponding to the activity boundary alert, wherein the second physical activity tracking function is different from the first physical activity tracking function, and wherein the second physical activity tracking function corresponding to the activity boundary alert tracks activity data detected after receiving the ninth user input (in some examples, the second physical activity tracking function tracks activity data detected after launching the second physical activity tracking function) (in some examples, one of the physical activity tracking functions corresponding to with the eleventh or twelfth affordance is the same physical activity tracking function corresponding to the thirteenth affordance).

In some examples, the eleventh affordance and the thirteenth affordance are visually highlighted (e.g., different color and/or bigger) as compared to the twelfth affordance, to indicate that the eleventh affordance and the thirteenth affordance are a different type of affordance from the twelfth affordance.

Note that details of the processes described above with respect to method 1100 (e.g., FIG. 11) are also applicable in an analogous manner to the methods described below/above. For example, method 1100 optionally includes one or more of the characteristics of the various methods described below with reference to method 700, method 900, or method 1300. For example, in response to the user interface of method 1100, the user interface of method 700 can be displayed. For another example, the user interface of method 1100 can lead (e.g., ending a workout can cause activity data to be generated) to the user interface of method 900 being displayed in response to activity data generated. For another example, a pace set using method 1100 can cause the user interface of method 1300 to be displayed. For brevity, these details are not repeated below.

FIGS. 12A-12AK illustrate exemplary user interfaces associated with configuring a pace alert for a workout application in accordance with some examples. The user interfaces allow a user to configure the dataset used to calculate a pace for the pace alert. For example, the dataset used can include data starting from the beginning of a workout (referred to as an average). For another example, the dataset used can be a previous amount of data relative to a current time such that the dataset does not include data from the beginning of the workout (referred to as a rolling average). The user interfaces in these figures are used to illustrate the processes described below, including the processes in FIG. 13.

FIG. 12A illustrates user interface 1256 displayed on touch-sensitive display 602A of device 600A. User interface 1256 includes multiple application affordances 1258 associated with applications. For example, affordance 1258A is associated with an audio application and affordance 1258B is associated with a workout application. In some examples, user interface 1256 can be displayed to present which application can be launched using device 600A. Selection of an affordance included in user interface 1256 can cause a corresponding application to be launched.

Figure 12B:
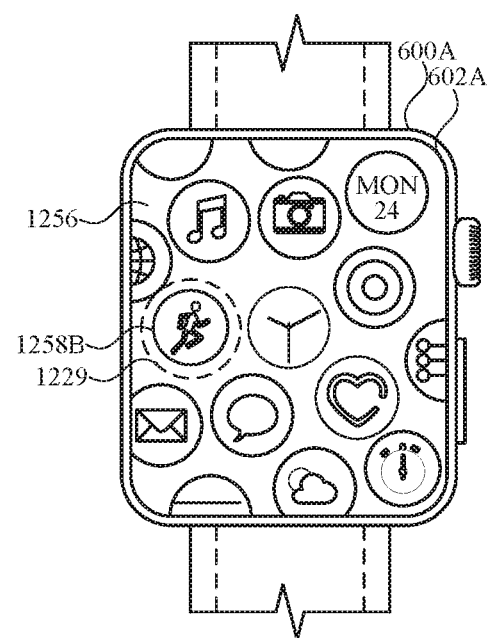

FIG. 12B again illustrates user interface 1256 (as depicted in FIG. 12A). As described above, user interface 1256 includes affordance 1258B. Referring to FIG. 12B, user input (e.g., tap input) 1229 is received, where user input 1229 corresponds to selection of affordance 1258B. In accordance with a determination that user input 1229 is detected at affordance 1258B, the workout application that corresponds to affordance 1258B is launched and user interface 1204 (which is discussed below and depicted in FIG. 12C) is displayed.

Figure 12C:
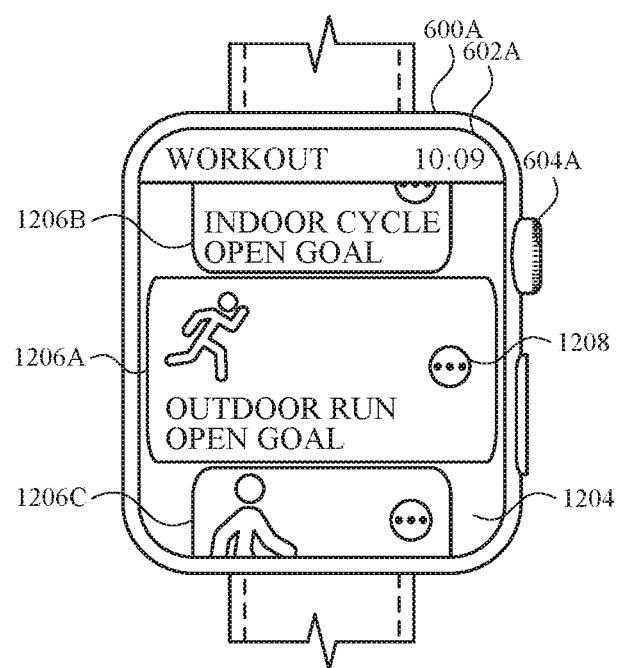

Referring to FIG. 12C, user interface 1204 includes a scrollable list of affordances 1206, which are associated with respective physical activity tracking functions for respective physical activities. For example, the scrollable list of affordances 1206 includes affordance 1206A (which corresponds to a physical activity tracking function for an outdoor run), affordance 1206B (which corresponds to a physical activity tracking function for an indoor cycling workout), and affordance 1206C (which corresponds to a physical activity tracking function for a walk). In some examples, the scrollable list of affordances 1206 can include additional affordances corresponding to other physical activity tracking functions that are not currently displayed but can be displayed in response to a scrolling input (e.g., rotation of rotatable input mechanism 604A). The scrollable list of affordances 1206 is configured such that a type of physical activity can be selected for a current workout.

In some examples, one or more affordances in the scrollable list of affordances 1206 includes an options affordance, as further discussed below. For example, affordance 1206A includes options affordance 1208.

Figure 12D:
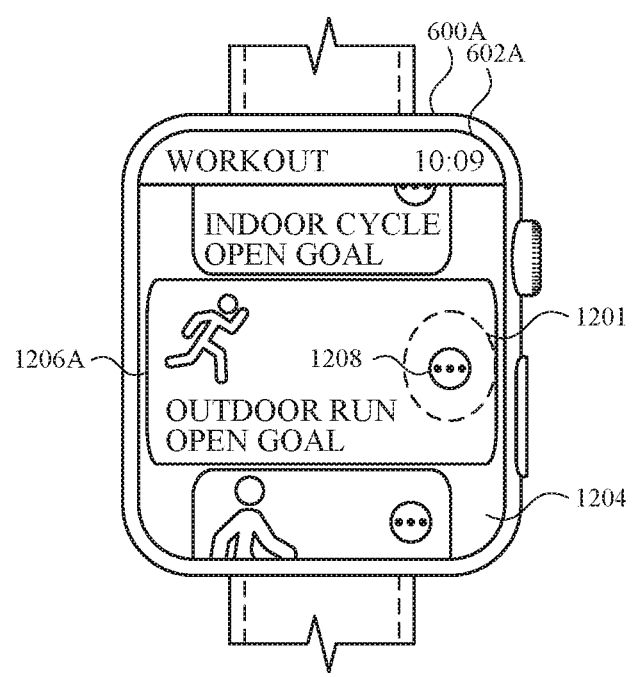

Referring to FIG. 12D, user input (e.g., tap input) 1201 is received, where user input 1201 corresponds to selection of options affordance 1208. In accordance with a determination that user input 1201 is detected at options affordance 1208, a user interface (e.g., user interface 1210 as depicted in FIG. 12E) is displayed with options related to a physical activity corresponding to affordance 1206A.

Figure 12E:
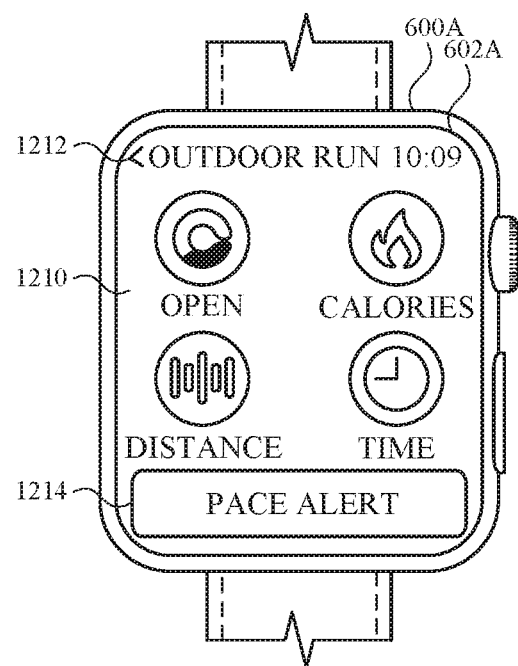

Referring to FIG. 12E, user interface 1210 is displayed in response to selection of options affordance 1208 (as depicted in FIG. 12D). User interface 1210 provides options to change how device 600A operates when executing a physical activity tracking function corresponding to affordance 1206A. User interface 1210 includes back affordance 1212 to cause user interface 1204 (as depicted in FIG. 12C) to be displayed. User interface 1210 further includes pace-alert affordance 1214 to allow a user to configure a pace alert for the physical activity tracking function corresponding to affordance 1206A.

Figure 12F:
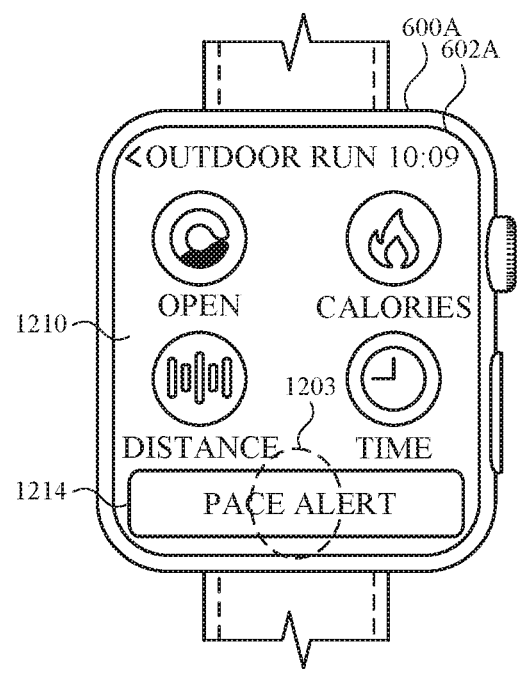

FIG. 12F again illustrates user interface 1210 (as depicted in FIG. 12E). As described above, user interface 1210 includes pace-alert affordance 1214. Referring to FIG. 12F, user input (e.g., tap input) 1203 is received, where user input 1203 corresponds to selection of pace-alert affordance 1214.

Figure 12G:
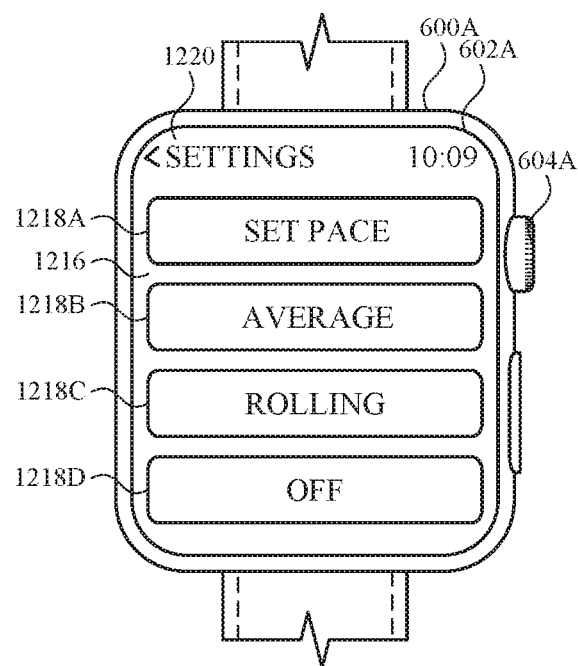
Figure 12H:
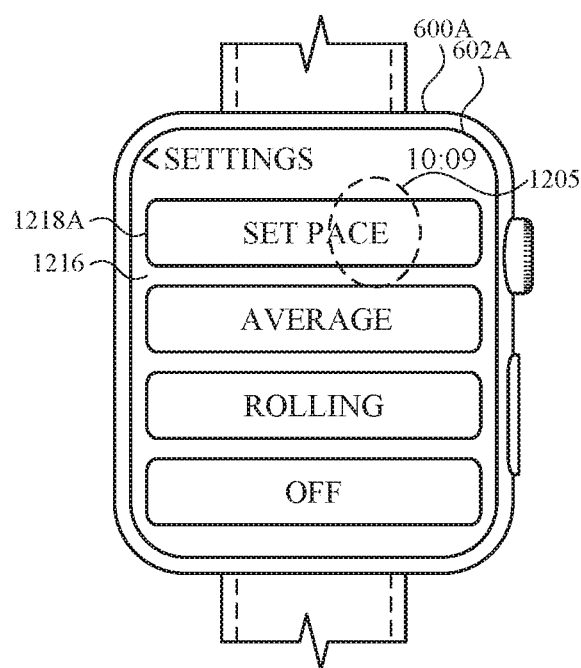
Figure 12I:
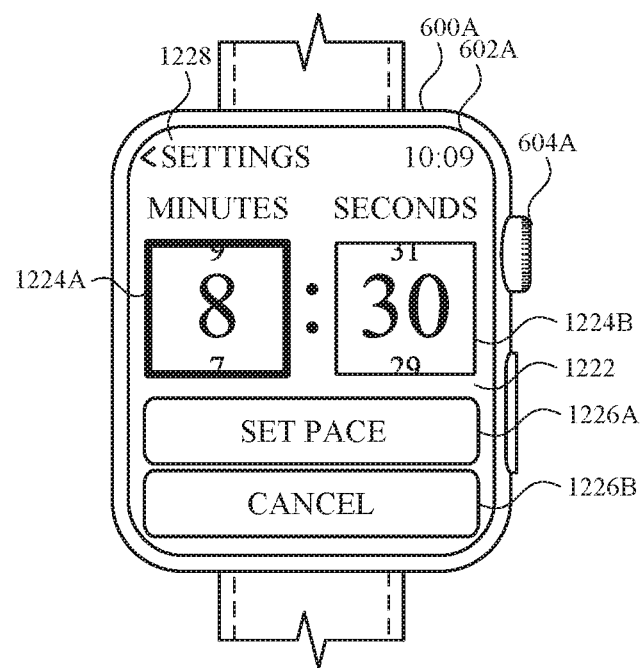

In some examples, in accordance with a determination that user input 1203 is detected at pace-alert affordance 1214, a user interface (e.g., user interface 1216 as depicted in FIG. 12G) is displayed with options related to a pace alert. In other examples, in accordance with a determination that user input 1203 is detected at pace-alert affordance 1214, a user interface (e.g., user interface 1222 as depicted in FIG. 12I) is displayed with options related to setting a pace for a pace alert.

Referring to FIG. 12G, user interface 1216 is displayed in response to selection of pace-alert affordance 1214. User interface 1216 provides options to configure a pace alert. User interface 1216 includes back affordance 1220 to cause user interface 1210 (as depicted in FIG. 12E) to be displayed.

User interface 1216 further includes a scrollable list of affordances 1218, which are associated with different operations. For example, the scrollable list of affordances 1218 includes set-pace affordance 1218A (which corresponds to causing a display for setting a pace to be displayed), average affordance 1218B (which corresponds to causing a pace to be calculated using data from an entire workout), rolling affordance 1218C (which corresponds to causing a pace to be calculated using a subset of data from a workout, where the subset is less than the entire workout), off affordance 1218D (which corresponds to turning off a pace alert), or any combination thereof. It is noted that, in some examples, the scrollable list of affordances 1218 might not fit within touch-sensitive display 602A; in which case one or more affordances not displayed can be displayed in response to a scrolling input (e.g., rotation of rotatable input mechanism 604A).

As used herein, pace can refer to speed (e.g., an amount of distance that a device travels in an amount of time or an amount of time that it takes for a device to travel an amount of distance). In regards to pace, the different calculations described herein (e.g., average and rolling) can refer to changing an amount of a dataset for a current workout that is used when performing a pace calculation. For example, for average, the pace calculation can be based upon data detected during the entire current workout. For rolling, the pace calculation can be based upon data detected during an amount prior to a current location (e.g., data detected for the last mile or data detected for the last 5 minutes).

FIG. 12H again illustrates user interface 1216 (as depicted in FIG. 12G). As described above, user interface 1216 includes set-pace affordance 1218A. Referring to FIG. 12H, user input (e.g., tap input) 1205 is received, where user input 1205 corresponds to selection of set-pace affordance 1218A. In accordance with a determination that user input 1205 is detected at set-pace affordance 1218A, a user interface (e.g., user interface 1222 as depicted in FIG. 12I) is displayed with options related to setting a pace for a pace alert.

Referring to FIG. 12I, user interface 1222 can be displayed in response to selection of set-pace affordance 1218A (as depicted in FIG. 12H) in some examples. In other examples, user interface 1222 can be displayed in response to selection of pace-alert affordance 1214 in user interface 1210 (as depicted in FIG. 12E). User interface 1222 can provide options to allow a user to set a pace for a pace alert. User interface 1222 can include back affordance 1228 to cause user interface 1210 to be displayed.

User interface 1222 further includes multiple affordances for setting a time (e.g., minutes-setting affordance 1224A and seconds-setting affordance 1224B). Minutes-setting affordance 1224A is used to set a number of minutes for a pace. Seconds-setting affordance 1224B is used to set a number of seconds for the pace.

As depicted in FIG. 12I, each affordance for setting the time is independently selectable. For example, each of minutes-setting affordance 1224A and seconds-setting affordance 1224B can be selected. When an affordance of the multiple affordances for setting a time is selected, the affordance can be visually distinguished. For example, in FIG. 12I, minutes-setting affordance 1224A has a thicker border than seconds-setting affordance 1224B, indicating minutes-setting affordance 1224A is selected (e.g., in focus).

User interface 1222 further includes a scrollable list of affordances 1226, which are each associated with different operations. For example, the scrollable list of affordances 1226 includes set-pace affordance 1226A (which corresponds to setting a pace identified using the multiple affordances for setting a time) and cancel affordance 1226B (which corresponds to displaying a user interface for providing options to configure a pace alert, such as user interface 1216 in FIG. 12G), or any combination thereof. It is noted that, in some examples, the scrollable list of affordances 1226 might not fit within touch-sensitive display 602A; in which case one or more affordances not displayed can be displayed in response to a scrolling input (e.g., rotation of rotatable input mechanism 604A).

Figure 12J:
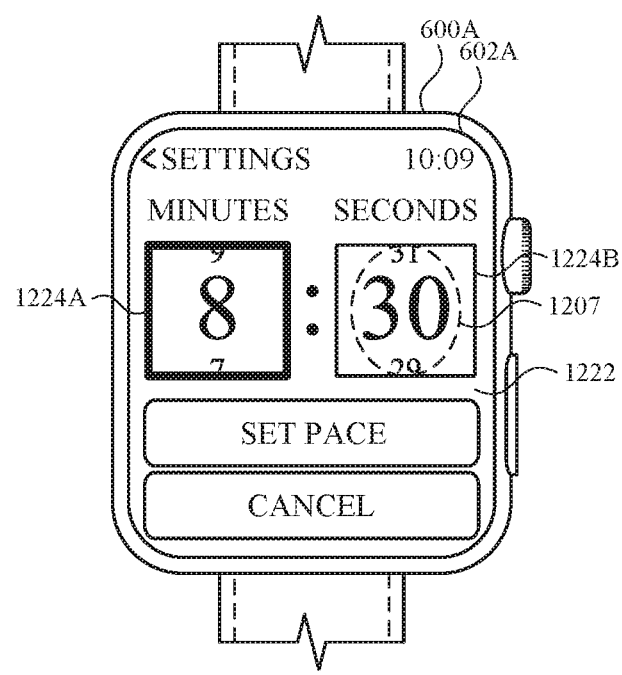

FIG. 12J again illustrates user interface 1222 (as depicted in FIG. 12I). As described above, user interface 1222 includes seconds-setting affordance 1224B. Referring to FIG. 12J, user input (e.g., tap input) 1207 is received, where user input 1207 corresponds to selection of seconds-setting affordance 1224B. In accordance with a determination that user input 1207 is detected at seconds-setting affordance 1224B, seconds-setting affordance 1224B can be visually distinguished from minutes-setting affordance 1224A. For example, selection of seconds-setting affordance 1224B can cause seconds-setting affordance 1224B to be visually distinguished instead of minutes-setting affordance 1224A.

Figure 12K:
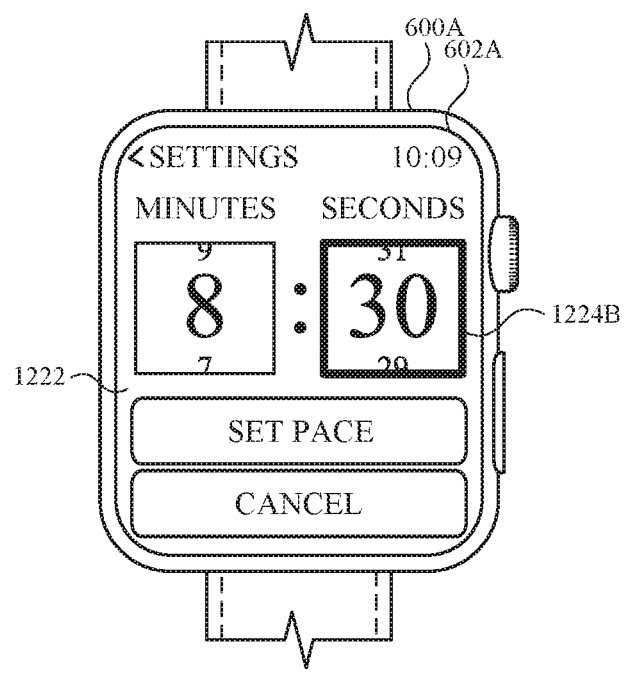

FIG. 12K again illustrates user interface 1222. Referring to FIG. 12K, seconds-setting affordance 1224B is visually distinguished instead of minutes-setting affordance 1224A. In particular, seconds-setting affordance 1224B has a thicker border than minutes-setting affordance 1224A, indicating seconds-setting affordance 1224B is selected (e.g., in focus).

Figure 12L:
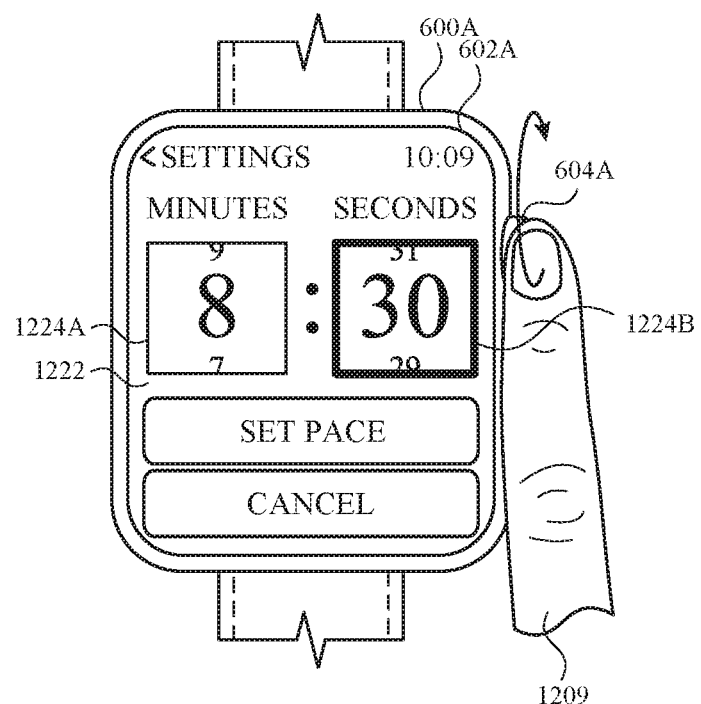
Figure 12M:
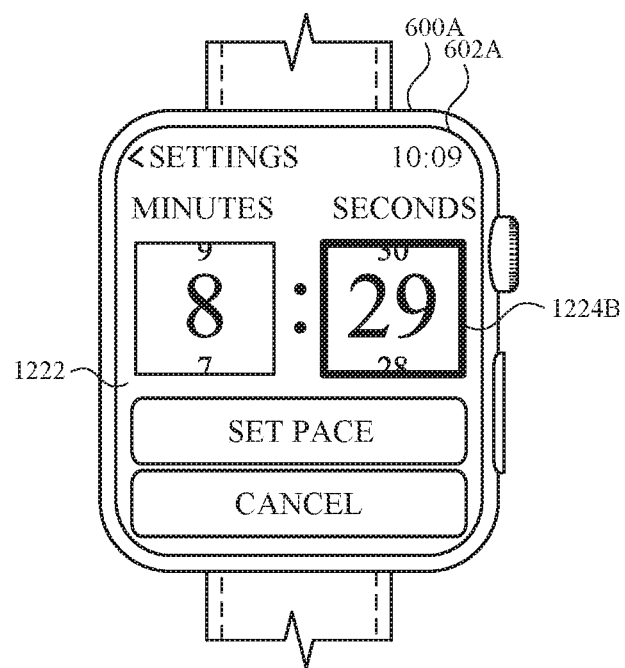

FIG. 12L depicts an example of user interface 1222 for scrolling of seconds-setting affordance 1224B. Referring to FIG. 12L, rotational input 1209 is received at rotatable input mechanism 604A. In response to rotational input 1209, options for seconds-setting affordance 1224B is scrolled in an upward direction such that different options for seconds-setting affordance 1224B are displayed, as depicted in FIG. 12M. For example, FIG. 12M depicts user interface 1222 changing seconds-setting affordance 1224B from "30" (as depicted in FIG. 12L) to "29" (as depicted in FIG. 12M). Similar scrolling can occur when minutes-setting affordance 1224A is selected and rotational input 1209 is received. Scrolling the opposite direction for both affordances may also be performed.

Figure 12N:
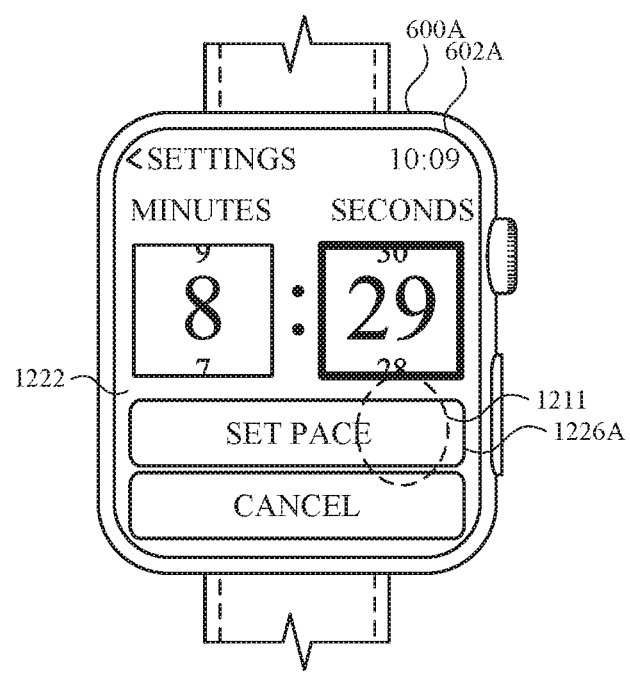

FIG. 12N again illustrates user interface 1222 (as depicted in FIG. 12M). As described above, user interface 1222 includes set-pace affordance 1226A. Referring to FIG. 12N, user input (e.g., tap input) 1211 is received, where user input 1211 corresponds to selection of set-pace affordance 1226A. In accordance with a determination that user input 1211 is detected at set-pace affordance 1226A, a user interface (e.g., user interface 1216 as depicted in FIG. 12O) is displayed with options related to a pace alert.

Figure 12O:
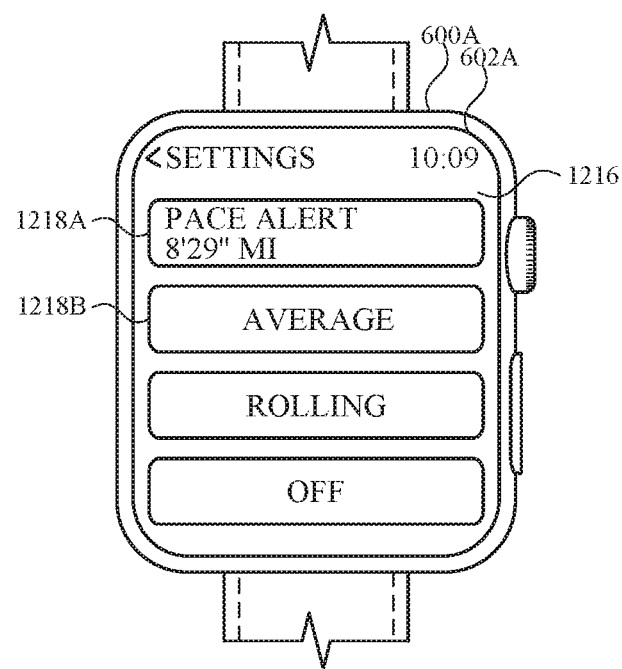

Referring to FIG. 12O, user interface 1216 can be displayed in response to selection of set-pace affordance 1226A. User interface 1216 can provide options to change how device 600A operates when executing a physical activity tracking function corresponding to affordance 1206A. As depicted in FIG. 12O, user interface 1216 can include a scrollable list of affordances 1218, which are associated with different operations. Text in set-pace affordance 1218A (as depicted in FIG. 12O) has been changed from "Set Pace" (as depicted in FIG. 12G) to a pace set by a user (e.g., "8'29" MI"), such as the pace set in FIG. 12N.

Figure 12P:
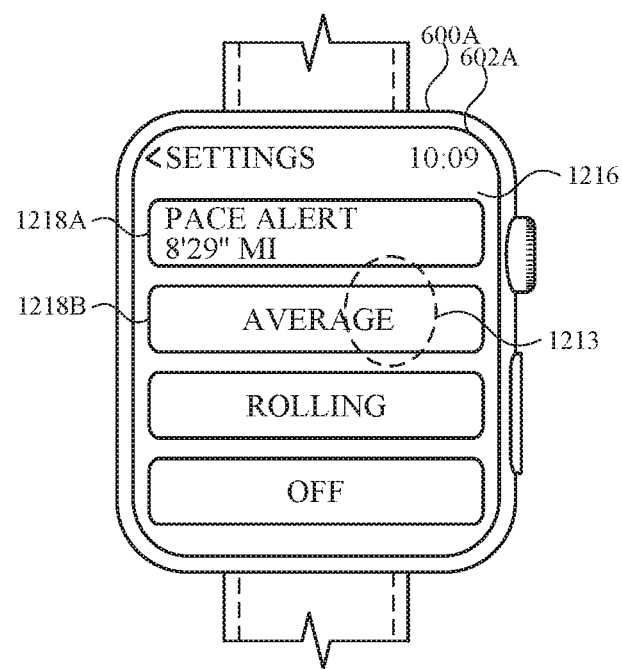

As discussed above, the scrollable list of affordances 1218 includes average affordance 1218B. Referring to FIG. 12P, user input (e.g., tap input) 1213 is received, where user input 1213 corresponds to selection of average affordance 1218B, causing the physical activity tracking function corresponding to affordance 1206A to use an average calculation.

Figure 12Q:
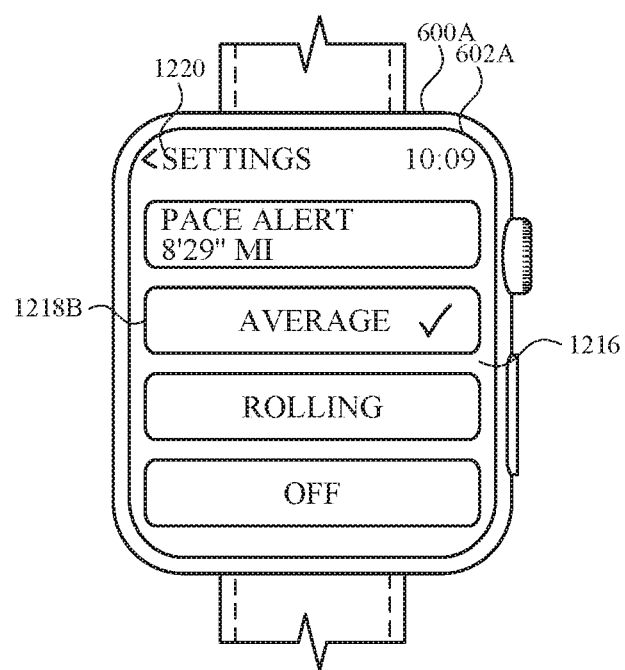

FIG. 12Q illustrates user interface 1216 in response to selection of average affordance 1218B. Referring to FIG. 12Q, average affordance 1218B is updated to include an indication (e.g., a check mark) that a pace will be calculated according to an average operation.

Figure 12R:
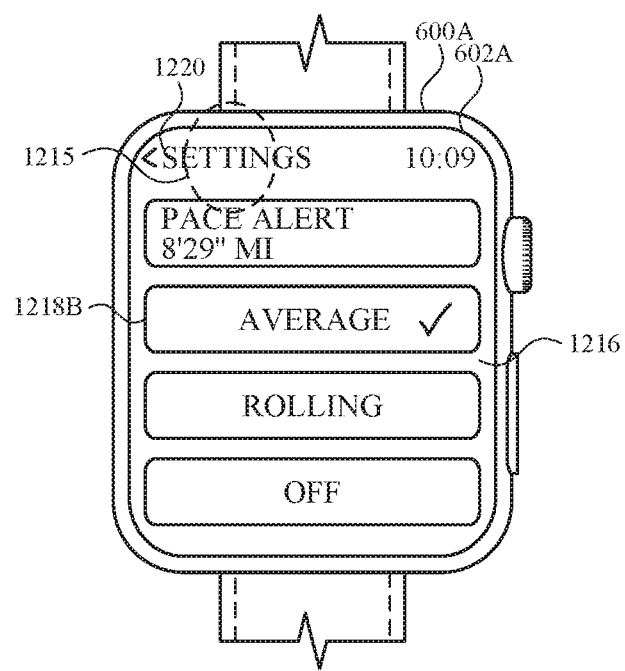

Referring to FIG. 12R, user input (e.g., tap input) 1215 is received, where user input 1215 corresponds to selection of back affordance 1220. In some examples, in accordance with a determination that user input 1215 is detected at back affordance 1220, a user interface (e.g., user interface 1210 as depicted in FIG. 12S) is displayed with options to change how device 600A operates when executing a physical activity tracking function corresponding to affordance 1206A.

Figure 12S:
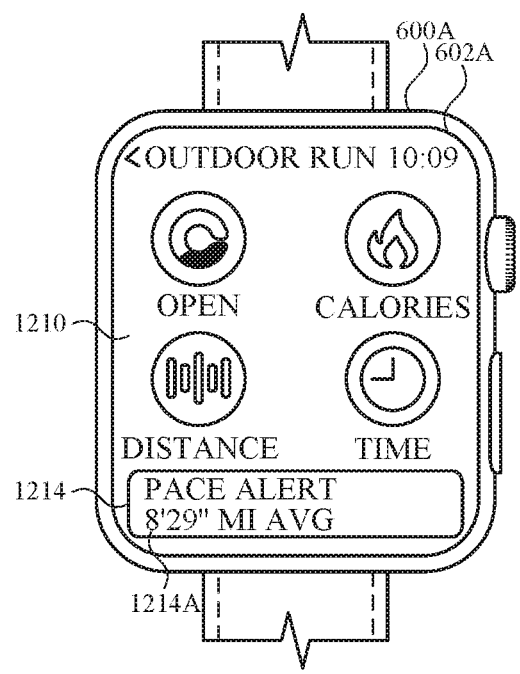

Referring to FIG. 12S, user interface 1210 can be displayed in response to selection of back affordance 1220. User interface 1210 can provide options to change how device 600A operates when executing a physical activity tracking function corresponding to affordance 1206A. Text in pace-alert affordance 1214 (as depicted in FIG. 12S) has been updated to include an indication of a pace set by a user (e.g., "8'29" MI AVG", as depicted at 1214A). In some examples, The text can be in the updated state any time device 600A is navigated to user interface 1210. By including "MI AVG" in the text, pace-alert affordance 1214 can indicate that the pace alert for a physical activity tracking function corresponding to affordance 1206A will be calculated using an average operation, as discussed herein.

Figure 12T:
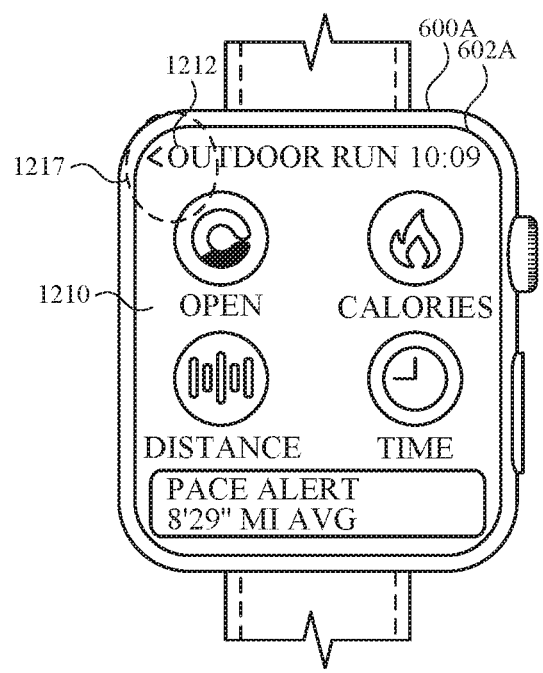

FIG. 12T again illustrates user interface 1210. Referring to FIG. 12T, user input (e.g., tap input) 1217 is received, where user input 1217 corresponds to selection of back affordance 1212. In some examples, in accordance with a determination that user input 1217 is detected at back affordance 1212, a user interface (e.g., user interface 1204 as depicted in FIG. 12U) is displayed.

Figure 12U:
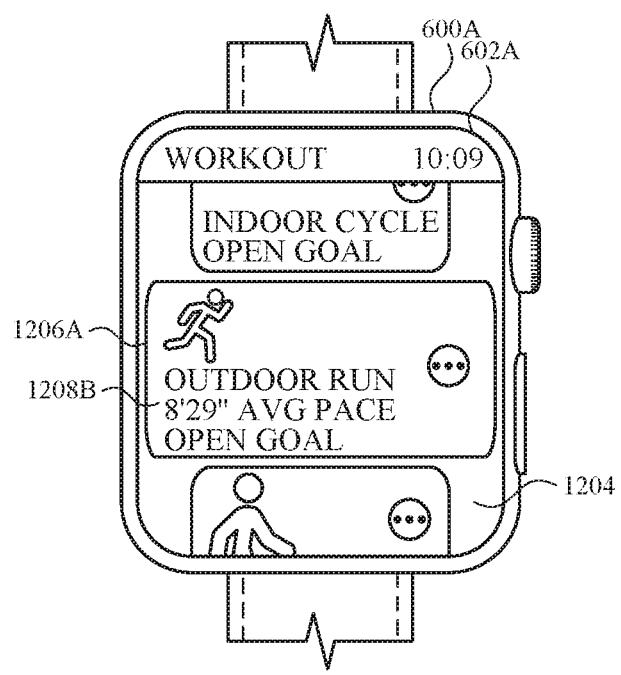

Referring to FIG. 12U, affordance 1206A is updated to include an indication of a pace set by a user (e.g., "8'29" AVG PACE", as depicted at 1208B). It should be recognized that multiple affordances in the list of affordances 1206 can include a pace set by a user. In some examples, different affordances in the list of affordances 1206 can include different paces set by a user.

Figure 12V:
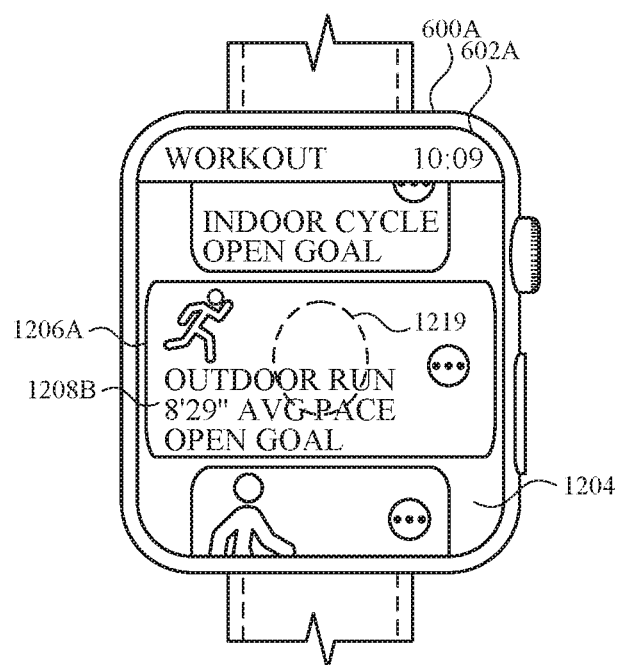

FIG. 12V again illustrates user interface 1204. Referring to FIG. 12V, user input (e.g., tap input) 1219 is received, where user input 1219 corresponds to selection of affordance 1206A. In accordance with a determination that user input 1219 is detected at affordance 1206A in the scrollable list of affordances 1206, a physical activity tracking function configured for outdoor runs is launched. The physical activity tracking function can include a pace alert when a user is below, on target, or above a user-specified pace for outdoor runs. The user-specified pace, as depicted in FIG. 12V is "8'29"".

Figure 12W:
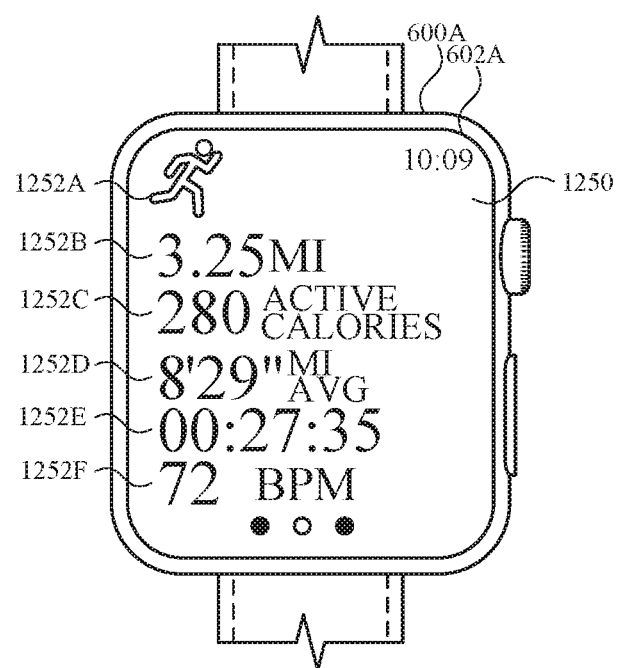

In response to selection of affordance 1206A, user interface 1250 (which is depicted in FIG. 12W) is displayed. User interface 1250 displays (e.g., provides feedback regarding) data detected by device 600A for an outdoor run. To display the data detected by device 600A, user interface 1250 includes representations 1252. In FIG. 12W, representations 1252 include icon 1252A (e.g., an animated icon of a running man to represent the outdoor run), total mileage 1252B (e.g., an indication of a number of miles traveled during the outdoor run), total calories 1252C (e.g., an indication of an amount of calories determined to be burned by the user during the outdoor run), average pace per mile 1252D (e.g., an indication of an average amount of time it has taken for device 600A to travel a mile during the outdoor run), total time 1252E (e.g., an indication of a duration of the outdoor run), and BPM 1252F (e.g., a calculated number of beats per minute for a heart of a user wearing device 600A). It should be recognized that, in some examples, user interface 1250 can include more or fewer representations, similar to as depicted in FIG. 12AK and discussed below.

While a user is performing the outdoor run, a pace of the user might goes above a pace set for the outdoor run. When the pace of the user is above the pace set for the outdoor run, an alert that the pace of the user is above the pace set for the outdoor run can be displayed, as depicted in FIG. 12X.

Figure 12X:
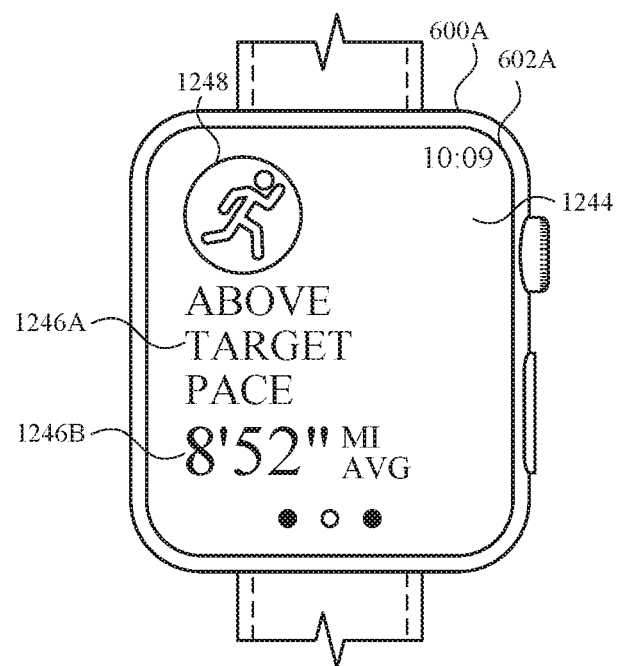
Figure 12Y:
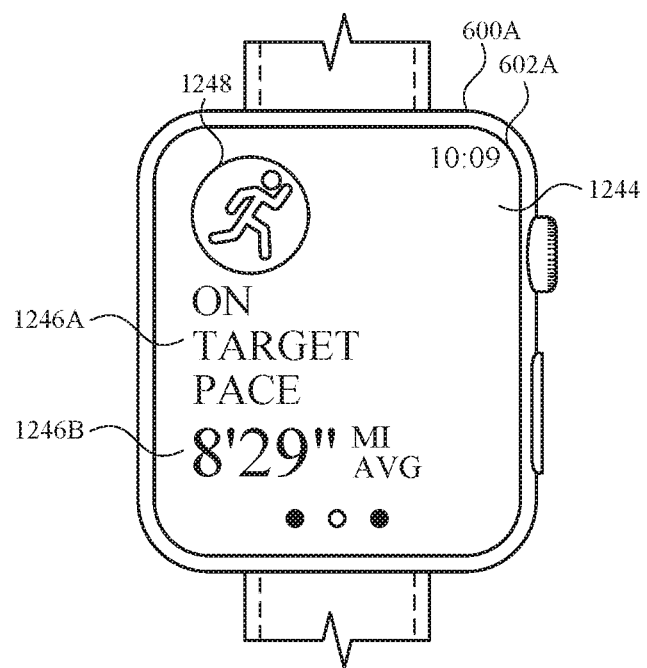

Referring to FIG. 12X, the alert can be included in user interface 1244. The alert can include an icon corresponding to a current workout and information 1246. Information 1246 can include status 1246A and current pace 1246B. Status 1246A can indicate whether the user is below, on target, or above a pace set for the current workout. Referring to FIG. 12X, status 1246A indicates that the user is "above target pace". Current pace 1246B can indicate a current pace for the user. For example, current pace 1246B (as depicted in FIG. 12X) indicates that the user is currently running at a "8'52"" pace, which (due to average being selected for calculating the pace) is calculated over the entire current workout. Because "8'52"" is above the pace set at "8'29"", the "above target pace" text can be displayed In response to the user running quicker and bringing their pace to "8'29"", user interface 1244 can be updated to reflect that the user is on target pace. Referring to FIG. 12Y, status 1246A can be updated to indicate that the user in "on target pace" and current pace 1246B can be updated to indicate that the user's current pace is "8'29"" when calculated over the entire current workout.

In response to the user running even quicker and bringing their pace to "7'57"", user interface 1244 can be updated to reflect that the user is below target pace. For example, status 1246A can be updated to indicate that the user in "on target pace" and current pace 1246B can be updated to indicate that the user's current pace is "7'57"" when calculated over the entire current workout. It should be recognized that what values constitute below, on target, and above a target pace can include one or more values around a target pace. For example, a number of seconds above and below target pace can still be considered on target.

Figure 12Z:
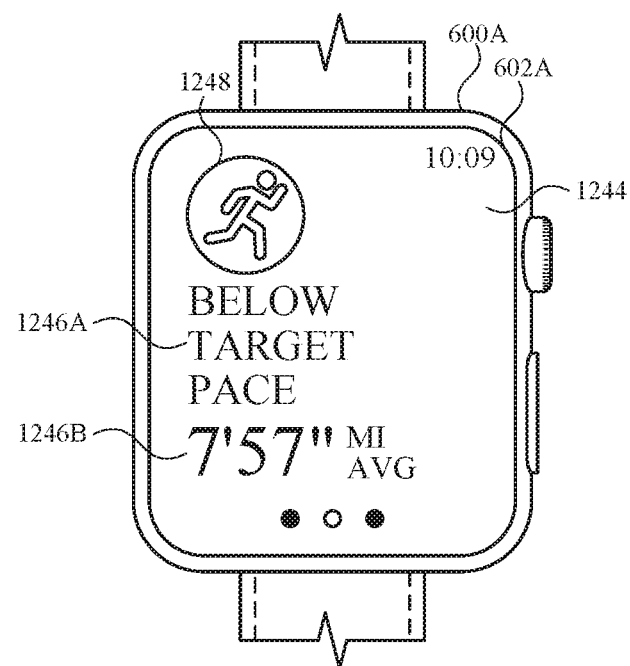
Figure 12A:
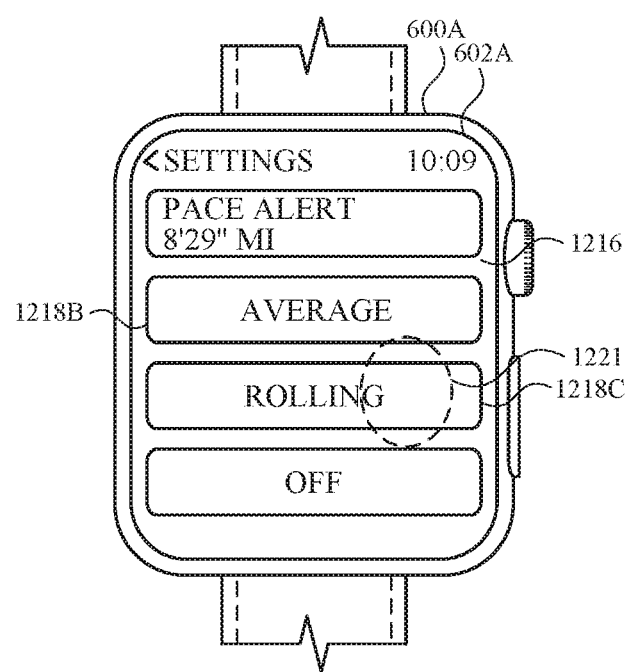
Figure 12A:
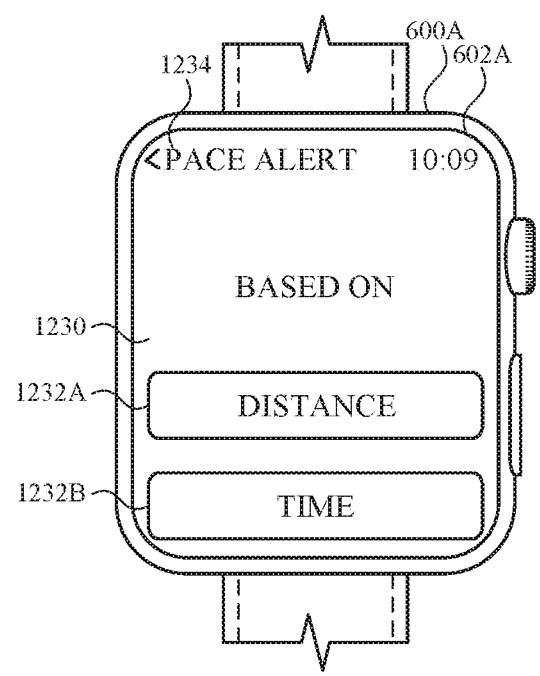
Figure 12A:
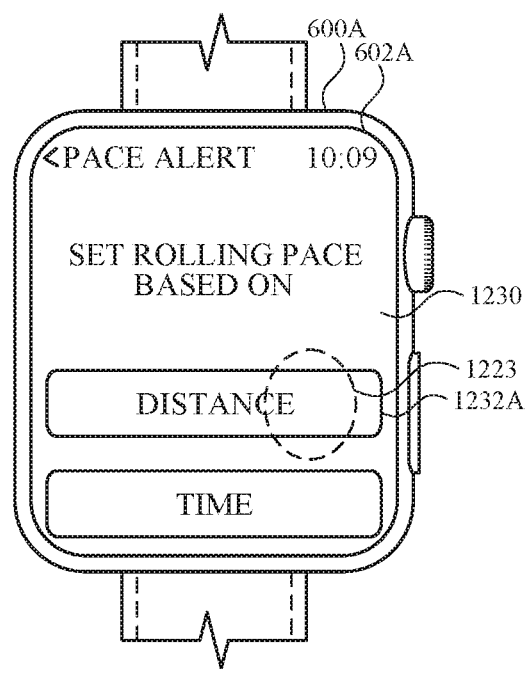
Figure 12A:
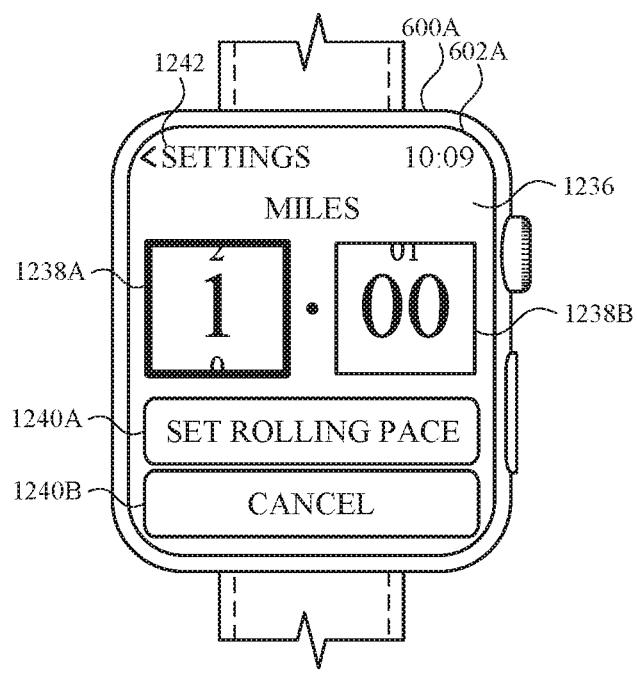
Figure 12A:
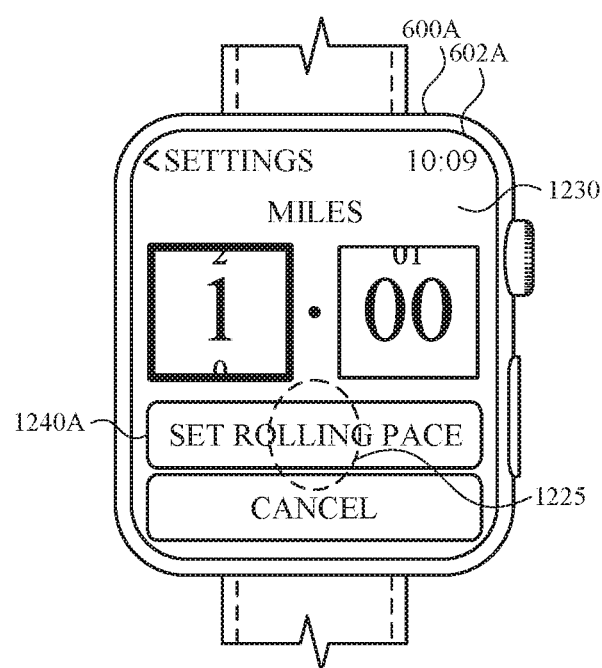
Figure 12A:
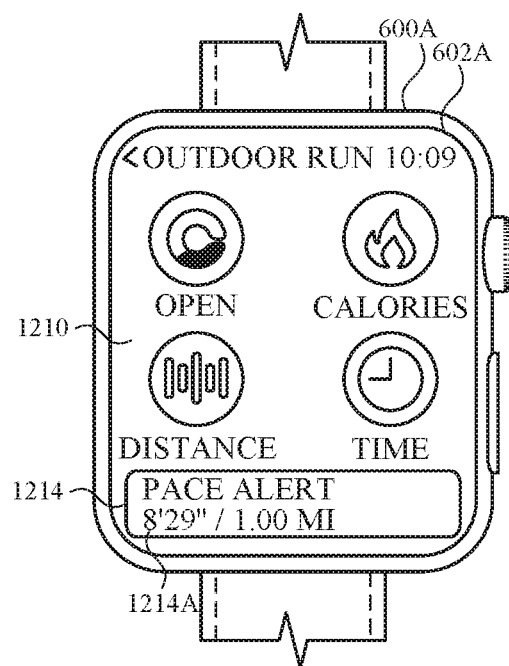
Figure 12A:
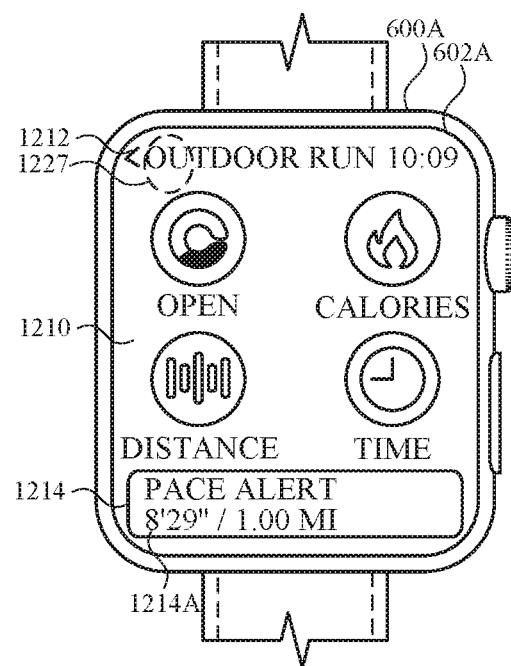
Figure 12A:
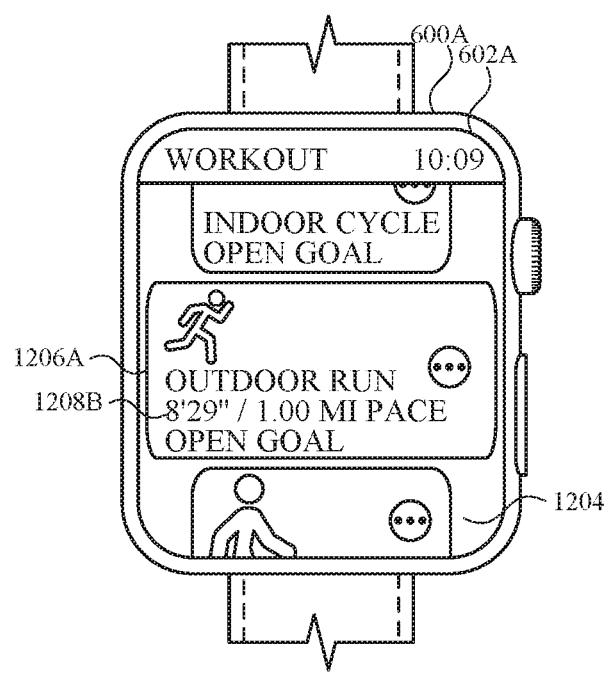
Figure 12A:
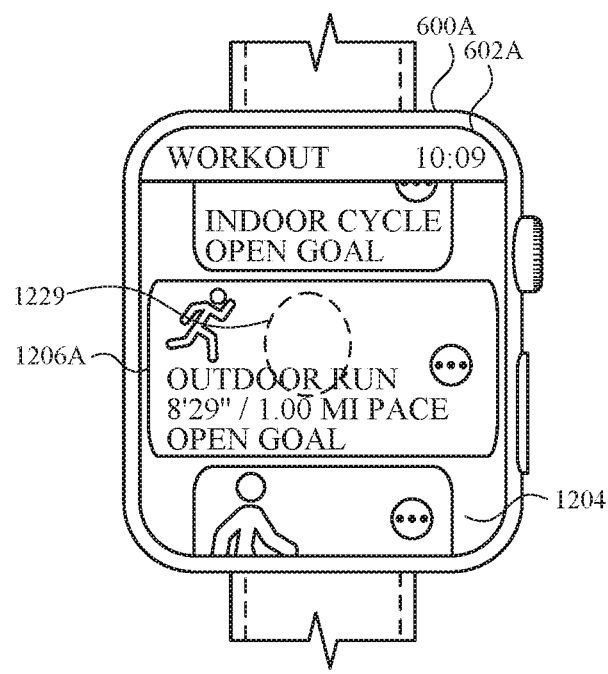
Figure 12A:
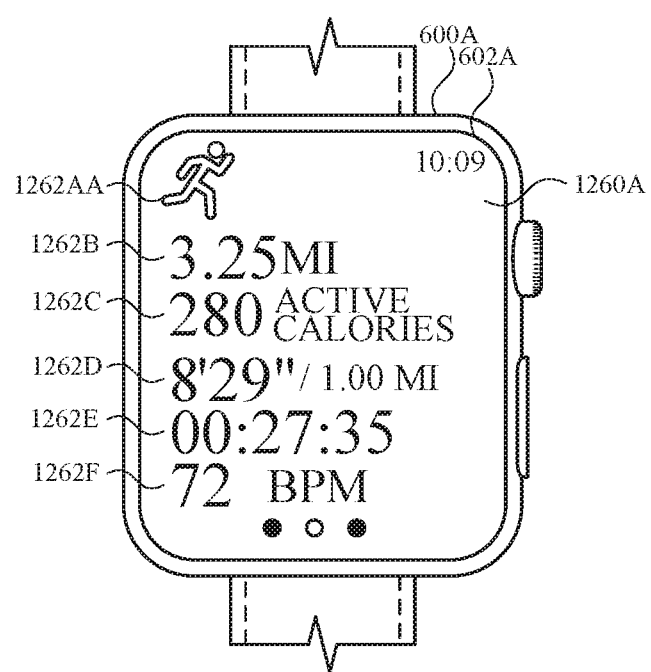
Figure 12A:
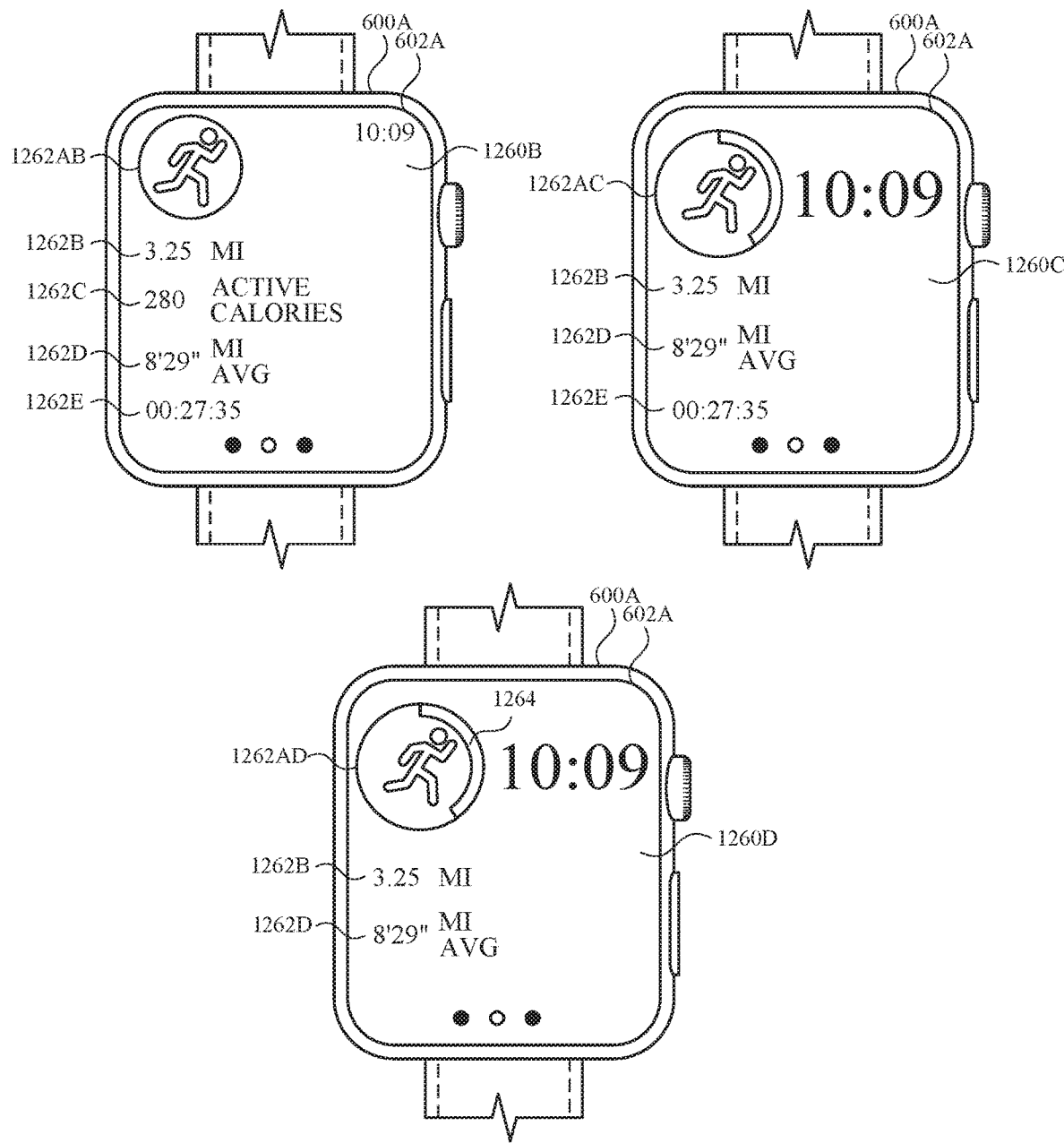

In some examples, interface 1244 (as depicted in each of FIG. 12X-12Z) can be displayed to the user once after it is determined that the user is below, on target, or above a target pace. The one time can be when a user brings device 600A into a position to look at device 600A. In such examples, additional views of device 600A while the same alert is applicable can cause user interface 1250 (as depicted in FIG. 12W) to be displayed. When user interface 1250 is displayed after an alert, average pace per mile 1252D can be visually highlighted such that it can easily be located on user interface 1250.

Referring back to after set-pace affordance 1226A is selected (as depicted in FIG. 12N), FIG. 12AA again illustrates user interface 1216. While average affordance 1218B is illustrated without a check mark in FIG. 12AA, it should be recognized that average affordance 1218B can include the check mark (as depicted in FIG. 12Q).

Referring to FIG. 12AA, user interface 1216 can include rolling affordance 1218C. Rolling affordance 1218C can correspond to calculating a pace using a rolling average during a physical activity. Rolling average can relate to using a subset of data for the physical activity. For example, while an average for the physical activity might use data from a beginning point to a present point of the physical activity, a rolling average can use an amount before the present point such that not all of the data from the beginning is used.

In one illustrative example, the user can run 2 miles in 10 minutes. The average for the run would be 5 minutes per mile. If the rolling average is calculated for the last 5 minutes, the rolling average for the run would be 5 divided by however much distance was covered in the last 5 minutes. For example, if the user ran 1.2 miles in the last 5 minutes, the rolling average for the user is 5 divided by 1.2 (i.e., 4 minutes and 10 seconds per mile).

Referring to FIG. 12AA, user input (e.g., tap input) 1221 is received, where user input 1221 corresponds to selection of rolling affordance 1218C. In accordance with a determination that user input 1221 is detected at rolling affordance 1218C in the scrollable list of affordances 1218, user interface 1230 can be displayed, as depicted in FIG. 12AB.

Referring to FIG. 12AB, user interface 1230 includes a list of affordances 1232 for configuring how a rolling calculation will be performed. The list of affordances 1232 can include first affordance 1232A and second affordance 1232B. First affordance 1232A corresponds to distance such that the rolling calculation includes data detected for a previous amount of distance. For example, an average can be calculated for data detected in the last mile. Selection of first affordance 1232A can cause a user interface (e.g., user interface 1236 as depicted in FIG. 12AD and discussed below) to be displayed to allow the user to select an amount of distance. Second affordance 1232B corresponds to time such that the rolling calculation includes data detected for a previous amount of time. For example, an average can be calculated for data detected in the last 5 minutes. Selection of second affordance 1232B can cause a user interface (e.g., similar to user interface 1222 as depicted in FIG. 12I) to be displayed to allow the user to select an amount of time.

FIG. 12AC again illustrates user interface 1230. As described above for FIG. 12AB, user interface 1230 includes first affordance 1232A, which corresponds to distance. Referring to FIG. 12AC, user input (e.g., tap input) 1223 is received, where user input 1223 corresponds to selection of first affordance 1232A. In accordance with a determination that user input 1223 is detected at first affordance 1232A in the scrollable list of affordances 1232, a user interface (user interface 1236 as depicted in FIG. 12AD) for selecting a distance is displayed.

Referring to FIG. 12AD, user interface 1236 can be displayed in response to selection of first affordance 1232A in user interface 1230. User interface 1236 includes multiple affordances 1238 for setting a rolling pace (e.g., integer-setting affordance 1238A and decimal-setting affordance 1238B). Integer-setting affordance 1238A is used to set a number of previous whole miles to use for the rolling pace. Decimal-setting affordance 1224B is used to set a number of previous fractional miles to use for the rolling pace.

As depicted in FIG. 12AD, each affordance for setting the rolling pace is independently selectable. For example, each of integer-setting affordance 1238A and decimal-setting affordance 1238B can be selected. When an affordance of multiple affordances 1238 for setting the rolling pace is selected, the affordance can be visually distinguished. For example, in FIG. 12AD, integer-setting affordance 1238A has a thicker border than decimal-setting affordance 1238B, indicating integer-setting affordance 1238A is selected (e.g., in focus).

User interface 1236 further includes a scrollable list of affordances 1240, which are associated with different operations. For example, the scrollable list of affordances 1240 includes set-pace affordance 1240A (which corresponds to setting a pace identified using the multiple affordances for setting the rolling pace) and cancel affordance 1240B (which corresponds to displaying a user interface for providing options to configure a pace alert, such as user interface 1230 in FIG. 12AB), or any combination thereof. It is noted that the scrollable list of affordances 1240 might not fit within touch-sensitive display 602A; in which case one or more affordances not displayed can be displayed in response to a scrolling input (e.g., rotation of rotatable input mechanism 604A).

Referring to FIG. 12AE, user input (e.g., tap input) 1225 is received, where user input 1225 corresponds to selection of set-pace affordance 1240A. In accordance with a determination that user input 1225 is detected at set-pace affordance 1240A in the scrollable list of affordances 1240, user interface 1210 can be displayed, as depicted in FIG. 12AF.

FIG. 12AF again illustrates user interface 1210. User interface 1210 can be displayed in response to selection of set-pace affordance 1240A. User interface 1210 can provide options to change how device 600A operates when executing a physical activity tracking function corresponding to affordance 1206A. Text in pace-alert affordance 1214 (as depicted in FIG. 12AF) has been updated to include an indication of a pace set by a user (e.g., "8'29"/1.00 MI", as depicted at 1214A). By including "/1.00 MI" in the text, pace-alert affordance 1214 can indicate that the pace alert for a physical activity tracking function corresponding to affordance 1206A will be calculated using a rolling operation, as discussed herein.

Referring to FIG. 12AG, user input (e.g., tap input) 1227 is received, where user input 1227 corresponds to selection of back affordance 1212. In accordance with a determination that user input 1227 is detected at back affordance 1212, user interface 1204 can be displayed, as depicted in FIG. 12AH.

Referring to FIG. 12AH, affordance 1206A is updated to include an indication of a pace set by a user (e.g., "8'29"/1.00 MI", as depicted at 1208B). It should be recognized that multiple affordances in the list of affordances 1206 can include a pace set by a user. In some examples, different affordances in the list of affordances 1206 can include different paces set by a user. In addition, different paces set by a user can be calculated using a different operation (e.g., average or rolling).

FIG. 12AI again illustrates user interface 1204. Referring to FIG. 12AI, user input (e.g., tap input) 1229 is received, where user input 1229 corresponds to selection of affordance 1206A. In accordance with a determination that user input 1229 is detected at affordance 1206A in the scrollable list of affordances 1206, a physical activity tracking function configured for outdoor runs is launched. Launching the physical activity tracking function can cause a user interface to be displayed (e.g., user interface 1260A as depicted in FIG. 12AJ).

Referring to FIG. 12AJ, user interface 1260A is displayed in response to selection of affordance 1206A. User interface 1260A displays (e.g., provides feedback regarding) data detected by device 600A for an outdoor run. To display the data detected by device 600A, user interface 1250A includes representations 1262. In FIG. 12W, representations 1262 include icon 1262AA (e.g., an animated icon of a running man to represent the outdoor run), total mileage 1262B (e.g., an indication of a number of miles traveled during the outdoor run), total calories 1262C (e.g., an indication of an amount of calories determined to be burned by the user during the outdoor run), average pace per mile 1262D (e.g., an indication of an average amount of time it has taken for device 600A to travel a mile during the last mile of the outdoor run), total time 1262E (e.g., an indication of a duration of the outdoor run), and BPM 1262F (e.g., a calculated number of beats per minute for a heart of a user wearing device 600A). It should be recognized that, in some examples, user interface 1260A can include more or fewer representations, similar to as depicted in FIG. 12AK and discussed below.

FIG. 12AK illustrates multiple user interfaces 1260. User interfaces 1260 can be alternatives for displaying (e.g., providing feedback regarding) data detected by device 600A for an outdoor run (e.g., an alternative to user interface 1250 as depicted in FIG. 12W or user interface 1260A as depicted in FIG. 12AJ). Each of user interfaces 1260 include a different number of representations 1262. For example, user interface 1260B includes 5 representations 1262, user interface 1260C includes 4 representations 1262, and user interface 1260D includes 3 representations 1262. Each of user interfaces 1260 are meant to be an example. It should be recognized that other subsets of representations 1262 can be used and/or a different order of representations 1262.

It should also be recognized that icon 1262A can be different depending upon a number of representations 1262. When there are less representations 1262 (e.g., user interface 1260C includes less representations 1262 than user interface 1260B), icon 1262A can be bigger, more detailed, and/or include additional information. For example, icon 1262AD in user interface 1260D includes a running man and portion 1264. In some examples, portion 1264 can indicate a percent of a daily goal completed using device 600A. In other examples, portion 1264 can indicate a percent of a current workout completed using device 600A.

FIG. 13 is a flow diagram illustrating a method for displaying a user interface to configure a dataset that is used to calculate a pace using an electronic device in accordance with some examples. Method 1300 is performed at a device (e.g., 100, 300, 500, 600A, 600B, 800) with a display. Some operations in method 1300 are, optionally, combined, the orders of some operations are, optionally, changed, and some operations are, optionally, omitted.

As described below, method 1300 provides an intuitive way for displaying a user interface to configure a dataset that is used to calculate a pace. The method reduces the cognitive burden on a user for configuring the dataset to calculate the pace, thereby creating a more efficient human-machine interface. For battery-operated computing devices, enabling a user to configure a pace faster and more efficiently conserves power and increases the time between battery charges.

At 1302, the device (e.g., 600A) displays a physical activity rate (e.g., a pace (e.g., a mile pace while running)) user interface (e.g., 1216) including a first setting affordance (e.g., 1218B) and a second setting affordance (e.g., 1218C). In some examples, the user interface father includes a third affordance (e.g., 1218A) for setting a pace.

At 1304, while displaying the physical activity rate user interface, the device (e.g., 600A) receives a first user input (e.g., 1213). In some examples, the user input is a finger gesture, such as a tap, on either the first or second affordance.

At 1306, in response to receiving the first user input, in accordance with the first user input corresponding to selection of the first setting affordance (e.g., 1213), the device configures a physical activity rate calculation to use a first portion of a dataset (e.g., average).

In some examples, the first portion of the dataset includes all of the dataset (e.g., for an average pace).

At 1308, in further response to receiving the first user input, in accordance with the first user input corresponding to selection of the second setting affordance (e.g., 1221), the device configures a physical activity rate calculation to use a second portion of the dataset (e.g., rolling) different than the first portion. In some examples, the first portion of the dataset and the second portion of the dataset overlap. Displaying an option to choose between different types of physical activity rate calculations provides additionally configurability regarding how the device operates. Providing additional control options without cluttering the UI enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, configuring the physical activity calculation to use the second portion of the dataset includes displaying a second user interface (e.g., 1230) with a first affordance (e.g., 1232A) and a second affordance (e.g., 1232B). In such examples while displaying the second user interface, the device receives a second user input (e.g., 1223). In response to receiving the second user input, in accordance with a determination that the second user input is detected at the first affordance, the device causes the second portion to be determined based upon an amount of time. In further response to receiving the second user input, in accordance with a determination that the second user input is detected at the second affordance (e.g., 1223), the device causes the second portion to be determined based upon an amount of distance.

In some examples, after a physical activity rate is set for a type of physical activity and while a physical activity tracking function corresponding to the type of physical activity is executing, the device detects a current physical activity rate (e.g., 1262D). In response to detecting the current physical activity rate, in accordance with a determination that the current physical activity rate does not satisfy a first set of one or more alert criteria, the device forgoes output of a first alert. In some examples, the first set of one or more alert criteria includes whether the current physical activity rate is off pace. In some examples, the first alert is a haptic, audio, or visual alert. In further response to detecting the current physical activity rate, in accordance with a determination that the current physical activity rate satisfies the first set of one or more alert criteria, the device outputs the first alert.

In some examples, after outputting the first alert (e.g., a haptic our audio alert), the device receives a third user input. In some examples, the third user input is finger tap or a movement of the device (e.g., detected using one or more accelerometers), such as a wrist raise. In response to determining that the third user input satisfies a first set of one or more visual alert criteria, the device displays a visual alert (e.g., 1244). In some examples, a criterion of the set of one or more visual alert criteria is that movement of the device corresponds to a wrist raise gesture. The visual alert, in accordance with a determination that the current physical activity rate is less than the physical activity rate assigned to the type of physical activity, includes a representation (e.g., FIG. 12Z, 1244) corresponding to being below the physical activity rate assigned to the type of physical activity (e.g., the current physical activity pace (e.g., a running pace) has transitioned from being on or above a target activity pace to being below the target activity pace). In some examples, less than is within a threshold. The visual alert, in accordance with a determination that the current physical activity rate is within a threshold of the physical activity rate assigned to the type of physical activity, includes a representation (e.g., FIG. 12Y, 1244) corresponding to being on target for the physical activity rate set assigned to the type of physical activity (e.g., the current physical activity pace has transitioned from being above or below a target activity pace to matching the target activity pace). The visual alert, in accordance with a determination that the current physical activity rate is more than the physical activity rate assigned to the type of physical activity, includes a representation (e.g., FIG. 12X, 1244) corresponding to being above the physical activity rate assigned to the type of physical activity (e.g., the current physical activity pace has transitioned from being on or below a target activity pace to being above the target activity pace).

In some examples, after displaying the visual alert (e.g., 1244), the device receives a fourth user input. In some examples, the fourth user input is a gesture (e.g., wrist raise gesture, a tap gesture, or the like) that is detected within a predetermined time since receiving a first input gesture (e.g., a third user input, described above). In response to determining that the fourth user input satisfies a second set of one or more visual alert criteria, the device displays a second visual alert (e.g., 1250) with additional information not in the first visual alert. In some examples, the additional information includes metrics for a current workout, such as mileage, time, or the like.

In some examples, a current pace is highlighted in the second visual alert.

In some examples, physical activities that are capable of being tracked by the device have animated affordances (e.g., running man animation with no ring, FIG. 10I) and physical activities that are not capable of being tracked by the device have static affordances. For example, one or more sensors of the device might not be able to detect that a particular physical activity is being performed (e.g., a physical activity that appears, to one or more sensors of the device, to be similar to a routine physical activity). In such an example, user interfaces with an affordance corresponding to the particular physical activity can include a static affordance to indicate that the particular physical activity is not capable of being tracked by the device.

In some examples, prior to displaying the physical activity rate user interface, the device displays a third user interface (e.g., 1210) with a third affordance (e.g., 1214). In such examples, the device receives a fifth user input (e.g., 1214) corresponding to the third affordance, where the physical activity rate user interface (e.g., 1216) is displayed in response to receiving the fifth user input. After receiving the first user input, the device redisplays the third user interface (e.g., 1210), wherein the third affordance (e.g., 1214) in the redisplayed third user interface includes an identification (e.g., 1214A) of whether the physical activity calculation is configured to use the first portion or the second portion of the dataset, and where the third affordance did not include the identification before receiving the first user input.

In some examples, prior to displaying the third user interface (e.g., 1210), the device displays a fourth user interface (e.g., 1204) with a scrollable list of affordances associated with different physical activities, where a fourth affordance (e.g., 1206A) in the scrollable list includes a fifth affordance (e.g., 1208). In some examples, the fourth affordance is to start an outdoor run workout. In some examples, the fifth affordance is an options button for the fourth affordance. The device receives a sixth user input (e.g., 1201) corresponding to selection of the fifth affordance, where the third user interface (e.g., 1210) is displayed in response to receiving the sixth user input. After receiving the first user input, the device redisplays the fourth user interface (e.g., 1204), where the fourth affordance (e.g., 1206A) in the redisplayed fourth user interface includes an identification (e.g., 1208B) of whether the physical activity calculation is configured to use the first portion or the second portion of the dataset, and where the fourth affordance did not include the identification before receiving the first user input.

In some examples, the fourth affordance (e.g., 1206A) includes an identification (e.g., 1208B) of a first pace assigned to a physical activity corresponding to the fourth affordance, where a sixth affordance (e.g., 1206B) in the scrollable list includes an identification of a second pace assigned to a physical activity corresponding to the sixth affordance, and where the second pace is different from the first pace.

In some examples, the physical activity rate user interface is displayed further in response to a physical activity rate being set (as depicted in FIGS. 12I-12N).

Note that details of the processes described above with respect to method 1300 (e.g., FIG. 13) are also applicable in an analogous manner to the methods described above. For example, method 1300 optionally includes one or more of the characteristics of the various methods described below with reference to method 700, method 900, or method 1100. For example, the user interface of method 700 can be based upon a number of pace alerts output that were configured using method 1300. For another example, the user interface of method 900 can be based upon a number of pace alerts output that were configured using method 1300. For another example, the user interface of method 1300 can configure a pace that is then used to determine a boundary of a workout (as provided in method 1100). For brevity, these details are not repeated below.

The foregoing description, for purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to increase interactions between users. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to display representations of the personal information. Accordingly, use of such personal information data enables users to view feedback regarding data received from other users. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates examples in which users selectively block the use of, or access to, personal information data. That is, the present disclosure contemplates that hardware and/or software elements can be provided to prevent or block access to such personal information data. For example, in the case of activity and workout services, the present technology can be configured to allow users to select to "opt in" or "opt out" of participation in the collection of personal information data during registration for services or anytime thereafter. In another example, users can select not to provide activity associated data for activity and/or workout services. In yet another example, users can select to limit the length that activity associated data is maintained or entirely prohibit the development of user interfaces described herein. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed examples, the present disclosure also contemplates that the various examples can also be implemented without the need for accessing such personal information data. That is, the various examples of the present technology are not rendered inoperable due to the lack of all or a portion of such personal information data. For example, content can be selected and delivered to users by inferring activity based on non-personal information data or a bare minimum amount of personal information, such as the content being requested by the device associated with a user, other non-personal information available to the services described herein, or publicly available information.

What is claimed is:

1. An electronic device comprising:
   a display;
   one or more sensors;
   one or more processors; and
   memory storing one or more programs configured to be executed by the one or more processors, the one or more programs including instructions for:
      detecting, via the one or more sensors, activity data for a current physical activity; and
      in response to detecting the activity data for the current physical activity:
         in accordance with a determination that the activity data for the current physical activity satisfies activity boundary alert criteria:
            displaying an activity boundary alert including a first affordance;
            receiving a first user input corresponding to selection of the first affordance;
            in response to receiving the first user input:
               initiating a physical activity tracking function corresponding to a type of physical activity, wherein the physical activity tracking function corresponds to the activity boundary alert, and wherein the physical activity tracking function corresponding to the activity boundary alert tracks activity data for the current physical activity detected prior to displaying the activity boundary alert; and
               displaying a representation of a cumulative metric that corresponds to the current physical activity, wherein at least the activity data for the current physical activity that was detected prior to displaying the activity boundary alert is used to calculate the cumulative metric; and
         in accordance with a determination that the activity data for the current physical activity does not satisfy the activity boundary alert criteria, forgoing display of the activity boundary alert.

2. The electronic device of claim 1, wherein the one or more sensors include an accelerometer, GPS sensor, heart rate monitor, clock, gyroscope, a camera, or any combination thereof.

3. The electronic device of claim 1, wherein the one or more programs further include instructions for:
   in response to detecting the activity data:
      in accordance with a determination that the activity data satisfies second activity boundary alert criteria, displaying a second activity boundary alert, wherein the activity boundary alert criteria and the activity boundary alert correspond to a first type of physical activity, and wherein the second activity boundary alert criteria and the second activity boundary alert correspond to a second type of physical activity different from the first type; and in accordance with a determination that the activity data does not satisfy the second activity boundary alert criteria, forgoing display of the second activity boundary alert.

4. The electronic device of claim 1, wherein the activity data is detected before a respective physical activity tracking function is active.

5. The electronic device of claim 1, wherein the activity boundary alert corresponds to a first physical activity tracking function, wherein displaying the activity boundary alert includes displaying a second affordance, and wherein the one or more programs further include instructions for:

receiving a second user input corresponding to selection of the second affordance in the activity boundary alert;

in response to receiving the second user input, displaying a first user interface including:

a third affordance corresponding to a second physical activity tracking function different from the first physical activity tracking function; and a fourth affordance corresponding to a third physical activity tracking function different from the first physical activity tracking function; and while displaying the first user interface receiving a third user input:

in accordance with the third user input corresponding to selection of the third affordance in the first user interface, configuring the electronic device to track activity data detected after selection of the third affordance using the second physical activity tracking function; and in accordance with the third user input corresponding to selection of the fourth affordance in the first user interface, configuring the electronic device to track activity data detected after selection of the fourth affordance using the third physical activity tracking function.

6. The electronic device of claim 1, wherein displaying the activity boundary alert includes displaying an animated affordance representing a type of workout associated with the activity boundary alert.

7. The electronic device of claim 1, wherein:

the activity data was detected via a first sensor of the one or more sensors; and initiating the physical activity tracking function includes detecting second activity data via a second sensor, different from the first sensor, of the one or more sensors.

8. The electronic device of claim 1, wherein the activity data is detected while an existing physical activity tracking function is active.

9. The electronic device of claim 1, wherein the activity data is detected while an existing physical activity tracking function is active, wherein displaying the activity boundary alert includes displaying a fifth affordance, and wherein the one or more programs further include instructions for:

receiving a fourth user input corresponding to selection of the fifth affordance; and in response to receiving the fourth user input:

ending the existing physical activity tracking function; and storing activity data detected prior to receiving the fourth user input as a previous workout.

10. The electronic device of claim 1, wherein displaying the activity boundary alert includes displaying a sixth affordance, and wherein the one or more programs further include instructions for:

receiving a fifth user input corresponding to selection of the sixth affordance; and in response to receiving the fifth user input, pausing execution of a physical activity tracking function.

11. The electronic device of claim 1, wherein the activity boundary alert corresponds to a first physical activity tracking function, wherein displaying the activity boundary alert includes displaying a seventh affordance, and wherein the one or more programs further include instructions for:

receiving a sixth user input corresponding to selection of the seventh affordance;

in response to receiving the sixth input:

initiating a process for ceasing execution of a first physical activity tracking function; and displaying a second user interface, including:

an eighth affordance corresponding to a second physical activity tracking function different from the first physical activity tracking function, and a ninth affordance corresponding to a third physical activity tracking function different from the first physical activity tracking function;

receiving a seventh user input;

in accordance with the seventh user input corresponding to selection of the eighth affordance in the second user interface, initiating the second physical activity tracking function; and in accordance with the seventh user input corresponding to selection of the ninth affordance in the second user interface, initiating the third physical activity tracking function.

12. The electronic device of claim 1, wherein the activity boundary alert is a first activity boundary alert, and wherein the one or more programs further include instructions for:

after a predetermined time has lapsed without initiating a physical activity tracking function corresponding to the first activity boundary alert, displaying a second activity boundary alert, wherein a physical activity tracking function corresponding to the second activity boundary alert tracks activity data detected prior to displaying the first activity boundary alert.

13. The electronic device of claim 1, wherein displaying the activity boundary alert includes displaying a tenth affordance, wherein the physical activity tracking function corresponding to the activity boundary alert is a first physical activity tracking function, and wherein the one or more programs further include instructions for:

receiving an eighth user input corresponding to selection of the tenth affordance; and in response to receiving the eighth user input, initiating a second physical activity tracking function corresponding to the activity boundary alert, wherein the second physical activity tracking function is different from the first physical activity tracking function.

14. The electronic device of claim 13, wherein the first affordance is highlighted as compared to the tenth affordance.

15. The electronic device of claim 1, wherein the activity boundary alert is a first activity boundary alert including first content, and wherein the one or more programs further include instructions for:

after displaying the first activity boundary alert, displaying a second activity boundary alert including second content, wherein the second content is different from the first content.

16. The electronic device of claim 1, wherein the one or more programs further include instructions for:
after displaying the activity boundary alert and before a respective physical activity tracking function is active:
displaying a third user interface including a scrollable list of affordances associated with physical activities;
receiving a ninth user input;
in accordance with a determination that the ninth user input is detected at an eleventh affordance in the scrollable list of affordances, launching the respective physical activity tracking function, wherein the respective physical activity tracking function corresponds to the activity boundary alert; and
in accordance with a determination that the ninth user input is detected at a twelfth affordance in the scrollable list of affordances, launching a physical activity tracking function (1) that does not correspond to the activity boundary alert and (2) that is different from the respective physical activity tracking function corresponding to the activity boundary alert.

17. The electronic device of claim 16, wherein the respective physical activity tracking function corresponding to the activity boundary alert is a first physical activity tracking function, and wherein the one or more programs further include instructions for:
in accordance with a determination that the ninth user input is detected at a thirteenth affordance in the scrollable list of affordances, launching a second physical activity tracking function corresponding to the activity boundary alert, wherein the second physical activity tracking function is different from the first physical activity tracking function, and wherein the second physical activity tracking function corresponding to the activity boundary alert tracks activity data detected after receiving the ninth user input.

18. The electronic device of claim 1, wherein at least activity data for the current physical activity that is detected after receiving the first user input is also used to calculate the cumulative metric.

19. A method comprising:
at an electronic device including a display and one or more sensors:
detecting, via the one or more sensors, activity data for a current physical activity; and
in response to detecting the activity data for the current physical activity:
in accordance with a determination that the activity data for the current physical activity satisfies activity boundary alert criteria:
displaying an activity boundary alert including a first affordance;
receiving a first user input corresponding to selection of the first affordance;
in response to receiving the first user input:
initiating a physical activity tracking function corresponding to a type of physical activity, wherein the physical activity tracking function corresponds to the activity boundary alert, and wherein the physical activity tracking function corresponding to the activity boundary alert tracks activity data for the current physical activity detected prior to displaying the activity boundary alert; and
displaying a representation of a cumulative metric that corresponds to the current physical activity, wherein at least the activity data for current physical activity that was detected prior to displaying the activity boundary alert is used to calculate the cumulative metric; and
in accordance with a determination that the activity data for the current physical activity does not satisfy the activity boundary alert criteria, forgoing display of the activity boundary alert.

20. The method of claim 19, wherein the one or more sensors include an accelerometer, GPS sensor, heart rate monitor, clock, gyroscope, a camera, or any combination thereof.

21. The method of claim 19, further comprising:
in response to detecting the activity data:
in accordance with a determination that the activity data satisfies second activity boundary alert criteria, displaying a second activity boundary alert, wherein the activity boundary alert criteria and the activity boundary alert correspond to a first type of physical activity, and wherein the second activity boundary alert criteria and the second activity boundary alert correspond to a second type of physical activity different from the first type; and
in accordance with a determination that the activity data does not satisfy the second activity boundary alert criteria, forgoing display of the second activity boundary alert.

22. The method of claim 19, wherein the activity data is detected before a respective physical activity tracking function is active.

23. The method of claim 19, wherein the activity boundary alert corresponds to a first physical activity tracking function, and wherein displaying the activity boundary alert includes displaying a second affordance, the method further including:
receiving a second user input corresponding to selection of the second affordance in the activity boundary alert;
in response to receiving the second user input, displaying a first user interface including:
a third affordance corresponding to a second physical activity tracking function different from the first physical activity tracking function; and
a fourth affordance corresponding to a third physical activity tracking function different from the first physical activity tracking function; and
while displaying the first user interface receiving a third user input:
in accordance with the third user input corresponding to selection of the third affordance in the first user interface, configuring the electronic device to track activity data detected after selection of the third affordance using the second physical activity tracking function; and
in accordance with the third user input corresponding to selection of the fourth affordance in the first user interface, configuring the electronic device to track activity data detected after selection of the fourth affordance using the third physical activity tracking function.

24. The method of claim 19, wherein displaying the activity boundary alert includes displaying an animated affordance representing a type of workout associated with the activity boundary alert.

25. The method of claim 19, wherein:
the activity data was detected via a first sensor of the one or more sensors; and
initiating the physical activity tracking function includes detecting second activity data via a second sensor, different from the first sensor, of the one or more sensors.

26. The method of claim 19, wherein the activity data is detected while an existing physical activity tracking function is active.

27. The method of claim 19, wherein the activity data is detected while an existing physical activity tracking function is active, and wherein displaying the activity boundary alert includes displaying a fifth affordance, the method further including:
receiving a fourth user input corresponding to selection of the fifth affordance; and
in response to receiving the fourth user input:
ending the existing physical activity tracking function; and
storing activity data detected prior to receiving the fourth user input as a previous workout.

28. The method of claim 19, wherein displaying the activity boundary alert includes displaying a sixth affordance, the method further including:
receiving a fifth user input corresponding to selection of the sixth affordance; and
in response to receiving the fifth user input, pausing execution of a physical activity tracking function.

29. The method of claim 19, wherein the activity boundary alert corresponds to a first physical activity tracking function, and wherein displaying the activity boundary alert includes displaying a seventh affordance, the method further including:
receiving a sixth user input corresponding to selection of the seventh affordance;
in response to receiving the sixth input:
initiating a process for ceasing execution of a first physical activity tracking function; and
displaying a second user interface, including:
an eighth affordance corresponding to a second physical activity tracking function different from the first physical activity tracking function, and
a ninth affordance corresponding to a third physical activity tracking function different from the first physical activity tracking function;
receiving a seventh user input;
in accordance with the seventh user input corresponding to selection of the eighth affordance in the second user interface, initiating the second physical activity tracking function; and
in accordance with the seventh user input corresponding to selection of the ninth affordance in the second user interface, initiating the third physical activity tracking function.

30. The method of claim 19, wherein the activity boundary alert is a first activity boundary alert, the method further including:
after a predetermined time has lapsed without initiating a physical activity tracking function corresponding to the first activity boundary alert, displaying a second activity boundary alert, wherein a physical activity tracking function corresponding to the second activity boundary alert tracks activity data detected prior to displaying the first activity boundary alert.

31. The method of claim 19, wherein displaying the activity boundary alert includes displaying a tenth affordance, and wherein the physical activity tracking function corresponding to the activity boundary alert is a first physical activity tracking function, the method further including:
receiving an eighth user input corresponding to selection of the tenth affordance; and
in response to receiving the eighth user input, initiating a second physical activity tracking function corresponding to the activity boundary alert, wherein the second physical activity tracking function is different from the first physical activity tracking function.

32. The method of claim 31, wherein the first affordance is highlighted as compared to the tenth affordance.

33. The method of claim 19, wherein the activity boundary alert is a first activity boundary alert including first content, the method further including:
after displaying the first activity boundary alert, displaying a second activity boundary alert including second content, wherein the second content is different from the first content.

34. The method of claim 19, further comprising:
after displaying the activity boundary alert and before a respective physical activity tracking function is active:
displaying a third user interface including a scrollable list of affordances associated with physical activities;
receiving a ninth user input;
in accordance with a determination that the ninth user input is detected at an eleventh affordance in the scrollable list of affordances, launching the respective physical activity tracking function, wherein the respective physical activity tracking function corresponds to the activity boundary alert; and
in accordance with a determination that the ninth user input is detected at a twelfth affordance in the scrollable list of affordances, launching a physical activity tracking function (1) that does not correspond to the activity boundary alert and (2) that is different from the respective physical activity tracking function corresponding to the activity boundary alert.

35. The method of claim 34, wherein the respective physical activity tracking function corresponding to the activity boundary alert is a first physical activity tracking function, the method further including:
in accordance with a determination that the ninth user input is detected at a thirteenth affordance in the scrollable list of affordances, launching a second physical activity tracking function corresponding to the activity boundary alert, wherein the second physical activity tracking function is different from the first physical activity tracking function, and wherein the second physical activity tracking function corresponding to the activity boundary alert tracks activity data detected after receiving the ninth user input.

36. The method of claim 19, wherein at least activity data for the current physical activity that is detected after receiving the first user input is also used to calculate the cumulative metric.

37. A non-transitory computer-readable storage medium storing one or more programs configured to be executed by one or more processors of an electronic device having a display and one or more sensors, the one or more programs including instructions for:

detecting, via the one or more sensors, activity data for a current physical activity; and in response to detecting the activity data for the current physical activity:
  in accordance with a determination that the activity data for the current physical activity satisfies activity boundary alert criteria:
    displaying an activity boundary alert including a first affordance;
    receiving a first user input corresponding to selection of the first affordance;
    in response to receiving the first user input:
      initiating a physical activity tracking function corresponding to a type of physical activity, wherein the physical activity tracking function corresponds to the activity boundary alert, and wherein the physical activity tracking function corresponding to the activity boundary alert tracks activity data for the current physical activity detected prior to displaying the activity boundary alert; and
      displaying a representation of a cumulative metric that corresponds to the current physical activity, wherein at least the activity data for current physical activity that was detected prior to displaying the activity boundary alert is used to calculate the cumulative metric; and
  in accordance with a determination that the activity data for the current physical activity does not satisfy the activity boundary alert criteria, forgoing display of the activity boundary alert.

38. The non-transitory computer readable storage medium of claim 37, wherein the one or more sensors include an accelerometer, GPS sensor, heart rate monitor, clock, gyroscope, a camera, or any combination thereof.

39. The non-transitory computer readable storage medium of claim 37, wherein the one or more programs further include instructions for:
  in response to detecting the activity data:
    in accordance with a determination that the activity data satisfies second activity boundary alert criteria, displaying a second activity boundary alert, wherein the activity boundary alert criteria and the activity boundary alert correspond to a first type of physical activity, and wherein the second activity boundary alert criteria and the second activity boundary alert correspond to a second type of physical activity different from the first type; and
    in accordance with a determination that the activity data does not satisfy the second activity boundary alert criteria, forgoing display of the second activity boundary alert.

40. The non-transitory computer readable storage medium of claim 37, wherein the activity data is detected before a respective physical activity tracking function is active.

41. The non-transitory computer readable storage medium of claim 37, wherein the activity boundary alert corresponds to a first physical activity tracking function, wherein displaying the activity boundary alert includes displaying a second affordance, and wherein the one or more programs further include instructions for:
  receiving a second user input corresponding to selection of the second affordance in the activity boundary alert;
  in response to receiving the second user input, displaying a first user interface including:
    a third affordance corresponding to a second physical activity tracking function different from the first physical activity tracking function; and
    a fourth affordance corresponding to a third physical activity tracking function different from the first physical activity tracking function; and
  while displaying the first user interface receiving a third user input:
    in accordance with the third user input corresponding to selection of the third affordance in the first user interface, configuring the electronic device to track activity data detected after selection of the third affordance using the second physical activity tracking function; and
    in accordance with the third user input corresponding to selection of the fourth affordance in the first user interface, configuring the electronic device to track activity data detected after selection of the fourth affordance using the third physical activity tracking function.

42. The non-transitory computer readable storage medium of claim 37, wherein displaying the activity boundary alert includes displaying an animated affordance representing a type of workout associated with the activity boundary alert.

43. The non-transitory computer readable storage medium of claim 37, wherein:
  the activity data was detected via a first sensor of the one or more sensors; and
  initiating the physical activity tracking function includes detecting second activity data via a second sensor, different from the first sensor, of the one or more sensors.

44. The non-transitory computer readable storage medium of claim 37, wherein the activity data is detected while an existing physical activity tracking function is active.

45. The non-transitory computer readable storage medium of claim 37, wherein the activity data is detected while an existing physical activity tracking function is active, wherein displaying the activity boundary alert includes displaying a fifth affordance, and wherein the one or more programs further include instructions for:
  receiving a fourth user input corresponding to selection of the fifth affordance; and
  in response to receiving the fourth user input:
    ending the existing physical activity tracking function; and
    storing activity data detected prior to receiving the fourth user input as a previous workout.

46. The non-transitory computer readable storage medium of claim 37, wherein displaying the activity boundary alert includes displaying a sixth affordance, and wherein the one or more programs further include instructions for:
  receiving a fifth user input corresponding to selection of the sixth affordance; and
  in response to receiving the fifth user input, pausing execution of a physical activity tracking function.

47. The non-transitory computer readable storage medium of claim 37, wherein the activity boundary alert corresponds to a first physical activity tracking function, wherein displaying the activity boundary alert includes displaying a seventh affordance, and wherein the one or more programs further include instructions for:
  receiving a sixth user input corresponding to selection of the seventh affordance;
  in response to receiving the sixth input:
    initiating a process for ceasing execution of a first physical activity tracking function; and displaying a second user interface, including:
    an eighth affordance corresponding to a second physical activity tracking function different from the first physical activity tracking function, and
    a ninth affordance corresponding to a third physical activity tracking function different from the first physical activity tracking function;
receiving a seventh user input;
in accordance with the seventh user input corresponding to selection of the eighth affordance in the second user interface, initiating the second physical activity tracking function; and
in accordance with the seventh user input corresponding to selection of the ninth affordance in the second user interface, initiating the third physical activity tracking function.

48. The non-transitory computer readable storage medium of claim 37, wherein the activity boundary alert is a first activity boundary alert, and wherein the one or more programs further include instructions for:
    after a predetermined time has lapsed without initiating a physical activity tracking function corresponding to the first activity boundary alert, displaying a second activity boundary alert, wherein a physical activity tracking function corresponding to the second activity boundary alert tracks activity data detected prior to displaying the first activity boundary alert.

49. The non-transitory computer readable storage medium of claim 37, wherein displaying the activity boundary alert includes displaying a tenth affordance, wherein the physical activity tracking function corresponding to the activity boundary alert is a first physical activity tracking function, and wherein the one or more programs further include instructions for:
    receiving an eighth user input corresponding to selection of the tenth affordance; and
    in response to receiving the eighth user input, initiating a second physical activity tracking function corresponding to the activity boundary alert, wherein the second physical activity tracking function is different from the first physical activity tracking function.

50. The non-transitory computer readable storage medium of claim 49, wherein the first affordance is highlighted as compared to the tenth affordance.

51. The non-transitory computer readable storage medium of claim 37, wherein the activity boundary alert is a first activity boundary alert including first content, and wherein the one or more programs further include instructions for:
    after displaying the first activity boundary alert, displaying a second activity boundary alert including second content, wherein the second content is different from the first content.

52. The non-transitory computer readable storage medium of claim 37, wherein the one or more programs further include instructions for:
    after displaying the activity boundary alert and before a respective physical activity tracking function is active:
        displaying a third user interface including a scrollable list of affordances associated with physical activities;
        receiving a ninth user input;
        in accordance with a determination that the ninth user input is detected at an eleventh affordance in the scrollable list of affordances, launching the respective physical activity tracking function, wherein the respective physical activity tracking function corresponds to the activity boundary alert; and
        in accordance with a determination that the ninth user input is detected at a twelfth affordance in the scrollable list of affordances, launching a physical activity tracking function (1) that does not correspond to the activity boundary alert and (2) that is different from the respective physical activity tracking function corresponding to the activity boundary alert.

53. The non-transitory computer readable storage medium of claim 52, wherein the respective physical activity tracking function corresponding to the activity boundary alert is a first physical activity tracking function, and wherein the one or more programs further include instructions for:
    in accordance with a determination that the ninth user input is detected at a thirteenth affordance in the scrollable list of affordances, launching a second physical activity tracking function corresponding to the activity boundary alert, wherein the second physical activity tracking function is different from the first physical activity tracking function, and wherein the second physical activity tracking function corresponding to the activity boundary alert tracks activity data detected after receiving the ninth user input.

54. The non-transitory computer readable storage medium of claim 37, wherein at least activity data for the current physical activity that is detected after receiving the first user input is also used to calculate the cumulative metric.

\* \* \* \* \*